US 8,637,253 B2
Jan. 28, 2014

(12) United States Patent
Piepenburg et al.

(54) RECOMBINASE POLYMERASE AMPLIFICATION

(75) Inventors: Olaf Piepenburg, Barnet (GB); Niall A. Armes, Fulbourn (GB); Mathew James David Parker, Letchworth Garden (GB)

(73) Assignee: Alere San Diego, Inc., San Diego, CA (US)

( * ) Notice: Subject to any disclaimer, the term of this patent is extended or adjusted under 35 U.S.C. 154(b) by 0 days.

(21) Appl. No.: 13/307,293

(22) Filed: Nov. 30, 2011

(65) Prior Publication Data

US 2012/0258499 A1    Oct. 11, 2012

Related U.S. Application Data

(63) Continuation of application No. 11/800,318, filed on May 4, 2007, now Pat. No. 8,071,308.

(60) Provisional application No. 60/798,060, filed on May 4, 2006.

(51) Int. Cl.
*C12Q 1/68* (2006.01)
*C12P 19/34* (2006.01)
*C07K 1/00* (2006.01)

(52) U.S. Cl.
USPC ............... 435/6.12; 435/91.2; 530/350

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,965,188 A | 10/1990 | Mullis et al. |
| 5,223,414 A | 6/1993 | Zarling et al. |
| 5,273,881 A | 12/1993 | Sena et al. |
| 5,326,692 A | 7/1994 | Brinkley et al. |
| 5,418,149 A | 5/1995 | Gelfand et al. |
| 5,430,136 A | 7/1995 | Urdea et al. |
| 5,536,649 A | 7/1996 | Fraiser et al. |
| 5,656,430 A | 8/1997 | Chirikjian |
| 5,665,572 A | 9/1997 | Ikeda et al. |
| 5,670,316 A | 9/1997 | Sena et al. |
| 5,705,366 A | 1/1998 | Backus |
| 5,792,607 A | 8/1998 | Backman et al. |
| 5,849,547 A | 12/1998 | Cleuziat |
| 5,858,652 A | 1/1999 | Laffler et al. |
| 6,087,112 A | 7/2000 | Dale |
| 6,165,793 A | 12/2000 | Stemmer |
| 6,251,600 B1 | 6/2001 | Winger et al. |
| 6,379,899 B1 | 4/2002 | Ullman |
| 6,387,621 B1 | 5/2002 | Wittwer |
| 6,699,693 B1 | 3/2004 | Marians et al. |
| 6,929,915 B2 | 8/2005 | Benkovic et al. |
| 7,252,940 B2 | 8/2007 | Kutyavin et al. |
| 7,270,981 B2 | 9/2007 | Armes et al. |
| 7,282,328 B2 | 10/2007 | Kong |
| 7,399,590 B2 * | 7/2008 | Piepenburg et al. ......... 435/6.14 |
| 7,435,561 B2 | 10/2008 | Piepenburg et al. |
| 7,485,428 B2 | 2/2009 | Armes et al. |
| 7,666,598 B2 * | 2/2010 | Piepenburg et al. ......... 435/6.16 |
| 7,763,427 B2 | 7/2010 | Piepenburg et al. |
| 8,017,339 B2 | 9/2011 | Piepenburg et al. |
| 8,030,000 B2 | 10/2011 | Piepenburg et al. |
| 8,062,850 B2 | 11/2011 | Piepenburg et al. |
| 8,071,308 B2 * | 12/2011 | Piepenburg et al. ......... 435/6.12 |
| 2001/0044111 A1 | 11/2001 | Carr et al. |
| 2002/0061530 A1 | 5/2002 | Belotserkovskii et al. |
| 2002/0155573 A1 | 10/2002 | Lanes et al. |
| 2003/0082565 A1 | 5/2003 | Jang |
| 2003/0108936 A1 | 6/2003 | Wagner |
| 2003/0143525 A1 | 7/2003 | Benkovic et al. |
| 2003/0219792 A1 | 11/2003 | Armes et al. |
| 2003/0228611 A1 | 12/2003 | Chruch et al. |
| 2004/0101893 A1 | 5/2004 | Kutyavin et al. |
| 2004/0137456 A1 | 7/2004 | Yokota et al. |
| 2004/0224336 A1 | 11/2004 | Wagner |
| 2005/0003395 A1 | 1/2005 | Gellibolian et al. |
| 2005/0059003 A1 | 3/2005 | Enoki et al. |
| 2005/0112631 A1 * | 5/2005 | Piepenburg et al. ............... 435/6 |
| 2005/0136443 A1 | 6/2005 | Shigemori |
| 2006/0110765 A1 | 5/2006 | Wang |
| 2007/0054296 A1 | 3/2007 | Piepenburg |
| 2007/0154914 A1 | 7/2007 | Gelfand et al. |
| 2008/0076160 A1 | 3/2008 | Armes et al. |
| 2008/0293045 A1 | 11/2008 | Piepenburg et al. |
| 2009/0017462 A1 | 1/2009 | Piepenburg et al. |
| 2009/0029421 A1 | 1/2009 | Piepenburg et al. |
| 2009/0269813 A1 | 10/2009 | Piepenburg et al. |

(Continued)

FOREIGN PATENT DOCUMENTS

| | | |
|---|---|---|
| CA | 2444649 | 10/2002 |
| CA | 2476481 | 9/2003 |

(Continued)

OTHER PUBLICATIONS

European Search Report, for the corresponding EP Application No. 11170060.5, dated Sep. 11, 2012.
Kim and Chae, "Optimized protocols for the detection of porcine circovirus 2 DNA from formalin-fixed paraffin-embedded tissues using nested polymerase chain reaction and comparison of nested PCR with in situ hybridization," J. Vir. Methods, 92:105-111, 2001.
Miyamoto et al., "Development of a New Seminested PCR Method for Detection of Legionella Species and Its Application to Surveillance of Legionellae in Hospital Cooling Tower Water," Applied and Environmental Microbiology, 63(7):2489-2494, 1997.
Monis and Saint, "Development of a Nested-PCR Assay for the Detection of Cryptosporidium Parvum in Finished Water," Wat. Res., 35(7):1641-1648, 2001.

(Continued)

*Primary Examiner* — Suryaprabha Chunduru
(74) *Attorney, Agent, or Firm* — Fish & Richardson P.C.

(57) ABSTRACT

The present invention features novel, diverse, hybrid and engineered recombinase enzymes, and the utility of such proteins with associated recombination factors for carrying out DNA amplification assays. The present invention also features different recombinase 'systems' having distinct biochemical activities in DNA amplification assays, and differing requirements for loading factors, single-stranded DNA binding proteins (SSBs), and the quantity of crowding agent employed.

47 Claims, 74 Drawing Sheets

(56) References Cited

U.S. PATENT DOCUMENTS

| | | | |
|---|---|---|---|
| 2009/0325165 | A1 | 12/2009 | Armes et al. |
| 2010/0311127 | A1 | 12/2010 | Piepenburg et al. |
| 2011/0053153 | A1 | 3/2011 | Piepenburg et al. |
| 2011/0059506 | A1 | 3/2011 | Piepenburg et al. |
| 2011/0065106 | A1 | 3/2011 | Armes et al. |
| 2012/0015367 | A1 | 1/2012 | Piepenburg et al. |
| 2012/0021462 | A1 | 1/2012 | Armes et al. |
| 2012/0058517 | A1 | 3/2012 | Piepenburg et al. |
| 2012/0082990 | A1 | 4/2012 | Piepenburg et al. |
| 2012/0129173 | A1 | 5/2012 | Piepenburg et al. |

FOREIGN PATENT DOCUMENTS

| | | | |
|---|---|---|---|
| EP | 0 624 643 | | 4/1994 |
| EP | 0 702 090 | | 3/1996 |
| EP | 0 810 436 | | 12/1997 |
| EP | 1 420 069 | | 5/2004 |
| EP | 1 564 306 | | 8/2005 |
| JP | 08-103300 | | 4/1996 |
| JP | 2000-500981 | | 2/2000 |
| WO | WO 91/17267 | | 11/1991 |
| WO | WO 93/05178 | | 3/1993 |
| WO | WO 97/20078 | | 6/1997 |
| WO | WO 98/08975 | | 3/1998 |
| WO | WO 00/41524 | | 7/2000 |
| WO | WO 00/46408 | | 8/2000 |
| WO | WO 02/086167 | | 10/2002 |
| WO | WO 03/027640 | | 4/2003 |
| WO | WO 03/038053 | | 5/2003 |
| WO | WO 03/072805 | | 9/2003 |
| WO | WO 2004/007078 | | 1/2004 |
| WO | WO 2004/027025 | | 4/2004 |
| WO | WO 2004/090169 | | 10/2004 |
| WO | WO 2005/118853 | | 12/2005 |
| WO | WO 2005118853 | A2 * | 12/2005 |
| WO | WO 2007/096702 | | 8/2007 |

OTHER PUBLICATIONS

Ozbas et al., "Development of a multiplex and semi-nested PCR assay for detection of *Yersinia enterocolitica* and *Aeromonas hydrophila* in raw milk," Food Microbiology, 17:197-203, 2000.
Accession: NP_861734 [GI: 32453528], Definition: UvsX RecA-like recombination protein [Enterobacteria phage RB69]. NCBI Sequence Revision History [online]; Mar. 30, 2006 uploaded, NCBI, <URL: http://www.ncbi.nlm.nih.gov/protein/32453528?sat=12&satkey=7706006> [retrieved on Aug. 30, 2011].
Accession: NP_861890 [GI: 32453681], Definition: UvsY recombination, repair and ssDNA binding protein [Enterobacteria phage RB69]. NCBI Sequence Revision History [online]; Mar. 30, 2006 uploaded, NCBI, <URL: http://www.ncbi.nlm.nih.gov/protein/32453681?sat=12&satkey=7706006> [retrieved on Aug. 30, 2011].
Adams et al., "Dissociation of RecA filaments from duplex DNA by the RuvA and RuvB DNA repair proteins," Proc. Natl. Acad. Sci. USA 91:9901-9905, 1994.
Alexseyev et al., "Genetic Characteristics of New *recA* Mutants of *Escherichia coli* K-12," J. Bacteriol., 178:2018-2024, 1996.
Amasino, "Acceleration of Nucleic Acid Hybridization Rate by Polyethylene Glycol," Anal. Biochem., 152:304-307, 1986.
Bains and Smith, "A Novel Method for Nucleic Acid Sequence Determination," J. Theor. Biol., 135:303-307, 1988.
Bar-Ziv and Libchaber, "Effects of DNA sequence and structure on binding of RecA to single-stranded DNA," PNAS USA, 98(16):9068-9073.
Baumann et al., "Purification of human Rad51 protein by selective spermidine precipitation," Mutat. Res., 384:65-72, 1997.
Benedict and Kowalczykowski, "Increase of the DNA Strand Assimiliation Activity of recA Protein by Removal of the C Terminus and Structure-Function Studies of the Resulting Protein Fragment," J. Biol. Chem., 263(30):15513-15520, 1988.
Benkovic et al., "Replisome-Mediated DNA Replication," Annu. Rev. Biochem., 70:181-208, 2001.

Bennett and Holloman, "A RecA Homologue in Ustilago maydis That Is Distinct and Evolutionarily Distant from Rad51 Actively Promotes DNA Pairing Reactions in the Absence of Auxiliary Factors," Biochemistry, 40:2942-2953, 2001.
Better and Helinski, "Isolation and Characterization of the recA Gene of Rhizobium meliloti," J. Bacteriol, 155:311-316, 1983.
Bianco and Weinstock, "Interaction of the RecA protein of *Escherichia coli* with single-stranded oligodeoxyribonucleotides," Nucleic Acids Research, 24(24):4933-4939, 1996.
Bianco et al"DNA Strand Exchange Proteins: A Biochemical and Physical Comparison," Frontiers in Bioscience, 3:D570-D603, 1998.
Borjac-Natour et al., "Divergence of the mRNA targets for the Ssb proteins of bacteriophages T4 and RB69," Virology J., 1(4):1-14, 2004.
Bork et al., "The RecOR proteins modulate RecA protein function at 5' ends of single-stranded DNA," EMBO J., 20:7313-7322, 2001.
Bork et al., "RecA Protein Filaments Disassemble in the 5' to 3' Direction on Single-stranded DNA," J. Biol. Chem., 276:45740-45743, 2001.
Butler et al., "Investigating Structural Changes Induced by nucleotide Binding to RecA Using Difference FTIR," Biophysical J., 82(4):2198-2210, 2002.
Byrd and Raney, "Protein displacement by an assembly of helicase molecules aligned along single-stranded DNA," Nat. Struct. Mol. Biol., 11(6):531-538, 2004.
Cai, "An inexpensive and simple nucleic acid dipstick for rapid pathogen detection," LAUR #05-9067 of Los Alamos National Laboratory, Aug. 22, 2006.
Chan et al., "Effects of Polyethylene Glycol on Reverse Transcriptase and Other polymerase Activities," Biochim. Biophys. Acta., 606(2):353-361, 1980.
Compton, "Nucleic acid sequence-based amplification," Nature, 350:91-92, 1991.
Conklin and Drake, "Isolation and Characterization of conditional Alleles of bacteriophage T4 Genes *uvsX* and *uvsY*," Genetics, 107:505-523, 1984.
Cox et al., "The importance of repairing stalled replication forks," Nature, 404:37-41, 2000.
Cox et al., "A Simple and Rapid Procedure for the Large Scale Purification of the recA protein of *Escherichia coli*," J. Biol. Chem., 256:4676-4678, 1981.
Cromie and Leach, "Control of Crossing Over," Mol. Cell., 6:815-826. 2000.
Decker et al., "*In Vitro* Initiation of DNA Replication in Simian Virus 40 Chromosomes," J. Biol. Chem., 262(22):10863-10872, 1987.
Demidov, "Rolling-circle amplification in DNA diagnostics: the power of simplicity," Expert Rev. Mol. Diagn., 2(6):89-95, 2002.
Digard et al., "The Extreme C Terminus of Herpes Simplex Virus DNA Polymerase Is Crucial for Functional Interaction with Processivity Factor UL42 and for Viral Replication," J. Virol., 67(1):398-406, 1993.
Dillingham and Kowalczykowski, "A Step Backward in Advancing DNA Replication: Rescue of Stalled Replication Forks by RecG," Mol. Cell., 8:734-736, 2001.
Dong et al., "A coupled complex of T4 DNA replication helicase (gp41) and polymerase (gp43) can perform rapid and processive DNA strand-displacement synthesis," Proc. Natl. Acad. Sci. USA, 93:14456-14461, 1996.
Drmanac, et al., "Sequencing of Megabase Plus DNA by Hybridization: Theory of the Method," Genomics, 4:114-128, 1989.
Edwards et al., "Genetic Variation at Five Trimeric and Tetrameric Tandem Repeat Loci in Four Human Population Groups," Genomics, 12:241-253, 1992.
Eggler et al., "The C Terminus of the Escherichia coli RecA Protein Modulates the DNA Binding Competition with Single-stranded DNA-binding Protein," J. Biol. Chem., 278:16389-16396, 2003.
Eggleston and West, "Cleavage of Holliday Junctions by the *Escherichia coli* RuvABC Complex," J. Biol. Chem., 275:26467-26476, 2000.
Elias-Arnanz and Salas, "Bacteriophage ø29 DNA replication arrest caused by codirectional collisions with the transcription machinery," EMBO J., 16:5775-5783, 1997.

(56) References Cited

OTHER PUBLICATIONS

Ellis, "Macromolecular crowding: obvious but underappreciated," Trends in Biochem. Sci., 26(10):597-604, 2001.
Ellouze et al., "Evidence for elongation of the helical pitch of the RecA filament upon ATP and ADP binding using small-angle neutron scattering," Eur. J. Biochem., 23392):579-583, 1995.
Enright et al., The evolutionary history of methicillin-resistant *Staphylococcus aureus* (MRSA), Proc. Natl. Acad. Sci. USA, 99:7687-7692, 2002.
Fahy et al., "Self-sustained sequence replication (3SR): an isothermal transcription-based amplification system alternative to PCR," Genome Res, 1:25-33, 1991.
Ferrari et al., "Co-operative Binding of *Escherichia coli* SSB Tetramers to Single-stranded DNA in the $(SSB)_{35}$ Binding Mode," J. Mol. Biol, 236:106-123, 1994.
Formosa et al., "Affinity purification of bacteriophage T4 proteins essential for DNA replication and genetic recombination," Proc. Natl. Acad. Sci. USA, 80:2442-2446, 1983.
Formosa and Alberts, "Purification and Characterization of the T4 Bacteriophage uvsX Protein," J. Biol. Chem., 261:6107-6118, 1986.
Formosa and Alberts, "DNA Synthesis Dependent on Genetic Recombination: Characterization of a Reaction Catalyzed by Purified Bacteriophage T4 Proteins," Cell, 47:793-806, 1986.
Fu et al., "Dynamics of DNA-tracking by two sliding-clamp proteins," EMBO J., 15(16):4414-4422, 1996.
Fuller et al., "Enzymatic replication of the origin of the *Escherichia coli* chromosome," Proc. Natl. Acad. Sci. USA, 78(12):7370-7374, 1981.
Giedroc et al., "The Function of Zinc in Gene 32 Protein from T4," Biochem., 26:5251-5259, 1987.
Giedroc et al., "Zn(II) Coordination Domain Mutants of T4 Gene 32 protein," Biochem., 31:765-774, 1992.
Ginocchio, "Life Beyond PCR: Alternative Target Amplification Technologies for the Diagnosis of Infectious Diseases, Part II," Clin. Microbiol. Newsletter, 26(17):129-136, 2004.
Glover and McHenry, "The DNA Polymerase III Holoenzyme: An Asymmetric Dimeric Replicative Complex with Leading and Lagging Strand Polymerases," Cell., 105:925-934.
Goodman et al., "Cloning and expression in *Escherichia coli* of a *recA*-like gene from *Bacteroides fragilis*," Gene, 58:265-271, 1987.
Hacker and Alberts, "Overexpression, Purification, Sequence Analysis, and Characterization of the T4 Bacteriophage dda DNA Helicase," J. Biol. Chem., 267:20674-20681, 1992.
Hammond et al., "Evaluation of 13 Short Tandem Repeat Loci for Use in Personal Identification Applications," Am. J. Hum. Genetics, 55:175-189, 1994.
Harris and Griffith, "UvsY Protein of Bacteriophage T4 is an Accessory Protein for in Vitro Catalysis of Strand Exchange," J. Mol. Biol., 206:19-27, 1989.
Harris and Griffith, "Visualization of the Homologous Pairing of DNA Catalyzed by the Bacteriophage T4 UvsX Protein," J. Biol. Chem., 262:9285-9292, 1987.
Harris and Griffith, "Formation of D Loops by the UvsX Protein of T4 Bacteriophage: A Comparison of the Reaction Catalyzed in the Presence or Absence of Gene 32 Protein," Biochem., 27:6954-6959, 1988.
Harvey et al., "Characterization and applications of CataCleave probe in real-time detection assays," Anal. Biochem., 333(2):246-255, 2004.
Heid et al., "Real time quantitative PCR," Genome Res., 6(10):986-994, 1996.
Heyer and Kolodner, "Purification and Characteirzation of a Protein from *Saccharomyces cerevisiae* That Binds Tightly to Single-Stranded DNA and Stimulates a cognate Strand Exchange Protein," Biochem. 28:2856-2862, 1989.
Hickson et al., "A Temperature Sensitive RecA Protein of *Escherichia coli*," Mol. Gen. Genet., 184:68-72, 1981.
Hopp et al., "A Short Polypeptide Marker Sequence Useful for Recombinant Protein Identification and Purification," Biotech., 6:1204-1210, 1988.
Hsieh et al., "The synapsis event in the homologous pairing of DNAs: RecA recognizes and pairs less than one helical repeat of DNA," Proc. Natl. Acad. Sci. USA, 89:6492-6496, 1992.
Huang et al., "Relationship between Bacteriophage T4 and T6 DNA Topoisomerases," J. Biol. Chem., 260(15):8973-8977, 1985.
Huletsky et al., "New Real-Time PCR Assay for Rapid Detection of Methicillin-Resistant *Staphylococcus aureus* Directly from Specimens Containing a Mixturre of *Staphylococci*," J. Clin. Microbiol., 42:1875-1884, 2004.
Ischenko and Saparbaev, "Alternative nucleotide incision repair pathway for oxidative DNA damage," Nature, 415(6868):183-187, 2002.
Ishmael et al., "Protein-Protein Interactions in the Bacteriophage T4 Replisome," J. Biol. Chem., 278(5):3145-3152, 2003.
Jarvis et al., "'Macromolecular Crowding': Thermodynamic Consequences for Protein-Protein Interactions with in the T4 DNA Replication Complex," J. Biol. Chem., 265(25):15160-15167, 1990.
Kaboord and Benkovic, "Rapid assembly of the bacteriophage T4 core replication complex on a linear primer/template construct," Proc. Natl. Acad. Sci. USA, 90:10881-10885, 1993.
Kaiser et al., "A Comparison of Eubacterial and Archaeal Structure-specific 5'-Exonucleases," J. Biol. Chem., 274(30):21387-21394, 1999.
Kato and Kuramitsu, "RecA Protein from an Extremely Thermophilic Bacterium, *Thermus thermophiles* HB8," J. Biochem., 114:926-929, 1993.
Katz and Bryant, "Interdependence of the Kinetics of NTP Hydrolysis and the Stability of the RecA-ssDNA Complex," Biochem., 40:11082-11089, 2001.
Kelman and O'Donnell, "DNA Polymerase III Holoenzyme: Structure and Function of a Chromosomal Replicating Machine," Annu. Rev. Biochem., 64:171-2000.
Khrapko et al., "An oligonucleotide hybridization approach to DNA sequencing," FEBS Lett., 256:118-122, 1989.
Komori et al., "Both RadA and RadB Are Involved in Homologous Recombination in *Pyrococcus furiosus*," J. Biol. Chem., 275:33782-33790, 2000.
Kool, "Replacing the Nucleobases in DNA with Designer Molecules," Acc. Chem. Res., 35:936-943, 2002.
Kowalczykowski et al., "Effects of the *Escherichia coli* SSB Protein on the Binding of *Escherichia coli* RecA Protein to Single-stranded DNA—Demonstration of Competitive Binding and the Lack of a Specific Protein-Protein Interaction," J. Mol. Biol., 193:81-95, 1987.
Kreader, "Relief of amplification inhibition in PCR with bovine serum albumin or T4 gene 32 protein," Appl. Env. Microbiol., 62:1102-1106, 1996.
Kuil et al., "The internal dynamics of gene 32 protein-DNA complexes studied by quasi-elastic light scattering," Biophys. Chem., 32:211-227, 1988.
Kuil et al., "A Refined Calculation of the Solution Dimensions of the Complex Between gene 32 Protein and Single Stranded DNA Based on Estimates of the Bending Persistence Length," J. Biomol. Struct. Dyn. 7(4):943-957, 1990.
Kuramitsu et al., "A Large-Scale Preparation and Some Physicochemical Properties of RecA Protein," J. Biochem., 90:1033-1045, 1981.
Kurumizaka et al., "A Chimeric RecA Protein Exhibits Altered Double-stranded DNA Binding," J. Biol. Chem., 269:3068-3075, 1994.
Lavery and Kowalczykowski, "Enhancement of recA Protein-promoted DNA Strand Exchange Activity by Volume-occupying Agents," J. Biol. Chem., 267:9301-9314, 1992.
Lavery and Kowalczykowski, "A Postsynaptic Role for Single-stranded DNA-binding Protein in recA Protein-promoted DNA Strand Exchange," J. Biol. Chem., 267(13):9315-9320, 1992.
LeBowitz and McMacken, "The bacteriophage ω0 and P protein initiators promote the replication of single-stranded DNA," 12(7):1-20, 1984.
Lerman, "A Transition to a Compact Form of DNA in Polymer Solutions," Proc. Nat. Acad. Sci. USA, 68(8):1886-1890, 1971.
Levin et al., "Homogeneous *Escherichia coli* Endonuclease IV," J. Biol. Chem., 263:8066-8071, 1988.
Liu et al., "The Ordered Assembly of the øX174-type Primosome," J. Biol. Chem., 271:15656-15661, 1996.

(56) References Cited

OTHER PUBLICATIONS

Lohman and Ferrari, "*Escherichia coli* Single-Stranded DNA-Binding Protein: Multiple DNA-Binding Modes and Cooperativities," Annu. Rev. Biochem., 63:527-570, 1994.

Lovett and Roberts, "Purification of a RecA Protein Analogue from *Bacillus subtilis*," J. Biol. Chem., 260:3305-3313, 1985.

Lusetti et al., "Magnesium Ion-dependent Activation of the RecA Protein Involves the C Terminus," J. Biol. Chem., 278(18):16381-16388, 2003.

Lutz-Freyermuth et al., "Quantitative determination that one of two potential RNA-binding domains of the A protein component of the U1 small nuclear ribonucleoprotein complex binds with high affinity to stem-loop II of U1 RNA," Proc. Natl. Acad. Sci. USA, 87:6393-6397, 1990.

Lysov et al., "Establishing Nucleotide Sequence of DNA using Oligonucleotide Hydridization. Novel Method," SSSR 303:1508-1511, 1988 (English Translation).

Maeshima et al., "Purification and characterization of XRad51.1 protein, Xenopus RAD51 homologue: recombinant XRad51.1 promotes strand exchange reaction," Genes Cells, 1:1057-1068, 1996.

Maki et al., "DNA Polymerase III Holoenzyme of *Escherichia coli*," J. Biol. Chem., 263(14):6570-6578, 1988.

Malkov and Camerini-Otero, Photocross-links between Single-stranded DNA and *Escherichia coli* RecA Protein Map to Loops L1 (Amino Acid Residues 157-164) and L2 (Amino Acid Residues 195-209),: J. Biol. Chem., 270(50):30230-30233, 1995.

Marians, "Prokaryotic DNA Replication," Annu. Rev. Biochem., 61:673-719, 1992.

Marians, "PriA: At the Crossroads of DNA Replication and Recombination," Prog. Nucleic Acid Res. Mol. Biol., 63:39-67, 1999.

Marras et al., "Multiplex detection of single-nucleotide variations using molecular beacons," Genet. Anal. Biomolec. Eng., 14:151-156, 1999.

Martin et al., "GAP Domains Responsible for Ras p21-Dependent Inhibition of Muscarinic Atrial $K^+$ $^C$hannel Currents," Science, 255:192-194, 1992.

Maxam and Gilbert, "A new method for sequencing DNA," Proc. Natl. Acad. Sci. USA, 74:560-564, 1877.

Mazin and Kowalczykowski, "The function of the secondary DNA-binding site of RecA protein during DNA strand exchange," Proc. Natl. Acad. Sci. USA, 74:560-564, 1977.

McGlynn and Lloyd, "RecG helicase activity at three- and four-strand DNA structures," Nucl. Acid Res., 27:3049-3056, 1999.

McGlynn et al., "Characterisation of the catalytically active form of RecG helicase," Nucl. Acid Res., 28:2324-2332, 2000.

Minton, "The Influence of Macromolecular Crowding and Macromolecular Confinement on Biochemical Reactions in Physiological Media," J. Biol. Chem., 276(14):10577-10580, 2001.

Mitra and Church, "In situ localized amplification and contact replication of many individual DNA molecules," Nucl. Acids Res., 27(24):e34i-e34vi.

Mizuuchi, "In Vitro Transposition of Bacteriophage Mu: A Biochemical Approach to a Novel Replication Reaction," Cell, 35:785-794, 1983.

Morel et al., "Recombination-dependent Repair of DNA Double-strand Breaks with Purified Proteins from *Escherichia coli*," J. Biol. Chem., 272:17091-17096, 1997.

Morrical et al., "Amplification of Snap-back DNA Synthesis Reactions by the uvsX Recombinase of Bacteriophage T4," J. Biol. Chem., 266:14031-14038, 1991.

Morrical and Alberts, "The UvsY Protein of Bacteriophage T4 Modulates Recombination-dependent DNA Synthesis in Vitro," J. Biol. Chem., 265:15096-15103, 1990.

Morris and Raney, "DNA Helicases Displace Streptavidin from Biotin-Labeled Oligonucleotides," Biochem., 38(16):5164-5171, 1999.

Morrison et al., "Quantification f Low-Copy Transcripts by Continuous SYBR Green I Monitoring during Amplification," BioTechniques, 24:954-962, 1998.

Mosig et al., "Two recombination-dependent DNA replication pathways of bacteriophage T4, and their roles in mutagenesis and horizontal gene transfer," Proc. Natl. Acad. Sci. USA, 98:8306-8311, 2011.

Nadler et al., "A Novel Function for Zinc(II) in a Nucleic Acid-binding Protein," J. Biol. Chem., 265(18):10389-10394, 1990.

Nadeau et al., "Real-Time, Sequence-Specific Detection of Nucleic Acids during Strand Displacement Amplification," Anal. Biochem., 276(2):177-187, 1999.

Nagai et al., "Additive Effects of Bovine Serum Albumin, Dithiothreitol, and Glycerol in PCR," 44:157-163, 1998.

Naimushin et al., "Effect of Polyethylene Glycol on the Supercoiling Free Energy of DNA," Biopolymers, 58(2):204-217, 2001.

Ng and Marians, "The Ordered Assembly of the øX174-type Primosome," J. Biol. Chem., 271:15642-15648, 1996.

Ng and Marians, "The Ordered Assembly of the øX174-type Primosome," J. Biol. Chem., 271:15649-15655, 1996.

Okazaki and Kornberg, "Enzymatic Synthesis of Deoxyribonucleic Acid," J. Biol. Chem., 239:259-268, 1964.

Paulus and Bryant, "Time-Dependent Inhibition of recA Protein-Catalyzed ATPHydrolysis by ATPyS: Evidence for a Rate-Determining Isomerization of the recA-ssDNA Complex," Biochem., 36:7832-7838, 1997.

Petrov et al., "Plasticity of the Gene Functions for DNA Replication in the T4-like Phages," J. Mol. Biol., 361:46-68, 2006.

Pevzner, "1-Tuple DNA Sequencing: Computer Analysis," J. Biomol. Struct. Dyn., 7:63-73, 1989.

Pham et al., "A model for SOS-lesion-targeted mutations in *Escherichia coli*," Nature, 409:366-370, 2001.

Piepenburg et al., "DNA Detection Using Recombination Proteins," PLOS Biology, 4(7):1115-1121, 2006.

Pierre and Paoletti, "Purification and Characterization of recA Protein from *Salmonella typhimurium*," J. Biol. Chem., 258:2870-2874, 1983.

Podust et al., "Replication Factor C Disengages from Proliferating Cell Nuclear Antigen (PCNA) upon Sliding Clamp Formation, and PCNA Itself Tethers Dna Polymerase 6 to DNA," J. Biol. Chem., 273(48):31992-31999, 1998.

Pomp and Medrano, "Organic Solvents as Facilitators of Polymerase chain Reaction," Biotechniques, 10(1):58-59, 1991.

Qiu and Giedroc, "Effects of Substitution of Proposed Zn(II) Ligand $His^{81}$ or $His^{64}$ in Phage T4 Gene 32 Protein: Spectroscopic Evidence for a Novel Zinc Coordination Complex," Biochem., 33(26):8139-8148, 1994.

Raap, "Advances in fluorescence in situ hybridization," Mutation Research, 400:287-298, 1998.

Raap et al., "Synthesis and Proton-NMR Studies of Oligonucleotides Containing and Apurinic (AP) Site," J. Biom. Structure & Dynamics, 5(2):219-247, 1987.

Rashid et al., "RecA/Rad51 Homolog from *Thermococcus kodakaraensis* KOD1," Methods Enzymol., 334:261-270, 2001.

Reddy et al., "Assembly of a functional replication complex without ATP hydrolysis: A direct interaction of bacteriophage T4 gp45 with T4 DNA polymerase," Proc. Natl. Acad. Sci. USA, 90:3211-3215, 1993.

Reddy et al., "Using Macromolecular Crowding Agents to Identify Weak Interactions within DNA Replication Complexes," Methods Enzymol., 262:466-476, 1995.

Riddles and Lehman, "The Formation of Plectonemic Joints by the recA Protein of *Escherichia coli*," J. Biol. Chem., 260:170-173, 1985.

Rivas et al., "Life in a crowded world—Workshop on the Biological Implications of Macromolecular Crowding," EMBO Reports, 5(1):23-27, 2004.

Ronaghi et al., "A Sequencing Method Based on Real-Time Pyrophosphate," Science, 281:363-365, 1998.

Rosselli and Stasiak, "Energetics of RecA-mediated Recombination Reactions Without ATP Hydrolysis RecA Can Mediate Polar Strand Exchange But Is Unable to Recycle," J. Mol. Biol., 216:335-352, 1990.

Roux, "Optimization and troubleshooting in PCR," Genome Res., 4:S185-S194, 1995.

Saiki et al., "Primer-Directed Enzymatic Amplification of DNA with a Thermostable DNA Polymerase," Science, 239:487-491, 1988.

(56) References Cited

OTHER PUBLICATIONS

Salinas et al., "Homology Dependence of UvsX Protein-catalyzed Joint Molecule Formation," J. Biol. Chem., 270:5181-5186.
Salinas and Benkovic, "Characterization of bacteriophage T4-coordinated leading- and lagging-strand synthesis on a minicircle substrate," PNAS, 97(13):7196-7201, 2000.
Sanders et al., "Use of a macromolecular crowding agent to dissect interactions and define functions in transcriptional activation by a DNA-tracking protein: Bacteriphage T4 gene 45 protein and late transcription," Proc. Natl. Acad. Sci. USA, 91:7703-7707, 1994.
Sanders et al., "Dual targets of a transcriptional activator that tracks on DNA," EMBO J., 16(11):3124-3132, 1997.
Sanger et al., "DNA sequencing with chain-terminating inhibitors," Proc. Natl. Acad. Sci. USA, 75:5463-5467, 1977.
Savva and Pearl, "Cloning and Expression of the Uracil-DNA Glycosylase Inhibitor (UGI) From Bacteriophage PBS-1 and Crystallization of a Uracil-DNA Glycosylase-UGI Complex," Proteins, 22(3):287-289, 1995.
Scheerhagen et al., "Binding Stoichiometry of the Gene 32 Protein of Phage T4 in the Complex with Single Stranded DNA Deduced from Boundary Sedimentation," J. Biomol. Struct. Dyn., 3:887-898, 1986.
Scheerhagen et al., "Hydrodynamic studies of a DNA-protein complex - Dimensions of the complex of single-stranded 145 base DNA with gene 32 protein of phage T4 deduced from quasi-elastic light scattering," FEBS Lett., 184(2):221-225, 1985.
Shan et al., "RecA Protein Filaments: End-dependent Dissociation from ssDNA and Stabilization by RecO and RecR Proteins," J. Mol. Biol., 265:519-540, 1997.
Shibata et al., "Purified *Escherichia coli* recA protein catalyzes homologous pairing of superhelical DNA and single-stranded fragments," Proc. Natl. Acad. Sci. USA, 76:1638-1642, 1979.
Shibata et al., "Homologous pairing in genetic recombination: Formation of D loops by combined action of recA protein and a helix-destabilizing protein," Proc. Natl. Acad. Sci. USA, 77:2606-2610, 1980.
Shibata et al, "Homologous pairing in genetic recombination: Complexes of recA protein and DNA," Proc. Natl. Acad. Sci. USA, 76(10):5100-5104, 1979.
Singleton et al., "Structural Analysis of DNA Replication Fork Reversal by RecG," Cell, 107:79-89, 2001.
Skinner et al., "Use of the Glu-Glu-Phe C-terminal Epitope for Rapid Purification of the Catalytic Domain of Normal and Mutant *ras* GTPase-activating Proteins," J. Biol. Chem., 266:14163-14166, 1991.
Southern et al., "Analyzing and Comparing Nucleic Acid sequences by Hybridization to Arrays of Oligonucleotides: Evaluation Using Experimental Models," Genomics, 13:1008-1017, 1992.
Spies et al., "The RadA protein from a hyperthermophilic archaeon *Pyrobaculum islandicum* is a DNA-dependent ATPase that exhibits two disparate catalytic modes, with a transition temperature at 75 °C.," Eur. J. Biochem., 267:1125-1137, 2000.
Steffen and Bryant, "Purification and Characterization of the RecA Protein from *Streptococcus pneumoniae*," Arch. Biochem. Biophys., 382:303-309, 2000.
Story et al., "Structural Relationship of Bacterial RecA Proteins to Recombination Proteins from Bacteriophage T4 and Yeast," Science, 259(5103):1892-1896, 1993.
Sun and Shamoo, "Biochemical characterization of Interactions between DNA Polymerase and Single-stranded DNA-binding Protein in Bacteriophage RB69," J. Biol. Chem., 278(6):3876-3881.
Takeshita et al., "Oligodeoxynucleotides Containing Synthetic Abasic Sites," J. Biol. Chem., 262:10171-10179, 1987.
Tang et al., "Roles of *E. coli*DNA polymerases IV and V in lesion-targeted and untargeted SOS mutagenesis," Nature, 404:1014-1018, 2000.
Tinker-Kulberg et al., "A direct interaction between a DNA-tracking protein and a promoter recognition protein: implications for searching DNA sequence," EMBO J., 15(18):5032-5039, 1996.
Tissier et al., "Purification and Characterization of a DNA Strand Transferase from Broccoli," Plant Physiol., 108:379-386, 1995.

Tracy and Kowalczykowski, "In vitro selection of preferred DNA pairing sequences by the *Escherichia coli* RecA protein," Genes Dev., 10:1890-1903, 1996.
Tsurimoto and Matsubara, "Replication of λ dv plasmid in vitro promoted by purified λ O and P proteins," Proc. Natl. Acad. Sci. USA, 79:7639-7643, 1982.
Tyagi et al., "Multicolor molecular beacons for allele discrimination," Nature Biotechnol., 16:49-53, 1998.
Van Ness et al., "Isothermal reactions for the amplification of oligonucleotides," Proc. Natl. Acad. Sci. USA, 100(8):4504-4509, 2003.
Villemain et al., "Mutations in the N-terminal Cooperativity Domain of Gene 32 protein Alter Properties of the T4 DNA Replication and Recombination Systems," J. Biol. Chem., 275:31496-31504, 2000.
Vincent et al., "Helicase-dependent isothermal DNA amplification," EMBO Rep., 5:795-800, 2004.
Volodin and Camerini-Otero, "Influence of DNA Sequence on the Positioning of RecA Monomers in RecA-DNA Cofilaments," J. Biol. Chem., 277(2):1614-1618, 2002.
Volodin et al., "Phasing of RecA monomers on quasi-random DNA sequences," FEBS Letters, 546:203-208, 2003.
Voloshin et al., "Homologous DNA Pairing Promoted by a 20-Amino Acid Peptide Derived from RecA," Science, 272:868-872, 1996.
Voloshin et al., "The Homologous Pairing Domain of RecA also Mediates the Allosteric Regulation of DNA Binding and ATP Hydrolysis: A Remarkable Concentration of Functional Residues," J. Mol. Biol., 303(5):709-720, 2000.
Waidner, et al., "Domain effects on the DNA-interactive properties of bacteriophage T4 gene 32 protein," J. Biol. Chem., 276:2509-16 (2001).
Walker et al., "Isothermal *in vitro* amplification of DNA by a restriction enzyme/DNA polymerase system," Proc. Natl. Acad. Sci. USA, 89:392-396, 1992.
Walker, "Empirical aspects of strand displacement amplification," Genome Res., 3:1-6, 1993.
Walker et al., "Distantly related sequences in the α- and β-subunits of ATP synthase, myosin, kinases and other ATP-requiring enzymes and a common nucleotide binding fold," EMBO J., 1:945-951, 1982.
Wang et al., "Modular Organization of T4 DNA Polymerase," J. Biol. Chem., 270(44):26558-26564, 1995.
Wang and Mosbaugh, "Uracil-DNA Glycosylase Inhibitor of Bacteriophage PBS2: Cloning and Effects of Expression of the Inhibitor Gene in *Escherichia coli*," J. Bacteriol., 170(3):1082-1091, 1988.
Webb et al., "An Interaction between the *Escherichia coli* RecF and RecR Proteins Dependent on ATP and Double-stranded DNA," J. Biol. Chem., 270:31397-31404, 1995.
Webb et al., "Recombinational DNA Repair: The RecF and RecR Proteins Limit the Extension of RecA Filaments beyond Single-Strand DNA Gaps," Cell, 91:347-356, 1997.
Webb et al., "ATP Hydrolysis and Dna Binding by the *Escherichia coli* RecF Protein," J. Biol. Chem., 274:15367-15374, 1999.
West et al., "Purification and Properties of the recA Protein of *Proteus mirabilis*," J. Biol. Chem., 258:4648-4654, 1983.
Wetmur et al, "Cloning, Sequencing, and Expressiono f RecA Proteins from Three Distantly Related *Thermophilic eubacteria*," J. Biol. Chem., 269:25928-25935, 1994.
Wittwer et al., "Continuous Fluorescence Monitoring of Rapid Cycle DNA Amplification," Biotechniques, 22(1):130-1, 134-138, 1997.
Xu and Marians, "A Dynamic RecA Filament Permits DNA Polymerase-catalyzed Extension of the Invading Strand in Recombination Intermediates," J. Biol. Chem., 277:14321-14328, 2002.
Yang et al., "Comparison of Bacteriophage T4 and UvsX and Human Rad51 Filaments Suggests that RecA-like Polymers May Have Evolved Independently," J. Mol. Biol., 312(5):999-1009, 2001.
Yeh et al., "Divergence of a DNA Replication Gene Cluster in the T4-Related Bacteriophage RB69," J. Bacteriol., 180(8):2005-2013, 1998.
Yonesaki et al., "Purification and some of the functions of the product of bacteriophage T4 recombination genes, *uvsX* and *uvsY* ," Eur. J. Biochem., 148:127-134, 1985.

(56) References Cited

OTHER PUBLICATIONS

Young et al., "The Kinetic Mechanism of Formation of the Bacteriophage T4 DNA polymerase Sliding Clamp," J. Mol. Biol., 264:440-452, 1996.

Zhang et al., "Ramification Amplification: A Novel Isothermal DNA Amplification Method," Mol. Diagn., 6:141-150, 2001.

Zimmerman and Trach, "Macromolecular crowding extends the range of conditions under which DNA polymerase is functional," Biochim. Biophys. Acta., 949:297-304, 1988.

Zimmerman and Minton, "Macromolecular Crowding: Biochemical, Biophysical, and Physiological Consequences," Annu. Rev. Biophys. Biomol. Struct., 22:27-65, 1993.

Zimmerman and Harrison, "Macromolecular crowding increases binding of DNA polymerase to DNA: An adaptive effect," Proc. Natl. Acad. Sci. USA, 84(7):1871-1875, 1987.

Zinchenko and Yoshikawa, "$Na^+$ Shows a Markedly Higher Potential than $K^+$ in DNA Compaction in a Crowded Environment," Biophysical Journal, 88:4118-4123, 2005.

International Search Report for corresponding PCT Application No. PCT/IB2007/003088, dated Nov. 25, 2008.

Office Action for U.S. Appl. No. 10/813,693 (U.S. counterpart to WO 00/41524—Foreign Patent Document No. 56 above), mailed May 28, 2009 (with claims attached).

EP Office Action, for corresponding EP Application No. 07848814.5, dated Jun. 5, 2009.

Response to EP Office Action, for the corresponding EP application No. 07848814.5, dated Nov. 2, 2009.

EP Office Action, for the corresponding EP Application No. 07848814.5, dated Dec. 3, 2009.

Response to European Office Action, for the corresponding EP Application No. 07848814.5, filed May 4, 2007, dated Jun. 25, 2010.

Response to EP Office Action, for the corresponding EP Application No. 07848814.5, dated Jan. 5, 2011.

Office Action, for the corresponding Japanese Patent Application No. 2009-508545, dated Aug. 30, 2011 (Mailing Date: Sep. 2, 2011).

European Office Action, for the corresponding EP Application No. 07848814.5, dated Jan. 27, 2012.

Barnes and Rowlyk, "Magnesium precipitate hot start method for PCR," Mol. and Cell. Probes, 16(3):167-171, 2002.

Crowe et al., "Is Trehalose Special for Preserving Dry Biomaterials?," Biophys. J., 71(4):2087-2093, 1996.

Mannarelli and Kurtzman, "Rapid Identification of *Candida albicans* and Other Human Pathogenic Yeasts by Using Short Oligonucleotides in a PCR," J. Clin. Microbiol., 36(6):1634-1641, 1998.

Ramos et al., "Stabilization of Enzymes against Thermal Stress and Freeze-Drying by Mannosylglycerate," Appl. and Env. Microbiol., 63(10):4020-4025, 1997.

English translation of Japanese Office Action, for corresponding Japanese Patent Application No. 2012-045874, dated Jul. 17, 2012 (Mailing Date: Jul. 19, 2012).

"UvsX RecA-like recombination protein [Enterobacteria phage RB69]", online NCBI, http://www.ncbi.nlm.nih.gov/protein/32350347?sat= I 38zsatkey=7100722, Apr. 5, 2005 (retrieved on Aug. 22, 2012).

"UvsX [Aeromonas phage Aehl]", online NCBI, http://www.ncbi.nlm.nih.gov/protein/38639939?&satkey=851579, Mar. 30, 2006 (retrieved on Aug. 22, 2012).

Desplats and Krisch, "The diversity and evolution of the T4-type bacteriophages," Res. Microbiol, 154(4):259-267, 2003.

Miller et al., "Complete Genome Sequence of the Broad-Host-Range vibriophage KVP40: Comparative Genomics of a T4-Related Bacteriophage," J. Bacteriol., 185(17):5220-5233, 2003.

Office action in corresponding Canadian application 2,476,481, dated May 16, 2013, 9 pages.

Australian Office Action, for corresponding Australian Application No. 2007298650, dated May 10, 2012.

Response to Office Action for corresponding Australian Application No. 2007298650, dated Sep. 19, 2012.

Australian Office Action, for Australian Application No. 2007298650, dated Nov. 22, 2012.

\* cited by examiner

Alignment of T4 UvsX and *E.coli* recA

```
T4    MS--DLKSRLIKASTSKLTAELTASKFFN-------EKDVVRTKIPMMNIALSGEITGGM
Coli  MAIDENKQKALAAALGQIEKQFGKGSIMRLGEDRSMDVETISTGSLSLDIALG---AGGL
      *:   :*.:  :*: .::  ::  ..::.       : :.: *       ::***.  :**:
                           Walker A motif
T4    QSGLLI-LAGPSKSFKSNFGLTMVSSYMRQYPDAVCLFYDSEFGITPAYLRSMGVDPERV
Coli  PMGRIVEIYGPESSGKTTLTLQVIAAAQRE--GKTCAFIDAEHALDPIYARKLGVDIDNL
       * ::  : **..* *:.: * ::::  *:  . .* * *:*..: * *  *.:*** :.:
                                              DNA binding loop1
T4    IHTPVQSLEQLRIDMVNQLDAIERGEKV-VVFIDSLGNLASKKETEDALNEKVVSDMTRA
Coli  LCSQPDTGEQ----ALEICDALARSGAVDVIVVDSVAALTPKAEIEGEIGDSHMG--LAA
      : :  ::  **       :: **: *. * *:;:.**:. *:.* *.  :::..;.    *
                  DNA binding loop2
T4    KTMKSLFRIVTPYFSTKNIPCIAINHT-YETQEMFS---KTVMGGGTGPMYSADTVFIIGK
Coli  RMMSQAMRKLAGNLKQSNTLLIFINQIRMKIGVMFGNPETTTGGNALKFYASVRLDIRRI
      : *.. :*  ::  :. .*  * **:    : **. :*. **.:   :*::   : *
T4    RQIKDGSDLQGYQFVLNVEKSRTVKEKSKFFIDVKFDGGIDPYSGLLDMALELGFVVKPK
Coli  GAVKEGENVVGSETRVKVVKNKIAAPFKQAEFQILYGEGINFYGELVDLGVKEKLIEK-A
       :*:*.:: *  :  ::* *.: .   .:  :::  :. **: *. *:*:::  ::  *
T4    NGWYAREFLDEETGEMIREEKSWRAKDTNCTTFWGPLFKHQPFRDAIKRAYQLGAIDSNE
Coli  GAWYSYK------GEKIGQGKA------NATAW---LKDNP-------------ETAK
      ..**: :      ** * : *:      :* *    :*.:*              :: :
T4    IVEAEVDELINSKVEKFKSPESKSKSAADLETDLEQLSDMEEFNE
Coli  EIEKKVRELLLS------NPNSTPDFSVD---DSEGVAETNE-DF
      ;* :* **: *      .*:*... :.*   * * ::: :* :
```

Fig. 2

Alignment of T4 and T6 gp32

```
t6  MFKRKSTAELAAQMAKLAGNKGGFSSEDKGEWKLKLDNAGNGQAVIRFLPSKNDEQAPFA
t4  MFKRKSTAELAAQMAKLNGNK-GFSSEDKGEWKLKLDNAGNGQAVIRFLPSKNDEQAPFA
    **************  * ****************************************** t6  ILVNHGFKKNGKWYIETCSSTHGDYDSCPVCQYISKNDLYNTDNKEYSLVKRKTSYWANI
t4  ILVNHGFKKNGKWYIETCSSTHGDYDSCPVCQYISKNDLYNTDNKEYSLVKRKTSYWANI
    ************************************************************ t6  LVVKDPAAPENEGKVFKYRFGKKIWDKINAMIAVDVEMGETPVDVTCPWEGANFVLKVKQ
t4  LVVKDPAAPENEGKVFKYRFGKKIWDKINAMIAVDVEMGETPVDVTCPWEGANFVLKVKQ
    ************************************************************ t6  VSGFSNYDESKFLNQSAIPNIDDESFQKELFEQMVDLSEMTSKDKFKSFEELSTKFSQVM
t4  VSGFSNYDESKFLNQSAIPNIDDESFQKELFEQMVDLSEMTSKDKFKSFEELNTKFGQVM
    *************************************************  * *** t6  GTAAMGGAAATAAKKADKVADDLDAFNVDDFNTKTEDDFMSSSSGSSSSADDTDLDDLLN
t4  GTAVMGGAAATAAKKADKVADDLDAFNVDDFNTKTEDDFMSSSSGSSSSADDTDLDDLLN
    * ****************************************************** t6  DL
t4  DL
    **
```

Alignment of T4 and T6 UvsY

```
t4  MRLEDLQEELKKDVFIDSTKLQYEAANNVMLYSKWLNKHSSIKKEMLRIEAQKKVALKAR
t6  MRLEDLQEELKKDVFIDSTKLQYEAANNVMLYSKWLNKHSSIKKEMLRIDAQKKVALKAK
    ************************************************:********:

t4  LDYYSGRGDGDEFSMDRYEKSEMKTVLSADKDVLKVDTSLQYWGILLDFCSGALDAIKSR
t6  LDYYSGRGDGDEFSMDRYEKSEMKTVLSADKDVLKVDTSLQYWGILLDFCSGALDAIKSR
    ************************************************************ t4  GFAIKHIQDMRAFEAGK
t6  GFAIKHIQDMRAFEAGK
    *****************
```

Fig. 4

ALIGNMENT OF UvsX RELATIVES

```
t4         MS-----------DLKSRLIKASTSKLTAELTASKFFNEKDV-VRTKIPMMNIALSGEI
t6         MS----------IADLKSRLIKASTSKMTAELTTSKFFNEKDV-IRTKIPMLNIAISGAI
Phage133   MS-----------SLKERLIKASTSKMTAELTKSKFFNDKTV-VRTRIPMLNIAISGAL
Rb69       MS-----------DLKSRLIKASTSKMTADLTKSKLFNNRDE-VPTRIPMLNIALGGAL
Aeh1       MAKGIKTAKTGNLGSLMSKLAGTSSNKMSSVLADSKFFNDKDC-VRTRVPLLNLAMSGEL
Ae65       MA---KKAKVVNSGDLLERLNGTSSNKMSAMLAESIFFNEKDT-IRTRVPIINLMMSGRL
Kvp40      MS----------DLMKSLKKSSTSGYAQVLSESQFMFDKDH-TRTYVPAINIAFSGEV
Rb43       MS----------NKALLKKLIKNSNSQSAAILSESDVFNNITK-TRTRVPILNLALSGAF
PSSM2      M------------DFLKEIVKEIGDEYTQVAAD---IQENERFIDTGSYIFNGLVSGSI
PSSM4      M------------NFLKDIAKEIGNDYASLVSEGVSAGDTAGFIDTGSYIFNALLSGSI
               *        :  .  :          :   :            *      :*  ..* .

recA GPESSGKTTLT _____ Walker A
t4         TGGMQSG-LLILAGPSKSFKSNFGLTMVSSYMRQYPDAVCLFYDSEFGITPAYLPSMGVD
t6         DGGMQSG-LTIFAGPSKHFKSNMSLTMVAAYLNKYPDAVCLFYDSEFGITPAYLPSMGVD
Phage133   MGGMQSG-LTIFAGPSKHFKSNMGLTMVAAYMKAFPDAVCMFYDSEFGITPAYLKAMGVD
Rb69       NAGLQSG-LTIFAAPSKHFKTLFGLTMVAAYMKKYKDAICLFYDSEFGASESYFRSMGVD
Aeh1       DGGLTPG-LTVLAGPSKHFKSNLSLVFVAAYLRKYPDAVCIFFDNEFGSTPGYFESQGVD
Ae65       DGGITPG-LTCIAGPSKHFKSNLSLVMVSAYLRKYPKAVCLFFDNEFGSTPDYFTSQGVD
Kvp40      DGGLTSG-LTVLAGPSKHFKSNLGLVGVAAYLKKYPDAVCVFIDTEFGITPSYLRSQGVD
Rb43       DGGLTSG-LTLFAGPSKHFKSNLGLVTVSAYLKANEDAVCLFYDSEKGVTKSYLKSMGVD
PSSM2      FGGVSSSRITAIAGESSTGKTYFSLAVVKNFLDNNPDGYCLYFDTEAAVNKGLLESRGID
PSSM4      YGGIPNNKITAIAGETSTGKTFFCLGMVQHFLESNPDAGVIYFESESAISKQMIEDRGID
             .*:       .  :  :*.    *. :  *  *  ::      ..   ::  :.*  ..    :   *:*

DNA binding loop1 _____ LTPKAEIEG
t4         PERVIHTPVQSLEQLRIDMVNQLDAI---------ERGEKVVVFIDSLGNLASKKETED
t6         PERVIHTPIQSVEQLKIDMVNQLEAI---------ERGEKVIVFIDSIGNMASKKETED
Phage133   PDRVIHTPVQSVEQLKIDMTNQLEEV---------KRGEKVIVFIDSIGNLASKKETED
Rb69       LDRVVHTPIQSVEQLKVDMTNQLDAI---------ERGDKVIIFIDSIGNTASKKETED
Aeh1       ISRVIHCPFKNIEELKFDIVKKLEAI---------ERGDRVIVFVDSIGNAASKKEIDD
Ae65       ISRVVHCPFIDVEELKFDIVKKLESI---------TRGDKVIIYIDSIGNVASKKELQD
Kvp40      PDRVLHIQCESVERMKFEMANQLKDLAERKRAKKAGEEPDRVIFFIDSVGNVASAKEIDD
Rb43       PDRVVYTRITTVEQLRNDVVSQLDAL---------ERGDKVIIFVDSVGNTASKKELAD
PSSM2      MNRLVVVNVVTIEEFRSKALRAVDIY-----LKTSEEERKPCMFVLDSLGMLSTEKEIRD
PSSM4      SNRMLLVPVTTVQEFRLQAIKILDKY-----NEQTAEERKPLMFVLDSLGMLSTSKEVED
              .*::     ::.::  .    :.       . .. . . :**:*   ::  **  *

DNA binding loop2 ─┐
           EIGDSHMG                    recA LINQIRMKIGVMFGNPETTTGG
t4         ALNEKVVSDMTRAKTMKSLFRIVTPYFSTKNIPCIAINHT-YETQEMF-SKTVMGGGTGP
t6         ALNEKSVADMTRAKSLKSLFRIVTPYFSIKNIPCVAVNHT-IETIEMF-SKTVMTGGTGV
Phage133   ALNEKTTADMTRAKALKSLFRIVTPYFSIKDIPCVAVNHT-LQTLEMF-SKEVMTGGTGV
Rb69       ALNEKVVGDMSRAKALKSLFRIVTPYLTIKDIPCVAINHTAMEIGGLY-PKEIMGGGTGI
Aeh1       AIDEKSVSDMTRAKQIKSLTRMMTPYLTVNDIPAIMVAHT-YDTQEMY-SKKVVSGGTGI
Ae65       AKDEKSAQDMTRAKQIKSLFRMVTPYLTVLDIPCIAVNHT-YETQEMF-SKTVMSGGTGP
Kvp40      AQNEKSVADMSRAKQLKSLFRIITPYFTMLDIPCIAINHT-YQTQEIY-SKTVMSGGTGI
Rb43       ALSDNDKQDMTRAKALKGMFRMVTPYLADLDIPMVCICHT-YDTQEMY-SKKVISGGTGL
PSSM2      ALDDKQVRDMTKSQLVKGAFRMLTLKLGQANIPLIVTNHT-YDVIGSYVPTKEMGGGSGL
PSSM4      SEAGKETRDMTRAQVVKSIFRVLTLKLGKANVPLIVTNHT-YDVVGAYIPTKEMGGGSGL
            :   :   **::::  :*.  *::*  :   ::*  :     **    :    ..  :  **:*
```

Fig. 5-1

ALIGNMENT OF UvsX RELATIVES

```
t4          MYSADTVFIIGKRQIKDGSDLQGYQFVLNVEKSRTVKEKSKFFIDVKFD-GGIDPYSGLL
t6          MYSADTVFIIGKRQIKDGSDLQGYQFVLNVEKSRTVKEKSKFFIDVKFD-GGIDPYSGLL
Phage133    MYSADTVFFIGKRQVKDGTELAGYEFILKAEKSRMVKEKSVFPITVKFD-GGIDPYSGLL
Rb69        LYSANTVFFISKRQVKEGTELTGYDFTLKAEKSRTVKEKSTFPITVNFD-GGIDPFSGLL
Aehl        TYSSDTVIIIGRQQEKDGKELLGYNFVLNMEKSRFVKEQSKLPLEVTFQ-GGINTYSGML
Ae65        MYSADTVIILGKQQDKDGKELLGYNFVMNAEKSRAIKEKSKLDLMVSFE-GGINTYSGLL
Kvp40       MYSADTVIILGKQQEKDGKDIIGYHFIMNIEKSRFVKEKMKVPLTVTYE-NGIDPFSGLL
Rb43        MYSADTAIILGKQQVKEGTEVVGYDFIMNIEKSRFVKEKSKFPLHVTYE-GGISMYSGLL
PSSM2       KYAASTIIYLSKKKEKDQKEVIGNLIKAKTHKSRLSKENKEVQIRLYYDERGLDRYYGLL
PSSM4       KYAASTIVYLSKKKEKNGKEVVGNIIKCKTAKSRLTKENSDVETRLYYD-RGLDRYYGLL
            *:: * . :.::: *: .:: *   :   :  * :   . :  ::  *:.  : *:* t4          DMALELGFVVKPKNGWYAREFLDEETGEMI--REEKSWRAKDTNCTTFWGPLFKHQPFRD
t6          DMALELGFVVKPKNGWYAREFLDEETGEMI--REEKSWRAKDTNCTTFWGPLFKHQPFRD
Phage133    EMATDLGFVVKPKVGWYKRAMMVD--GVMQ--HEEKSWRAKDTDSIDFWGPLFKHDEFRK
Rb69        EMATEIGFVVKPKAGWYAREFLDEETGEMI--REEKSWRAKATDCVEFWGPLFKHKPFRD
Aehl        DIALEVGFVVKPSNGWFSRAFLDEETGELV--EEDKKWRRADTNCLEFWKPMFAHQPFKT
Ae65        KIAQELGFVTKPQNARYQRNFLDLEPGEMVIPEDEKKWTEEESDSLEFWKPMFSHKPFMD
Kvp40       DIALQTGHVVKPSNGWYQRATVDEETGEMI--VEEKKYRAKETQTISFWKDIINSPTFKE
Rb43        DLAMEMNFVQTPTKGWRGRAFLNTETGELE--LEEKKWRESETNSIEFWRPLFTHQPFLD
PSSM2       ELG-EIGGMWKNVAGRYEMNGKKIYAKEIL--KNPTEYFTDDI----------MEQLDN
PSSM4       ELG-EKHGVFSRKGNRVVVGDSSVYPSAIL--ADPLKYFTEEL----------MEKLDE
            .:. :   :  .       :     :   .:                          :

t4          AIKRAYQLGAIDSNEIVEAEVDELINSKVEKFKSP--ESKSKSAADLETDLEQLSDMEEF
t6          AIKRAYQLGAIDSNEIVEAEVDELINSKVEKFKSP--ESKSKSAADLETDLEQLSDMEEF
Phage133    AIETRYQLGSIESDAEVDAEVDALIGSKTTAKISGVNFGPAESAADKEQQLEDFVD----
Rb69        AIETKYKLGAISSIKEVDDAVNDLINCKATTKV-PVKTSDAPSAADIENDLDEMED---F
Aehl        ACSDMFKLKSVAVKDEVFDEVDELFSGEAEMPVNMGRKLDTADQEEIDQLEEVDVEGSDS
Ae65        AVSNAYKLKAVEVSQEVFDEVDQLFG----------------------------------
Kvp40       GVKRIYCLGQLD-ESELFGEVDSLFD----------------------------------
Rb43        AIQDKYRIPDKEITDG--AALEDLYSTDEPESNKIDLDDDIPDDIGIDQDEEPIM-----
PSSM2       IAKEHFSYGTN-------------------------------------------------
PSSM4       AAAKEFRYGN--------------------------------------------------
              :

t4          NE------
t6          NE------
Phage133    ED------
Rb69        DE------
Aehl        DELFANLD
Ae65        --------
Kvp40       --------
Rb43        --------
PSSM2       --------
PSSM4       --------
```

Fig. 5-2

ALIGNMENT OF UvsY PROTEINS

```
t4          MR---LEDLQEELKKDVFIDSTKLQYEAANNVMLYSKWLNKHSSIKKEMLRIEAQKKVAL
t6          MR---LEDLQEELKKDVFIDSTKLQYEAANNVMLYSKWLNKHSSIKKEMLRIDAQKKVAL
Rb69        MK---LEDLQEELDADLAIDTTKLQYETANNVKLYSKWLRKHSFIRKEMLRIETQKKTAL
Phage133    MT---LEDLQAELKKDLVLDMTQLQTEAAENINLYCKWSTKYSNIRKSILSLDAQRKKHT
Aeh1        MT---LDELKEELKADLPIKLTAVQTEVAENPVLYGKWNRYLADINREITRLDAERKKML
Rb43        MTELKLEDLQAELEQDMLIDPLKLQSESADIPKIWSKWLRYHSNAKKKLIQLQARKEADV
Kvp40       MK---LQDLKAEYHEDVKIDTTALETAAIRIPVLHAKWLAYRADARQLLIKAEMKMEAVR
PSSM2       MN---LDKIQEMWERDAVIDPDNLHDESLKIPQLHSKYYTVYNTVTLMREKAREQYNKTR
PSSM4       MN---LEQIQEMWKKDSVIDNDLYCEESTKIPQLHMRYMELYTTFGLMKKEREIEMKRLI
                 *   *:.::     . *  :.          :  ::              . :

t4          KARLDYYSGRGDGDEFSMD------RYEKS-EMKTVLSADKDVLKVDTSLQYWGILLDFC
t6          KAKLDYYSGRGDGDEFSMD------RYEKS-EMKTVLSADKDVLKVDTSLQYWGILLDFC
Rb69        KARLDYYSGRGDGDEFSMD------RYEKS-EMKTVLAADKDVLKIETTLQYWGILLEFC
Phage133    KTKLDYYDGR--GDEVSMD------RYERS-EMKTVLSGDADILTVETKIQYFTIMLEFC
Aeh1        RDRFMFYTGR-SEDEVCMD------VYSPT-ELKTVIAGDEEVIKKNAAVELSQAKADFC
Rb43        KERLLYYTGR-HETEMTDV------IYTGSGEIKIAINGDPKIVEVNKLIQYFELIAEFT
Kvp40       KDRWLFYSGK-HDDEVCDF------IVEKS-EMKYALAGDEALQLAIARFQHMKDVLSFI
PSSM2       LERHNYYTGK-APAEVYIEEPFGYKVREKD-AIQRYMEADEKMSKIDLKIRYYDTTLKFL
PSSM4       REKWLYYKGK-APSSVYKELPFDLKLTTKE-EVNMFIEGDDDVRKLQYKIEYVEQCLNYL
             :  :*.*:       ..            ::  : .*  :       ..       . :

t4          SGALDAIKSRGFAIKHIQDMRAFEAG-K
t6          SGALDAIKSRGFAIKHIQDMRAFEAG-K
Rb69        SGALDAVKSRSFALKHIQDMREFEAG-Q
Phage133    GNAMDAIKSRGFAIKNIIDLRQFEAG-K
Aeh1        RQSMEAVRQRGFSLRAIIDCRKLEAG-E
Rb43        SKALDIVKNKGYSIKNMLEIRKLESG-A
Kvp40       EEALKGISQMGFTIKHIIDNRKIESGIV
PSSM2       EEIIKNISNRTFQIKNAIEWNKFQAG-M
PSSM4       DGVLRQINNRNFQIKNAIDWTKFQNG-L
              :   : .   :  ::    :   :: *
```

Fig. 6

ALIGNMENT OF gp32 PROTEINS

CLUSTAL (-like) formatted alignment by MAFFT (v5.667)

```
t4      M--FKRKSTA-------ELAAQMAKLNGNK-GFSSEDKGEWKLKLDNAGNGQAVIRFLPS
tg      M--FKRKSTA-------ELAAQMAKLAGNKGGFSSEDKGEWKLKLDNAGNGQAVIRFLPS
Rb69    M--FKRKSTA-------DLAAQMAKLNGNK-GFSSEDKGEWKLKLDASGNGQAVIRFLPA
Aeh1    MSIFKRKDPS-------QLQQQLAAFSAKK-GFES-DATEWKLTQGKDGNGAAVIRFLPA
Rb43    MSFFKRQDPT-------KLQEQVAALKGSS-GFQK-DEKEWKLTLDAQKNGSAVIRFLPN
Kvp40   M--FKRKSPA-------QLQEKLEKMSSKK-SFDNAD--EWKLTTDKLGNGSAVIRFLPA
PSSM2   MSFAKLKKQSKLGSLTQKLVKEVEKMNNTG---GQGDDRLWKLEVDKGGNGYDVIRFLPA
PSSM4   MSFASLKKAASAGSTLSKLTQEIEKINQPQ-QNNSADERFWKPELDKSGNGFAVIRFLPA
         *  .  : .  :        .*   ::   :      - *  **   -   **  ******
                        ↓               ↓             ↓↓
t4      KNDEQAPFAILVNHGFKKNGK-WYIETCSSTHGDYD-SCPVCQYISKNDLYNTDNKE---
tg      KNDEQAPFAILVNHGFKKNGK-WYIETCSSTHGDYD-SCPVCQYISKNDLYNTDNKE---
Rb69    KTDDALPFAILVNHGFKKNGK-WYIETCSSTHGDYD-SCPVCQYISKNDLYNTNKTE---
Aeh1    KGDNATTFVKLVNHGFQRNGK-WYIENCSSTHGDYD-NCPACQWIKEQNWDYNVEAD---
Rb43    RSDDELAFVRIVNHSFKKQNQ-WYIENCPSTHGDYD-GCPVCQYITDNDLFEKAKANKGG
Kvp40   KGEDDLPFVKIFTHGFKENGN-WFIENCPST---IDLPCPCCAA---NGELWKTEIE---
PSSM2   PDGEDLPFVKLYSHAFQGPGG-WYIENSLTTLGQKD---PVSEF---NSQLWNNGTD---
PSSM4   PEGEEMPWAKVWSHAFKGPGGQWYIENSLTTIGKDD---PVGEY---NRELWNSGKE---
            : .: .  :.*.*:  .  *:**..  :*    *     *         :   . :

t4      -----YSKVKRKTSYWANILVVKDPAAPENEGKVFKYRFGKKIWDKINAMIAVDVEMGET
tg      -----YSLVKRKTSYWANILVVKDPAAPENEGKVFKYRFGKKIWDKINAMIAVDVEMGET
Rb69    -----YSQLKRKTSYWANILVVKDPQAPDNEGKVFKYRFGKKIWDKINAMIAVDTEMGET
Aeh1    KKAMYASGVTRKTAFWANILVIKDPANPDNEGKVFKFRFGKKIMDKIQAEVDVNTDLGEE
Rb43    EADKLLGQIGRKQSFWANILVIKDPGNPENEGKVFKFRFGKKIMDKITATIAGNPDLDEP
Kvp40   DNQNIARKRKRTLSYWANIVVIKDDAAPENEGKVFKYRFGKKILDKITQAAQADEDLGVP
PSSM2   AGKDTARKQKRKLTYISNIYVVKDPANPENEGKTFLYKYGKKIFDKLTAAMQPEFE-DEE
PSSM4   SDKNIARAQKRKLSYYSNIYVVSDPAHPENEGKVFLYKYGKKIFDKLVEAMQPAFA-DET
              *.  :: :**  *:..*   *:****.*  *:****  **:           
```

Fig. 7-1

ALIGNMENT OF gp32 PROTEINS

```
t4      PVDVTCPWEGANFVLKVKQVSGFSNYDESKFLNQSAIPNIDDESFQKELFEQMVDLSEMT
t6      PVDVTCPWEGANFVLKVKQVSGFSNYDESKFLNQSAIPNIDDESFQKELFEQMVDLSEMT
Rb69    PVDVTCPWEGANFVLKVKQVSGFSNYDESKFLNQSAIPNIDDESFQKELFEQMVDLSEMT
Aeh1    PCDVTCPFEGKNFTIKIKKVGGNNNYDDSVFGKQSQIANIEDEAYQAQLFEQMHDIMDLI
RB43    GIAVTCPFAGANFTLKAKKVGDWPNYDDSTFGVPGPIKGIDDEAVQKAIFEGMSDLRPIT
Kvp40   GMDVTCVFDGANFSLKAKKVSGFPNYDDSKFGPSTELYG-GDEAKLKEVWDAMHDLNAII
PSSM2   AIDPFDFWQGANFKLKAKNVAGYRNYDSSEFAATSALLD-DDDAME-AIWKKEYSLAELV
PSSM4   PLDPFNFWKGADFKLKIRKLDGYWNYDKSEFAATSTLGGFDDSKLE-SIWKEGYSLTEFE
         : * :* :* ::: .  ***.* *          :  .   *.       ::.    .:   :

t4      SKDKFKSFEELNTKFGQVMGTAVMGGAAATAAKKADKVADDLDAFNVD--DF-NTKTE--
t6      SKDKFKSFEELSTKFSQVMGTAAMGGAAATAAKKADKVADDLDAFNVD--DF-NTKTE--
Rb69    SKDKFKSFEELNTKFNQVLGTAALGGAAAAAASVADKVASDLDDFDKDMEAFSSAKTE--
Aeh1    AKDKFKSMEDLTTVFNRVMGAEKRSNARAA------------DDFEKQMEQFENTPASKP
RB43    APDQFKPTAELTAKFTKVFGGGAAMGAGSSAGADLD---SELNSFDADLKNFDNGNQSGS
Kvp40   APSAFKSEAELQKRFLQVTGAAQPKASAAQ-------------NLEAQLNTSAPAQANAP
PSSM2   ATDQFKSYDELKTRLGYVLGNKPVRNDAET--------------VEQEVEDVRASAPV--
PSSM4   SAKNFKDYDALKKRLDLVLGLTIPHPTTEDESLEDLSEGKTPSSWGQEVSDFREKAVA--
         :  . **      *     :   * *                                    :

t4      -----------------DDFMSSSSGSSSSADDTDLDDLLNDL-----
t6      -----------------DDFMSSSSGSSSSADDT--------------
Rb69    -----------------DDFM-----SSSSSDDGDLDDLLAGL-----
Aeh1    EKE--------------DDDVPFNT-GSAGTVDTDLDDLLNEI-----
RB43    VKESGGVNQLNVGGSVPEDDTPFDLDNTSG--DDDLDKLL-DL-----
Kvp40   KAAAKPA---------AASVDVDSEPVTDSVDDELDALLADLELGDD
PSSM2   ----------------VETVESVSRSSATEDEDDTLSYFAKL--AES
PSSM4   -------------------------SSPVQDEEDTLSYFSRL-AEED
                                                    :
```

Fig. 7-2

T6 UvsX may substitute for T4 UvsX in RPA reactions

Conditions
100mM Potassium acetate
50mM Tris.acetate pH 8.3
50mM Phosphocreatine
3mM ATP
200 micromolar dNTPs
300nM Rs8179145-2 primer
300nM Rs8179145-3 primer
150ng/microliter T4 or T6 UvsX
1000ng/microliter T4 gp32
40ng/microliter T4 UvsY
42 copies human genomic DNA
5% Carbowax 20M
32ng/microliter Bsu polymerase 90 mins 37*C Cleanup through Qiagen spin column Rs8179145-2    CCTTTCTTTGGGACTGTGTGGACCAAGGAGCTTCCATC
Rs8179145-3    CCTGAAGGAGACAGCCTTGAAACCTTGAAGGATTCC Expected amplicon size 205 bp from human locus Rs8179145

Fig. 8

HETEROLOGOUS AMPLIFICATION WITH rb69 gp32 AND Aeh1 Uvsx
AND Aeh1 UvsY

| gp32 | rb69 | rb69 | T4 |
| UvsX | KVP40 | Aeh1 | rb69 |
| UvsY | KVP40 | Aeh1 | rb69 |

← EXPECTED PRODUCT

PRIMERS ARE Apo300 AND ApoB4 WHICH GENERATE A ~300bp BAND
TARGET IS HUMAN GENOMIC DNA

MANGANESE IONS CAN SUPPORT RPA REACTIONS

AMPLIFICATION PRIMERS J1 AND K2 (BACILLUS SUBTILIS GENOMIC TARGET)
EXPECTED PRODUCT SIZE 260 bp

DNA AMPLIFICATION IN THE ABSENCE OF UvsY

DNA AMPLIFICATION IN THE ABSENCE OF UvsY

■ CORRECT SIZED PRODUCTS MARKED

OLIGO PAIR:    1  2  3  4  5    1  2  3  4  5
UvsY                  +                    −

| OLIGO PAIRS: | EXPECTED PRODUCT SIZE |
|---|---|
| 1 | 100bp |
| 2 | 141bp |
| 3 | 174bp |
| 4 | 228bp |
| 5 | 101bp |

DNA TEMPLATE = 1000 COPIES MS2 cDNA
uvsX USED = T6H66S
gp32 USED = rb69

UvsY PRESENCE AND ABSENCE TEST USING A SHORT DNA TEMPLATE

■ CORRECT SIZED PRODUCTS MARKED

← 500bp
← 200bp
← 100bp

OLIGO PAIR:   1  2  3  4  WATER  1  2  3  4

UvsY                 +                ..

| OLIGO PAIRS: | EXPECTED PRODUCT SIZE |
|---|---|
| 1 | 305bp |
| 2 | 210bp |
| 3 | 143bp |
| 4 | 141bp |

DNA TEMPLATE = 1000 COPIES 305bp AMPLICON PRODUCT, AMPLIFIED FROM HUMAN GENOMIC DNA

UvsX USED = T6H66S gp32 USED = rb69

DNA AMPLIFICATION IN THE ABSENCE
OF UvsY OCCURS WHEN USING GENOMIC DNA

■ CORRECT SIZED PRODUCTS MARKED

← 500bp
← 200bp
← 100bp

UvsY      +  -  +  -  +  -  +  -  +  -
OLIGO PAIR:   1     2     3     4    WATER

| OLIGO PAIRS: | EXPECTED PRODUCT SIZE |
|---|---|
| 1 | 305bp |
| 2 | 210bp |
| 3 | 143bp |
| 4 | 141bp |

DNA TEMPLATE = 1000 COPIES HUMAN GENOMIC DNA
UvsX USED = T6H66S
gp32 USED = rb69

NO DNA AMPLIFICATION IN THE ABSENCE OF UvsY FOLLOWING THE REMOVAL OF PEG
■ CORRECT SIZED PRODUCTS MARKED
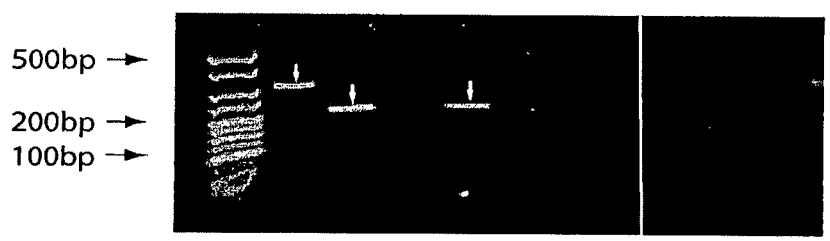
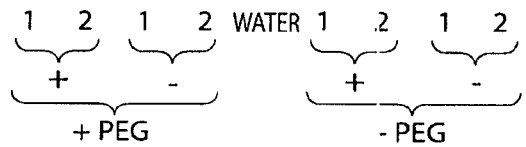
| OLIGO PAIRS: | EXPECTED PRODUCT SIZE | |
|---|---|---|
| 1 | 305bp | DNA TEMPLATE = 1000 COPIES HUMAN GENOMIC DNA |
| 2 | 210bp | UvsX USED = T6H66S |
| | | gp32 USED = rb69 |
Fig. 56

DNA AMPLIFICATION IN THE ABSENCE OF UvsY USING T4 gp32
■ CORRECT SIZED PRODUCTS MARKED
← 500bp
← 200bp
← 100bp
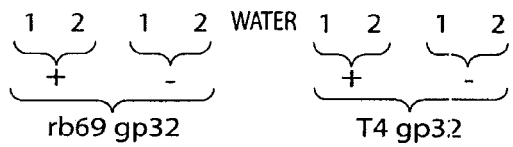
| OLIGO PAIRS: | EXPECTED PRODUCT SIZE |
|---|---|
| 1 | 305bp |
| 2 | 210bp |
DNA TEMPLATE = 1000 COPIES HUMAN GENOMIC DNA
UvsX USED = T6H66S
gp32 USED = rb69 OR T4
Fig. 57

POOR DNA AMPLIFICATION IN THE ABSENCE OF UvsY USING Ach1 gp32

■ CORRECT SIZED PRODUCTS MARKED

←500bp
←200bp
←100bp

OLIGO PAIR: 1 2 1 2 WATER 1 2 1 2
UvsY:          +      −            +      −
              rb69 gp32         Aeh1 gp32

| OLIGO PAIRS: | EXPECTED PRODUCT SIZE | |
|---|---|---|
| 1 | 305bp | DNA TEMPLATE = 1000 COPIES HUMAN GENOMIC DNA |
| 2 | 210bp | UvsX USED = T6H66S |
| | | gp32 USED = rb69 OR Aeh1 |

NO DNA AMPLIFICATION IN THE ABSENCE
OF UvsY USING T4 uvsX WITH rb69 gp32

| OLIGO PAIRS: | EXPECTED PRODUCT SIZE | |
|---|---|---|
| 1 | 305bp | DNA TEMPLATE = 1000 COPIES HUMAN GENOMIC DNA |
| 2 | 210bp | UvsX USED = T6H66S OR T4 |
| | | gp32 USED = rb69 |

NO DNA AMPLIFICATION IN THE ABSENCE
OF UvsY USING rb69 UvsX

■ CORRECT SIZED PRODUCTS MARKED

← 500bp
← 200bp
← 100bp

OLIGO PAIR:   1  2  1  2  WATER  1  2  1  2
UvsY              +      −              +      −
            T6H66S UvsX         rb69 UvsX

|  | EXPECTED PRODUCT | |
| --- | --- | --- |
| OLIGO PAIRS: | SIZE | DNA TEMPLATE = 1000 COPIES HUMAN GENOMIC DNA |
| 1 | 305bp | UvsX USED = T6H66S OR rb69 |
| 2 | 210bp | gp32 USED = rb69 |

NO DNA AMPLIFICATION IN THE ABSENCE
OF UvsY USING Aeh 1 UvsX

■ CORRECT SIZED PRODUCTS MARKED

OLIGO PAIR:  1  2  1  2 WATER 1  2  1  2
UvsY         \_+_/ \_-_/       \_+_/ \_-_/
              rb69 UvsX         Aeh1 uvsX

| OLIGO PAIRS: | EXPECTED PRODUCT SIZE | |
|---|---|---|
| 1 | 305bp | DNA TEMPLATE = 1000 COPIES HUMAN GENOMIC DNA |
| 2 | 210bp | UvsX USED = T6H66S OR Aeh 1 |
|   |       | gp32 USED = rb69 |

NO DNA AMPLIFICATION IN THE ABSENCE
OF UvsY USING Rb69 T6loop2H64S
2xLDE UvsX

■ CORRECT SIZED PRODUCTS MARKED

OLIGO PAIR:     1  2   1  2  WATER  1  2   1  2
UvsY              +       -             +       -
               T6H66S UvsX      rb69 T6loop2H64S
                                      UvsX

| OLIGO PAIRS: | EXPECTED PRODUCT SIZE |
|---|---|
| 1 | 305bp |
| 2 | 210bp |

DNA TEMPLATE = 5000 COPIES HUMAN GENOMIC DNA
UvsX USED = T6H66S OR rb69 T6loop2H64S 2xLDE
gp32 USED = rb69

REACTION SETUP (IN IxNEB4 BUFFER):
• PRESENT AT START: 100nM PROBE (SATamra2:Tamra/THF/BHQ2)
• PRESENT AT START: INDICATED AMOUNTS OF rb69 gp32
• PRESENT AT START: Nfo (PREP17/1; FINAL DILUTION 1 IN 300)

CONCLUSION:
DOSE RESPONSE FOR PROBE PROTECTION BY gp32

RECOMBINASE POLYMERASE AMPLIFICATION

RELATED APPLICATIONS

This application is a continuation of U.S. application Ser. No. 11/800,318 filed, May 4, 2007, which claims the benefit of U.S. Provisional Application No. 60/798,060, filed May 4, 2006. The contents of the foregoing applications are incorporated herein by reference in their entirety.

FIELD OF THE INVENTION

The present invention relates to novel hybrid and engineered recombinase enzymes, and the use of such enzymes for the amplification of nucleic acids. More specifically, the present invention relates to the use of T6, Rb69, Aeh1, and KVP40 hybrid and engineered proteins, and the use of such proteins in recombinase polymerase amplification assays.

BACKGROUND

Recombinase Polymerase Amplification (RPA) is a process in which recombinase-mediated targeting of oligonucleotides to DNA targets is coupled to DNA synthesis by a polymerase (Armes and Stemple, U.S. application Ser. No. 10/371,641). RPA depends upon components of the cellular DNA replication and repair machinery. The notion of employing some of this machinery for in vitro DNA amplification has existed for some time (Zarling et al. U.S. Pat. No. 5,223,414), however the concept has not transformed to a working technology until recently as, despite a long history of research in the area of recombinase function involving principally the *E. coli* RecA protein, in vitro conditions permitting sensitive amplification of DNA have only recently been determined (Piepenburg et al. U.S. patent application Ser. No. 10/931,916, also Piepenburg et al., PlosBiology 2006). Development of a 'dynamic' recombination environment having adequate rates of both recombinase loading and unloading that maintains high levels of recombination activity for over an hour in the presence of polymerase activity proved technically challenging and needed specific crowding agents, notably PEG molecules of high molecular weight (Carbowax 20M molecular weight 15-20,000, and others described herein, particularly PEG molecular weight 35,000), in combination with the use of recombinase-loading factors, specific strand-displacing polymerases and a robust energy regeneration system.

The RPA technology depended critically on the empirical finding that high molecular weight polyethylene glycol species (particularly >10,000 Daltons or more) very profoundly influenced the reaction behaviour. It has previously been discovered that polyethylene glycol species ranging in size from at least molecular weight 12,000 to 100,000 stimulate RPA reactions strongly. While it is unclear how crowding agents influence processes within an amplification reaction, a large variety of biochemical consequences are attributed to crowding agents and are probably key to their influence on RPA reactions.

Crowding agents have been reported to enhance the interaction of polymerase enzymes with DNA (Zimmerman and Harrison, 1987), to improve the activity of polymerases (Chan E. W. et al., 1980), to influence the kinetics of RecA binding to DNA in the presence of SSB (Layery and Kowalczykowski, 1992). Crowding agents are reported to have marked influence on systems in which co-operative binding of monomers is known to occur such as during rod and filament formation (Rivas et al., 2003) by increasing association constants by potentially several orders of magnitude (see Minton, 2001). In the RPA system multiple components rely on co-operative binding to nucleic acids, including the formation of SSB filaments, recombinase filaments, and possibly the condensation of loading agents such as UvsY. Crowding agents are also well known to enhance the hybridization of nucleic acids (Amasino, 1986), and this is a process that is also necessary within RPA reactions. Finally, and not least, PEG is known to drive the condensation of DNA molecules in which they change from elongated structures to compact globular or toroidal forms, thus mimicking structures more common in many in vivo contexts (see Lerman, 1971; also see Vasilevskaya. et. al., 1995; also see Zinchenko and Anatoly, 2005) and also to affect the supercoiling free energy of DNA (Naimushin et al., 2001).

Without intending to be bound by theory, it is likely that crowding agents influence the kinetics of multiple protein-protein, protein-nucleic acid, and nucleic acid-nucleic acid interactions within the reaction. The dependence on large molecular weight crowding agents for the most substantial reaction improvement (probably greater than about 10,000 Daltons in size) may reflect a need to restrict the crowding effect to reaction components over a certain size (for example oligonucleotides, oligonucleotide:protein filaments, duplex products, protein components) while permitting efficient diffusion of others (say nucleotides, smaller peptides such as UvsY). Further, it may also be that the high molecular weight preference might reflect findings elsewhere that as PEG molecular weight increases the concentration of metal ions required to promote DNA condensation decreases. In any case it is an empirical finding that RPA is made effective by the use of high molecular weight polyethylene glycols.

In addition to a need for specific type of 'crowded' reaction conditions as described above (reaction in the presence of crowding agents), effective RPA reaction kinetics depend on a high degree of 'dynamic' activity within the reaction with respect to recombinase-DNA interactions. In other words, the available data which includes (i) reaction inhibition by ATP-γ-S, or removal of the acidic C terminus of RecA or UvsX, and (ii) inhibition by excessive ATP (Piepenburg et al., 2006) suggest that not only is it important that recombinase filaments can be formed rapidly, but also important that they can disassemble quickly. This data is consistent with predictions made in earlier U.S. patent application Ser. No. 10/371,641. Rapid filament formation ensures that at any given moment there will be a high steady state level of functional recombinase-DNA filaments, while rapid disassembly ensures that completed strand exchange complexes can be accessed by polymerases.

Other processes must be adequately supported in the reaction environment in addition to highly dynamic recombinase loading/unloading. For the benefit of later discussions there now follows a more complete list of factors to note when considering how RPA reaction may be affected by changes in activity/properties of the components:

1. As stated above there must be a high overall level of active, correctly loaded, recombinase-DNA filaments at any given moment to ensure rapid kinetics of invasion and strand exchange. This is required to drive rapid reaction kinetics at low target numbers early in the reaction, as predicted by standard bi-molecular reaction kinetics, as well as to ensure non-limiting quantities of active filaments late in the reaction when targets become highly abundant and could easily out-titrate the loaded filaments.

2. Filaments must be dynamic, capable of rapid disassembly as well as assembly, to ensure that strand exchange processes work rapidly, and to avoid filament 'lock-up' in unproductive protein-DNA conformations (should they arise).

3. Recombinases should have a strong preference for single-stranded DNA, and a relatively weaker preference for double-stranded DNA. This ensures the correct partitioning of recombinase onto the oligonucleotides, and is very important in the late phase of the reaction when significant quantities of duplex DNA accumulate. This duplex DNA may otherwise compete too effectively for recombinase and slow the reaction too rapidly. A difference in disassembly rates on duplex DNA would also enhance factor (ii) insofar as accelerating disassembly of productive exchange complexes. Observations consistent with 'out-titration' activity of excess duplex DNA, such as decreases in reaction rate late in the reaction, or if excess DNA is present early in the reaction, have been made.

4. Hybridization of single-stranded DNA's to one another must be supported under any given reaction condition. RPA has the potential to generate single-stranded DNA products which may only be converted to new duplex targets following hybridization of the complementary priming oligonucleotide to initiate DNA synthesis. As saturating quantities of single-stranded DNA binding proteins (i.e. loading proteins, single-stranded DNA binding proteins and recombinases) are present in the reaction environment, these hybridization processes must be supported/aided by these proteins. SSB's and recombinases have some melting/hybridization activities on duplex/single-stranded DNA's, and probably demonstrate differential levels of melting/hybridization activity. Thus the relative proportions of recombinase and SSB of loading may influence the rate behaviour for hybridization, and this may also depend on the species of SSB and recombinase employed. If either the SSB or recombinase does not, or only poorly, supports hybridization of single-stranded DNAs to one another, then the reaction may be compromised.

5. The temporal change in reaction composition with regard to pH, anion accumulation, generation of ADP, of AMP, pyrophosphate, and other nucleotide species may be strongly influenced by the recombinase employed. Furthermore recombinases may respond differentially to the ionic and pH environment. Rates of nucleotide hydrolysis affect the accumulation of the afore-mentioned species, and their accumulation may in turn influence the activity in the reaction of recombinases and polymerases. For example accumulation of phosphate and pyrophosphate may inhibit recombinase processes, while the accumulation of ADP (and possibly AMP) can affect DNA on-off kinetics of the recombinase. Notably bacteriophage T4 UvsX protein has been reported to hydrolyse ATP to both ADP and AMP, a property not attributed to other recombinases to date. Recombinases may also hydrolyse dATP, UTP and potentially other nucleotides. Different nucleotides may affect the DNA binding stabilities of complexes on ssDNA and dsDNA, for example dATP has been noted to increase the stability of RecA on ssDNA. Without intending to be bound by theory, the particular properties of a recombinase with respect to its DNA binding domains and nucleotide binding/catalysis domains may have significant impact on reaction rate and effectiveness in generating strong signals late in the reaction.

Previously Established RPA Conditions.

Effective RPA reactions have previously been demonstrated using both *E. coli* RecA (in a heterologous system with compromised gp32 protein) and with the T4 phage UvsX protein (when combined with the T4 phage UvsY protein) (Piepenburg et al., 2006). In both cases the employment of polyethylene glycol was found to be absolutely necessary for amplification to occur with any useful efficiency when templates were present at concentrations below roughly nanomolar levels (or roughly below the order of about $10^{10}$ target molecules per microliter).

Experimentation showed the importance of PEG in stimulating secondary, tertiary and yet further invasion events when using oligonucleotides directed towards the ends of linear templates, said oligonucleotide initially having a 5' overhang relative to the initial target, but being flush to later targets due to the activity of 'backfire' synthesis (Piepenburg et al. U.S. Ser. No. 10/931,916). Fully embedded targets proved to be even more intractable, almost certainly due to the topological constraints associated with the recombination products caused by the outgoing strand being wound unfavourably around the newly formed duplex. Without intending to be bound by any theory, the huge increase in efficiency of initiating replication from these more unstable intermediates in the presence of PEG may depend on stability conferred by the crowding agent on the complexes, on altered DNA conformation and coiling (such as DNA condensation), on much higher association constants for the polymerase gaining access to the intermediates, and/or a very great increase in the frequency of recombination events leading to more 'chances' of the polymerase grabbing the intermediate and elongating.

An RPA system utilizing bacteriophage T4 UvsX, T4 UvsY, and T4gp32, a *B. subtilis* PolI large fragment, and PEG compound (carbowax 20M) is effective for amplifying duplex DNA sequences up to about 1 kilobase in length (Piepenburg et al., 2006). Average doubling times of as little as 40 seconds or less have been attained for fragments of roughly 300 nucleotides, and DNA accumulates to levels useful for detection by a variety of means, even when targets are initially present at levels below 10 copies. Despite this robust behaviour there exists a need for the identification of other recombinases, their associated loading components and single stranded DNA binding proteins, due to the strict necessity for very rapid kinetics and strong signals for the implementation of the RPA system in commercially useful products. The present invention meets these needs and other needs.

SUMMARY OF THE INVENTION

This disclosure provides enabling data on the use of alternative recombinase/accessory factor systems for performing RPA reactions. As evidenced herein, bacteriophage T6 UvsX, bacteriophage Rb69 UvsX, UvsY and gp32, and bacteriophage Aeh1 UvsX, UvsY, and gp32 can be employed successfully in RPA reactions. Additionally, evidence that bacteriophage KVP40 UvsX and UvsY may also be able to support RPA reactions is included, although problems were encountered in the production of KVP40 gp32 that limited this analysis. In general it was discovered that variation in the concentration of reactants must be performed to identify optimal conditions for each system, and there are observable differences in overall kinetic activity. The present invention provides evidence of limited cross-compatibility between reaction components generated from different species. In general the requirement for co-employment of UvsX and UvsY from the same or similar species was observed, while gp32 may be less stringently matched. Also provided herein are mutant and chimeric recombinase proteins, in particular the use of altered T6 and Rb69 UvsX proteins, and chimeric T4 and Rb69 UvsY proteins, and the analysis thereof. This analysis leads to identification of residues influencing the assayable behaviour of the proteins in RPA reactions. As provided herein, some, but not all, of the character of the T4 UvsX protein derives from a unique serine residue within the Walker A motif.

Without intending to be bound by any theory, the resulting re-iteration of a lysine-serine dipeptide within the motif may underpin the hydrolysis of ATP to both ADP and AMP by this protein. Modification of T6 UvsX protein to contain this re-iteration results in altered (improved) RPA activity when monitored in real-time. Such modified UvsX demonstrates changed reaction kinetics when assayed by proprietary fluorescent probes, in particular exhibiting steeper fluorescent signal-generation curves during the late phase of the amplification reaction. Also provided herein is the discovery that regions of myoviridae UvsX proteins which are predicted to be equivalents to DNA binding loop 2 of *E. coli* are variable and impart distinctive activities UvsX hybrids used in RPA reactions. Rb69 UvsX is an unusual UvsX molecule in regard to this sequence, more closely resembling the bacterial homologs. The present invention provides a model for structure/sequence compatibility in the surface region of recombinase enzymes that binds both nucleic acids and ATP, and how this evidence may be employed to 'tune' and improve (alter) recombinase activity. Surprisingly it was discovered that T6 UvsX, in particular, can function moderately well with a complete absence of UvsY protein. This property may be evident for other UvsX species although less markedly. Finally the present invention provides the use of manganese ions to support RPA reactions, the use of heparin to improve signal:noise ratios, the use *S. aureus* Pol I as the polymerase employed in RPA reactions, and *E. coli* exonuclease III to process and unblock primer ends in some cases to permit elongation.

The first RPA embodiment of the invention is directed to a process (method) of recombinase polymerase amplification of a double stranded target nucleic acid molecule. In the first step of the process, a first and a second single stranded nucleic acid primer is contacted with a recombinase (e.g., UvsX), a recombinase loading agent (e.g., UvsY) and a single strand DNA binding protein (e.g., gp32) to form a first and a second nucleoprotein primer. The single stranded nucleic acid primers are specific for and are complementary to the target nucleic acid molecule. In this case each of the recombinase (e.g., UvsX), recombinase loading agent (e.g., UvsY) and single strand DNA binding protein (e.g., gp32) are derived from a myoviridae phage. Further, no more than two of the recombinase (e.g., UvsX), recombinase loading agent (e.g., UvsY) and single strand DNA binding protein (e.g., gp32) are T4 phage proteins.

In the second step, the first nucleoprotein primer is contacted to the double stranded target nucleic acid molecule to create a first D loop structure at a first portion of the double stranded target nucleic acid molecule (Step 2a). Further, the second nucleoprotein primer is contacted to the double stranded target nucleic acid molecule to create a second D loop structure at a second portion of the double stranded target nucleic acid molecule (Step 2b). The D loop structures are formed such that the 3' ends of the first nucleic acid primer and said second nucleic acid primer are oriented toward each other on the same double stranded target nucleic acid molecule without completely denaturing the target nucleic acid molecule. It should be noted that step 2a and step 2b can be performed in any order or simultaneously.

In a D loop structure, the primer is hybridized to one strand of the double stranded target nucleic acid molecule to form a double stranded structure. The second strand of the target nucleic acid molecule is displaced by the primer. The structure resembles a capital D where the straight part of the D represents the double stranded part of the structure and the curved part of the D represents the single stranded displaced second strand of the target nucleic acid.

In the third step, the 3' end of the first and the second nucleoprotein primer is extended with one or more polymerases capable of strand displacement synthesis and dNTPs to generate a first and second double stranded target nucleic acid molecule and a first and second displaced strand of nucleic acid. The first and second double stranded target nucleic acid molecules may serve as target nucleic acid molecules in step two during subsequent rounds of amplification.

Steps two and step 3 are repeated until a desired degree of amplification of the target nucleic acid is achieved. A desired degree of amplification may be at least $10^3$, $10^4$, $10^5$, $10^6$, $10^7$, $10^8$, or $10^9$ fold amplification.

During the amplification process described above, the first and second displaced strand of nucleic acid may hybridize to each other after step (c) to form a third double stranded target nucleic acid molecule.

In any of the processes of this disclosure, the recombinase (e.g., UvsX), recombinase loading agent (e.g., UvsY) and single strand DNA binding protein (e.g., gp32) may be derived from a myoviridae phage. The myoviridae phage may be, for example, T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, or phage LZ2. In a preferred embodiment, the combination of Rb69 UvsX, Rb69 UvsY and Rb69 gp32 may be used. In another preferred embodiment, the combination of Aeh1 UvsX, Aeh1 UvsY and Rb69 gp32 may be used. In another preferred embodiment, the combination of T4 UvsX, T4 UvsY and Rb69 gp32 may be used. In another preferred embodiment, the combination of T4 UvsX, Rb69 UvsY and T4 gp32 may be used.

Further, in any of the processes of this disclosure, the recombinase (e.g., UvsX), recombinase loading agent (e.g., UvsY) and single strand DNA binding protein (e.g., gp32) can each be native, hybrid or mutant proteins from the same or different myoviridae phage sources. A native protein may be a wildtype or natural variant of a protein. A mutant protein (also called a genetically engineered protein) is a native protein with natural or manmade mutations such as insertions, deletions, substitutions, or a combination thereof, that are at the N terminus, C terminus, or interior (between the N terminus and the C terminus. A hybrid protein (also called a chimeric protein) comprises sequences from at least two different organisms. For example, a hybrid UvsX protein may contain an amino acid from one species (e.g., T4) but a DNA binding loop from another species (e.g., T6). The hybrid protein may contain improved characteristics compared to a native protein. The improved characteristics may be increased or more rapid RPA amplification rate or a decreased or more controllable RPA amplification rate.

In any process of this disclosure, the recombinase (e.g., UvsX) may be a mutant UvsX. In a preferred embodiment, the mutant UvsX is an Rb69 UvsX comprising at least one mutation in the Rb69 UvsX amino acid sequence, wherein the mutation is selected from the group consisting of (a) an amino acid which is not histidine at position 64, a serine at position 64, the addition of one or more glutamic acid residues at the C-terminus, the addition of one or more aspartic acid residues at the C-terminus, and a combination thereof. In another preferred embodiment, the mutant UvsX is a T6 UvsX having at least one mutation in the T6 UvsX amino acid sequence, wherein the mutation is selected from the group consisting of (a) an amino acid which is not histidine at position 66; (b) a serine at position 66; (c) the addition of one or more glutamic acid residues at the C-terminus; (d) the addition of one or more aspartic acid residues at the C-terminus; and (e) a combination thereof.

In any process of this disclosure where a hybrid protein is used, the hybrid protein may be a UvsX protein comprising at least one region which comprises an amino acid sequence from a different UvsX species. The region may be, for example, the DNA-binding loop-2 region of UvsX.

Any of the RPA process of this disclosure may be performed in the presence of a crowding agent. The crowding agent may be selected from the group comprising polyethylene glycol, polyethylene oxide, polyvinyl alcohol, polystyrene, Ficoll, dextran, PVP, albumin. In a preferred embodiment, the crowding agent has a molecular weight of less than 200,000 daltons. Further, the crowding agent may be present in an amount of about 0.5% to about 15% weight to volume (w/v).

Any of the RPA processes of this disclosure may be performed with a polymerase which is a large fragment polymerase. The large fragment polymerase may be selected from the group consisting of E. Coli Pol I, Bacillus subtilis Pol I, Staphylococcus aureus Pol I, and homologues thereof.

Any of the RPA processes of this disclosure may be performed in the presence of heparin. Heparin may serve as an agent to reduce the level of non-specific primer noise, and to increase the ability of E. coli exonuclease III or E. Coli exonuclease IV to rapidly polish 3' blocking groups or terminal residues from recombination intermediates.

Further, any of the RPA processes of this disclosure may be performed with a blocked primer. A blocked primer is a primer which does not allow elongation with a polymerase. Where a blocked primer is used, an unblocking agent is also used to unblock the primer to allow elongation. The unblocking agent may be an endonuclease or exonuclease which can cleave the blocking group from the primer. Preferred unblocking agents include E. coli exonuclease III and E. coli endonuclease IV.

Any of the RPA processes of this disclosure may be performed in the presence of about 1 mM to about 3 mM divalent manganese ions. In a preferred embodiment, the manganese ions replace the magnesium ions and the reaction may be performed with or without magnesium.

Furthermore, UvsY may be optionally omitted from any of the RPA reactions of this disclosure. That is, any of the RPA reactions of this disclosure may be performed in the absence of UvsY.

The second RPA embodiment of the invention is directed to a process (method) of recombinase polymerase amplification of a double stranded target nucleic acid molecule. In the first step of the process, recombinase (e.g., UvsX), recombinase loading agent (e.g., UvsY) and single strand DNA binding protein (e.g., gp32) are contacted with a first single stranded nucleic acid primer specific for the double stranded target nucleic acid molecule to form a population of first nucleoprotein primer, wherein the recombinase (e.g., UvsX), recombinase loading agent (e.g., UvsY) and single strand DNA binding protein (e.g., gp32) are each derived from a myoviridae phage, and wherein no more than two of the recombinase (e.g., UvsX), recombinase loading agent (e.g., UvsY) and single strand DNA binding protein (e.g., gp32) are T4 phage proteins.

In the second step, the first nucleoprotein primer is contacted with the double stranded target nucleic acid molecule to form a first D loop structure at a first portion of said double stranded target nucleic acid molecule without completely denaturing the target nucleic acid molecule;

In the third step, the 3' end of the first nucleoprotein primer is extended with one or more polymerases capable of strand displacement synthesis and dNTPs to generate a double stranded target nucleic acid molecule and a displaced strand of nucleic acid molecule;

In the fourth step, a second single stranded nucleic acid primer is hybridized to the displaced strand of nucleic acid molecule to form a hybridized second single stranded nucleic acid primer;

In the fifth step, the hybridized second single stranded nucleic acid primer is elongated to generate a double stranded target nucleic acid molecule;

The second through fifth steps of the reaction is continued until a desired degree of amplification is reached.

All other aspects of this second RPA embodiment is similar to that of the first RPA embodiment including the desired degree of amplification and the choice of proteins (recombinase, loading agent, single stranded DNA binding protein) etc. These parameters are described above for the first RPA embodiment. We have found, surprisingly, that RPA would function even if only one of the nucleic acid primers was coated with recombinase/recombinase loading agent/single stranded DNA binding protein. That is, an RPA may be performed with one primer which is uncoated and one primer which is coated with any one or a combination of recombinase, recombinase loading agent, and single stranded DNA binding protein.

The production of a coated primer and an uncoated primer may be made in a number of methods. In one method, only one primer is contacted to any one or a combination of recombinase, recombinase loading agent, and single stranded DNA binding protein before commencement of RPA. In another method, both primers are contacted to any one or a combination of recombinase, recombinase loading agent, and single stranded DNA binding protein. However, one primer is incapable of attaching sufficient protein to be able to generate a D loop on a target double stranded nucleic acid. This may be because the primer is too short or contain unusual nucleic acids such that it cannot bind sufficient protein for recombination. Nevertheless, to our surprise, RPA is possible even if only one primer is capable of forming D loops. RPA is possible in this circumstance because the primer which cannot form a D loop can hybridize to any displaced strand generated from the D loop capable primer (the recombinase coated primer) to initiate DNA synthesis.

Another embodiment of the invention is directed to a mutant or hybrid Rb69 UvsX protein with an amino acid sequence selected from the group consisting of (a) an amino acid which is not histidine at position 64; (b) a serine at position 64; (c) the addition of one or more glutamic acid residues at the C-terminus; (d) the addition of one or more aspartic acid residues at the C-terminus; (e) the replacement of DNA-binding loop-2 region with a DNA-binding loop-2 region from a UvsX protein which is not Rb69 UvsX; and (f) a combination thereof. An example of such mutants or hybrids may be found, for example, in SEQ ID NO:114, SEQ ID NO:115, SEQ ID NO:116, SEQ ID NO:117, SEQ ID NO:118, SEQ ID NO:119, SEQ ID NO:120, or SEQ ID NO:121.

Another embodiment of the invention is directed to a mutant or hybrid T6 UvsX protein having at least one mutation in the amino acid sequence, wherein the mutation is selected from the group consisting of (a) an amino acid which is not histidine at position 66; (b) a serine at position 66; (c) the addition of one or more glutamic acid residues at the C-terminus; (d) the addition of one or more aspartic acid residues at the C-terminus; (e) the replacement of DNA-binding loop-2 region with a DNA-binding loop-2 region from a UvsX protein which is not T6 UvsX; (f) a valine at position 164, (g) a serine at position 166, and (h) a combination thereof. See, for example, SEQ ID NO:105 and SEQ ID NO:106.

BRIEF DESCRIPTION OF THE FIGURES

FIG. 2 shows a primary sequence alignment of bacteriophage T4 UvsX with *E. coli* recA. T4 UvsX sequence is: MSDLKSRLIK ASTSKLTAEL TASKFFNEKD VVRTKIPMMN IALSGEITGG MQSGLLILAG PSKSFKSNFG LTMVSSYMRQ YPDAVCLFYD SEFGITPAYL RSMGVDPERV IHTPVQSLEQ LRIDMVNQLD AIERGEKVVV FIDSLGNLAS KKETEDALNE KVVSDMTRAK TMKSLFRIVT PYFSTKNIPC IAINHTYETQ EMFSKTVMGG GTGPMYSADT VFIIGKRQIK DGSDLQGYQF VLNVEKSRTV KEKSKFFIDV KFDGGIDPYS GLLDMALELG FVVKPKNGWY AREFLDEETG EMIREEKSWR AKDTNCTTFW GPLFKHQPFR DAIKRAYQLG AIDSNEIVEA EVDELINSKV EKFKSPESKS KSAADLETDL EQLSDMEEFN E (SEQ ID NO:1). The *E. Coli* RecA sequence is as follows: MAIDENKQKA LAAALGQIEK QFGKGSIMRL GEDRSMDVET ISTGSLSLDI ALGAGGLPMG RIVEIYGPES SGKTTLTLQV IAAAQREGKT CAFIDAEHAL DPIYARKLGV DIDNLLCSQP DTGEQALEIC DALARSGAVD VIVVDSVAAL TPKAEIEGEI GDSHMGLAAR MMSQAMRKLA GNLKQSNTLL IFINQIRMKI GVMFGNPETT TGGNALKFYA SVRLDIRRIG AVKEGENVVG SETRVKVVKN KIAAPFKQAE FQILYGEGIN FYGELVDLGV KEKLIEKAGA WYSYKGEKIG QGKANATAWL KDNPETAKEI EKKVRELLLS NPNSTPDFSV DDSEGVAETN EDF (SEQ ID NO:2).

FIG. 3 shows a representative 3-D structure of a model of an active *E. coli* recA filament with superimposition and labelling of equivalent T4 UvsX residues based on primary sequence alignment.

FIG. 4 shows the primary sequence alignment of T4 and T6 g32 and UvsY proteins. The T6 gp32 sequence is as follows: MFKRKSTAEL AAQMAKLAGN KGGFSSEDKG EWKLKLDNAG NGQAVIRFLP SKNDEQAPFA ILVNHGFKKN GKWYIETCSS THGDYDSCPV CQYISKNDLY NTDNKEYSLV KRKTSYWANI LVVKDPAAPE NEGKVFKYRF GKKIWDKINA MIAVDVEMGE TPVDVTCPWE GANFVLKVKQ VSGFSNYDES KFLNQSAIPN IDDESFQKEL FEQMVDLSEM TSKDKFKSFE ELSTKFSQVM GTAAMGGAAA TAAKKADKVA DDLDAFNVDD FNTKTEDDFM SSSSGSSSSA DDTDLDDLLN DL (SEQ ID NO:3). The T4 gp32 sequence is as follows: MFKRKSTAELAAQMAKLNGN KGFSSEDKGE WKLKLDNAGN GQAVIRFLPS KNDEQAPFAI LVNHGFKKNG KWYIETCSST HGDYDSCPVC QYISKNDLYN TDNKEYSLVK RKTSYWANIL VVKDPAAPEN EGKVFKYRFG KKIWDKINAM IAVDVEMGET PVDVTCPWEG ANFVLKVKQV SGFSNYDESK FLNQSAIPNI DDESFQKELF EQMVDLSEMT SKDKFKSFEE LNTKFGQVMG TAVMGGAAAT AAKKADKVAD DLDAFNVDDF NTKTEDDFMS SSSGSSSSAD DTDLDDLLND L (SEQ ID NO:4). The T4 UvsY sequence is as follows: MRLEDLQEEL KKDVFIDSTK LQYEAANNVM LYSKWLNKHS SIKKEMLRIE AQKKVALKAR LDYYSGRGDG DEFSMDRYEK SEMKTVLSAD KDVLKVDTSL QYWGILLDFC SGALDAIKSR GFAIKHIQDM RAFEAGK (SEQ ID NO:5). The T6 UvsY sequence is as follows: MRLEDLQEEL KKDVFIDSTK LQYEAANNVM LYSKWLNKHS SIKKEMLRID AQKKVALKAK LDYYSGRGDG DEFSMDRYEK SEMKTVLSAD KDVLKVDTSL QYWGILLDFC SGALDAIKSR GFAIKHIQDM RAFEAGK (SEQ ID NO:6).

FIG. 5 (FIG. 5-1 continued onto FIG. 5-2) shows the primary sequence alignment of diverse UvsX proteins. The T4UvsX sequence is as follows: MSDLKSRLIK ASTSKLTAEL TASKFFNEKD VVRTKIPMMN IALSGEITGG MQSGLLILAG PSKSFKSNFG LTMVSSYMRQ YPDAVCLFYD SEFGITPAYL RSMGVDPERV IHTPVQSLEQ LRIDMVNQLD AIERGEKVVV FIDSLGNLAS KKETEDALNE KVVSDMTRAK TMKSLFRIVT PYFSTKNIPC IAINHTYETQ EMFSKTVMGG GTGPMYSADT VFIIGKRQIK DGSDLQGYQF VLNVEKSRTV KEKSKFFIDV KFDGGIDPYS GLLDMALELG FVVKPKNGWY AREFLDEETG EMIREEKSWR AKDTNCTTFW GPLFKHQPFR DAIKRAYQLG AIDSNEIVEA EVDELINSKV EKFKSPESKS KSAADLETDL EQLSDMEEFN E (SEQ ID NO:7). The t6 UvsX sequence is as follows: MSIADLKSRL IKASTSKMTA ELTTSKFFNE KDVIRTKIPM LNIAISGAID GGMQSGLTIF AGPSKHFKSN MSLTMVAAYL NKYPDAVCLF YDSEFGITPA YLRSMGVDPE RVIHTPIQSV EQLKIDMVNQ LEAIERGEKV IVFIDSIGNM ASKKETEDAL NEKSVADMTR AKSLKSLFRI VTPYFSIKNI PCVAVNHTIE TIEMFSKTVM TGGTGVMYSA DTVFIIGKRQ IKDGSDLQGY QFVLNVEKSR TVKEKSKFFI DVKFDGGIDP YSGLLDMALE LGFVVKPKNG WYAREFLDEE TGEMIREEKS WRAKDTNCTT FWGPLFKHQP FRDAIKRAYQ LGAIDSNEIV EAEVDELINS KVEKFKSPES KSKSAADLET DLEQLSDMEE FNE (SEQ ID NO:8). The Phage133 UvsX sequence is as follows: MSSLKERLIK ASTSKMTAEL TKSKFFNDKT VVRTRIPMLN IAISGALNGG MQSGLTIFAG PSKHFKSNMG LTMVAAYMKA FPDAVCMFYD SEFGITPAYL KAMGVDPDRV IHTPVQSVEQ LKIDMTNQLE EVKRGEKVIV FIDSIGNLAS KKETEDALNE KTTADMTRAK ALKSLFRIVT PYFSIKDIPC VAVNHTLQTL EMFSKEVMTG GTGVMYSADT VFFIGKRQVK DGTELAGYEF ILKAEKSRMV KEKSVFPITV KFDGGIDPYS GLLEMATDLG FVVKPKVGWY KRAMMVDGVM QHEEKSWRAK DTDSIDFWGP LFKHDEFRKA IETRYQLGSI ESDAEVDAEV DALIGSKTTA KISGVNFGPA ESAADKEQQL EDFVDED (SEQ ID NO:9). The Rb69 UvsX sequence is as follows: MSDLKSRLIK ASTSKMTADL TKSKLFNNRD EVPTRIPMLN IALGGALNAG LQSGLTIFAA PSKHFKTLFG LTMVAAYMKK YKDAICLFYD SEFGASESYF RSMGVDLDRV VHTPIQSVEQ LKVDMTNQLD AIERGDKVII FIDSIGNTAS KKETEDALNE KVVGDMSRAK ALKSLFRIVT PYLTIKDIPC VAINHTAMEI GGLYPKEIMG GGTGILYSAN TVFFISKRQV KEGTELTGYD FTLKAEKSRT VKEKSTFPIT VNFDGGIDPF SGLLEMATEI GFVVKPKAGW YAREFLDEET GEMIREEKSW RAKATDCVEF WGPLFKHKPF RDAIETKYKL GAISSIKEVD DAVNDLINCK ATTKVPVKTS DAPSAADIEN DLDEMEDFDE (SEQ ID NO:10). The AehlUvsX sequence is as follows: MAKGIKTAKT GNLGSLMSKL AGTSSNKMSS VLADSKFFND KDCVRTRVPL LNLAMSGELD GGLTPGLTVL AGPSKHFKSN LSLVFVAAYL RKYP-DAVCIF FDNEFGSTPG YFESQGVDIS RVIHCPFKNI EELKFDIVKK LEAIERGDRV IVFVDSIGNA ASKKEID-DAI DEKSVSDMTR AKQIKSLTRM MTPYLTVNDI PAIMVAHTYD TQEMYSKKVV SGGTGITYSS DTVII-IGRQQ EKDGKELLGY NFVLNMEKSR FVKEQSKLPL EVTFQGGINT YSGMLDIALE VGFVVKPSNG WFS-RAFLDEE TGELVEEDRK WRRADTNCLE FWKPM-FAHQP FKTACSDMFK LKSVAVKDEV FDEVDELFSG EAEMPVNMGR KLDTADQEEI DQLEEVDVEG SDS-DELFANL D (SEQ ID NO:11). The Ae65UvsX sequence is as follows: MAKKAKVVNS GDLLERLNGT SSNKM-SAMLA ESIFFNEKDT IRTRVPIINL MMSGRLDGGI TPGLTCIAGP SKHFKSNLSL VMVSAYLRKY PKAV-CLFFDN EFGSTPDYFT SQGVDISRVV HCPFIDVEEL KFDIVKKLES ITRGDKVIIY IDSIGNVASK KELQDAKDEK SAQDMTRAKQ IKSLFRMVTP YLTVL-DIPCI AVNHTYETQE MFSKTVMSGG TGPMYSADTV IILGKQQDKD GKELLGYNFV MNAEKSRAIK EKSKLDLMVS FEGGINTYSG LLKIAQELGF VTK-PQNARYQ RNFLDLEPGE MVIPEDEKKW TEEESD-SLEF WKPMFSHKPF MDAVSNAYKL KAVEVSQEVF DEVDQLFG (SEQ ID NO:12). The Kvp40UvsX sequence is as follows: MSDLMKSLKK SSTSGYAQVL SESQFM-FDKD HTRTYVPAIN IAFSGEVDGG LTSGLTVLAG PSKHFKSNLG LVGVAAYLKK YPDAVCVFID TEF-GITPSYL RSQGVDPDRV LHIQCESVER MKFEMAN-QLK DLAERKRAKK AGEEPDRVIF FIDSVGNVAS AKEIDDAQNE KSVADMSRAK QLKSLFRIIT PYFTML-DIPC IAINHTYQTQ EIYSKTVMSG GTGIMYSADT VIILGKQQEK DGKDIIGYHF IMNIEKSRFV KEKMKV-PLTV TYENGIDPFS GLLDIALQTG HVVKPSNGWY QRATVDEETG EMIVEEKKYR AKETQTISFW KDIIN-SPTFK EGVKRIYCLG QLDESELFGE VDSLFD (SEQ ID NO:13). The Rb43 UvsX sequence is as follows: MSNKALLKKL IKNSNSQSAA ILSESDVFNN ITKTR-TRVPI LNLALSGAFD GGLTSGLTLF AGPSKHFKSN LGLVTVSAYL KANEDAVCLF YDSEKGVTKS YLKSMGVDPD RVVYTRITTV EQLRNDVVSQ LDAL-ERGDKV IIFVDSVGNT ASKKELADAL SDNDKQD-MTR AKALKGMFRM VTPYLADLDI PMVCICHTYD TQEMYSKKVI SGGTGLMYSA DTAIILGKQQ VKEG-TEVVGY DFIMNIEKSR FVKEKSKFPL HVTYEGGISM YSGLLDLAME MNFVQTPTKG WRGRAFLNTE TGELELEEKK WRESETNSIE FWRPLFTHQP FLDAIQDKYR IPDKEITDGA ALEDLYSTDE PESNKIDLDD DIPDDIGIDQ DEEPIM (SEQ ID NO:14). The PSSM2 UvsX sequence is as follows: MDFLKEIVKE IGDEYTQVAA DIQENERFID TGSYIFNGLV SGSIFG-GVSS SRITAIAGES STGKTYFSLA VVKNFLDNNP DGYCLYFDTE AAVNKGLLES RGIDMNRLVV VNV-VTIEEFR SKALRAVDIY LKTSEEERKP CMFVLD-SLGM LSTEKEIRDA LDDKQVRDMT KSQLVKGAFR MLTLKLGQAN IPLIVTNHTY DVIGSYVPTK EMGGGSGLKY AASTIIYLSK KKEKDQKEVI GNLIKAKTHK SRLSKENKEV QIRLYYDERG LDRYYGLLEL GEIGGMWKNV AGRYEMNGKK IYAKEILKNP TEYFTDDIME QLDNIAKEHF SYGTN (SEQ ID NO:15). The PSSM4 UvsX sequence is as follows: MNFLKDIAKE IGNDYASLVS EGVSAGDTAG FIDTG-SYIFN ALLSGSIYGG IPNNKITAIA GETSTGKTFF CLG-MVQHFLE SNPDAGVIYF ESESAISKQM IEDRGIDSNR MLLVPVTTVQ EFRLQAIKIL DKYNEQTAEE RKPLM-FVLDS LGMLSTSKEV EDSEAGKETR DMTRAQVVKS IFRVLTLKLG KANVPLIVTN HTYDVVGAYI PTKEMGGGSG LKYAASTIVY LSKKKEKNGK EVVG-NIIKCK TAKSRLTKEN SDVETRLYYD RGLDRYYGLL ELGEKHGVFS RKGNRVVVGD SSVYPSAILA DPDKY-FTEEL MEKLDEAAAK EFRYGN (SEQ ID NO:16).

FIG. 6 shows the primary sequence alignment of diverse UvsY proteins. The T4UvsY sequence is as follows: MRLEDLQEEL KKDVFIDSTK LQYEAANNVM LYSKWLNKHS SIKKEMLRIE AQKKVALKAR LDYYS-GRGDG DEFSMDRYEK SEMKTVLSAD KDV-LKVDTSL QYWGILLDFC SGALDAIKSR GFAIKHIQDM RAFEAGK (SEQ ID NO:17). The T6UvsY sequence is as follows: MRLEDLQEEL KKDVFIDSTK LQYEAANNVM LYSKWLNKHS SIKKEMLRID AQKKVALKAK LDYYSGRGDG DEFSMDRYEK SEMKTVLSAD KDVLKVDTSL QYWGILLDFC SGAL-DAIKSR GFAIKHIQDM RAFEAGK (SEQ ID NO:18). The Rb69UvsY sequence is as follows: MKLEDLQEEL DAD-LAIDTTK LQYETANNVK LYSKWLRKHS FIRKEML-RIE TQKKTALKAR LDYYSGRGDG DEFSMDRYEK SEMKTVLAAD KDVLKIETTL QYWGILLEFC SGAL-DAVKSR SFALKHIQDM REFEAGQ (SEQ ID NO:19). The phage133UvsY sequence is as follows: MTLEDLQAEL KKDLVLDMTQ LQTEAAENIN LYCKWSTKYS NIRK-SILSLD AQRKKHTKTK LDYYSGRGDE VSMDRYERSE MKTVLSGDAD ILTVETKIQY FTIMLEFCGN AMDAIK-SRGF AIKNIIDLRQ FEAGK (SEQ ID NO:20). The Aeh1UvsY sequence is as follows: MTLDELKEEL KADLPIKLTA VQTEVAENPV LYGKWNRYLA DINRE-ITRLD AERKKMLRDR FMFYTGRSED EVCMDVYSPT ELKTVIAGDE EVIKKNAAVE LSQAKADFCR QSMEAVRQRG FSLRAIIDCR KLEAGE (SEQ ID NO:21). The Rb43UvsY sequence is as follows: MTELKLEDLQ AELEQDMLID PLKLQSESAD IPKIWSKWLR YHSNAKKKLI QLQARKEADV KERLLYYTGR HET-EMTDVIY TGSGEIKIAI NGDPKIVEVN KLIQYFELIA EFTSKALDIV KNKGYSIKNM LEIRKLESGA (SEQ ID NO:22). The Kvp40UvsY sequence is as follows: MKLQDL-KAEY HEDVKIDTTA LETAAIRIPV LHAKWLAYRA DARQLLIKAE MKMEAVRKDR WLFYSGKHDD EVCDFIVEKS EMKYALAGDE ALQLAIARFQ HMKDV-LSFIE EALKGISQMG FTIKHIIDNR KIESGIV (SEQ ID NO:23). The PSSM2UvsY sequence is as follows: MNLD-KIQEMW ERDAVIDPDN LHDESLKIPQ LHSKYYTVYN TVTLMREKAR EQYNKTRLER HNYYTGKAPA EVYIEEPFGY KVREKDAIQR YMEADEKMSK IDLKIRYYDT TLKFLEEIIK NISNRTFQIK NAIEWNK-FQA GM (SEQ ID NO:24). The PSSM4UvsY sequence is as follows: MNLEQIQEMW KKDSVIDNDL YCEESTKIPQ LHMRYMELYT TFGLMKKERE IEMKRLIREK WLYYKGKAPS SVYKELPFDL KLTTKEEVNM FIEGD-DDVRK LQYKIEYVEQ CLNYLDGVLR QINNRNFQIK NAIDWTKFQN GL (SEQ ID NO:25).

FIG. 7 (FIG. 7-1 continued onto FIG. 7-2) shows the primary sequence alignment of diverse gp32 proteins. The T4 gp32 sequence is as follows: MFKRKSTAEL AAQMAKL-NGN KGFSSEDKGE WKLKLDNAGN GQAVIRFLPS KNDEQAPFAI LVNHGFKKNG KWYIETCSST HGDYD-SCPVC QYISKNDLYN TDNKEYSLVK RKTSYWANIL VVKDPAAPEN EGKVFKYRFG KKIWDKINAM IAVD-VEMGET PVDVTCPWEG ANFVLKVKQV SGFSNY-DESK FLNQSAIPNI DDESFQKELF EQMVDLSEMT SKDKFKSFEE LNTKFGQVMG TAVMGGAAAT AAKKADKVAD DLDAFNVDDF NTKTEDDFMS SSSGSSSSAD DTDLDDLLND L (SEQ ID NO:26). The T6 gp32 sequence is as follows: MFKRKSTAEL AAQMAK-LAGN KGGFSSEDKG EWKLKLDNAG NGQAVIRFLP SKNDEQAPFA ILVNHGFKKN GKWYIETCSS THGDYDSCPV CQYISKNDLY NTDNKEYSLV KRKTSYWANI LVVKDPAAPE NEGKVFKYRF GKKI- WDKINA MIAVDVEMGE TPVDVTCPWE GANFV-LKVKQ VSGFSNYDES KFLNQSAIPN IDDESFQKEL FEQMVDLSEM TSKDKFKSFE ELSTKFSQVM GTAAMGGAAA TAAKKADKVA DDLDAFNVDD FNT-KTEDDFM SSSSGSSSSA DDT(SEQ ID NO:27). The Rb69 gp32 sequence is as follows: MFKRKSTADL AAQMAKL-NGN KGFSSEDKGE WKLKLDASGN GQAVIRFLPA KTDDALPFAI LVNHGFKKNG KWYIETCSST HGDYD-SCPVC QYISKNDLYN TNKTEYSQLK RKTSYWANIL VVKDPQAPDN EGKVFKYRFG KKIWDKINAM IAVDTEMGET PVDVTCPWEG ANFVLKVKQV SGFS-NYDESK FLNQSAIPNI DDESFQKELF EQMVDLSEMT SKDKFKSFEE LNTKFNQVLG TAALGGAAAA AAS-VADKVAS DLDDFDKDME AFSSAKTEDD FMSSSSS-DDG DLDDLLAGL (SEQ ID NO:28). The Aeh1 gp32 sequence is as follows: MSIFKRKDPS QLQQQLAAFS AKKGFESDAT EWKLTQGKDG NGAAVIRFLP AKGD-NATTFV KLVNHGFQRN GKWYIENCSS THGDYDNCPA CQWIKEQNWD YNVEADKKAM YAS-GVTRKTA FWANILVIKD PANPDNEGKV FKFRFGK-KIM DKIQAEVDVN TDLGEEPCDV TCPFEGKNFT IKIKKVGGNN NYDDSVFGKQ SQIANIEDEA YQAQLFEQMH DIMDLIAKDK FKSMEDLTTV FNRVMGAEKR SNARAADDFE KQMEQFENTP ASK-PEKEDDD VPFNTGSAGT VDTDLDDLLN EI (SEQ ID NO:29). The Rb43 gp32 sequence is as follows: MSFFKRQDPT KLQEQVAALK GSSGFQKDEK EWKLTLDAQK NGSAVIRFLP NRSDDELAFV RIVNHS-FKKQ NQWYIENCPS THGDYDGCPV CQYITDNDLF EKAKANKGGE ADKLLGQIGR KQSFWANILV IKD-PGNPENE GKVFKFRFGK KIMDKITATI AGNPDLDEPG IAVTCPFAGA NFTLKAKKVG DWPNYDDSTF GVPG-PIKGID DEAVQKAIFE GMSDLRPITA PDQFKPTAEL TAKFTKVFGG GAAMGAGSSA GADLDSELNS FDADLKNFDN GNQSGSVKES GGVNQLNVGG SVPEDDTPFD LDNTSGDDDL DKLLDL (SEQ ID NO:30). The Kvp40 gp32 sequence is as follows: MFKRK-SPAQL QEKLEKMSSK KSFDNADEWK LTTDKLGNGS AVIRFLPAKG EDDLPFVKIF THGFKENGNW FIENCP-STID LPCPCCAANG ELWKTEIEDN QNIARKRKRT LSYWANIVVI KDDAAPENEG KVFKYRFGKK ILD-KITQAAQ ADEDLGVPGM DVTCVFDGAN FSLKAKKVSG FPNYDDSKFG PSTELYGGDE AKLKEVWDAM HDLNAIIAPS AFKSEAELQK RFLQVTGAAQ PKASAAQNLE AQLNTSAPAQ ANAP-KAAAKP AAASVDVDSE PVTDSVDDEL DALLA-DLELG DD (SEQ ID NO:31). The PSSM2 gp32 sequence is as follows: MSFAKLKKQS KLGSLTQKLV KEVEK-MNNTG GQGDDRLWKL EVDKGGNGYD VIRFLPA-PDG EDLPFVKLYS HAFQGPGGWY IENSLTTLGQ KDPVSEFNSQ LWNNGTDAGK DTARKQKRKL TYIS-NIYVVK DPANPENEGK TFLYKYGKKI FDKLTAAMQP EFEDEEAIDP FDFWQGANFK LKAKNVAGYR NYDSSEFAAT SALLDDDDAM EAIWKKEYSL AEL-VATDQFK SYDELKTRLG YVLGNKPVRN DAETVEQEVE DVRASAPVVE TVESVSRSSA TEDED-DTLSY FAKLAES (SEQ ID NO:32). The PSSM4 gp32 sequence is as follows: MSFASLKKAA SAGSTLSKLT QEIEKINQPQ QNNSADERFW KPELDKSGNG FAVIR-FLPAP EGEEMPWAKV WSHAFKGPGG QWYIENSLTT IGKDDPVGEY NRELWNSGKE SDKNIARAQK RKL-SYYSNIY VVSDPAHPEN EGKVFLYKYG KKIFD-KLVEA MQPAFADETP LDPFNFWKGA DFKLKIRKLD GYWNYDKSEF AATSTLGGFD DSKLESIWKE GYS-LTEFESA KNFKDYDALK KRLDLVLGLT IPHPTTEDES LEDLSEGKTP SSWGQEVSDF REKAVASSPV QDEEDTLSYF SRLAEED (SEQ ID NO:33).

FIG. 8 is a picture of an ethidium bromide stained agarose gel showing RPA products using T6 UvsX and T4 UvsX for amplification. Rs8179145-2 is (SEQ ID NO:34) and RS8179145-3 is (SEQ ID NO:35).

FIG. 56, is a picture of an ethidium bromide stained agarose gel showing RPA products using T6 H66S UvsX and Rb69 gp32 in the presence or absence of UvsY loading agent and in the presence or absence of PEG.

FIG. 57 is a picture of an ethidium bromide stained agarose gel showing RPA products using T6 H66S UvsX with T4 gp32 or Rb69 gp32 in the presence or absence of UvsY loading agent.

DETAILED DESCRIPTION OF THE INVENTION

Figure 1:
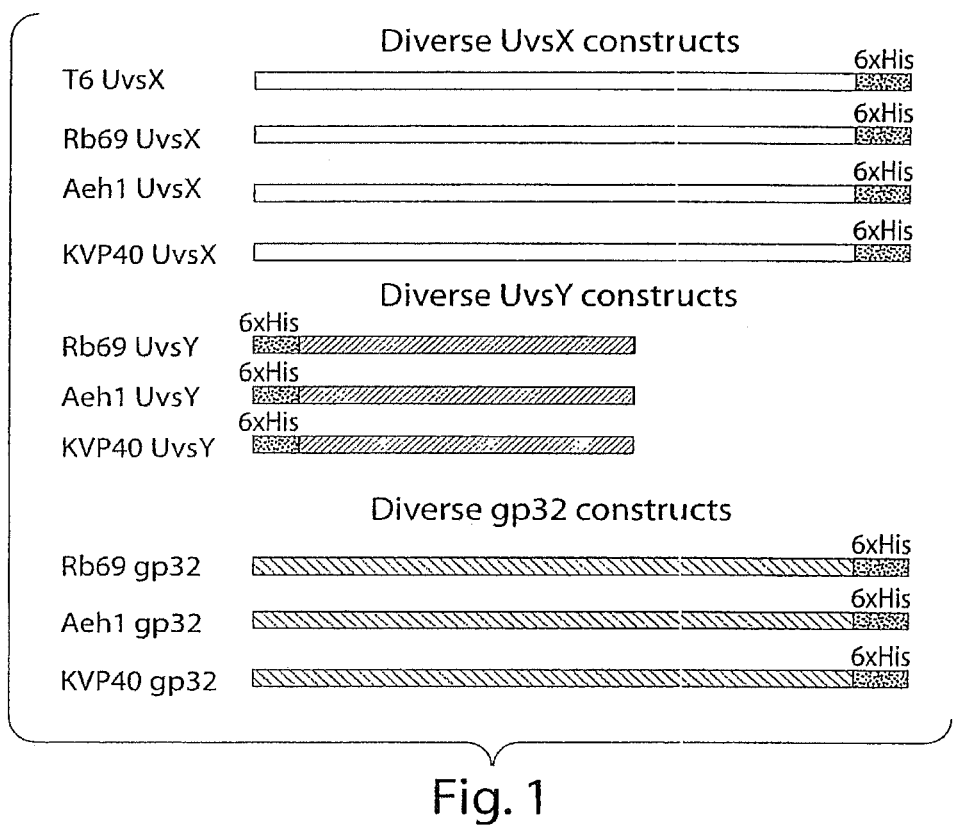
FIG. 1 shows a schematic representation of clones used to generate variant UvsX, UvsY and gp32 proteins.

This invention constitutes novel enabling data on the use of diverse, hybrid and engineered recombinase enzymes. The utility of a variety of recA/UvsX-like recombination proteins and associated recombination factors for carrying out RPA reactions is shown.

Surprisingly, it was discovered that variant recombinases (e.g., novel engineered chimeric and mutant recombinases) and their associated components display differences in kinetics, differences in optimal PEG concentrations and SSB concentrations, and differences in dependence on recombinase loading factors. Furthermore, the novel chimeric and mutant proteins of the invention have permitted the elucidation of specific peptide regions that profoundly influence these behaviours.

The origin of some of the observed variation, and location of some key amino acids residues influencing activities in RPA assays is described herein. Particularly important are a mobile DNA-binding loop, as well residues in the Walker A motif found in ATPases. Notably it was discovered that the peptide corresponding to DNA binding loop 2 in *E. coli* RecA is very important, and that this peptide is generally unrelated to *E. coli* RecA, and quite variant among RecA/UvsX-like proteins from the myoviridae. Surprisingly, it was discovered that the T6 UvsX protein, and derivatives of it, display very significant UvsY-independent activity in RPA reactions. This UvsY-independent activity may also be extended to other UvsX species under conditions which particularly favour UvsX-loading but is most obvious for T6 and its derivatives. This analysis has permitted the engineering of altered T6 and Rb69 UvsX recombinase proteins for use in RPA, and has set the stage for further optimization and the development of engineered super-recombinases for the RPA system. Surprisingly, T6-derived recombinases show only partial requirement for loading proteins, albeit loading proteins improve reaction performance and robustness. Hybrid proteins can be utilized which display altered activities in the RPA process. Systems comprising heterologous combinations of recombination components may also be effectively used.

Additional components and conditions to improve RPA reactions are also provided herein. For example, the present invention provides other crowding agents which impart similar or even greater effects than Carbowax 20M (PEG compound) on RPA reactions. The inclusion of crowding agents, in particular those having a molecular weight of at least 10,000 and less than 100,000 was found to be highly stimulatory in RPA reactions. Such crowding agents include but are not limited to polyethylene glycol, polyethylene oxide, polyvinyl alcohol, polystyrene, Ficoll, dextran, PVP, and albumin. In particular, PEG molecular weight 35,000 was found to be very effective in RPA reactions. The present invention also provides the use of heparin in RPA reactions, as an agent to reduce the level of non-specific primer noise, and the ability of *E. coli* exonuclease III or *E. Coli* exonuclease IV to rapidly polish 3' blocking groups or terminal residues from recombination intermediates. Additionally, manganese ions are shown to be able to replace Magnesium, but at much lower concentrations.

Further, the present invention provides the use alternative polymerases capable of strand displacement synthesis for use in RPA reactions, including repair class polymerases, and polymerases which lack proof-reading activity. Surprisingly, the large fragment, not the full protein, of bacterial polymerase I repair enzymes which bear homology to the Pol I class of *E. coli, Bacillus subtilis*, and *Staphylococcus aureus* were found to be effective in RPA reactions, thus extending the repertoire of polymerases shown to be effective and further supporting the view that repair class, strand-displacing, polymerases from prokaryotes (and possibly phage) are generally effective.

Brief Description of RPA

RPA is a method (process) for amplifying DNA fragments. RPA employs enzymes, known as recombinases, that are capable of pairing oligonucleotide primers with homologous sequence in duplex DNA. In this way, DNA synthesis is directed to defined points in a sample DNA. Using two gene-specific primers, an exponential amplification reaction is initiated if the target sequence is present. The reaction progresses rapidly and results in specific amplification from just a few target copies to detectable levels within as little as 20-40 minutes.

RPA reactions contain a blend of proteins and other factors that are required to support both the activity of the recombination element of the system, as well as those which support DNA synthesis from the 3' ends of olignucleotides paired to complementary substrates. The key protein component of the recombination system is the recombinase itself, which may originate from prokaryotic, viral or eukaryotic origin. Additionally, however, there is a requirement for single-stranded DNA binding proteins to stabilize nucleic acids during the various exchange transactions that are ongoing in the reaction. A polymerase with strand-displacing character is requires specifically as many substrates are still partially duplex in character. Reduction to practice has established that in order to make the reaction capable of amplifying from trace levels of nucleic acids precise in vitro conditions are required that include the use of crowding agents and loading proteins. An effective system comprising bacteriophage T4 UvsX recombinase, bacteriophage T4 UvsY loading agent, bacteriophage T4 gp32 and *Bacillus subtilis* polymerase I large fragment has been reported earlier.

Analysis of Key Residues and Engineering Novel Recombinase Proteins

In an effort to learn more about the optimal conditions and proteins for performing RPA reactions efforts to clone and produce RecA/UvsX-like proteins from the myoviridae bacteriophages which are relatives of the T4 bacteriophage were made. Additionally other key protein components were identified, which might be required for RPA reactions from each respective phage, e.g., equivalents to the gp32 protein and the UvsY protein. FIG. 1 shows a schematic representation of clones used to generate variant UvsX, UvsY and gp32 proteins. Hexahistidine tags were engineered at the N or C termini via incorporation of extra bases in oligonucleotides into PCR amplification primers used in their cloning. Templates were genomic phage DNA. T6 was obtained from the DSMZ stock centre in Germany, while Rb69, Aeh1 and KVP40 phages were obtained from the Institute Felix D'herelle in Canada.

A comparison of the biological activity of these proteins and analysis of the relationship of any biochemical differences to variation in the amino acids sequence of these proteins was made. Although none of the bacteriophage UvsX or UvsY proteins have been crystallized (or are unavailable in public databases, UvsX proteins are close relatives of bacterial RecA proteins for whom the structure is known. It has been hypothesized that RecA and UvsX originated from a common ancestor (Story et al., 1993). Although RecA and UvsX proteins share only weak homology at the primary sequence level, they show very similar geometries and pitches when assembled onto DNA and share blocks of homology comprising the potential subunit interfaces. They also share other features associated with bacterial RecA proteins such as acidic C-terminal residues likely involved in modulating DNA affinity on duplex and single-stranded DNA (Benedict and Kowalczykowski, 1988). As described herein, UvsX proteins were modeled onto the known RecA protein sequence using a standard primary protein sequence alignment as template. This allowed the effects of primary peptide sequence variation to structural position and known biological function of regions involved in DNA binding, ATP binding and hydrolysis, subunit interface, etc., to be observed.

RecA and T4 UvsX

FIGS. 2 and 3 show a primary sequence alignment of bacteriophage T4 UvsX with *E. coli* RecA, and a representative 3-D structure of a model of an active *E. coli* RecA filament. These two proteins share 23% identity and are 43% similar at the primary sequence level. Various key regions of the RecA molecule which are implicated in biological activity and relevant to the discussion here are indicated on the alignment and the structure. The regions involved in binding and hydrolysing nucleotides are found intimately associated with the face of the protein involved in contacting the DNA backbone. Note that key residues defining the so-called Walker A motif (found in all ATP-hydrolysing enzymes) are found in both proteins. The Walker A consensus is often stated as A/G XXXXGK S/T (SEQ ID NO:43), where X is any amino acid (Walker et al., 1982). The *E. coli* RecA protein Walker A motif perfectly matches this consensus, while T4 UvsX notably lacks the second glycine immediately preceding the lysine. Most phage UvsX proteins other than T4 also lack this second glycine (see FIG. 5), having a phenylalanine instead, however this is not the case for the somewhat more divergent recombinases of cyanophages SSM2 and SSM4. These latter proteins do possess the second glycine, and on the whole significantly more closely resemble RecA with regard to the Walker A sequence.

Other peptide sequences of interest for later discussions include those regions described as DNA binding loops 1 and 2 in *E. coli* RecA. These loops have been described as highly mobile, are implicated in direct contacts to DNA (Malkov and Camerini-Otero, 1995), and also as participating in the nucleotide hydrolysis process (Voloshin et al., 2000). It is thus significant to note that both the DNA binding loops (disordered in some crystal structures), and the Walker A motif are all located in close proximity to one another on a common face of the protein. One can readily imagine that the dependence of ATP interaction for DNA binding, and the concomitant stimulation of ATP hydrolysis caused by DNA binding, are intimately interdependent processes involving direct interactions between these various peptides, ATP and DNA.

A last region of interest is the very C terminus of the *E. coli* RecA and T4 UvsX proteins. In both cases there is an acidic peptide sequence. This has previously been shown to influence the DNA binding properties of *E. coli* RecA, in particular when removed promoting stronger binding to double-stranded DNA and a reduction in dependence in magnesium ions and various salt and pH conditions (Eggler et al. 2003; Lusetti et al. 2003). Notably removal of this acidic sequence may decrease the frequency with which disassembly of recombinase filaments occurs. In earlier work, it was reported that removal of this acidic sequence from either RecA or T4 UvsX altered the activity of the proteins in RPA reactions having a generally detrimental effect which may result from undesirably high DNA affinity on duplex substrates (Piepenburg et al. U.S. Ser. No. 10/931,916).

T4 vs T6 UvsX Protein

An Unexpected Number of Amino Acid Substitutions

A number of UvsX-like protein molecules are aligned in FIG. 5. The T6 UvsX protein was cloned, sequenced, and expressed in *E. coli* with a histidine tag sequence at the C terminus. A similar draft sequence of the T6 UvsX protein was discovered in a database provided at Tulane University. A surprising discovery was that quite a number of amino acid residues were variant between T4 and T6 UvsX proteins. There were 38 substitutions between the two proteins and a 2 amino acid insertion at the N-terminus. The reason that this significant level of heterology was a surprise is that T2, T4, and T6 (the so-called T-even phages) are regarded as fairly close relatives of one another. Oddly, all the substituted amino acid residues were confined to more- or -less the N-terminal half of the protein, while the C-terminal half was completely conserved. This seemed particularly odd because when UvsX relatives from more diverged myoviridae members were studied it was noted that other regions such as the last C-terminal 30-40 residues were the least conserved. It was also noted that the primary DNA sequence was fairly well-conserved in the coding sequence for the C-terminal half of the protein with few base changes even on wobble positions, while the N-terminal half showed concentrated clusters of base changes. Indeed many of the substituted amino acids required 2 base changes to achieve the amino acid substitutions observed. As described below, some of these substitutions have occurred in regions important for function of the recombinase, and it is proposed that rather than supporting a model of mutations occurring principally at silent positions, in this case many substitutions may have been selected due to conferring measurable biochemical variation to the polypeptide.

Relative Activity of T4 and T6 UvsX Proteins

Figure 9:
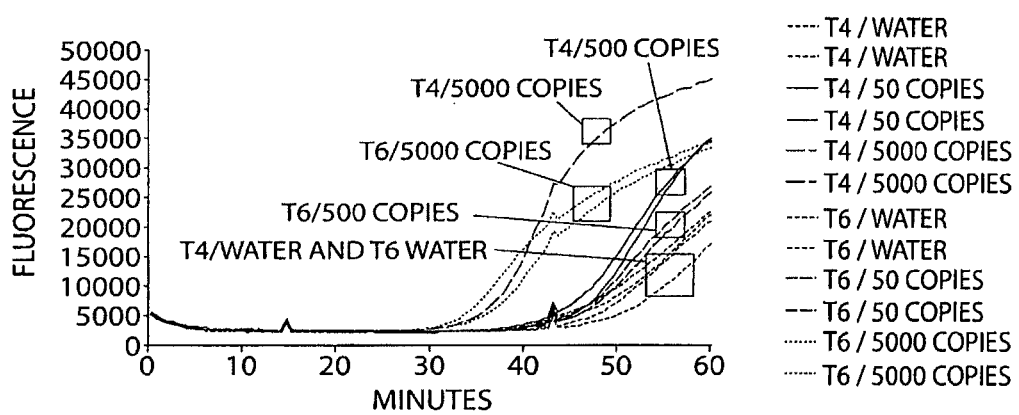
FIG. 9 is a graph showing a comparison the kinetic behaviour of T6 and T4 UvsX in an RPA reaction using SYBR green dye.
Figure 10:
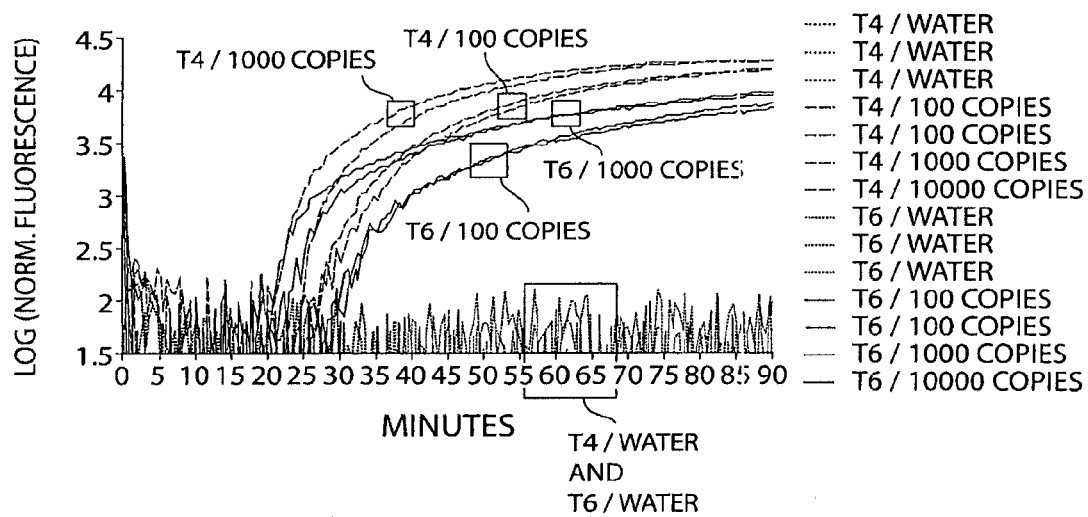
FIG. 10 is graph showing a comparison of kinetic behaviour of T6 and T4 UvsX in an RPA reaction using a fluorescent probe.

The activity of the T6 UvsX protein in DNA amplification assays was tested and monitored in real-time with a fluorescent probe or minor-groove binding dye, as well as some experiments in which products at end-point were monitored on agarose gels. In these experiments gp32 and UvsY proteins from T4 were employed. This approach was taken as the gp32 and UvsY proteins from T4 and T6 appeared very similar. T6 UvsY was sequenced and only 2 highly conservative substitutions were found (see FIG. 4). T6 gp32 had only 4 substitutions, and a single amino acid insertion. It was determined that the T6 UvsX protein was indeed active and worked effectively to amplify targets in this heterologous system. When assayed on agarose gels there was no significant consistent differences between reactions performed with T4 and T6 UvsX proteins (90 minute reactions) (small differences in final product accumulation were observed here, but were not consistent and may arise through pipetting inaccuracies) (see FIG. 8). However, when assayed in real-time using SYBR-green or with a probe-based approach, a measurable difference in reaction kinetics was observed. Reactions performed with T6 UvsX were consistently shallower in the curve of signal accumulation than those performed with T4 UvsX, although generally the time at which the signal threshold was crossed were similar (see FIGS. 9 and 10 showing comparison of T4 and T6 UvsX amplification kinetics using SYBR-green or a probe). Without intending to be bound by any theory, the reproducibility of this effect appears to have been underpinned by real biochemical differences between these 2 proteins. Note here however that one concern should be raised about the interpretation of experiments performed with a probe-based system. In order to generate strong signals in probe-based experiments, an asymmetric ratio of amplification primers were employed to encourage an excess of single-stranded DNA complementary to the probe late in the reaction. Should variant recombinases influence the ability of this single-stranded DNA to interact with the probe then it may mask signals generated in this system and lead to lower overall fluorescence. This effect could have a mechanistically different origin to a similar response caused by poorer overall amplification. In either case, however, it would reflect biochemical differences in the amplification components.

Source of Variability Between T4 and T6 UvsX

Walker A Motif

In an effort to understand a possible relationship between the differing primary amino acid sequences of T4 and T6 UvsX and the observed biochemical differences the known structural and functional information available for RecA was studied, and the information was translated to the phage proteins. Of particular interest were the regions potentially involved in DNA binding and nucleotide hydrolysis. As discussed earlier, the affinity of recombinases for ssDNA and dsDNA, and their turnover rates which are related to ATP hydrolysis rate, are factors likely to critically affect the behaviour of RPA reactions. Thus, the sequence of, and surrounding, the so-called Walker A motif (or 'P-loop') (consensus normally described as A/G XXXXGK S/T (SEQ ID NO:43)) which is highly conserved among most known (non-cyanophage) UvsX-like proteins, but is slightly eccentric in that it lacks the second glycine of the canonical Walker A motif (see FIG. 5, sequence GPSKHFKS (SEQ ID NO:44) in most proteins and APSKHFKT (SEQ ID NO:45) in Rb69), and is slightly different in T4 UvsX (GPSKSHFKS(SEQ ID NO:46))) was of particular interest. This motif is implicated in the binding and hydrolysis of ATP, possessing residues involved in co-ordinating the triphosphate backbone, and polar residues implicated in stimulating hydrolysis. T4 UvsX possesses a serine residue at position 64 which is a histidine in all other UvsX proteins except the distant cyanophage homologs (which have a P-loop more reminiscent of RecA proteins). It was noted that this novel arrangement resulted in the generation of a new lysine-serine dipeptide in the middle of the Walker A motif, a feature normally found only at the C-terminus of the motif, and hence a re-iteration. Crucially the lysine and serine (or threonine) residues of the Walker A motif are key to the co-ordination of the gamma phosphate (lysine) and hydrolysis of the phosphate-phosphate bond (serine/threonine). It was known from early studies that T4 UvsX demonstrated the unusual property that the protein hydrolysed ATP to AMP and pyrophosphate, as well as to ADP and phosphate, the more traditional reaction (Formosa and Alberts, 1986). This raised the question whether this catalytic plasticity was imparted by this central lysine-serine dipeptide which could perhaps co-ordinate the beta-phosphate and catalyse hydrolysis of the alpha-beta phosphate-phosphate bond in a manner equivalent to the more traditional reaction (analysis of the RecA protein structure suggested that these central residues might be appropriately positioned, see FIG. 3). If true then it was anticipated that non-T4 UvsX proteins would not generate AMP and pyrophosphate, and this could have significant implications on their relative behaviours in RPA reactions. For example, in T4 UvsX, this activity might increase the overall total ATP hydrolysis activity with implications for the degree of dynamicity of the recombinase in the reaction. Also, as ATP and ADP are reported to be associated with different nucleoprotein helical pitches (Ellouze et al., 1995), so AMP might promote yet a third pitch which could be significant. Thus, this variant residue might underpin some or all of the variation observed between T4 and T6 UvsX.

Figure 12:
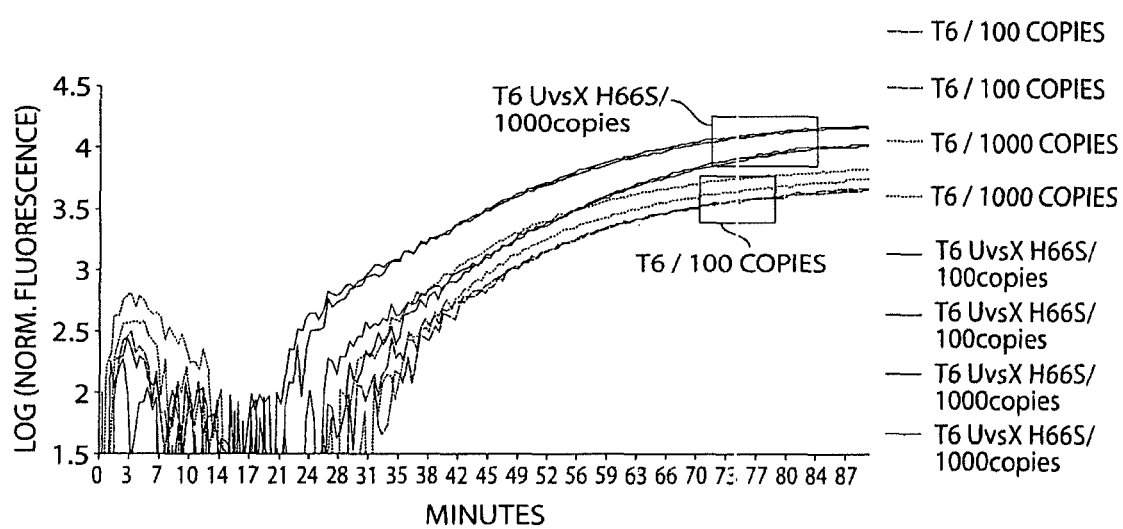
FIG. 12 a graph showing a comparison of the kinetic behaviour of T6 UvsX H66S and wild type T6 UvsX using a fluorescent probe.

Mutant T6 proteins were generated in which the histidine residue was replaced with serine at the equivalent central Walker A motif position as found in T4. This resulted in a protein which appeared improved relative to the original T6 protein sequence. In a variety of experiments involving sensing product accumulation in real-time, the slope was steeper and maximal signal generated was higher for the mutant T6 protein (FIG. 12). It was concluded that this mutation directly benefits the behaviour of RPA reactions, particularly late in the reaction. This may result from one or more of several sources; (i) The recombinase may less efficiently bind duplex DNA, thus suffering less from out-titration of recombinase by product, (ii) The recombinase may hydrolyse ATP more effectively on duplex DNA, thus recycling more efficiently from duplex DNA, (iii) the hydrolysis the generate AMP and PPi from ATP may be associated with a new nucleoprotein pitch which is useful for maintaining high dynamic activity late in the reaction. Other explanations are, of course, possible.

Residues C Terminal to Walker A Motif

Despite significant improvement in the activity of T6 UvsX once histidine 66 had been mutated to serine, the protein still seemed to remain slightly different in behaviour to the T4 UvsX. Thus, other amino acids were examined. As mentioned earlier, the 38 amino acid substitutions between T6 and T4 are clustered in the N-terminal half of the protein. Substitutions were found in several places that might be influential, namely residues directly C-terminal to the Walker A motif as well as those in the putative mobile DNA-binding loops (see more below). FIG. 5 shows that T6 has 2 amino acids directly after the Walker A motif, namely methionine 71 and serine 72, that are different to T4 in which these residues are phenylalanine and glycine. In FIG. 3, Panel B, the putative position of the T4 residues phenylalanine (F69) and glycine (G70) are indicated (assuming similar positioning in T4 UvsX as in *E. coli* RecA). Note that they are very close to the other important residues of the Walker A motif (or 'P' loop), and also to the putative mobile DNA binding loop2 whose beginning and end is indicated.

Figure 13:
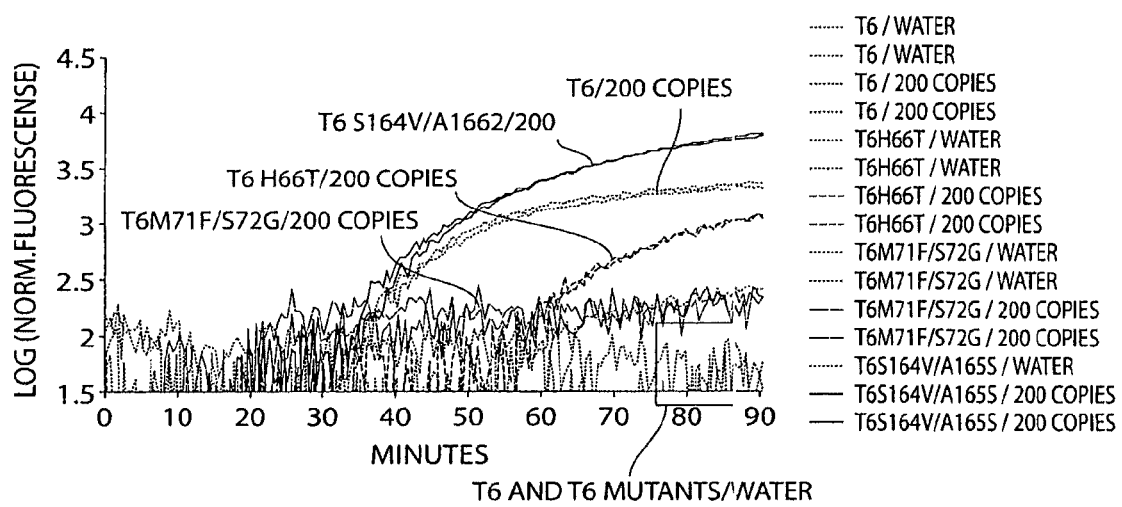
FIG. 13 is a graph showing a comparison of the kinetic behaviour various T6 UvsX mutants in an RPA reaction using a fluorescent probe.

These variant residues were mutated in T6 UvsX to generate clone T6UvsX M71F/S72G the protein was made. This protein was tested in real-time assays and was found to be totally inactive (FIG. 13). It was concluded that one or both of these residues are non-substitutable in isolation and that they must have a biochemical interaction with other substituted residues which are also altered in T6 UvsX to compensate and allow correct folding and/or activity. Further evidence that one or both of these residues confer measurable interaction with some other peptide regions is suggested by data presented later analysing Rb69 chimeras. In summary these two residues (M71 and S72), at least in isolation, are not silent substitutions between T4 and T6, nor do they in isolation appear responsible for conferring the slight difference between T4 and T6 UvsX.

DNA Binding Loop 1

Comparison of T4 and T6 peptide sequences suggested that those sequences likely comprising the equivalent of DNA binding loop 1 of *E. coli* RecA were generally very highly conserved between T4 and T6 UvsX (FIG. 5). Nonetheless, 2 residues at the end of the putative region were variant, namely serine 164 of T6 which is valine in T4, and alanine 166 of T6 which is serine in T4. These residues were both mutated together in T6 to generate the clone T6 UvsX S164V/A166S. This protein was expressed, purified, and tested it in real-time assays. The first experiment performed with this protein is shown in FIG. 13, in which it performs well, and slightly better than wild type T6. It was noted that in later experiments its behaviour seemed almost indistinguishable from wild type even in complete isolation from the whole protein (Voloshin et al., 1996). The loop has also been variously implicated in stimulating ATP hydrolysis when recombinase is bound to DNA, and even to have a catalytic role in ATP hydrolysis (Voloshin et al., 2000). It was anticipated that the equivalent sequence would be of great importance to UvsX function. Note however that this peptide is unrelated to the RecA peptide.

As illustrated in FIG. 5, T6 and T4 have 3 substitutions in the region of the putative DNA binding loop 2 region. An additional alignment of all known UvsX-like proteins in this region is shown below. Sequences have been loosely grouped by similarity. An alignment of the RecA loop is shown in this region also.

| | DNA binding loop 2 sequences | |
|---|---|---|
| T6 | NHT IETIEMFSKT VMT GG | (SEQ ID NO: 47) |
| RB3 | NHT IETIEMFSKT VMT GG | (SEQ ID NO: 48) |
| LZ2 | NHT IETIEMFSKT VMT GG | (SEQ ID NO: 49) |
| RB14 | NHT IETIEMFSKT VMT GG | (SEQ ID NO: 50) |
| RB32 | NHT IETIEMFSKT VMT GG | (SEQ ID NO: 51) |
| 133 | NHT LQTLEMFSKI VMT GG | (SEQ ID NO: 52) |
| T4 | NHT YETQEMFSKT VMG GG | (SEQ ID NO: 53) |
| AE65 | NHT YETQEYFSKT VMS GG | (SEQ ID NO: 54) |
| PHI 1 | NHT YETQEMFSKT VMS GG | (SEQ ID NO: 55) |
| RB49 | NHT YETQEMFSKT VMS GG | (SEQ ID NO: 56) |
| RB16 | CHT YDTQEMLSKS VIS GG | (SEQ ID NO: 57) |
| RB43 | CHT YDTQEMLSKS VIS GG | (SEQ ID NO: 58) |
| AEH1 | AHT YDTQEMLSKS VVS GG | (SEQ ID NO: 59) |
| KVP40 | NHT YQTQEILSKT VMS GG | (SEQ ID NO: 60) |
| NT1 | NHT YQTQEMLSKT VMS GG | (SEQ ID NO: 61) |
| PSSM2 | NHT YVIGSNVPTK EMG GG | (SEQ ID NO: 62) |
| PSSM4 | NHT YVVGANIPTK EMG GG | (SEQ ID NO: 63) |
| SPM2 | NHT YVVGSNVPTK EMG GG | (SEQ ID NO: 64) |
| RB69 | NHT AMEKGLYPKE IMG GG | (SEQ ID NO: 65) |
| JS98 | NHT AMEKGMYPKE IMG GG | (SEQ ID NO: 66) |
| RECA | QI RMKIGVMFGNPETTT GG | (SEQ ID NO: 67) |
| Required RecA | * *     * * ** | |
| Hydrolysis Involvement | o o o    o | |

T6. Consequently, within the boundaries of error of the experiments, it is suggested that these substitutions are silent between T4 and T6 polypeptides and do not contribute significantly to the assayable characteristics addressed in these experiments.

DNA Binding Loop 2

One of the most interesting peptide sequences in *E. coli* RecA is the so-called mobile DNA binding loop 2. This peptide has been shown to possess DNA binding activity, It was noted that residue isoleucine 199 and isoleucine 202 were not only different in T6 (being respectively a tyrosine and glutamine in T4 UvsX), but were T4-like in many of the loops from other UvsX relatives. This latter observation suggested that they might not be trivially substituted. Furthermore it was noted that using the best possible alignment generated with the RecA loop, isoleucine 199 corresponded to a RecA residue shown to be necessary for activity. The consequence of altering either I199 or I202 to the T4 equivalents was investigated. Mutant clones were generated and the proteins were expressed. Substitution of either I199 or I202 to their T4 equivalents completely inactivated the protein. This result was something of a surprise, but once again highlights the fact that these substitutions are not silent and have significant biological consequences. It was assumed that each of these substitutions in T6 UvsX is matched by at least one other compensating substitution elsewhere. Furthermore, all UvsX molecules with a loop length similar to T4 and T6 (see below) possess a tyrosine and glutamine like T4 at these positions apart from those in the T6 group and phage 133, and in these cases both residues are altered to either isoleucine (T6 group) or leucine (133). It was hypothesized that these particular residues have key interactions with one another and must be substituted in unison. To test this hypothesis, a double mutant T6 UvsX molecule was generated with both of these residues changed to the T4 equivalents. It was found that the double mutant protein also failed to demonstrate activity in amplification assays suggesting that other variant residues which are substituted between T4 and T6 underpin the substitution compatibility problem. This highlights the fact that a number of the substitutions between T4 and T6 UvsX proteins occur in non-silent positions and have real influence on protein biochemistry.

Amplification Systems Employing Rb69, Aeh1 and KVP40 Proteins

Clones encoding the UvsX, UvsY and Gp32 proteins of bacteriophages Rb69, Aeh1 and KVP40 were generated, as indicated in FIG. 1. Alignments of these 3 proteins are shown in FIGS. 5, 6, and 7 and include other known homologs. A possible error in the NCBI Genbank database was noted with regard to the Rb69 UvsY sequence. According to the database the Rb69 UvsY would have an N-terminal extension relative to the sequence shown here, however attempts to express this longer polypeptide were unsuccessful and lead to the re-examination of the sequence. It was noted that all other identifiable UvsY proteins begin at a near-identical point and that the database entry included a methionine at the equivalent position to the first methionine of the others. It was deduced that the automatic annotation software was erroneous. Probable errors in annotation were also identified for some of the cyanophage entries for UvsY and Gp32 which had been artificially truncated at the N terminus compared to the sequences shown in the alignments herein.

All of the proteins illustrated in FIG. 1 expressed and purified robustly with the exception of KVP40 gp32. Only relatively limited amounts of this protein were recovered despite no apparent errors in the sequence of the clone. A possible source of this biochemical oddity was speculated. Study of the alignment of gp32 molecules shown in FIG. 7 reveals that KVP40 is eccentric relative to T4, T6, Rb69, and Aeh1 gp32 molecules in the part of the primary sequence corresponding to residues implicated in co-ordinating Zinc atoms in T4 gp32. More specifically 4 residues have been implicated to be involved in binding zinc in T4 gp32, these are either histidine 64, cysteine 77, cysteine 87, and cysteine 90 (Qiu and Giedroc D. P., 1994) or Histidine 81 cysteine 77, cysteine 87, and cysteine 90 which were reported earlier (Giedroc et al., 1987). In T4, T6, Rb69, and Aeh1 gp32's these 4 residues are highly conserved with identical spacings and very high conservation of residues in general between histidine 64 and cysteine 90.

Zinc co-ordination has been shown to be critical for the cooperative behavior of T4 gp32 (Nadler et al., 1990), and the apoprotein does not support effective RPA reactions (see Piepenburg et al.). However KVP40 gp32 has significant disruption to the spacing of putative coordinating residues in the C-terminal half of this region, and little or no homology with other residues in T4, T6, RB69, and Aeh1 in this region. It was proposed that this disruption has altered the metal-binding properties of KVP40 gp32 relative to T4, T6, Rb69 etc. Without intending to be bound by any theory, it is possible that KVP40 no longer binds Zinc, or instead uses another metal atom such as Cobalt. It was noted that KVP40, a broad spectrum vibriophage, was isolated from a marine environment in which trace metal conditions may be different to those inhabited by coliphages. Without intending to be bound by any theory, perhaps an altered metal dependency and folding characteristics have influenced the efficiency of expression in *E. coli*. Furthermore it was noted that the cyanophage SSM2 and SSM4 putative protein sequences are conspicuous in the absence of any of the conserved coordinating cysteine residues. It was assumed that these gp32 molecules do not contain a zinc, or similar, metal atom. This is of some considerable interest as occasional problems in the activity of gp32 have been encountered, likely caused by co-purification of apoprotein, or by loss of zinc from the protein under poor storage conditions. Furthermore as gp32 loses the zinc atom when heat denatured, it has consequently has been of limited use in PCR or other techniques requiring a heat denaturation step. If the SSM2 and SSM4 gp32 proteins have engineered a way to have similar co-operative behavior without zinc atoms, and still have all the other properties required for RPA, then they could be very useful agents for RPA or other techniques.

RPA with Rb69 Proteins

Figure 14:
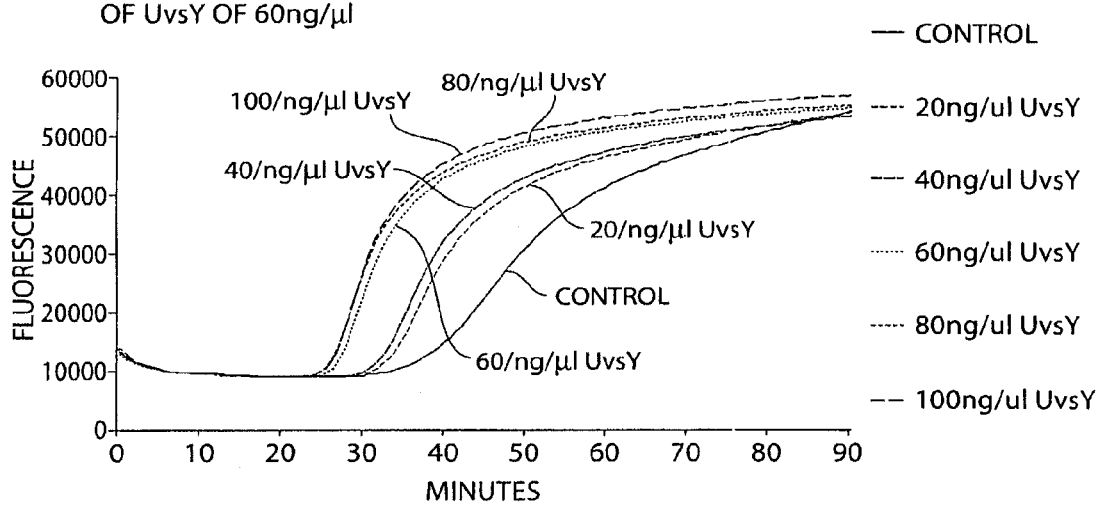
FIG. 14 is graph showing a comparison of the DNA amplification by Rb69 components in an RPA reaction. Samples were analyzed using SYBR green dye.
Figure 23:
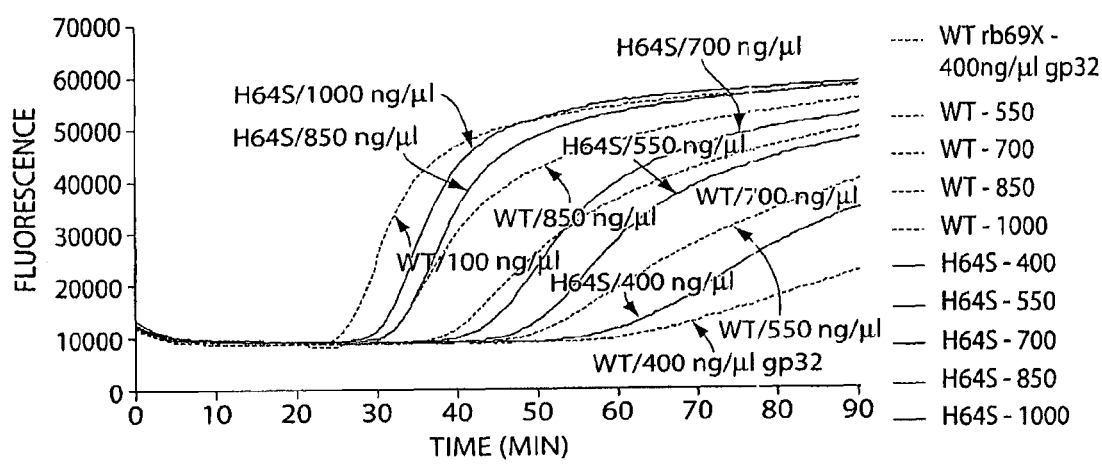
FIG. 23 is a graph showing a comparison of the effects of Rb69 gp32 titration on RPA using wildtype Rb69 UvsX or mutant Rb69 UvsX H64S. Samples were analyzed using SYBR green dye.
Figure 24:
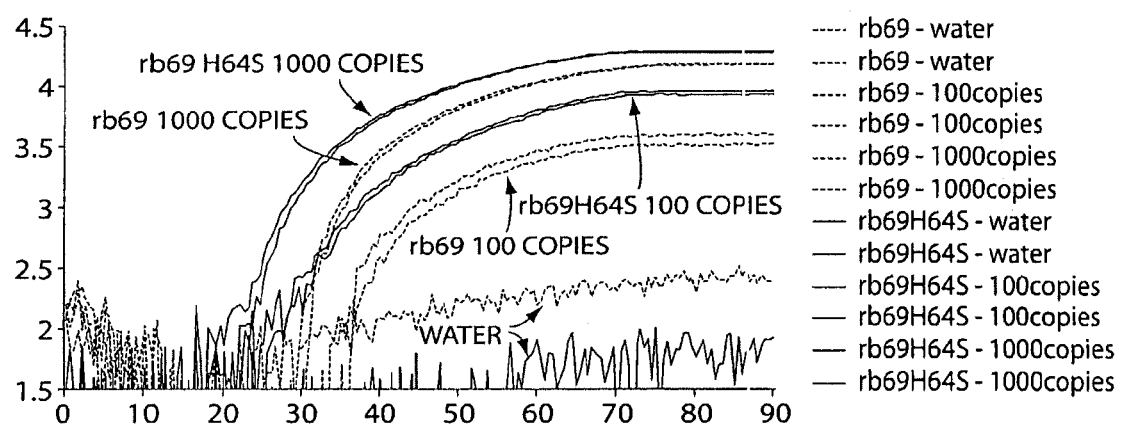
FIG. 24 is a graph showing a comparison of the kinetic behaviour of mutant Rb69 H64S UvsX protein to wildtype Rb69 UvsX in an RPA reaction. Samples were analyzed using a fluorescent probe.

RPA reactions were configured with Rb69 UvsX, Rb69 UvsY, and Rb69 gp32. Limited investigation into optimal component concentrations established that reaction behavior was notably distinct from T4 or T6 UvsX-based systems. It was found that higher quantities of UvsY were required for optimal activity. FIG. 14 shows amplifications performed with SYBR green and FIG. 24 shows reactions monitored with a fluorescent probe system. Reactions work well but have slightly slower kinetics than T4 or T6 based reactions. Oddities in the behavior of the Rb69 amplification system were noted. For example the amplification system was strangely very sensitive to overtitration of both Rb69 gp32 (see FIG. 23), and sensitive to overtitration of Rb69 UvsX (see FIGS. 26 and 27). Both these sensitivities were distinctive and different from observations made with T4 (and T6) amplification systems. Significant efforts were made to address the underlying source of these differences which are later described. However, it was noted that despite these variations, highly effective RPA reactions may be configured with Rb69 components, again confirming the generality of the RPA system and the possibility of using a wide range of recombinase agents and associated factors.

RPA with Aeh1 Proteins

Figure 15:
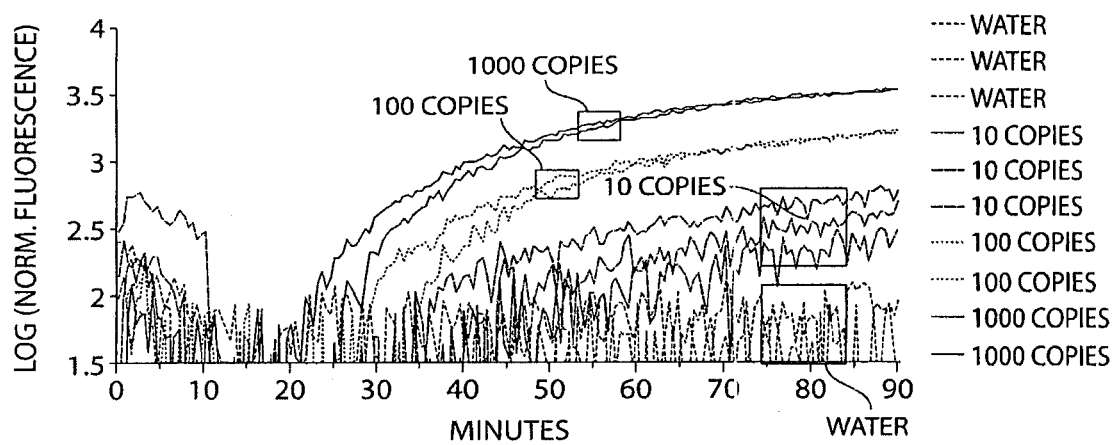
FIG. 15 is a graph showing a comparison of the DNA amplification by Aeh1 components in an RPA reaction. Samples were analyzed using a fluorescent probe.
Figure 16:
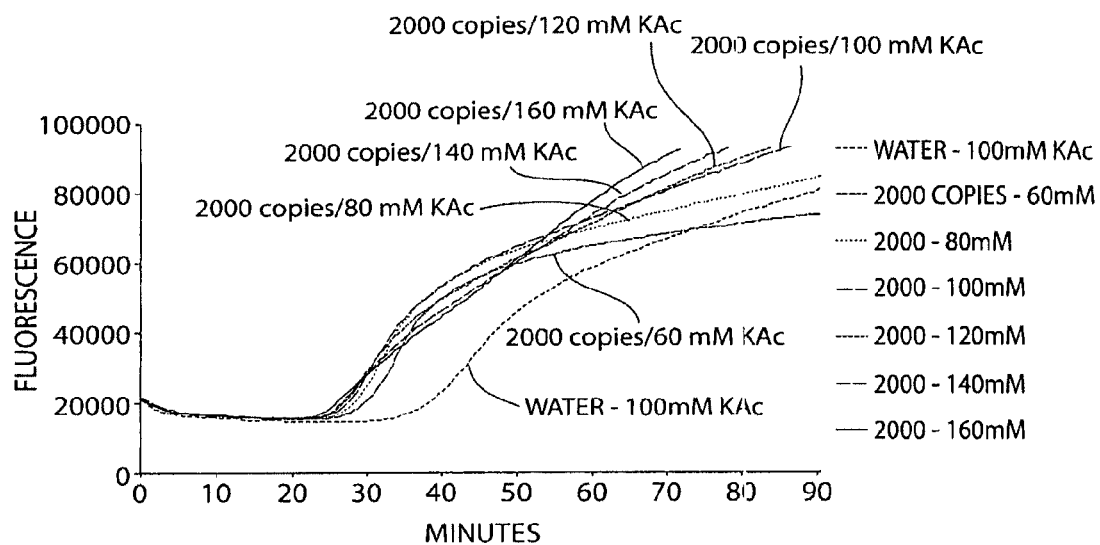
FIG. 16 is a graph showing a comparison of the DNA amplification by Aeh1 components and the effect of salt titration in an RPA reaction. Samples were analyzed using SYBR green dye.
Figure 17:
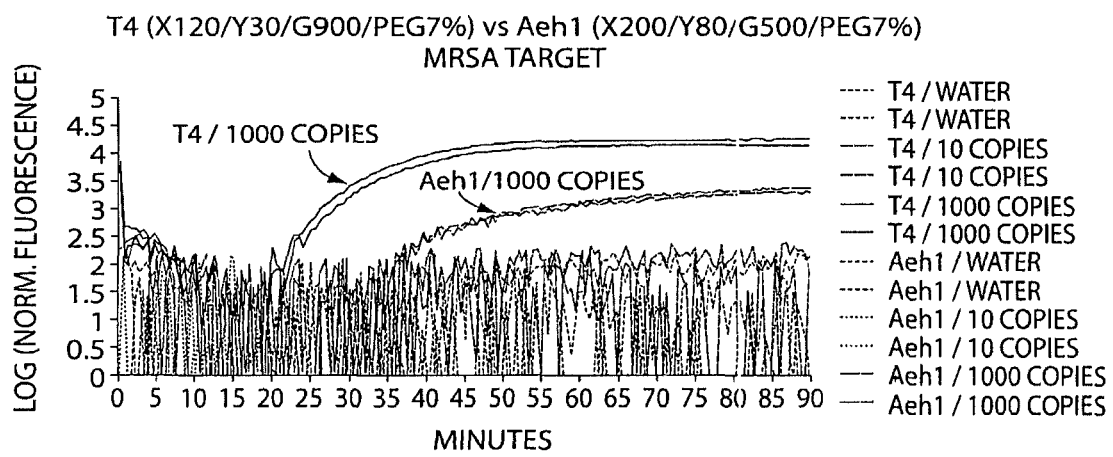
FIG. 17 is graph showing a comparison of the kinetic behaviour of the Aeh1 system to the T4 system in an RPA reaction. Samples were analyzed using a fluorescent probe.

RPA reactions were configured with Aeh1 UvsX, Aeh1 UvsY, and Aeh1 gp32 (see FIGS. 15, 16, and 17). As with the Rb69 system it was found that the Aeh1 system was clearly functional, but showed differences to the T4 and T6 based systems. There appeared to be dependency on higher quantities of polyethylene glycol, and once again kinetics tended to be somewhat slower than observed with T4 and T6.

One observation that was made using both gel-based assays (FIG. 19) and real-time assays (FIG. 18) is that an amplification system could be configured that used Rb69 gp32 in combination with Aeh1 UvsX and Aeh UvsY, albeit perhaps not as robust as when all Aeh1 components are used. This interesting result suggests that the gp32 species used may not absolutely need to match the UvsX and UvsY species.

RPA with KVP40 Proteins

KVP40 gp32 did not express robustly in E. coli under the conditions of growth and induction used. Consequently an amplification system using KVP40 components was unable to be established. Nevertheless there is some reason to believe that KVP40 UvsX and UvsY may possess basic biochemical activities required for establishing RPA reactions. In one experiment KVP40 UvsX and UvsY were combined with either gp32 from Rb69, or gp32 from Aeh1. Under these conditions there was evidence of DNA synthesis and while a product of expected size was not generated the presence of apparently amplified primer artifacts lends support to the idea that recombination-mediated polymerase priming was occurring. This suggests partial functionality of this heterologous systems, and it is proposed that KVP40 might also in principle be adapted to a useful RPA system.

Rb69 Chimeras

Figure 27:
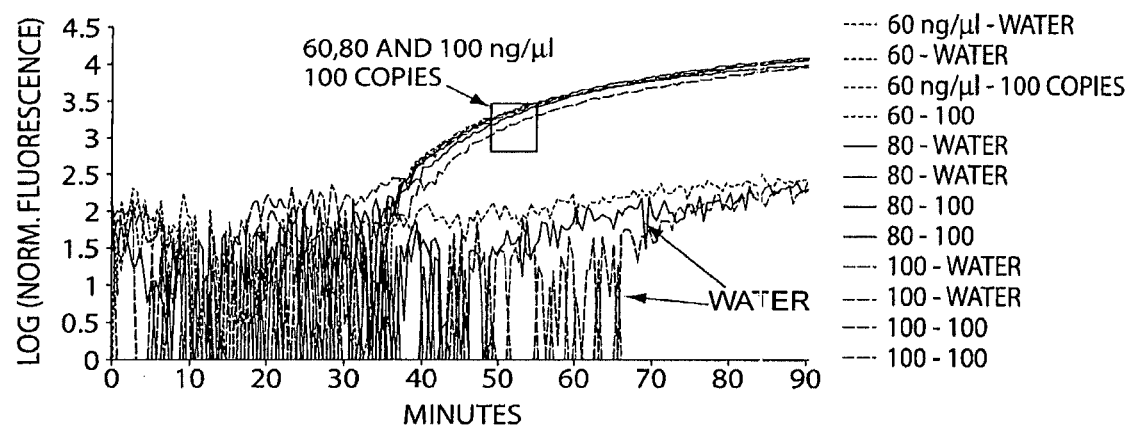
FIG. 27 is a graph showing additional titration of mutant Rb69 UvsX in RPA (60, 80 or 100 ng/µl Rb69 H64S UvsX). Samples were analyzed using a fluorescent probe.
Figure 28:
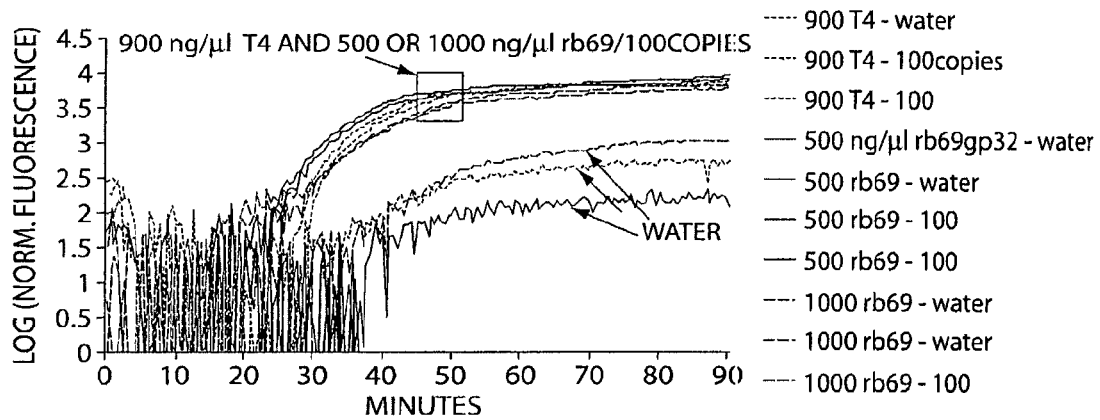
FIG. 28 is graph showing the effectiveness of Rb69 gp32 in RPA reactions with T4 UvsX and UvsY. Samples were analyzed using a fluorescent probe.
Figure 29:
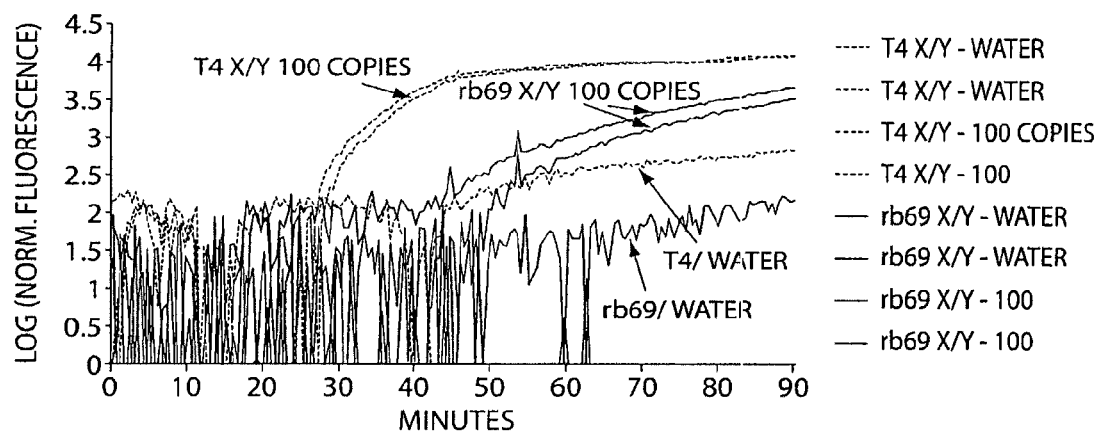
FIG. 29 is a graph showing a comparison of the kinetic behaviour of T4 and the Rb69 UvsX/UvsY system in RPA when Rb69 gp32 is used at high concentrations. Samples were analyzed using a fluorescent probe.
Figure 32:
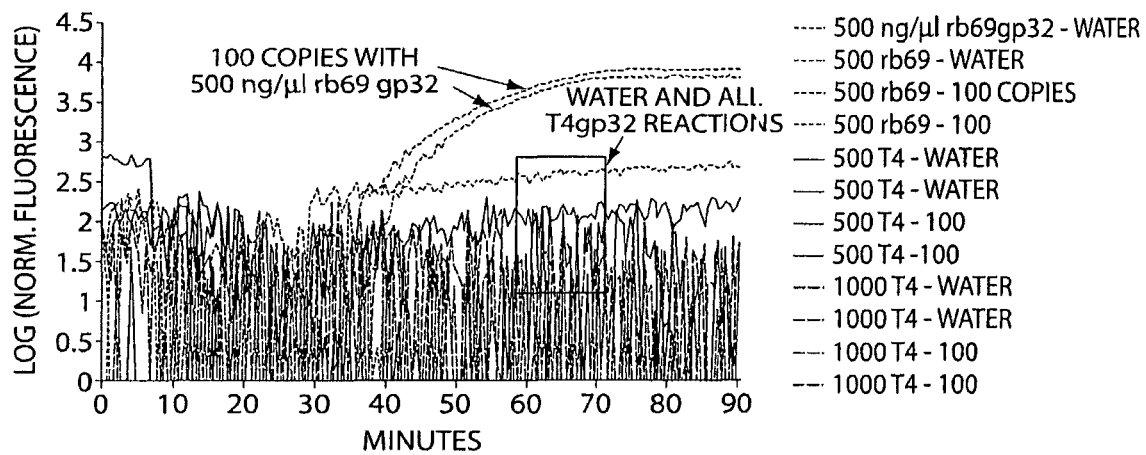
FIG. 32 is a graph showing the effect of T4 gp32 on Rb69 UvsX and UvsY in RPA. Samples were analyzed using a fluorescent probe.
Figure 37:
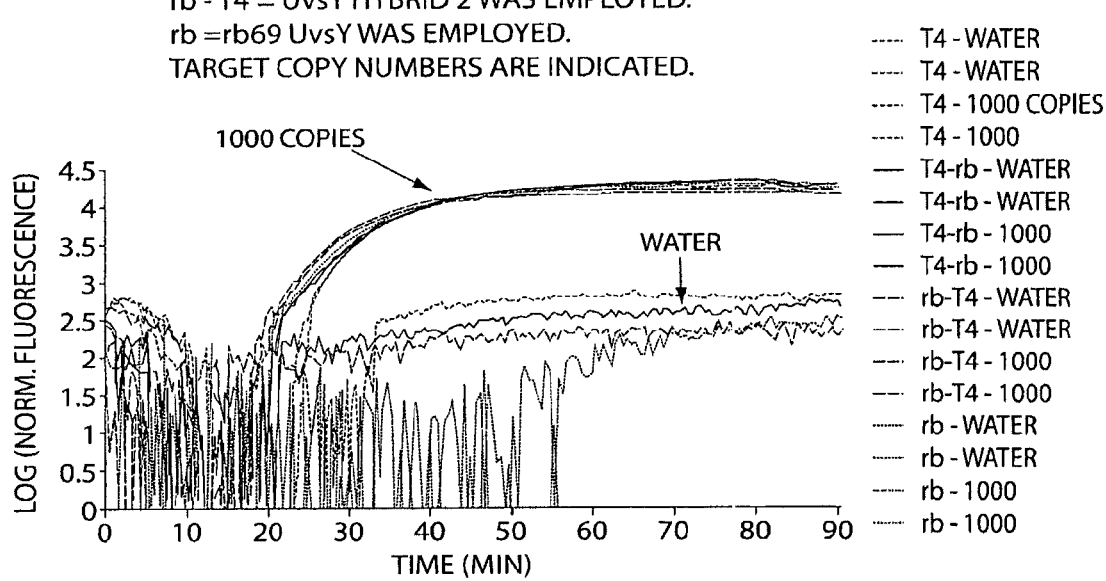
FIG. 37 is a graph showing the kinetic behaviour of novel UvsY hybrid constructs with T4 UvsX and T4 gp32 in RPA. Samples were analyzed using a fluorescent probe.
Figure 38:
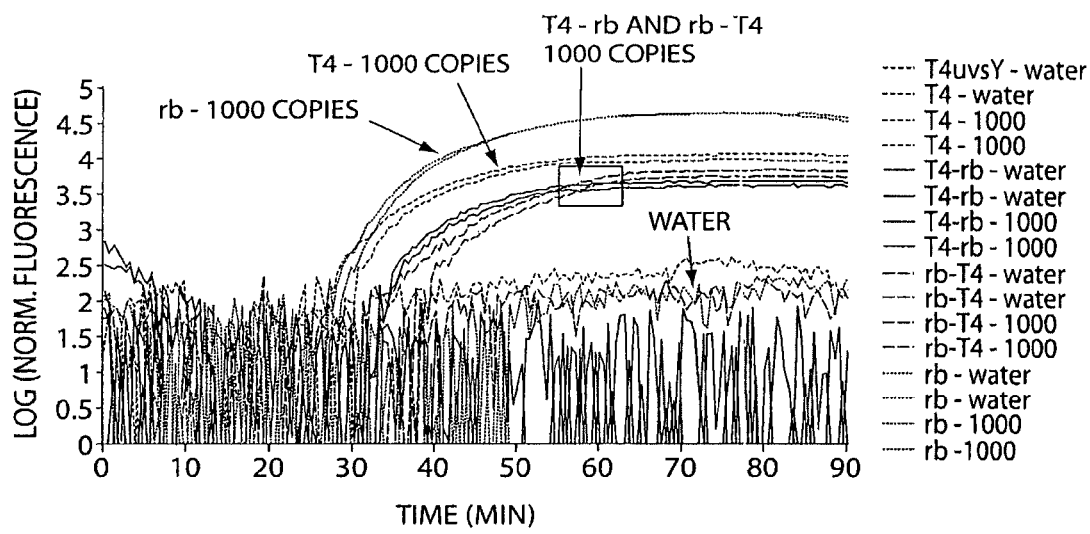
FIG. 38 is a graph showing a comparison of novel UvsY hybrid constructs with Rb69 UvsX and Rb69 UvsY in RPA.

The source of some of the most marked differences in RPA reactions using Rb69 components rather than those of T4 and T6 are addressed herein. FIG. 14 reveals one of the first oddities of the Rb69 system, namely that Rb69 seems to require more UvsY than the T4 or T6 systems. A second oddity is that the Rb69 system is very sensitive to the concentration of gp32 that is employed as revealed in FIG. 23. Such a high degree of sensitivity was not noted for the T4 system. A third oddity is that the Rb69 RPA system is very sensitive to the concentration of UvsX employed as revealed in FIGS. 26 and 27, in particular suffering if excess protein is employed. Other peculiarities were discovered in addition to these as protein in heterologous mixtures were compared with other proteins. For example it was found that Rb69 UvsX could not tolerate T4 gp32 at all, while Rb69 gp32 worked very efficiently with T4 UvsX and T4 UvsY (FIGS. 28, 29, and 32). Similarly it was found that Rb69 UvsY would readily support amplification with heterologous T4 components (FIG. 37), but when Rb69 UvsX was employed the type of UvsY used had a significant impact on the outcome of the experiment (FIG. 38). Rb69 UvsY gave the highest stimulation, while T4 UvsY or hybrids between T4 and Rb69 UvsY were markedly less effective.

A possible explanation to rationalize the above data is presented herein. Without intending to be bound by any theory, it is suggested that Rb69 UvsX is mainly responsible for the variant behavior of the Rb69 amplification system. Perhaps Rb69 UvsX has relatively poor DNA binding behavior in comparison with T4 UvsX, at least under the salt, pH, and other conditions employed by us here. As a consequence perhaps Rb69 UvsX has relative difficulty in coping with the excess quantities of gp32 present in the system, being a poor DNA-binding competitor, and, as such it is more dependant on highly effective UvsY behavior, is inhibited by excessive gp32, and sensitive to the fecundity of the gp32 and UvsY species employed which are presumably subtly different between Rb69 and T4 proteins (thus explaining why T4 UvsX is largely unaffected by the species of gp32 or UvsY used while Rb69 UvsX is affected).

This theory could account for most of the observations made about RPA reactions using RB69 components. However one aspect that is left unanswered by this is the question of why the reactions should be sensitive to overtitration of Rb69 UvsX, which on the face of it one would expect to help rather than hinder reaction kinetics. Without intending to be bound by any theory, perhaps a second factor that might be in play is that Rb69 UvsX may not support the hybridization of complementary oligonucleotides to one another. It is reported that RecA and UvsX support the hybridization of complementary oligonucleotides, a property essential to effective RPA reactions as strand displacement DNA synthesis must generate quantities of ssDNA that require conversion to duplex DNA via hybridization, not invasion, based priming. If true then the situation might be explained as follows: Rb69 UvsX has a low affinity for, or residence time on ssDNA, compared with T4/T6 UvsX which means that it competes poorly with excess gp32 (hence sensitivity to gp32 overtitration), however it also fails to support oligonucleotide hybridizations and thus encouraging overly high oligonucleotide-recombinase loading also leads to impaired amplification reactions as few primers are available for hybridization. Consequently a middle ground would have to be struck in which roughly half the primers are coated with UvsX and half are coated with gp32. That the maximal optimum RB69 UvsX concentration was found to be ~100 ng/µl, which is roughly half that required to saturate all primers in the reaction may be no coincidence.

Despite the above 'theory' there exist other reasonable explanations, and other data exists that is somewhat inconsistent with this model. For example gel analysis of Rb69 component-mediated amplifications (not shown here) reveal larger amounts of product DNA than is typically generated found with a T4-based system. Overall such reactions gave the impression of extremely high recombinase activity somewhat inconsistent with the interpretation that Rb69 UvsX has weak DNA-binding behavior. This suggests that Rb69 UvsX might show altered ssDNA/dsDNA partitioning relative to T4 or T6 UvsX, perhaps showing less inhibition by duplex DNA build-up.

Whatever the rationale for the differences in behavior of Rb69 and T4/T6 UvsX molecules, which are speculative at this time, one peptide region that is prime suspect in all of this is the putative mobile DNA binding loop2. FIG. 5 showing the alignment of UvsX proteins reveals how very unusual the Rb69 loop2 sequence is compared to its nearest homologous neighbors. Unlike T4, T6, Aeh1, KVP40, phage 133 (and all UvsX molecules apart from JS98 which is a close Rb69 relative), and the cyanophage proteins, the Rb69 loop 2 has a different number of amino acids and appears completely recoded in comparison to the others. This is most unexpected, and given the attention paid to this loop in studies of RecA, and the results described above regarding subtle alterations found in the T4 and T6 loops, it was anticipated that this variant loop sequence might underpin much of the measurable differences.

Figure 20:
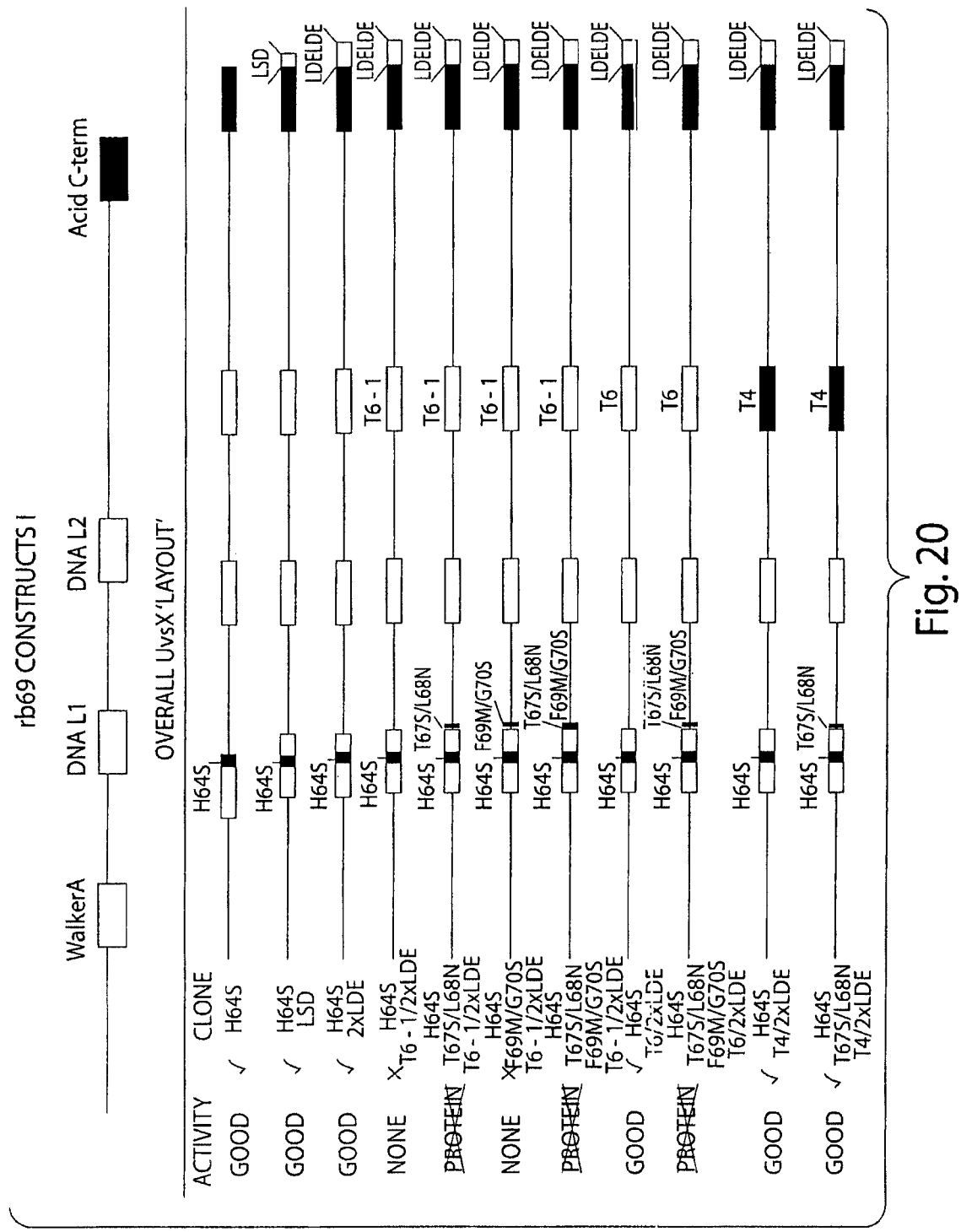
FIG. 20 is a schematic representation of novel Rb69 engineered constructs (LDELDE peptide is disclosed as SEQ ID NO: 132).
Figure 21:
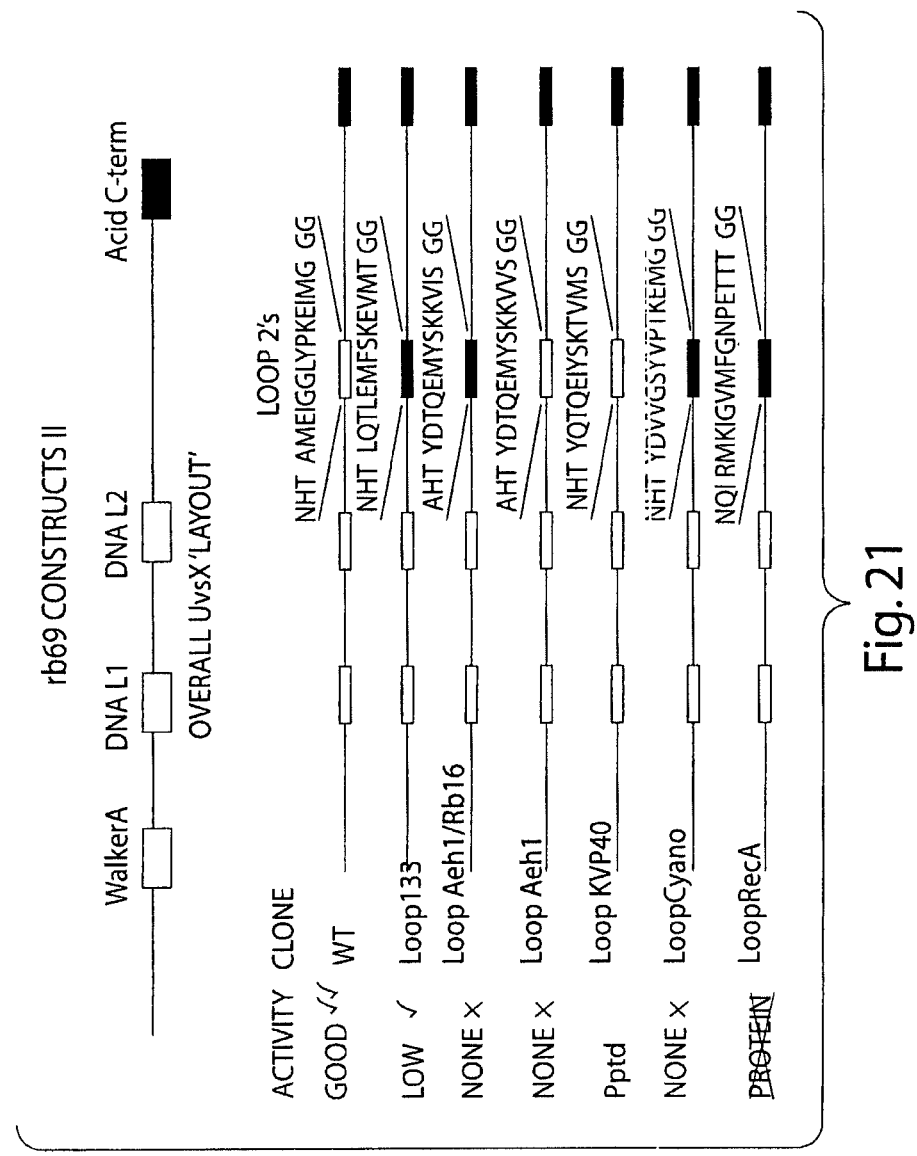
FIG. 21 is a schematic representation of additional novel Rb69 engineered constructs. The sequences, from top to bottom are SEQ ID NO:36, SEQ ID NO:37, SEQ ID NO:38, SEQ ID NO:39, SEQ ID NO:40, SEQ ID NO:41, and SEQ ID NO:42.

Other putative UvsX-like loop2 sequences and Walker A amino acids were employed and used to replace the Rb69 version. Additionally, changes to the acidic C-terminus of the protein were investigated. FIGS. 20 and 21 show schematic representations of clones that were generated in order to express mutant proteins. These experiments followed a temporal flow of investigation which means that most data was generated by successive steps of alteration of clones which were generated in an Rb69 protein backbone.

Figure 22:
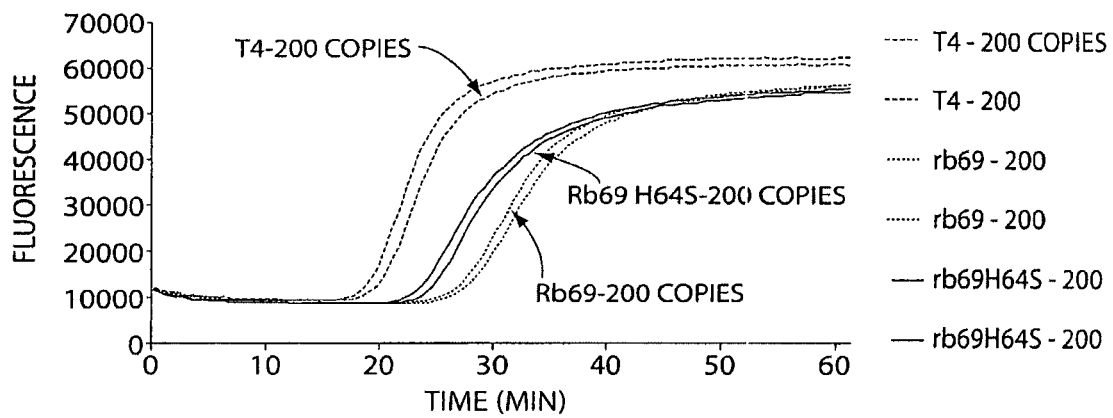
FIG. 22 is a graph showing a comparison of the kinetic behaviour of Rb69 and Rb69 H64S in an RPA reaction. Samples were analyzed using SYBR green dye.
Figure 33:
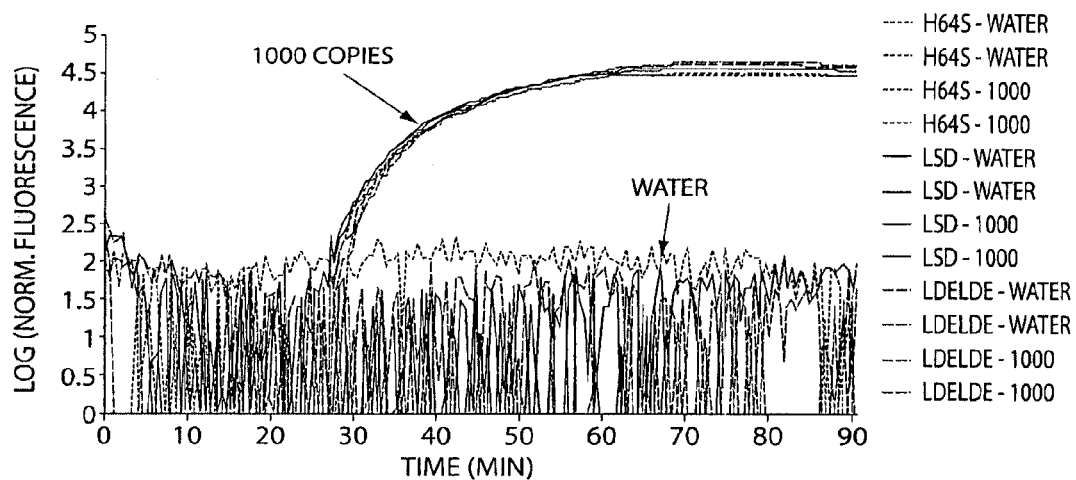
FIG. 33 is a graph showing a comparison of the kinetic behaviour of mutant Rb69 UvsX constructs having modifications to the C-terminus, in an RPA reaction. Samples were analyzed using a fluorescent probe.
Figure 34:
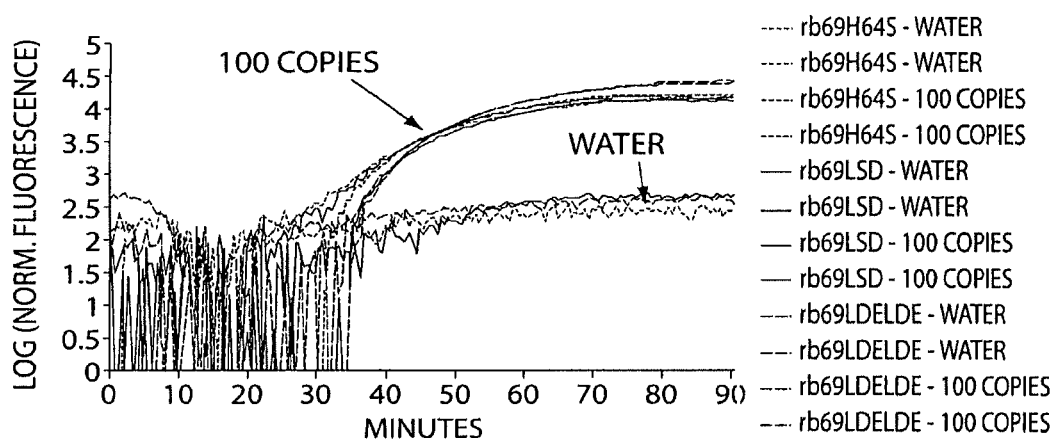
FIG. 34 is a graph showing a comparison of the kinetic behaviour of additional mutant Rb69 UvsX constructs having modifications to the C-terminus, in an RPA reaction. Samples were analyzed using a fluorescent probe.

Initially the histidine in the Walker A motif was substituted for serine as was done for T6. FIGS. 22 and 24 show experiments performed to compare Rb69 UvsX wild type with Rb69 H64S. FIGS. 22 and 24 show that Rb69 H64S performs better than the wild type equivalent. Samples were analyzed using either SYBR green or using a probe-based approach. This finding nicely mirrors the finding made with T6, and suggests that altering this histidine residue may be universally beneficial for UvsX proteins used for RPA. Second, the utility of altering the nature of the very C-terminus of the protein was investigated. It was noted (see FIG. 5) that Rb69 was very slightly shorter at the very C terminus relative to T6 and T4 UvsX. Examination of these proteins lead to the conclusion that the acidic residues found at the C terminus were loosely arranged in threes at the very protein terminus according to the rules (hydrophobic/structural)-(acidic)-(acidic). According to this model Rb69 was lacking one unit of this repeat relative to T4 and T6. It was hypothesized that the length of this acidic region would influence the RPA performance. To test this hypothesis, 2 novel clones with slightly extended the C-terminal Rb69 sequence were generated; in one case inserting the triplet of amino acids 'LSD' and in the second case inserting a tandem repeat of the triplet 'LDE' and thus 6 new residues (see FIG. 20). The proteins containing these alterations were tested in assays using a probe-based detection approach. Although not every experiment gave completely consistent results (possibly in part because different start copy numbers were used), in general a clear trend was noted. It was usually the case that the shape of the accumulation curve was slightly different between wild type Rb69. the 'LSD' mutant, and the '2xLDE' mutant. The mutants generally showed a very slightly later onset of detection, but then had a slightly sharper signal accumulation incline, and a slightly higher final total fluorescence (FIGS. 33 and 34). Although the extent of this effect was somewhat variable between different experiments performed under slightly variable conditions, it was nonetheless sufficiently clear to conclude that these alterations had significant biological effect. Without intending to be bound by any theory, these alterations may slightly reduce the affinity/stability of recombinase for certain substrates, particularly perhaps duplex DNA, and as such alter the reaction kinetics with a particular emphasis on reducing the late phase reaction slowing that is precipitated by the accumulation of product.

Figure 39:
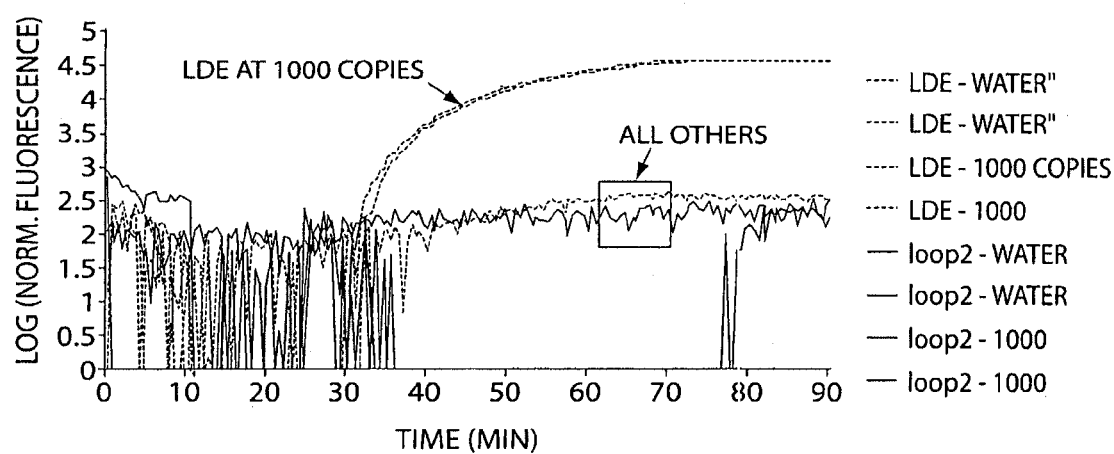
FIG. 39 is a graph showing the kinetic behaviour of mutant Rb69 UvsX H64S/T6-1 2xLDE in RPA. Samples were analyzed using a fluorescent probe.

The next steps were to investigate the DNA binding loop2 sequences which were suspected of underpinning much variation. The Rb69 loop2 sequence NHT AMEIGGLYPKE IMG GG (SEQ ID NO:68) was substituted for the T6 loop NHT IETIEMFSKT VMT GG (SEQ ID NO:69) except for the last variant threonine (bolded and underlined here) which was left as the native glycine found in Rb69. This was done because the T4 loop had a similar glycine to the Rb69 sequence, and assuming this residue was unimportant (or not strictly in the flexible loop region) it was left to avoid a more complex mutagenesis protocol. This new protein which had been generated in the backbone of the functional Rb69 H64S/2xLDE protein was tested. This protein was designated Rb69 H64S/T6-1/2xLDE in which T6-1 refers to the T6 DNA-binding loop2 lacking the last native threonine that precedes the pair of C-terminal glycines (see FIG. 20 and legend). This protein was found to have no activity in RPA assays (FIG. 39). It was speculated that this lack of activity might result from incompatibility between the DNA-binding loop and the residues in the nearby Walker motif Rb69 has an unusual Walker motif in several respects. First, it does not have a serine but rather a threonine as the main putative catalytic residue of the motif in contrast to the other non-cyanophage proteins. This threonine is followed by another atypical residue, leucine, which is also not found in other UvsX proteins. In addition to this the glycine found at the beginning of the Walker A consensus is an alanine in Rb69 UvsX unlike any other UvsX molecule (apart from the near-identical J598 protein) or even *E. coli* RecA.

In addition to the eccentric differences between Rb69 UvsX and other UvsX molecules, T6 UvsX also has eccentric residues in this region. In particular methionine 71 is not found in most other UvsX proteins except those that are near-identical to T6, or phage 133 (see FIG. 5). It was noted that phage 133 also had changes in the DNA-binding loop2 region (having leucines at the positions substituted to isoleucine in T6) which possibly represented evidence of a direct contact between these various residues. In all, the Rb69 Walker motif in its C-terminal region differs from T4 by 2 residues (compare Rb69 KTLFGL (SEQ ID NO:70) to T4 KSNFGL (SEQ ID NO:71)) and differs from T6 by 4 residues (compare Rb69 KTLFGL (SEQ ID NO:72) to KSNMSL (SEQ ID NO:73)). Changes in the Walker region in the backbone context of clone Rb69 H64 S/2xLDE/T6-1 were generated making it like T4 (KSNFGL(SEQ ID NO:74)), like T6 (KSNMSL(SEQ ID NO:75)) or with changes made that are characteristic uniquely to T6 (KTLMSL(SEQ ID NO:76)). Attempts to express some of these clones failed despite the use of multiple sequenced clones apparently containing no errors. In fact it appeared that those clones that had been made equivalent to T4 or T6 sequences (KSNFGL (SEQ ID NO:77) or KSNMSL(SEQ ID NO:78)) would not express and purify properly. It was concluded that the 'SN' motif is not tolerated when the T6-1 DNA loop is inserted to replace the Rb69 DNA-binding Loop2. This was most perplexing because this exchange is well-tolerated if the T4 DNA-binding loop 2 is used to replace Rb69, as later described. The one expressed clone (KTLMSL) (SEQ ID NO: 76) appeared to have no activity in assays when tested.

A Complete T6 DNA-Binding Loop2 Sequence Demonstrates Activity

Figure 46:
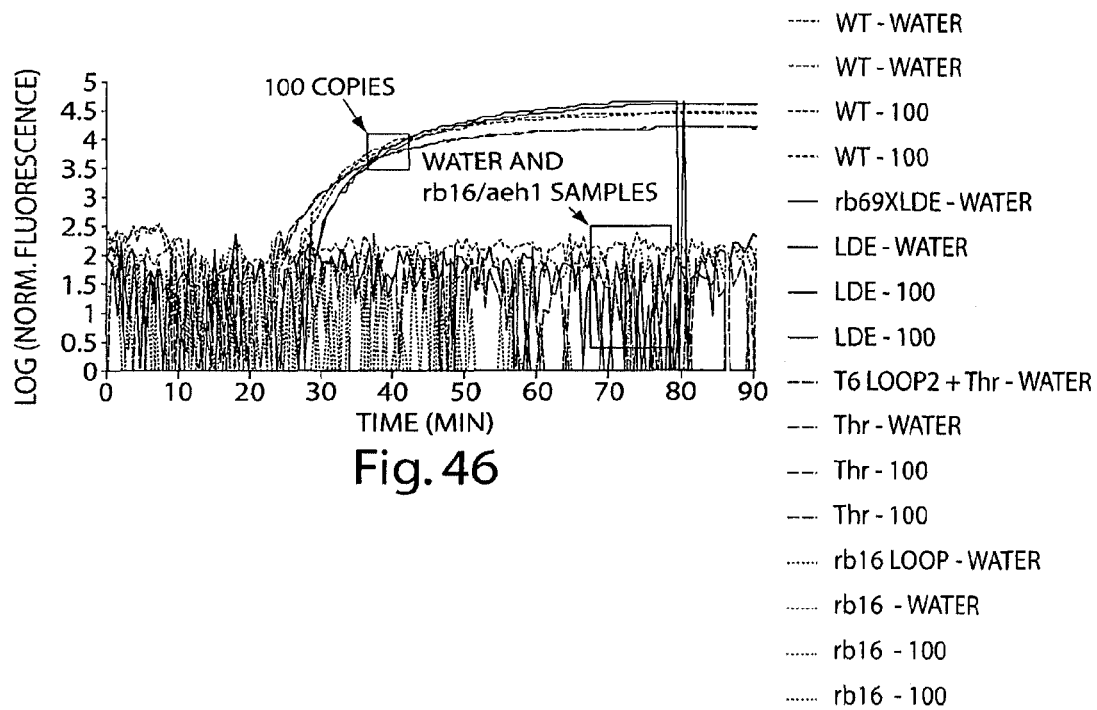
FIG. 46 is a graph showing the activity of mutant Rb69 UvsX H64S T6 2xLDE in RPA. Samples were analyzed using a fluorescent probe.

Clones were generated in which the last variant residue of the T6 DNA-binding loop 2 (NHT IETIEMFSKT VMT GG (SEQ ID NO:79)) in the chimeric Rb69-T6 constructs were restored. Clones corresponding to Rb69 H64S/2xLDE/T6-1/KSNMSL (SEQ ID NO:80) and Rb69 H64S/2xLDE/T6-1/wtRb69 Walker were generated but with the repaired threonine and thus designated Rb69 H64S/2xLDE/T6/KSNMSL (SEQ ID NO:81) and Rb69 H64S/2xLDE/T6/wtRb69 Walker. Once again, the clone with an altered Walker motif would not express and purify. Without intending to be bound by any theory, this implies close biochemical context between these Walker A residues and the variant isoleucines present in the T6 DNA-binding loop2. However, a surprising discovery was that the latter clone possessing only a repaired T6 DNA-binding loop and no alterations to the native Rb69 Walker A motif did express and proved to be functionally active (FIG. 46). Thus it appears that this last variant threonine residue is absolutely critical to the function of the T6 DNA-binding loop, at least when transferred to an Rb69 backbone. It was concluded that functional chimeric proteins may be generated, and that all of the three substitutions between T4 and T6 DNA-binding loop 2 sequences have measurable functional implications.

Rb69 Chimeras Containing T4 DNA-Binding Loop2 Sequences are Active

Further chimeric molecules containing the DNA-binding loop2 sequence of T4 UvsX were generated. In contrast to the Rb69/T6 chimeras these proteins were active regardless of whether the Walker motif was left unaltered in the native state or changed to be T4-like (KSNFGL (SEQ ID NO:82)) even though such a Walker A motif was not tolerated when the T6 DNA-binding loop was employed. Again it is stressed that this could reflect direct contacts between the 'SN' motif and the first few residues of the DNA-binding loop2. Some tendency of the protein made with a native Rb69 Walker motif to precipitate more readily from concentrated stocks was observed, which could indicate a slight incompatibility between heterologous sequences, but this was only a slight effect.

Improved Recombinase Behaviour for Rb69 Chimeras

Figure 43:
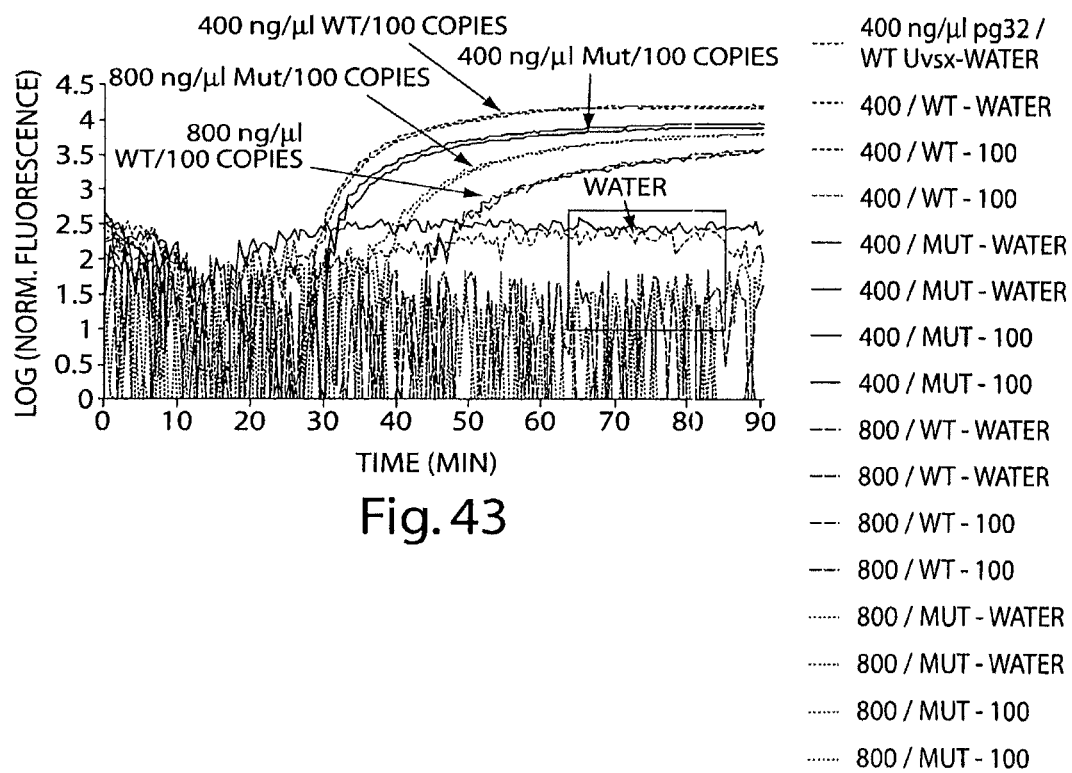
FIG. 43 is a graph showing the effect of titration of Rb69 gp32 when using mutant Rb69 UvsX H64S T67S/L68N/T4/2xLDE in RPA. Samples were analyzed using a fluorescent probe.

From the above it may be concluded that DNA-binding loop 2 sequences may be exchanged between UvsX molecules from different origins to generate functional proteins in some cases. The Rb69 chimeric molecules generated were tested to determine whether they might display different characteristics to those exhibited by native Rb69. First, the protein was assayed to determine whether more resistant to overtitration of gp32 protein. FIG. 43 shows that the delay in signal onset that is measured when mutant protein containing a T4 DNA-binding loop is used is decreased when higher quantities of gp32 are used than is the case with native Rb69. It was concluded that the engineered design contributed some of the more tolerant activity found in T4 and T6 UvsX proteins to the Rb69 chimera. Next the protein was assayed to determine whether T4 gp32 could be employed to replace Rb69 gp32, something that had not been possible with the native Rb69 protein. It was found that indeed amplification reactions could now be carried out using Rb69 protein containing the T4 DNA-binding loop (see FIG. 44).

Thus it is possible to engineer UvsX proteins with novel biochemical activities by substituting key residues, and some of these are relatively improved compared to their native parents in RPA assays.

Other DNA-Binding Loop2 Sequences

To extend this analysis further and to its logical conclusion Rb69 proteins containing all the various classes of DNA-binding loop2 sequences that were available were generated. To ease this process a 'cassette' structure to the Rb69 clones were engineered, having a unique Bal I restriction enzyme site on one side and a KpnI restriction site on the other. Synthetic oligonucleotides were cloned into Rb69 UvsX clones cut with these enzymes. The clones were generated as illustrated schematically in FIG. 21. Problems were encountered when attempting to express some of these proteins. Purified protein for the RecA-substituted loop could not be recovered, and the KVP40-substituted loop aggregated during dialysis and could not be re-solubilised effectively afterwards. Of the remaining proteins, the Aeh1, Rb16/Aeh1 and Cyanophage-substituted loops were expressed well but had no activity in the assays. The phage 133-substituted loop did possess, albeit weak, activity in the assays.

Without intending to be bound by any theory, these clones were possibly slightly at a disadvantage relative to the studies done on T4 and T6 DNA-binding loops because in this case they were engineered into a wild-type Rb69 backbone rather than one containing H64S, and a more acidic C-terminus. No engineering of other parts of the Walker A motif were made either. Nevertheless the results provide a useful diagnostic on the likely tolerance of altered sequences in this region. First, it was noted that like T4 and T6, phage 133 DNA-binding loop could confer some activity to the hybrid protein. It can be concluded that to some extent there is a general tolerance to the short 'standard' loop lengths found in most sequenced phage UvsX molecules. Second, it was noted that Aeh1 failed, but this protein has a very unexpected mutation of the asparagine that begins the loop and is otherwise very highly conserved. It is anticipated that other substitutions would be necessary in order to tolerate this change. Finally, neither the cyanophage, nor the RecA loop appeared to be tolerated. In the case of the RecA loop this is not unexpected as this loop does not even conserve the loop length, being longer in RecA. Without intending to be bound by any theory, there may be problems for this protein to fold correctly, or it may tend to aggregate. The cyanophage loop is the same length as the parent Rb69 loop, however the sequence is almost completely different. As the cyanophage proteins are very diverged from Rb69, and have radically different Walker A motifs, it is expected that changing this loop in isolation will not suffice to generate a functional molecule.

T6 UvsX and Derivatives Exhibit UvsY-Independent Activity

An experiment was performed investigating the effects of modified DNA backbones in oligonucleotides used in RPA, in particular to assess whether they influenced a need for UvsY. In the course of this work it was observed that UvsY was not essential for the amplification of DNA in experiments performed with T6 UvsX with the histidine 66 to serine mutation (T6 H66S). This unexpected phenomenon was further investigated, and the data described below confirmed that this property is substantially, although perhaps not entirely, attributable to the T6 origin of the recombinase species in the reaction.

Figure 52:
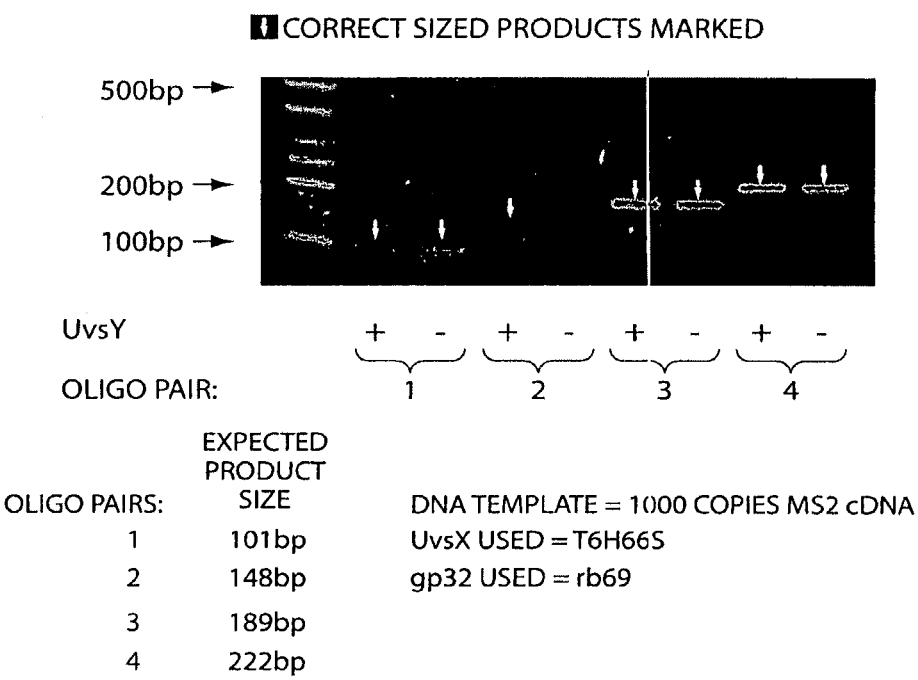
FIG. 52 is a picture of an ethidium bromide stained agarose gel showing RPA products using T6 H66S UvsX and Rb69 gp32 in the presence or absence of UvsY loading agent.
Figure 53:
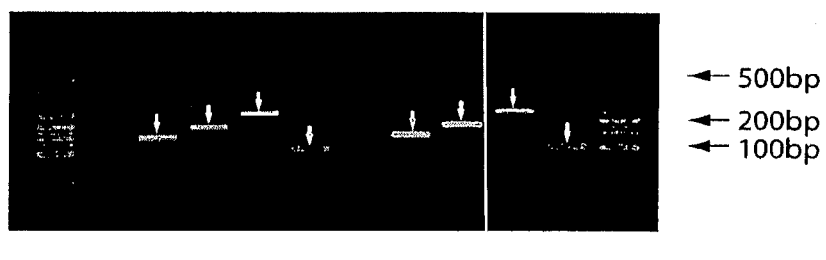
FIG. 53 is another picture of an ethidium bromide stained agarose gel showing RPA products using T6 H66S UvsX and Rb69 gp32 in the presence or absence of UvsY loading agent.

FIG. 52 illustrates an experiment performed to assess whether UvsY was required for amplification of DNA fragments from a template (generated by PCR) using a variety of primers. The experiment clearly indicated that for 3 of the 4 primer pairs used in this experiment (all combinations shared one common primer paired with an opposing primer a variable distance away in the template) products were generated in the absence of UvsY which were of the expected molecular weight. A follow-up experiment is shown in FIG. 53 in which the same template was employed, but some variable primer combinations were used (see legend). In this case 4 of the 5 combinations were successful regardless of the presence or absence of UvsY. Differences in product intensity were observed, and in some cases products were more abundant in the absence of UvsY. The results indicate UvsY is partially dispensable in at least some amplification reactions performed with this recombinase (T6 H66S), SSB (Rb69 gp32), PEG 35,000 and polymerase (Sau Pol).

Figure 54:
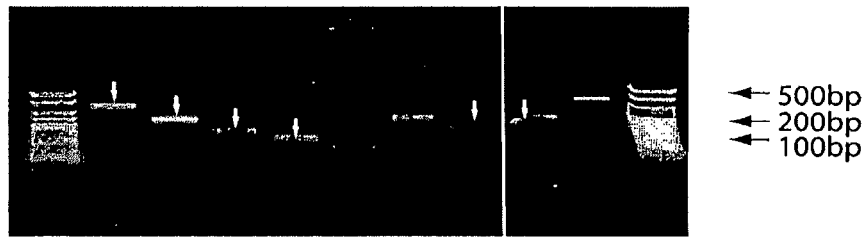
FIG. 54 is a picture of an ethidium bromide stained agarose gel showing DNA amplification of small genomic DNA targets using T6 H66S UvsX and Rb69 gp32 in the presence or absence of UvsY loading agent.

Investigations were extended to templates which were provided as complex genomic DNA. Of particular concern was that the extraordinary efficiency observed with the MS2 template might arise because this template had first been generated by PCR and might contain denatured or single-stranded templates. These situation could remove some 'constraints' placed on initiating RPA on true embedded sequences which are potentially difficult because of their tendency to from topologically strained structures during early cycles of amplification. The experiment shown in FIG. 54 depicts the amplification of DNA from human genomic DNA using pairs of primers (one common primer) which generate progressively larger fragments. In this case the results were rather more variable than observed with the MS2 template. However, at least two of the combinations generated fragments that were considered to be the expected length even when UvsY was omitted (all reactions functioned in the presence of UvsY). This work was extended in the experiment shown in FIG. 55. Once again, in some cases, DNA products of the expected sizes were generated in paired reactions even when UvsY was omitted, and once again there was significant variability on the outcome depending on the primer pairs and/or anticipated product size. It was believed that reactions 2 and 4 were successful in both cases.

Another set of experiments were performed to assess whether this remarkable and previously unnoticed activity, believed to be attributable to of T6 derivative recombinase, (and possibly associated factors used here) extended to a difference in requirement for polyethylene glycol. FIG. 56 shows that despite a partial resistance to the need for UvsY, the omission of PEG results in the absence of significant DNA synthesis. It was concluded that PEG was still required to achieve useful DNA amplification from low target concentration samples.

Figure 58:
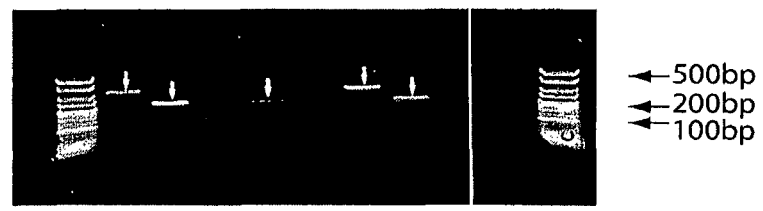
FIG. 58 is a picture of an ethidium bromide stained agarose gel showing RPA products using T6 H66S UvsX with Rb69 gp32 or Aeh1 gp32 in the presence or absence of UvsY loading agent.

Next assessed was whether the type of gp32 employed affected the UvsY-independent nature of these amplification reactions. FIG. 57 shows the results of an experiment in which T4 gp32 is employed instead of Rb69 gp32. As shown in FIG. 57, DNA was still amplified in the presence of T4 gp32, albeit with slightly different ratios of products. FIG. 58 extends this work and shows that DNA is still synthesized in a heterologous system employing Aeh1 gp32, although no products of the expected size were generated in the absence of UvsY. Note however that DNA of some description was made in the absence of UvsY which was consistent with a significant biochemical difference between these reactions and earlier reactions using all T4 reagents. In the models described herein, to synthesise/amplify any DNA visible on gels at endpoint a minimum number of loaded recombinase filaments are required, which were considered to be too few in the absence of UvsY acting as a re-loading/stabilizing agent. Thus, it was concluded that exchanging gp32 species does influence the efficacy of reactions under these conditions, but that in all cases DNA synthesis does occur even in the absence of UvsY in contrast to earlier results attained with T4 reagents. It was concluded that the T6-derivative UvsX is primarily responsible for permitting high-loading of recombinase filaments in contrast to the situation with T4 UvsX. This presumably could reflect difference in the DNA-binding domains as well as inter-subunit surfaces involved in stabilizing the co-operative filament structure.

Figure 59:
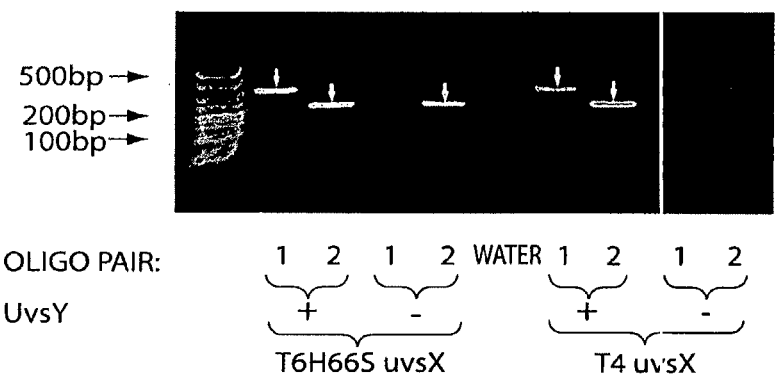
FIG. 59 is a picture of an ethidium bromide stained agarose gel showing RPA products using T6 H66S UvsX or T4 UvsX with Rb69 gp32 in the presence or absence of UvsY loading agent.
Figure 60:
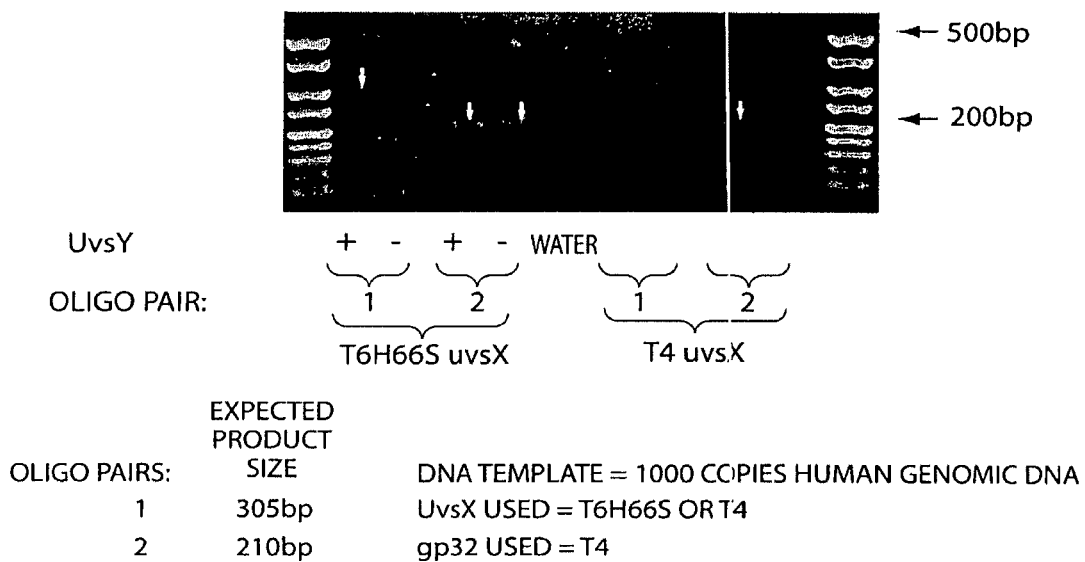
FIG. 60 is a picture of an ethidium bromide stained agarose gel showing RPA products using T6 H66S UvsX or T4 UvsX with T4 gp32 in the presence or absence of UvsY loading agent.
Figure 61:
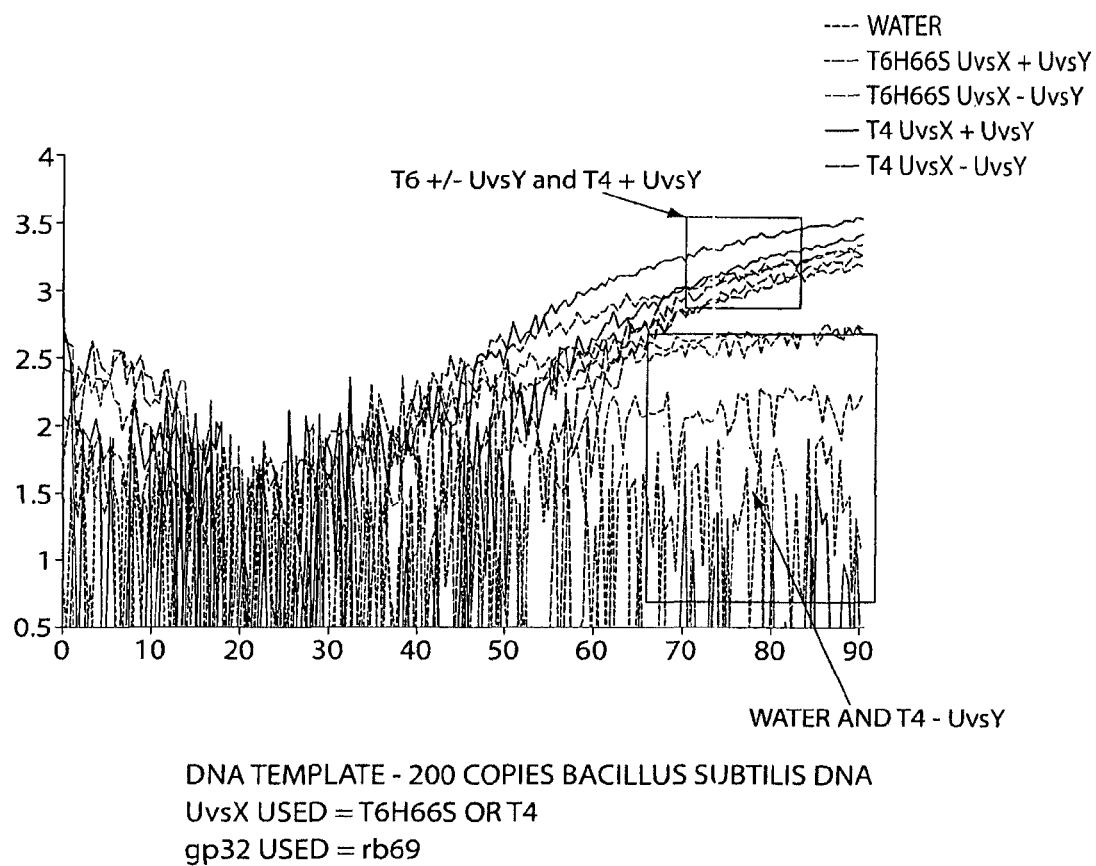
FIG. 61 is a graph showing DNA amplification using T4 UvsX or T6 H66S UvsX with Rb69 gp32, in the presence of absence of UvsY loading agent. Samples were analyzed using a fluorescent probe system.

This difference in UvsX behaviour was further confirmed in the experiment shown in FIG. 59, showing a complete absence of DNA synthesis when T4 UvsX is substituted for T6 H66S UvsX, and then UvsY is omitted. Similar results were obtained in the experiment shown in FIG. 60 in which a similar experiment is performed but using T4 gp32 throughout—T4 UvsX absolutely requires UvsY while T6 H66S does not in these experiments. A kinetic experiment is shown in FIG. 61. As shown in FIG. 61, detection kinetics are moderately similar between T4 and T6 H66S experiments. However when UvsY is omitted there is little consequence for the T6 H66S amplification kinetics, while the T4 recombinase shows no activity. In other experiments with other templates, an obligate need for UvsY even when using T6 H66S, was noted. Thus it was concluded that UvsY is only partially dispensable when using this recombinase, and it can still improve reaction behaviour and play a role in robust and consistent RPA behaviour between targets.

Figure 62:
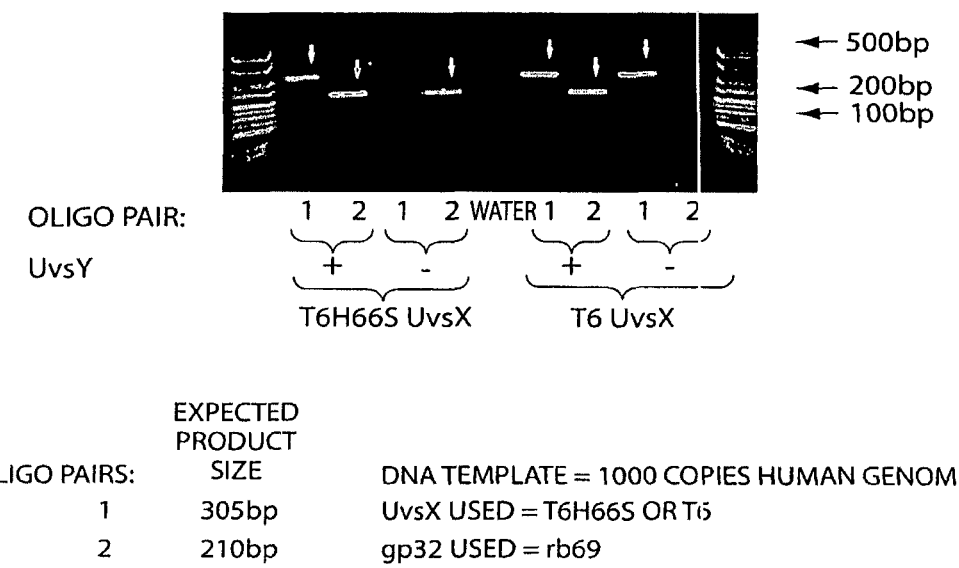
FIG. 62 is a picture of an ethidium bromide stained agarose gel showing RPA products using T6 UvsX or T6 H66S UvsX with Rb69 gp32 in the presence of absence of UvsY loading agent.

Next, investigations into whether this unusual property was observed with unmodified T6 UvsX, and whether it extended to other recombinases (such as Rb69 UvsX and Aeh1 UvsX) were performed. FIG. 62 shows very clearly that DNA is efficiently synthesized with at least one oligonucleotide combination when T6 recombinase is employed in the absence of UvsY. It was concluded that the unusual property of UvsY-independence not observed with T4 UvsX extends to the unmodified T6 UvsX, albeit there were differences in product accumulation levels between T6 UvsX and T6 H66S UvsX confirming their biochemical distinction.

Figure 63:
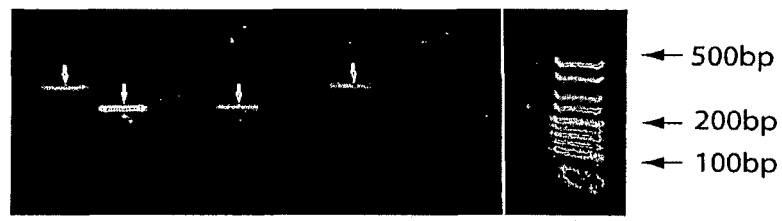
FIG. 63 is a picture of an ethidium bromide stained agarose gel showing RPA products using T6 H66S UvsX or Rb69 UvsX with Rb69 gp32 in the presence of absence of UvsY loading agent.
Figure 64:
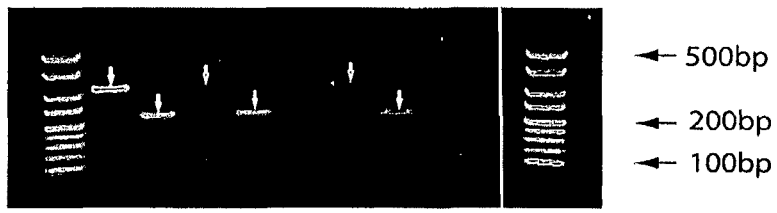
FIG. 64 is a picture of an ethidium bromide stained agarose gel showing RPA products using Rb69 UvsX or Aeh1 UvsX with Rb69 gp32 in the presence or absence of UvsY loading agent.

FIG. 63 shows that results of an experiment to determine whether Rb69 UvsX could operate in the absence of UvsY. While caution is advised on interpretation of the results because one of the amplicons did not amplify even with UvsY, the principle observation was the lack of DNA generated when UvsY was omitted. Without intending to be bound by any theory, this implies that, like T4 UvsX, Rb69 UvsX cannot readily support efficient amplification without the presence of UvsY. FIG. 64 extends this analysis to the employment of phage Aeh1 components. As shown in FIG. 64, amplification is efficient in a heterologous system comprising Aeh1 UvsX, Aeh1 UvsY and Rb69 gp32, however if Aeh1 UvsY is omitted no amplification is seen. Next, the activity of a modified Rb69 UvsX containing, amongst other things, the DNA binding loop2 sequence of T6, was assessed. This experiment was performed to assess whether the activity of T6 derivatives might arise from the distinct T6 DNA binding loop2 sequence. In this case, no amplification in the absence of UvsY was observed, although caution is advised as amplification seemed rather weak in the presence of UvsY. However, taken at face value, this result does not support that the T6 DNA binding loop 2 is wholly responsible for the unusual behavior of T6 UvsX and its derivatives, or that this property cannot be trivially transferred in isolation.

These results collectively show that T6 UvsX and its derivatives are unusual insofar as when co-incubated in the presence of gp32 species of various types (T4, Rb69 and Aeh1) it is capable of supporting significant recombination activity without a need for UvsY. Without intending to be bound by any theory, existing models suggest that a limiting component of recombinase-driven amplification systems is the concentration of recombinase-loaded filaments. These are not considered to be abundant when T4 UvsX is co-incubated in the presence of T4 gp32, and in the absence of UvsY and crowding agents. However the evidence suggests that for T6 UvsX this competitive environment is perhaps shifted in the favor of recombinase, so much so that UvsY can be dispensed with in some cases. For this to occur, it could be inferred that T6 UvsX may have a higher affinity for single-stranded DNA than T4 UvsX, and/or that it is less likely to disassemble from filaments as a consequence of active ATP hydrolysis. In turn these properties could arise due to higher affinity of the DNA binding elements of the recombinase for nucleic acids, and/or via higher affinity between protein subunits in the filaments leading to a reduction in disassembly behaviour. However, it is noteworthy that reactions appeared more robust on the whole when UvsY was included. Occasionally, in its absence, DNA was synthesized but products of the expected size did not accumulate. This outcome could reflect an abundance of active filaments but some other fundamental flaw in the RPA reaction cycle.

Without intending to be bound by any theory, two possible mechanisms to explain why UvsY enhances RPA functionality even when it is not strictly required for some amplification activity are proposed herein. First, UvsY could confer full and even loading of filaments on oligonucleotides ensuring that they are coated to their 5' ends, and undergo efficient recombination along their length. In the absence of UvsY, according to this rationale, filaments may only be partially loaded and this could lead to a situation in which recombination leads to constrained intermediates (no free unwinding possible at the substrate 5' ends) most of the time which are unstable and lead to disassembly of recombinase/synthesis intermediates before complete synthesis along a target has occurred. This could favor very short products such as primer dimers that require little processive DNA synthesis. A second alternative is that UvsY plays an active role in the DNA synthesis process as it is ongoing. For example, UvsY could promote recombinase-loading of the outgoing strand and re-invasion to cause a 'bubble migration' activity. Such bubble migration synthesis could act to decrease topological strain on the synthetic complex. Similarly, the processivity of elongation complex might rely on accessing the 3' end of DNA which is still partly coated with UvsX, and this might require UvsY presence. In any case, the data support the notion that UvsY may play a role in the RPA process that is more sophisticated than simply increasing the steady state number of recombinationally active filaments in the reaction environment.

Furthermore the use of different gp32 species may influence the UvsY-dependence of RPA reactions. Experimental data provided here, including competition oligonucleotide competition data and thermal stability data presented below, suggest that T4 gp32 may have a particularly high affinity for DNA when compared to Rb69 gp32 and Aeh1 gp32. Thus, according to a model in which UvsX and gp32 compete for common substrates as described earlier, it may be beneficial for the recombinase if a gp32 with a lower DNA affinity is employed. Thus Rb69 gp32 is likely to favor recombinase-loading in such a competitive environment.

Manganese can Support RPA Reactions

Figure 47:
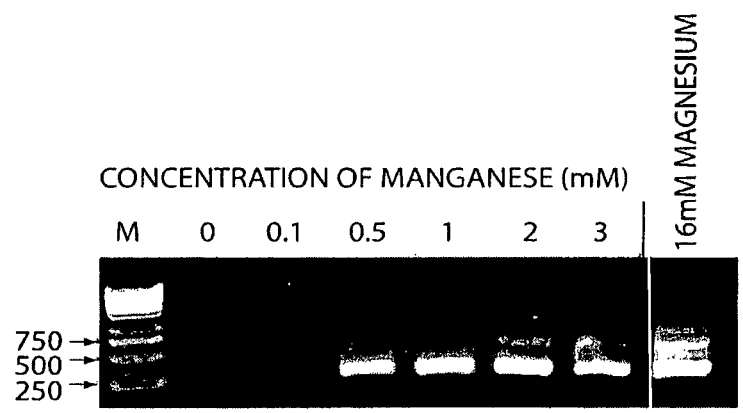
FIG. 47 is a picture of an ethidium bromide stained gel showing amplified DNA products from RPA reactions using 0.1 mM, 0.5 mM, 1 mM, 2 mM, 3 mM manganese.

Manganese can replace magnesium ions to support DNA amplification by the RPA system. In particular the useful range of manganese ions for supporting robust amplification is significantly lower than that found for magnesium. The most effective amplification occurs when manganese is present at roughly 1 to 3 mM (FIG. 47). Higher concentrations are progressively inhibitory to significant product accumulation. These low levels of supporting ion are something of a surprise as in some cases this is an insufficient quantity to saturate the abundant ATP and dNTP species in the reaction (ATP is used at 3 mM).

Heparin can Act as a Noise-Suppressing Reagent

Figure 49:
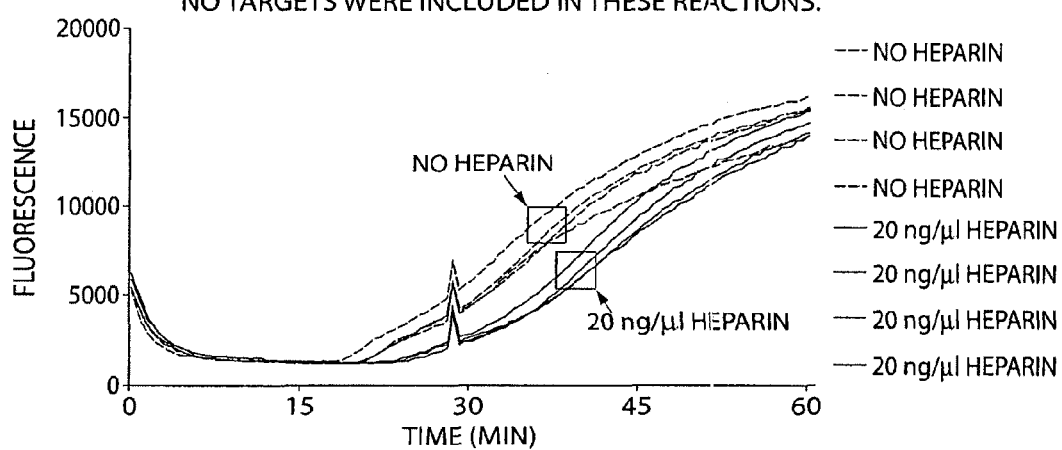
FIG. 49 is graph showing heparin the onset of noise detection using water as a control in RPA reactions. Samples were analyzed using SYBR green dye.
Figure 50:
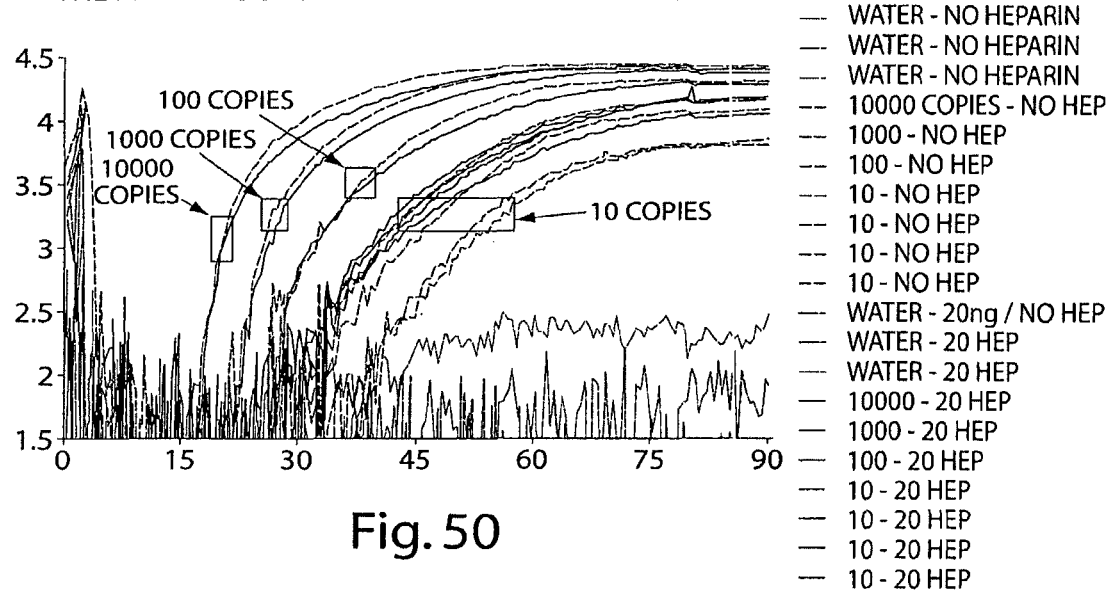
FIG. 50 is a graph showing improved resolution of low copy target numbers by the use of Heparin in RPA reactions. Samples were analyzed using a fluorescent probe.

The effects of heparin on RPA reactions were investigated. This was in part in an effort to establish the resistance of RPA reactions to agents commonly found in clinical and environmental samples. It was surprising to discover that RPA was rather resistant to the inclusion of heparin in the amplification reactions. Indeed it even appeared that heparin could improve the outcome of RPA reactions, apparently by reducing the rate at which primer artefacts accumulate in RPA reactions. FIG. 49 reveals how the inclusion of heparin at 20 ng/μl results in a delay in the accumulation of primer artefacts which appear if RPA is permitted to run without a target present in the reaction. Using a probe-based sensing approach, inclusion of heparin in RPA was tested to determine whether it would improve the behaviour of RPA reactions. FIG. 50 explores the effects of including heparin in amplification reactions. The following phenomena are observed: the time of onset of signal detection are similar regardless of the presence of heparin, however when present heparin leads to more consistent time of onset of detection at low copy numbers. Heparin slightly decreases the total signal which develops in the reaction. It was concluded that probably heparin acts as a 'sink' for UvsX or other DNA binding proteins and can help to buffer it from excessive activity which may benefit noise rather than signal under certain circumstances.

E. coli Exonuclease III can Function as a Primer Polishing Agent in RPA

E. coli endonuclease IV (Nfo) or E. coli exonuclease III were included in RPA reactions that include proprietary fluorescent probe sensing system (Piepenburg et al., 2006) as an agent to process abasic-site containing probes. However during investigations into novel probe structures some surprising and unexpected observations were made, namely that supposedly 3'-blocked primers could be efficient amplification primers when used in reactions containing exonuclease III, and perhaps to a lesser extent if containing endonuclease IV (Nfo) (see FIG. 51). It was hypothesized that blocked primers employed in these cases were being unblocked by the activity of the enzymes. Both of these enzymes have reported activities which include 3'-exonuclease activity as well as having 3'-diesterase or phosphatase activities. Without intending to be bound by any theory, it is likely they either 'polish' the blocking group from the final base, or remove the final base with the blocking group on it. It is not possible to distinguish between these possibilities from these experiments. However the potential ability to 'unblock' primers in a sequence-dependent manner has certain potentially useful applications.

S. aureus Pol I Large Fragment is Functional in RPA Reactions

Figure 48:
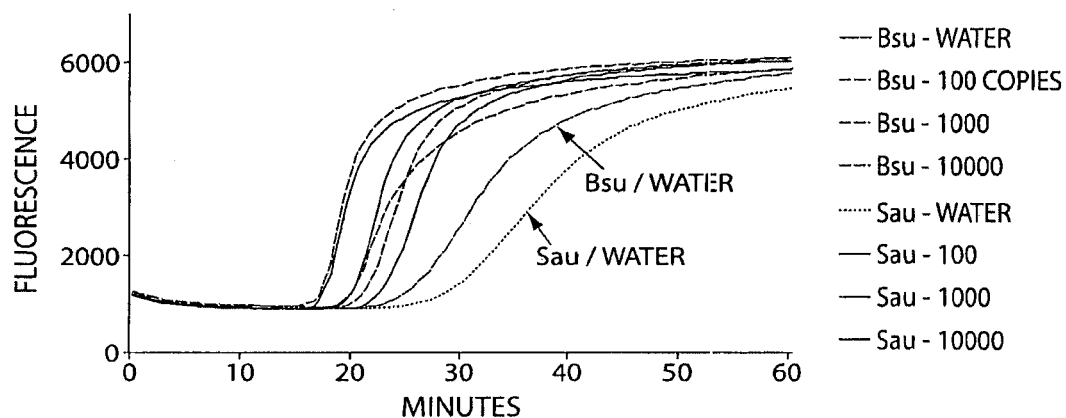
FIG. 48 is a graph showing DNA amplification using S. Aureus Pol I in RPA. Samples were analyzed using SYBR green dye.

RPA works efficiently with Bsu polymerase as previously shown (See Piepenburg et al. U.S. Ser. No. 10/931,916). It has also been shown to function with the Klenow fragment of E. coli Pol I, and with Bst polymerase. Other polymerases were examined in attempts to extend the breadth of polymerases that may be used in RPA reactions. The polymerases examined included repair class polymerases, and polymerases which lack proof-reading activity. The large fragment of such polymerases, as opposed to the full protein, were also examined. A sequence corresponding to the S. aureus Pol I was identified in the Genbank entry locus BX571857 which is the genome sequence of methicillin-sensitive S. aureus strain MSSA476. The complete polymerase coding sequence corresponds to the complement to positions 1740769 to 1743399 of the genomic sequence and the putative encoded polypeptide has the TrEMBL accession number Q6G8N6. A fragment of this coding region was amplified from MSSA476 genomic DNA corresponding to position 865 to 2631 of the coding region, thus omitting the first 288 amino acid residues which correspond principally to the 5'-3' exonuclease domain. This fragment was cloned into pET21+ and included a hexahistidine-encoding tag incorporated into the PCR primers at the 5' end. This protein expressed efficiently and was readily purified on Ni-NTA agarose. This protein was tested in RPA reactions as shown in FIG. 48. It was observed that the S. aureus enzyme (referred to as Sau polymerase) works very well and seems at least as efficient as the Bsu polymerase.

gp32 Activity

Figure 66:
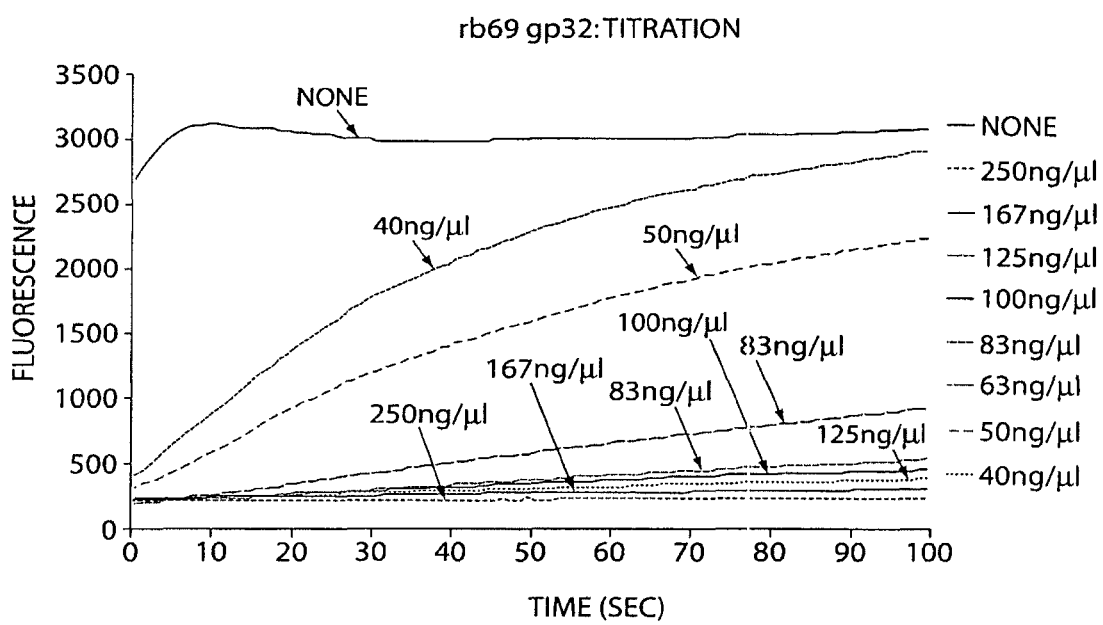
FIG. 66 is graph showing the results of the effects of titrating Rb69 gp32 in an assay designed to detect gp32 activity. Samples were analyzed using a fluorescent probe.

As demonstrated below, novel activity assays for gp32 proteins demonstrate their distinct biochemical activities. gp32 proteins were derived from several different bacteriophages. In one experiment, gp32 activity was assessed by establishing a reaction environment in which the mass of gp32 contained in the reaction was titrated until it was just limiting in activity as assessed by a nuclease-protection assay. FIG. 66 illustrates such assay, which was performed to determine the quantity (mass) of Rb69 gp32 required to inhibit the cutting of a reporter probe oligonucleotide by the endonuclease IV (Nfo) of E. coli. In this assay, cutting was monitored by rising fluorescence which occurs as a consequence of nucleolytic attack on a tetrahydrofuran (abasic mimic) positioned between a fluorophore and dark quencher in the probe. In the absence of gp32 the probe was cut so rapidly that by the time the tube was transferred to the fluorometer for measurement it was already almost completely degraded (high fluorescence). Conversely, when 250 ng/μL of Rb69 gp32 was included in the reaction, cutting was completely abolished and a flat line resulted throughout the assay time (100 seconds). Intermediary quantities of the gp32 protein resulted in fluorescence increase curves of various slopes consistent with a strict relationship between protein mass and protective capacity. The results demonstrate the utility of this assay in establishing the 'activity' of a gp32 preparation.

Figure 67:
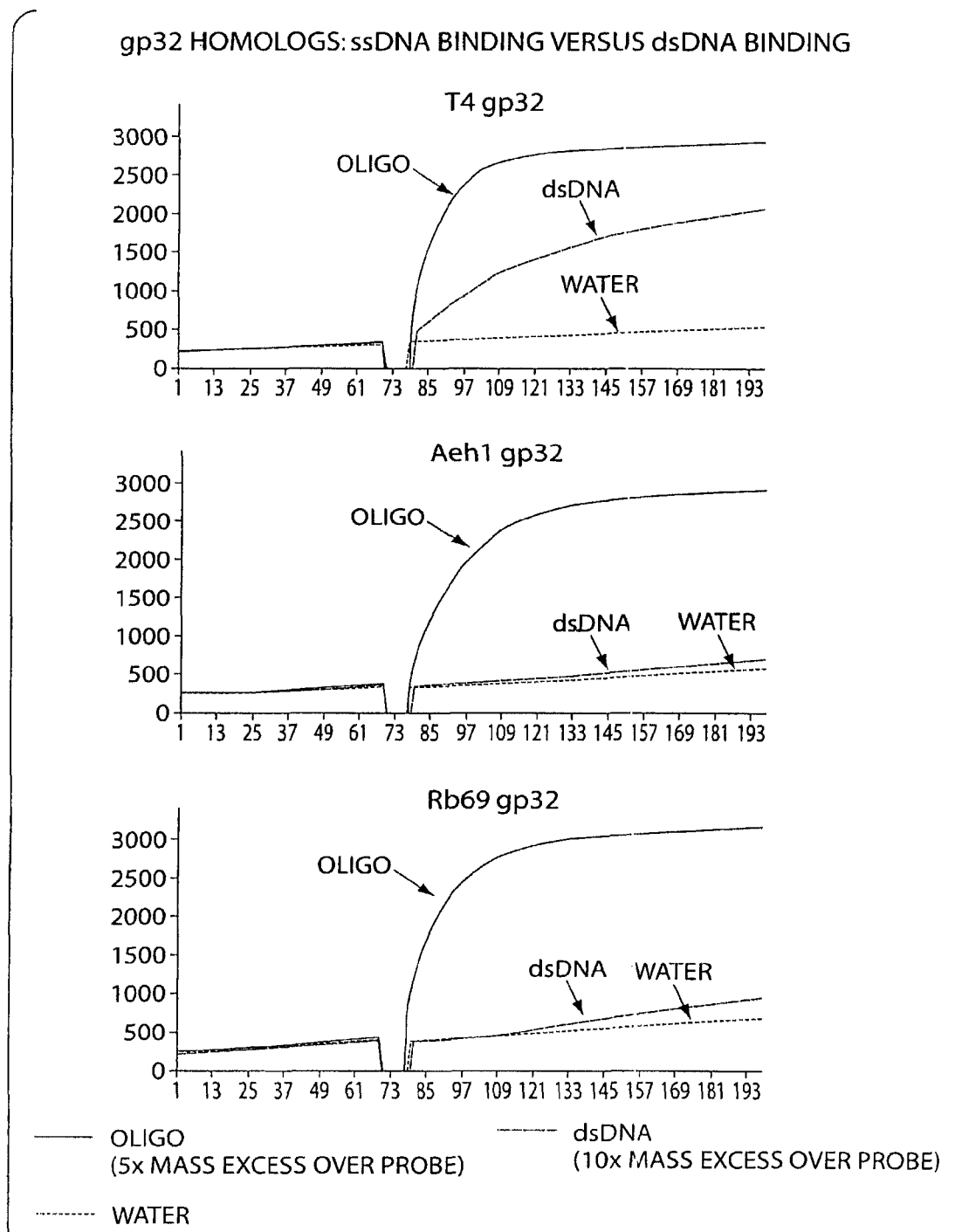
FIG. 67 shows graphs comparing the activity of T4, Aehl and Rb69 gp32 molecules in an assay designed to detect gp32 activity. Samples were analyzed using a fluorescent probe.

As shown in FIG. 66, it is possible to establish a ratio of probe oligonucleotide and gp32 protein that is on the boundary of complete protection, such as between 83 and 100 ng/μL. At this concentration of gp32 cutting occurred, but only slowly, and any changes in gp32 activity were likely to be easily observed by difference in cutting rate. At such a concentration, the reaction was challenged with additional added reagents or changes in environmental conditions, such as temperature, and the efficacy of gp32 in probe protection was assessed. FIG. 67 shows the results of an experiment in which the consequences of challenging the reaction with additional single-stranded or double-stranded DNA were assessed. In this experiment, the effects of these challenges on Rb69 gp32, T4 gp32 and Aeh1 gp32 were compared. In all cases challenge with competitor ssDNA at a defined time resulted in a sharp increase in probe attack.

The results demonstrate that the distribution of gp32 must be highly dynamic, supporting the notion that both association and dissociation events occur frequently in RPA reactions (although in the presence of crowding agents and other RPA reagents the kinetics may be altered). While this competitive effect of ssDNA was strong and similar between different gp32 species, significant differences were noted when the system was challenged with double-stranded DNA. When challenged with 10 times the mass of dsDNA (compared to probe) Aeh1 and RB69 gp32 showed only very slight increases in cutting activity. In contrast T4 gp32 showed a very significant increase in cutting activity. While not intending to be bound by any theory, the results suggest that the relative affinities of the gp32 species to double-stranded DNA were significantly variant. These results further suggest that there are could be significant differences in the late RPA reaction behaviour depending on the species of gp32. Rb69 or Aeh1 gp32 are likely to be more strongly partitioned between single-stranded and double-stranded DNA, while T4 gp32 in likely to be titrated out onto the duplex products. This may account for some of the improved activity noted with Rb69 gp32 in some RPA reactions. It is possible that T4 gp32 simply has a higher overall DNA affinity, which would be consistent with the results of the next experiment detailed below.

Figure 68:
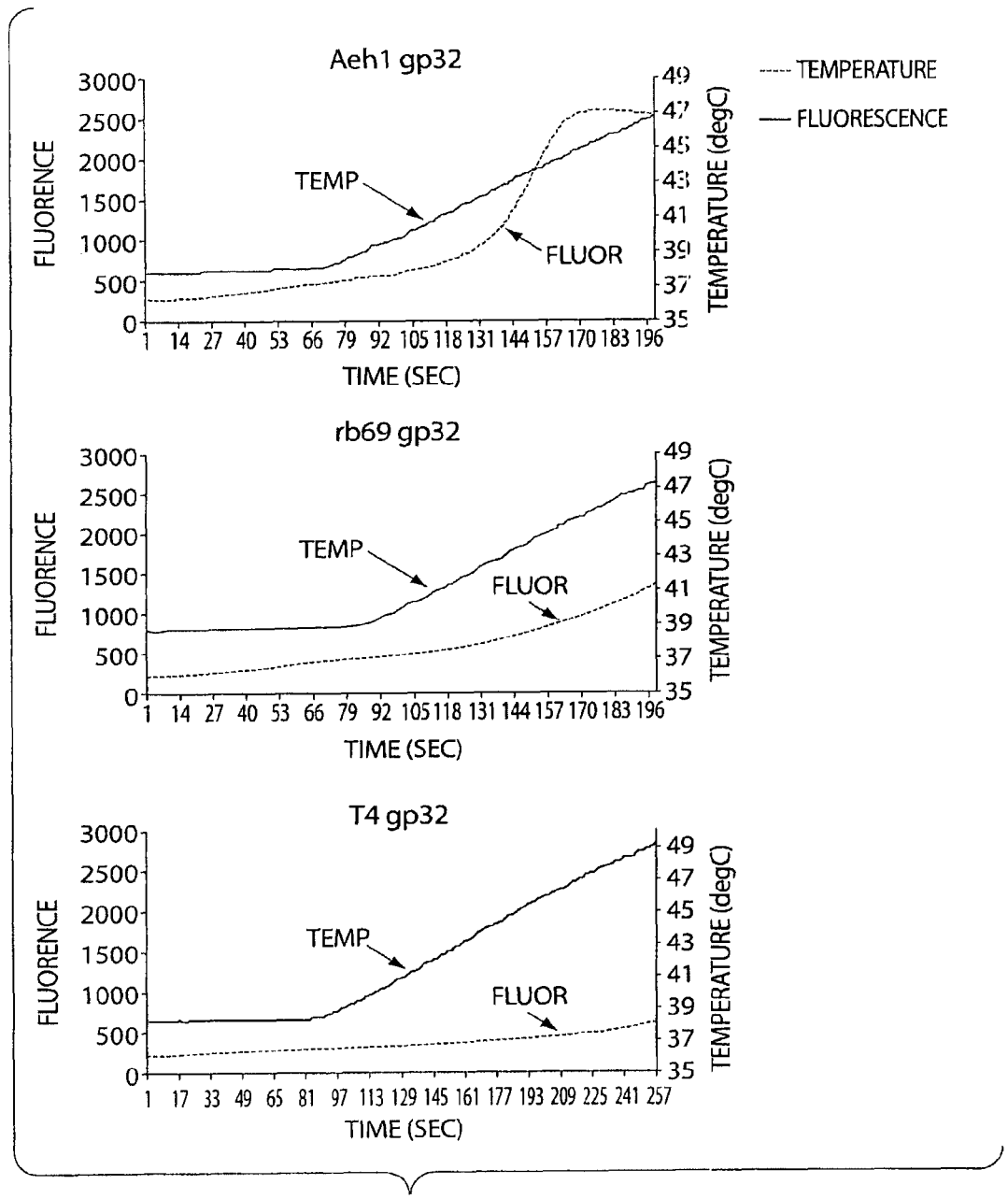
FIG. 68 shows graphs comparing the upper temperature limits of T4, Aehl and Rb69 gp32 molecules in an assay designed to detect gp32 activity. Samples were analyzed using a fluorescent probe.

In another variation of the probe protection assay the effects of temperature on the activity of the gp32 in protecting the probe were investigated. FIG. 68 shows the effects of progressively increasing the temperature of the reaction environment over time and reveals that at a certain point the protective properties of the gp32 suddenly decrease. This presumably represents the upper temperature at which the protein functions efficiently. It was noted that the profiles are markedly different between the 3 species tested here. Aeh1 gp32 became less effective above about 40 degrees centigrade and losing protective capacity very quickly above this temperature. By 42 degrees it lost almost all of its activity. In contrast Rb69 gp32 retains full activity up until about 42 degrees and then slowly starts to lose activity. While compromised, it still affords some protective capacity up until 47 degrees in this assay. The most powerful protective capacity was, however, observed for T4 gp32 which only started to show a slight decrease in effectiveness at 49 degrees, the highest temperature assayed in this experiment. Thus was deduced that the operational temperature range for these 3 proteins is clearly and measurably distinct. This should have some considerable significance when deciding which gp32 species is most suitable for a given application, and may reflect both the thermal stability of the protein itself as well as the relative DNA binding affinity of the protein.

It is understood that "acid C-term," acidic C terminus, acid N-term, and acidic N terminus refer to the optional addition of one or more acid amino acids, such as $(LDE)_n$ or $(LSD)_n$ where n=1 to 4 or 10 or fewer acidic amino acids to the C or N terminus of the protein. In addition, any of the proteins described anywhere in this specification, including the recombinase (e.g., UvsX), recombinase loading agent (e.g., UvsY), and single stranded binding protein (e.g., gp32) may optionally include a His tag at the N terminus, at the C terminus, or between the N terminus and C terminus of the protein in addition to any other modification (such as acidic C or N terminus). His tag is understood to mean 10 or fewer amino acids comprising Histidines in series or Histidine and Glutamine (HQ, or QH) in series—in a preferred embodiment, the number is 6. Furthermore, His tags may also refer to amino acids such as HQHQHQHQHQ (SEQ ID NO:83) which is less than 10 amino acids in length such as HQHQHQ (SEQ ID NO:84). For example, if a protein has both an acidic C terminus and a C-terminus histidine tag, the protein may have a configuration such as [protein]-[acidic residues]-[histidine tag] or such as [protein]-[histidine tag]-[acidic residues]. Alternatively, a protein with both an acidic N terminus and a N terminus histidine tag may have a configuration of [acidic residues]-[histidine tag]-[protein] or such as [histidine tag]-[acidic residues]-[protein].

EXAMPLES

The invention, having been generally described, may be more readily understood by reference to the following examples, which are included merely for purposes of illustration of certain aspects and embodiments of the present invention, and are not intended to limit the invention in any way. Other aspects, advantages, and modifications are within the scope of the following claims.

Example 1

Cloning and Protein Expression

All DNA manipulations were performed using standard techniques, in particular cloning using PCR, PCR-based mutagenesis procedures, and standard restriction digestion and ligation. Sequencing was performed by Lark technologies Ltd, Saffron Walden, UK. All proteins were expressed in *E. coli* and purified in 1M NaCl following lysis using lysozyme at 1 mg/ml and 2-3 freeze thaw cycles. Ni-NTA resin was purchased from Qiagen.

Amplification Reactions

The conditions for individual amplification reactions are described in the detailed descriptions provided below. In general reactions were monitored in real-time either by the inclusion of SYBR green dye, or more often by employment of a probe-based approach developed by us (see Piepenburg et al. 2006). In this case the probe is a third DNA primer which contains an internal tetrahydrofuran residue (abasic site mimic) flanked by a fluorophore and a quencher. On hybridization to amplified DNA this probe becomes a substrate for the endonucleolytic activity of endonuclease IV (Nfo) or exonuclease III which are enzymes included in the reaction.

The sequence of fluorescent probes described here are as follows:

```
SATamra1
                                                          (SEQ ID NO: 85)
5'-tgttaattgaacaagtgtacagagcatt(T)a(H)ga(q1)tatgcgtggag-Biotin-3'

SATamra2
                                                          (SEQ ID NO: 86)
5'-tgttaattgagcaagtgtatagagcatt(T)a(H)ga(q2)tatgcgtggag-Biotin-3'
```

BsFlc (SEQ ID NO: 87)
5'-catgattggatgaataagctgcagc(F)g(H)t(q3)aaaggaaactta-Biotin-3'

Where (T) is dT-TAMRA, (F) is dT-Fluorescein, (H) is THF, (q1) is dT-BHQ1, (q2) is dT-BHQ2, (q3) is dT-DDQ1. Nfo enzyme was used at 200 ng/µl, but almost all probe-based experiments employed exonuclease III at 65 ng/µl. Excitation/detection was at 485/525 nm (SYBR green or probe BsFlc) or 530/575 nm (SATamra1/2). Measurements were taken every 30 or 45 seconds. Fluorescence probe data was normalised against water controls, and the pre-amplification baseline was adjusted. In general the logarithm of the normalised fluorescence read-out was plotted against time for the probe-based experiments.

Amplification primers:

*Bacillus subtilis*:

(SEQ ID NO: 88)
J1      5'-acggcattaacaaacgaactgattcatctgcttgg (SEQ ID NO: 89)
K2      5'-ccttaatttctccgagaacttcatattcaagcgtc

MRSA:

sccIII
(SEQ ID NO: 90)
5'-ccaatatttcatatatgtaattcctccacatctca orfx45a (aka orfx)
(SEQ ID NO: 91)
5'- cccaagggcaaagcgactttgtattcgtcattggcggatcaaacg sccII-35 IV
(SEQ ID NO: 92)
5'- ctcaaagctagaactttgcttcactataagtattc (SEQ ID NO: 93)
MS2 down RT2-5' - cttaagtaagcaattgctgtaaagtcgtcac (SEQ ID NO: 94)
MS2 down 5-5' - ccagtagcgacagaagcaattgattggtaaatt (SEQ ID NO: 95)
MS2 up 2-5' - ttccgactgcgagcttattgttaaggcaatg (SEQ ID NO: 96)
MS2 up 4-5' - cctcgcgatctttctctcgaaatttaccaatca (SEQ ID NO: 97)
MS2 up 5-5' - ccatgtcgaagacaacaaagaagttcaactctt (SEQ ID NO: 98)
MS2 up 6-5' - catctactaatagacgccggccattcaaacatg (SEQ ID NO: 99)
MS2 up 7-5' - cccgattccctcagcaatcgcagcaaactccgg Apolipoprotein B:

ApoB4
(SEQ ID NO: 100)
5'- cagtgtatctggaaagcctacaggacaccaaaa

ApoB300
(SEQ ID NO: 101)
5'- tgctttcatacgtttagcccaatcttggatag

ApoB3
(SEQ ID NO: 102)
5'- tgacaagtgtgctataaacctggcctaccagag

ApoB7
(SEQ ID NO: 103)
5'- ttgatacattcggtctcgtgtatcttctata

ApoB10
(SEQ ID NO: 104)
5'- gatacattcggtctcgtgtatcttctagg

Clones were constructed by PCR using genomic DNA of T6 phage, Rb69 phage, Aeh1 phage, or phage KVP40. FIG. 1 shows the schematic layout of novel clones encoding diverse recombination machinery from the myoviridae. A modified pET21+ plasmid (Novagen) was used, and hexahistidine tags were engineered into the PCR primers to encode in-frame tags at either the N terminus (UvsY proteins) or at the C terminus (UvsX and gp32 proteins). In alignments and discussions later the amino acid residue numbers refer to the position in the native proteins as documented in the relevant databases. In the case of UvsY there will be 6 histidines and a methionine preceding this in the clones used.

Example 2

Primary Sequence Alignment of Diverse Recombinase Proteins

Primary Sequence Alignment of T4 UvsX and *E. coli* RecA

The web-based tool MAFFT (accessed via the Expasy proteomics server) was used to align the primary polypeptide sequences of T4 UvsX and *E. coli* RecA, as shown in FIG. 2. This alignment was consistent with those generated and discussed elsewhere. Based on the known crystal structure of *E. coli* RecA the position of three regions of interest namely the Walker A motif involved in ATP binding and hydrolysis, the mobile DNA binding loop 1, and the mobile DNA binding loop 2 sequences are boxed. Under the alignment symbols indicate amino acid identity between all homologs (*), conserved substitutions (:), or semi-conserved substitutions (.).

Figure 3A:
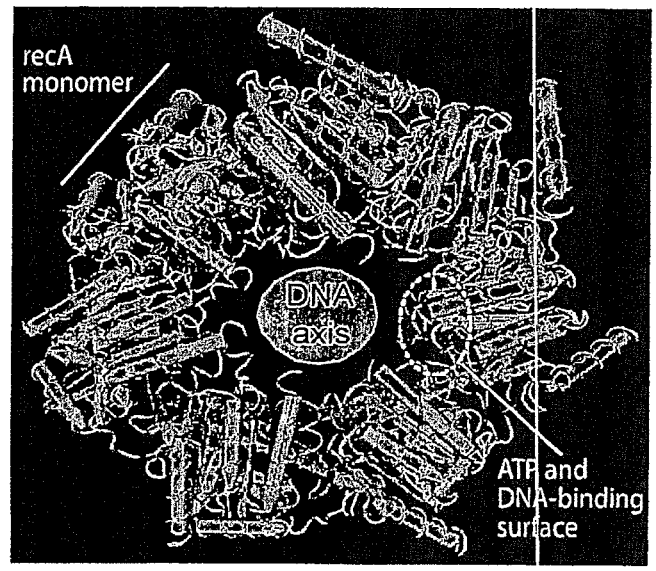
FIG. 3A is a screenshot looking down the axis of the model RecA filament with the central hole being the approximate location of bound DNA. The approximate location of the Walker A motif and mobile DNA binding loops is indicated for a single subunit and is on the surface facing the nucleic acid.
Figure 3B:
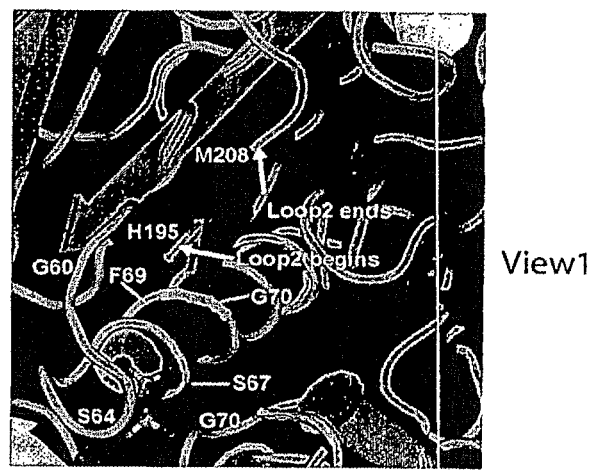
FIGS. 3B and 3C are two zoomed shots taken of the region to which ATP is bound on the surface indicated in 3A.
Figure 3C:
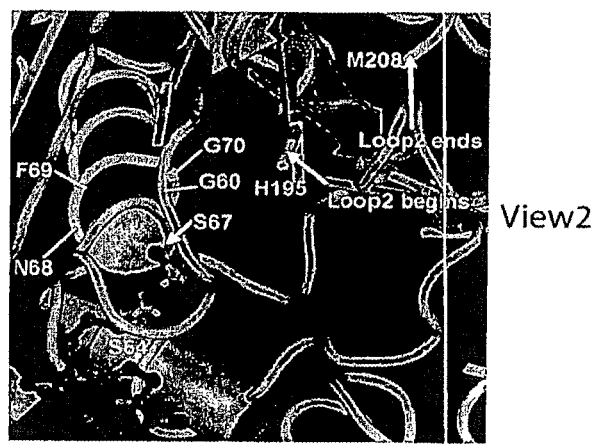

Model of RecA Structure with Superimposition and Labelling of Equivalent T4 UvsX Residues A model of the RecA nucleoprotein filament was generated using CN3D and a dataset downloaded from the NCBI database, PDB entry 1N03 (associated citation Vanloock M S et al., Structure 2003 February; 1 (2):187-96). Using the alignment in FIG. 2 the putative position of T4 UvsX residues was mapped to this RecA structure as an exercise in providing insight into the possible position of UvsX amino acids of interest and their proximity to one another. FIG. 3 shows the model of RecA structure with superimposition and labelling of equivalent T4 UvsX residues based on primary sequence alignment. FIG. 3A shows the screenshot looking down the axis of the model RecA filament with the central hole being the approximate location of bound DNA. The approximate location of the Walker A motif and mobile DNA binding loops is indicated for a single subunit and is on the surface facing the nucleic acid. FIGS. 3B and 3C show two zoomed shots are taken of the region to which ATP is bound on the surface indicated in (A). the putative positions of T4 UvsX residues G60, S64, S67, F69, G70, H195, and M208 are indicated in FIG. 3. Also indicated are the approximate locations of the beginning and end of mobile DNA-binding loop 2. That these amino acids are positioned exactly as shown in this model is unlikely given the significant divergence between RecA and UvsX, however these approximations are probably of meaningful utility for the study herein.

Primary sequence alignment of T4 and T6 g32 and UvsY proteins

The web-based tool MAFFT (accessed via the Expasy proteomics server) was used to align the primary polypeptide sequences of T4 and T6 gp32 and UvsY proteins, as shown in FIG. 4. This alignment revealed only small differences between these proteins. The UvsY proteins had only 2 highly conservative substitutions. Under the alignment symbols indicate amino acid identity between all homologs (*), conserved substitutions (:), or semi-conserved substitutions (.).

Primary Sequence Alignment of Diverse UvsX Proteins

The web-based tool MAFFT (accessed via the Expasy proteomics server) was used to align the primary polypeptide sequences of T4, T6, phage 133, Rb69, Aeh1, Ae65, KVP40, Rb43, PSSM2, and PSSM4 UvsX proteins, as shown in FIG. 5. Several regions of interest were boxed, namely the Walker A motif (or 'P-loop') involved in DNA binding and hydrolysis, the mobile DNA binding loop 1, and the mobile DNA binding loop 2. Certain residues under discussion have been highlighted. All amino acid differences between T4 and T6 UvsX are shown in bold. Under the alignment symbols indicate amino acid identity between all homologs (*), conserved substitutions (:), or semi-conserved substitutions (.).

Primary Sequence Alignment of Diverse UvsY Proteins

The web-based tool MAFFT (accessed via the Expasy proteomics server) was used to align the primary polypeptide sequences of T4, T6, phage 133, Rb69, Aeh1, KVP40, Rb43, PSSM2, and PSSM4 UvsX proteins, as shown in FIG. 6. In this alignment the PSSM4 sequence was derived from our own translation of the genomic DNA, the NCBI entry apparently erroneously omitting the first 43 residues from the polypeptide sequence. Under the alignment symbols indicate amino acid identity between all homologs (*), conserved substitutions (:), or semi-conserved substitutions (.).

Primary Sequence Alignment of Diverse gp32 Proteins

The web-based tool MAFFT (accessed via the Expasy proteomics server) was used to align the primary polypeptide sequences of T4, T6, Rb69, Aehl, KVP40, Rb43, PSSM2, and PSSM4 gp32 proteins, as shown in FIG. 7. In this alignment the PSSM2 sequence was derived from our own translation of the genomic DNA, the NCBI entry apparently erroneously omitting the first 25 residues from the polypeptide sequence. Under the alignment symbols indicate amino acid identity between all homologs (*), conserved substitutions (:), or semi-conserved substitutions (.). Also indicated by arrows are the positions of residues implicated in the co-ordination of zinc in T4 gp32. Also indicated by a line above the sequence is a common sequence, FKRK fSEQ ID NO: 129) (or FKRQ (SEQ ID NO: 130) in Rb43) which is absent in cyanophage gp32 proteins, and is implicated in co-operative binding as is the zinc atom of T4 gp32. Lack of co-ordinating residues in cyanophage gp32 proteins suggests that these proteins may not require metals such as zinc, cobalt, nickel etc. for activity. The re-organised status of the KVP40 metal-binding region suggests that this protein may not bind zinc, but rather a different metal atom, or that is may show altered requirements for zinc during growth, or altered sensitivity to replacement assault by competitor metal atoms.

Example 3

T6 UvsX Substituted for T4 UvsX in RPA Reactions Using Heterologous Components

RPA reactions were configured using primers Rs8179145-2 and Rs8179145-3 whose sequences are indicated. Target DNA was human genomic DNA, and reaction conditions were as follows: 100 mM potassium acetate, 50 mM Tris Acetate pH 8.3, 50 mM phosphocreatine, 3 mMP ATP, 200 µM dNTPs, 300 nM Rs8179145-2 primer, 300 nM Rs8179145-3 primer, 150 ng/µL T4 or T6 UvsX, 1000 ng/ng/µL T4 gp32, 40 ng/µL T4 UvsY, 42 copies of human genomic DNA, 5% Carbowax 20 M, and 32 ng/µL Bsu polymerase. After 90 minutes samples were purified via centrifugation through a Qiagen PCR product clean-up column. Purified samples were analyzed on an ethidium bromide stained agarose gel. The expected amplicon size from the human locus Rs817945 was 205 bp. Asterisks on the gel shown in FIG. 8 indicate the position of the expected band, 205 bp and the position of marker bands is indicated on the left. As shown in FIG. 8, T6 UvsX can effectively be substituted for T4 UvsX in RPA reactions using heterologous components.

RPA reactions were established to compare the kinetics of T6 and T4 UvsX using SYBR green dye, using primers J1 and K2 under the following conditions: 50 mM Tris.acetate pH 7.9, 100 mM Potassium acetate, 14 mM Magnesium acetate, 50 mM Creatine phosphate (Calbiochem), 3 mM ATP (Roche), 200 micromolar dNTPs, 50 ng/µl creatine kinase (Roche), 120 ng/µl UvsX of T4 or T6, 30 ng/µl UvsY, 900 ng/µl gp32, 30 ng/µl Bsu polymerase, 5% Carbowax 20M, 300 nM amplification primers, 1:50,000 dilution from stock of SYBR green (Invitrogen). Reactions were established on ice in a 96-well plate, and then transferred to a BIOTEK Flx-800 fluorescence microplate reader with stage set to 38° C. at which time measurements were taken periodically from a top-reading probe. Samples contained either no target (water) or 50 or 5000 copies of B. subtilis genomic DNA containing the target sequence. Samples contained either T4 or T6 UvsX, and the recombinase and presence of target is shown in the legend. Each sample was run in duplicate.

Positive signals developed in all samples during the 60 minute incubation, and the time of signal increase was earlier in the target-containing samples than in non-target samples as expected. As shown in FIG. 9, the time at which signal increase was first detected was similar between T4 and T6 samples. However the curves developed with different slopes and final maxima. T6 gave less sharp signal accumulation and less high final signals.

RPA reactions were also established to compare the kinetics of T6 and T4 UvsX using fluorescent probe, using primers orfx45a (120 nM) and sccii35IV (480 nM) under the following conditions: 50 mM Tris.acetate pH 7.9, 100 mM Potassium acetate, 14 mM Magnesium acetate, 50 mM Creatine phosphate (Calbiochem), 3 mM ATP (Roche), 200 micromolar dNTPs, 50 ng/µl creatine kinase (Roche), 120 ng/µl UvsX of T4 or T6, 30 ng/µl UvsY, 900 ng/µl gp32, 50 ng/µl Bsu polymerase, 5% Carbowax 20M, 120 nM fluorescent probe SATamra2. Exonuclease III was included at 65 ng/µl. Reactions were established on ice in a 384-well plate, and then transferred to a BIOTEK Flx-800 fluorescence microplate reader with stage set to 38° C. at which time measurements were taken periodically from a bottom-reading probe. Samples contained either no target (water) 100, or 1000 copies of MRSA 3 (mecI) genomic DNA containing the target sequence. Samples contained either T4 or T6 UvsX, and the recombinase and presence of target is shown in the legend. Each sample was run in duplicate.

Positive signals developed in the template positive samples during the 90 minute incubation, and the time of signal increase was earliest in the highest target-containing samples. As shown in FIG. 10, the time at which signal increase was first detected was similar between T4 and T6 samples, particularly for the 1000 copies samples, however the curves developed with different slopes and final maxima. T6 gave less sharp signal accumulation and less high final signals.

Example 4

Engineered T6 UvsX Protein Constructs

Figure 11:
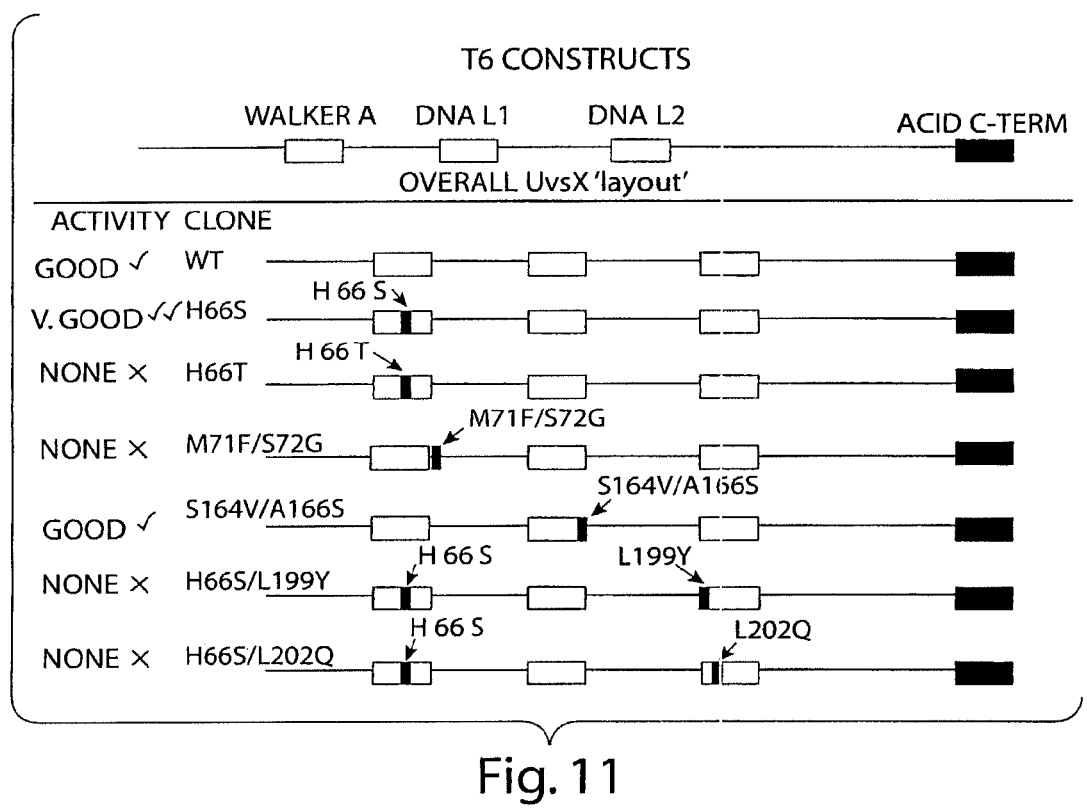
FIG. 11 is a schematic layout of novel, engineered T6 UvsX protein constructs of the present invention.

The parent plasmid clone containing T6 UvsX in a modified pET21+ vector was altered using standard PCR mutagenesis protocols. A schematic layout of the relation of the coding region/primary polypeptide sequence to putative structural elements is shown at the top of FIG. 11. Modifications were made to three regions which are shown as boxes on the schematic, the Walker A motif, the DNA binding loop1 and, DNA binding loop2. Several regions and amino acids were targeted and these are indicated on the lower schematics next to the name given to the clone. Numbers refer to the position of the amino acid in the wild type T6 UvsX protein, hence H66S means that the histidine present as amino acid 66 in wild type T6 was altered to a serine. On the left of the FIG. 11, a simple representation of the general activity of the protein produced for this clone when tested in RPA assays is shown.

Comparison of T6 UvsX H66S and Wild Type T6 UvsX

RPA reactions were established to compare T6 UvsX H66S and wild type T6 UvsX using primers J1 (120 nM) and K2 (480 nM) under the following conditions: 50 mM Tris.acetate pH 7.9, 100 mM Potassium acetate, 14 mM Magnesium acetate, 50 mM Creatine phosphate (Calbiochem), 3 mM ATP (Roche), 200 micromolar dNTPs, 50 ng/μl creatine kinase (Roche), 120 ng/μl UvsX of T4 or T6 UvsX H66S, 45 ng/μl T4 UvsY, 900 ng/μl T4 gp32, 30 ng/μl Bsu polymerase, 5% Carbowax 20M, 120 nM fluorescent probe BsFlc. Exonuclease III was included at 65 ng/μl. Reactions were established on ice in a 384-well plate, and then transferred to a BIOTEK Flx-800 fluorescence microplate reader with stage set to 38° C. at which time measurements were taken periodically from a bottom-reading probe. Samples contained either 100, or 1000 copies of B. subtilis genomic DNA containing the target sequence. Samples contained either T4 or T6 UvsX H66S, and the recombinase and presence of target is shown in the legend in FIG. 12. Each sample was run in duplicate.

The sequence of T6 UvsX H66S is as follows: MSIADLKSRL IKASTSKMTA ELTTSKFFNE KDVIRTKIPM LNIAISGAID GGMQSGLTIF AGPSKSFKSN MSLTMVAAYL NKYPDAVCLF YDSEFGITPA YLRSMGVDPE RVIHTPIQSV EQLKIDMVNQ LEAIERGEKV IVFIDSIGNM ASKKETEDAL NEKSVADMTR AKSLKSLFRI VTPYFSIKNI PCVAVNHTIE TIEMFSKTVM TGGTGVMYSA DTVFIIGKRQ IKDGSDLQGY QFVLNVEKSR TVKEKSKFFI DVKFDGGIDP YSGLLDMALE LGFVVKPKNG WYAREFLDEE TGEMIREEKS WRAKDTNCTT FWGPLFKHQP FRDAIKRAYQ LGAIDSNEIV EAEVDELINS KVEKFKSPES KSKSAADLET DLEQLSDMEE FNE (SEQ ID NO:105).

As shown in FIG. 12, positive signals developed in the samples during the 90 minute incubation, and the time of signal increase was earliest in the highest target-containing samples. Signals developed earlier in the T6 UvsX H66S— containing samples, particularly for the 1000 copies samples, and the curves developed higher final maxima. Based on this study, it was concluded that T6 UvsX H66S performs better in these assays than wild type T6

UvsX. However the slope of the signal accumulation using this system was similar between the 2 proteins, and therefore it is unlikely that T6 UvsX H66S exactly reproduces the activity of T4 UvsX in this assay.

Kinetic Behaviour of Other Mutants of T6 UvsX

RPA reactions were established using mutant T6 UvsX components, using primers J1 (120 nM) and K2 (480 nM) under the following conditions: 50 mM Tris.acetate pH 7.9, 100 mM Potassium acetate, 14 mM Magnesium acetate, 50 mM Creatine phosphate (Calbiochem), 3 mM ATP (Roche), 200 micromolar dNTPs, 50 ng/μl creatine kinase (Roche), 120 ng/μl UvsX of T6 or T6 UvsX H66T or T6 UvsX M71F/S72G or T6 UvsX S164V/A166S, 45 ng/μl T4 UvsY, 1000 ng/μl T4 gp32, 30 ng/μl Bsu polymerase, 6% Carbowax 20M, 120 nM fluorescent probe BsFlc. Exonuclease III was included at 65 ng/μl. Reactions were established on ice in a 384-well plate, and then transferred to a BIOTEK Flx-800 fluorescence microplate reader with stage set to 38° C. at which time measurements were taken periodically from a bottom-reading probe. Samples contained either water or 200 copies of B. subtilis genomic DNA containing the target sequence as indicated in the legend.

As shown in FIG. 13, positive signals developed in some samples during the 90 minute incubation. Signals developed earliest in the T6 UvsX S164V/A166S and then wild-type samples. Signal accumulated much later in the T6 UvsX H66T sample, and no signal accumulated in the T6 UvsX M71F/S72G sample. It was concluded that T6 UvsX S164V/A166S performs well in these assays, however in some later experiments little or no difference to the wild type T6 UvsX was found. It was further concluded that T6 UvsX H66T has poor activity, and T6 UvsX M71F/S72G is inactive.

The sequence of T6 UvsX S164V/A166S is as follows: MSIADLKSRL IKASTSKMTA ELTTSKFFNE KDVIRTKIPM LNIAISGAID GGMQSGLTIF AGPSKHFKSN MSLTMVAAYL NKYPDAVCLF YDSEFGITPA YLRSMGVDPE RVIHTPIQSV EQLKIDMVNQ LEAIERGEKV IVFIDSIGNM ASKKETEDAL NEKVV SDMTR AKSLKSLFRI VTPYFSIKNI PCVAVNHTIE TIEMFSKTVM TGGTGVMYSA DTVFIIGKRQ IKDGSDLQGY QFVLNVEKSR TVKEKSKFFI DVKFDGGIDP YSGLLDMALE LGFVVKPKNG WYAREFLDEE TGEMIREEKS WRAKDTNCTT FWGPLFKHQP FRDAIKRAYQ LGAIDSNEIV EAEVDELINS KVEKFKSPES KSKSAADLET DLEQLSDMEE FNE (SEQ ID NO:106).

Example 5

RPA Using Rb69 Components

RPA reactions were established using Rb69 components, using primers J1 and K2 under the following conditions: 50 mM Tris.acetate pH 7.9, 100 mM Potassium acetate, 14 mM Magnesium acetate, 50 mM Creatine phosphate (Calbiochem), 3 mM ATP (Roche), 200 micromolar dNTPs, 50 ng/μl creatine kinase (Roche), 100 ng/μl UvsX of Rb69, 20-100 ng/μl Rb69 UvsY, 400 ng/μl Rb69 gp32, 30 ng/μl Bsu polymerase, 7% Carbowax 20M, 300 nM amplification primers, 1:50,000 dilution from stock of SYBR green (Invitrogen). Reactions were established on ice in a 384-well plate, and then transferred to a BIOTEK Flx-800 fluorescence microplate reader with stage set to 38° C. at which time measurements were taken periodically from a bottom-reading probe. Samples contained either no target (control—water) or 2500 copies of *B. subtilis* genomic DNA containing the target sequence. Samples contained varying concentrations of Rb69 UvsY, and the quantities used are indicated in the legend.

As shown in FIG. 14, positive signals developed in all samples during the 90 minute incubation, and the time of signal increase was earlier in the samples containing higher quantities of UvsY underlying an ideal requirement for concentrations of Rb69 UvsY of 60 ng/µl or over. The control sample was performed under identical conditions to the positive sample containing 60 ng/µl of UvsY, but lacking target DNA. This experiment shows that Rb69 components can be employed to configure a sensitive and specific amplification system.

Example 6

RPA Using Aeh1 Components

RPA reactions were established using Aeh1 components, using primers J1 (120 nM) and K2 (480 nM) under the following conditions: 50 mM Tris acetate pH 7.9, 100 mM Potassium acetate, 14 mM Magnesium acetate, 50 mM Creatine phosphate (Calbiochem), 3 mM ATP (Roche), 200 micromolar dNTPs, 50 ng/µl creatine kinase (Roche), 200 ng/µl Aeh1 UvsX, 80 ng/µl Aeh1 UvsY, 500 ng/µl Aeh1 gp32, 30 ng/µl Bsu polymerase, 7% PEG compound, 120 nM fluorescent probe BsFlc. Exonuclease III was included at 65 ng/µl. Reactions were established on ice in a 384-well plate, and then transferred to a BIOTEK Flx-800 fluorescence microplate reader with stage set to 38° C. at which time measurements were taken periodically from a bottom-reading probe. Samples contained either water, 10, 100, or 1000 copies of *B. subtilis* genomic DNA containing the target sequence as indicated in the legend shown in FIG. 15.

Salt Titration

RPA reactions were also established using Aeh1 components testing salt titration, using primers J1 and K2 under the following conditions: 50 mM Tris.acetate pH XX, 60 or 80 or 100 or 120 or 140 or 160 mM Potassium acetate, 14 mM Magnesium acetate, 50 mM Creatine phosphate (Calbiochem), 3 mM ATP (Roche), 200 micromolar dNTPs, 50 ng/µl creatine kinase (Roche), 150 ng/µl UysX of Aeh1, 50 ng/µl Aeh1 UvsY, 500 ng/µl Aeh1 gp32, 30 ng/µl Bsu polymerase, 7% Carbowax 20M, 300 nM amplification primers, 1:50,000 dilution from stock of SYBR green (Invitrogen). Reactions were established on ice in a 384-well plate, and then transferred to a BIOTEK Flx-800 fluorescence microplate reader with stage set to 38° C. at which time measurements were taken periodically from a bottom-reading probe. Samples contained 2000 copies of *B. subtilis* genomic DNA containing the target sequence.

As shown in FIG. 16, positive signals developed in all samples during the 90 minute incubation. This experiment suggests that Aeh1 components can be employed successfully to amplify DNA over a broad range of salt concentrations.

Aeh1 Compared to T4

RPA reactions were established to compare Aeh1 amplification to the T4 amplification system, using primers orfx45a (100 ng/µl) and sccii35IV (500 ng/µl) under the following conditions: 50 mM Tris.acetate pH 7.9, 100 mM Potassium acetate, 14 mM Magnesium acetate, 50 mM Creatine phosphate (Calbiochem), 3 mM ATP (Roche), 200 micromolar dNTPs, 50 ng/µl creatine kinase (Roche), 200 ng/µl Aeh1 UvsX, 80 ng/µl Aeh1 UvsY, 500 ng/µl Aeh1 gp32, 70 ng/µl Bsu polymerase, 7% PEG Compound (Sigma), 120 nM fluorescent probe SATamra2, OR under similar conditions but with the following recombination components: 120 ng/µl T4 UvsX, 30 ng/µl T4 UvsY and 900 ng/µl T4 gp32. Exonuclease III was included at 65 ng/µl. Reactions were established on ice in a 384-well plate, and then transferred to a BIOTEK Flx-800 fluorescence microplate reader with stage set to 38° C. at which time measurements were taken periodically from a bottom-reading probe. Samples contained either water, 10 or 1000 copies of MRSA genomic DNA containing the target sequence as indicated in the legend. As shown in FIG. 17, no signals were detected with either recombination system when an estimated 10 copies had been provided. Based on later experiments it was believed that the DNA dilutions used for this experiment were compromised and hence that actual copy numbers were significantly lower than those expected. As shown in FIG. 17, the Aeh1 recombination system reaches detection threshold later than T4 and achieves a lower total signal strength in this experiment.

Aeh1 UvsX and UvsY can Amplify Using Heterologous gp32

RPA reactions were established using primers J1 and K2 under the following conditions: 50 mM Tris.acetate pH 7.9, 100 mM Potassium acetate, 14 mM Magnesium acetate, 50 mM Creatine phosphate (Calbiochem), 3 mM ATP (Roche), 200 micromolar dNTPs, 50 ng/µl creatine kinase (Roche), 200 ng/µl UvsX of Aeh1, 100 ng/µl Aeh1 UvsY, 300 ng/µl Aeh1 gp32 OR 500 ng/µl Rb69 gp32 OR 700 ng/µl T4 gp32, 30 ng/µl Bsu polymerase, 7% Carbowax 20M, 300 nM amplification primers, 1:50,000 dilution from stock of SYBR green (Invitrogen). Reactions were established on ice in a 384-well plate, and then transferred to a BIOTEK Flx-800 fluorescence microplate reader with stage set to 38° C. at which time measurements were taken periodically from a bottom-reading probe. Samples contained 2000 copies of *B. subtilis* genomic DNA containing the target sequence.

Figure 18:
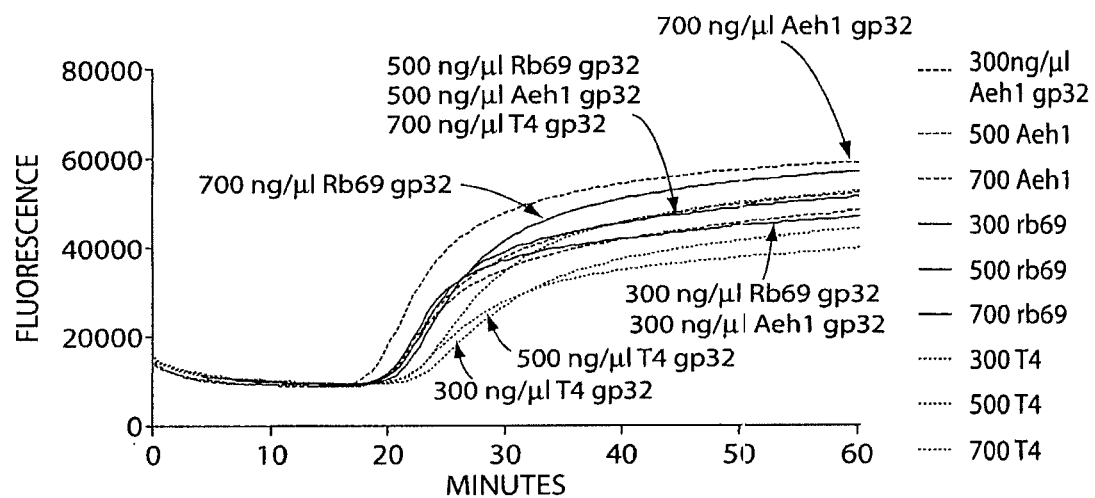
FIG. 18 is a graph showing Aeh1 UvsX and UvsY and heterologous gp32 can amplify DNA using an RPA reaction. Samples were analyzed using SYBR green dye.

As shown in FIG. 18, signals developed in all samples indicating that DNA amplification had occurred in all cases. The fastest and strongest signals developed when Aeh1 gp32 was employed, then Rb69 gp32, then T4 gp32. One should interpret the relative effectiveness of the gp32 molecules cautiously as they were not employed at the same concentrations.

Example 7

RPA Using Heterologous Reaction Components

Figure 19:
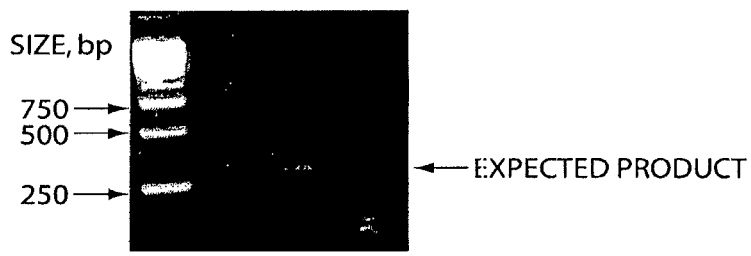
FIG. 19 is a picture of an ethidium bromide stained agarose gel showing DNA amplification in an RPA reaction using heterologous reaction components: Rb69, gp32 and Aeh1 UvsX, and Aeh1 UvsY.

RPA reactions were established using primers Apo300 and ApoB4 which amplify a roughly 300 base pair duplex product from human genomic DNA. The following conditions were employed: 50 mM Tris.acetate pH 8.3, 100 mM Potassium acetate, 14 mM Magnesium acetate, 50 mM Creatine phosphate (Calbiochem), 3 mM ATP (Roche), 200 micromolar dNTPs, 50 ng/µl creatine kinase (Roche), 200 ng/µl UvsX of KVP40, Aeh1 or Rb69, 32 ng/µl UvsY of KVP40, Aeh1 or T4 as indicated, 600 ng/µl Rb69 gp32 or T4 gp32, 30 ng/µl Bsu polymerase, 5% Carbowax 20M, 300 nM amplification primers. Reactions were established and left at 37° C. for 90 minutes. All samples contained 1000 copies of human genomic DNA containing the target sequence. The precise composition of each reaction with regard to species of gp32, UvsX and UvsY is indicated. Samples were cleaned by passage through a Qiagen PCR clean-up column and electrophoresed on a 2% agarose gel containing ethidium bromide. As shown in FIG. 19, amplification had occurred in the sample containing a heterologous mixture of Rb69 gp32 with Aeh1 UvsX and UvsY.

Example 8

Engineered Rb69 Constructs

Alterations to our parent clone of Rb69 UvsX in a modified pET21+ vector were engineered. The overall layout of the coding/primary amino acid sequence of RB69 drawing attention to regions of interest is shown at the top of the FIG. 20. Changes in the coding sequence were engineered, specifically to alter encoded amino acids in and around the Walker A motif, in and around the DNA-binding loop 2, and at the very C-terminus of the protein. Alterations in and around the Walker motif are as indicated by specific lettering and numeration referring to the position of the amino acid in the Rb69 wild-type protein, what the amino acid is, and to what it is mutated. For example H64S refers to alteration of histidine 64 of the native protein to a serine. Altered sequences in the region of DNA-binding loop 2 are indicated according to a different scheme. In this case most or all of the DNA binding loop sequences was replaced by the loop from T6 or T4 UvsX. When T6-1 is shown, this refers to replacement of the sequence NHT AMEIGGLYPKE IMG GG (SEQ ID NO:107) with the sequence NHT IETIEMFSKT VMG GG (SEQ ID NO:108), in which the underlined glycine is similar to the Rb69 sequences not the T6 native sequence. When T6 is shown, this refers to replacement of the Rb69 sequence with NHT IETIEMFSKT VMT GG (SEQ ID NO:109), in which the underlined threonine is the native T6 sequence in this position. When T4 is shown, this refers to replacement of the Rb69 sequence with the T4 sequence, that is NHT YETQEMFSKT VMG GG (SEQ ID NO:110). In the case of modifications to the C terminus the symbol 'LSD' indicates alteration of the native sequence of Rb69 at the very C terminus from the encoded amino acid sequence END LDE MEDFDE (SEQ ID NO:111) to the sequence END LDE LSD MEDFDE (SEQ ID NO:112). The symbol 'LDE LDE' or sometimes in the legends '2xLDE' refers to changing the Rb69 C-terminal sequence to END LDE MEDFDE LDELDE (SEQ ID NO:113). Note that in all cases the very C-terminal sequence is followed by 18 bases encoding 6 histidine residues that are used for protein purification.

Briefly, selected sequences discussed above are listed below.

The Rb69 UvsX H64S sequence is as follows: MSDLKSRLIK ASTSKMTADL TKSKLFNNRD EVPTRIPMLN IALGGALNAG LQSGLTIFAA PSKSFKTLFG LTMVAAYMKK YKDAICLFYD SEFGASESYF RSMGVDLDRV VHTPIQSVEQ LKVDMTNQLD AIERGDKVII FIDSIGNTAS KKETEDALNE KVVGDMSRAK ALKSLFRIVT PYLTIKDIPC VAINHTAMEI GGLYPKEIMG GGTGILYSAN TVFFISKRQV KEGTELTGYD FTLKAEKSRT VKEKSTFPIT VNFDGGIDPF SGLLEMATEI GFVVKPKAGW YAREFLDEET GEMIREEKSW RAKATDCVEF WGPLFKHKPF RDAIETKYKL GAISSIKEVD DAVNDLINCK ATTKVPVKTS DAPSAADIEN DLDEMEDFDE (HHHHHH) (SEQ ID NO:114). The six "H" at the end is optional.

The Rb69 UvsX H64S LSD sequence is as follows: MSDLKSRLIK ASTSKMTADL TKSKLFNNRD EVPTRIPMLN IALGGALNAG LQSGLTIFAA PSKSFKTLFG LTMVAAYMKK YKDAICLFYD SEFGASESYF RSMGVDLDRV VHTPIQSVEQ LKVDMTNQLD AIERGDKVII FIDSIGNTAS KKETEDALNE KVVGDMSRAK ALKSLFRIVT PYLTIKDIPC VAINHTAMEI GGLYPKEIMG GGTGILYSAN TVFFISKRQV KEGTELTGYD FTLKAEKSRT VKEKSTFPIT VNFDGGIDPF SGLLEMATEI GFVVKPKAGW YAREFLDEET GEMIREEKSW RAKATDCVEF WGPLFKHKPF RDAIETKYKL GAISSIKEVD DAVNDLINCK ATTKVPVKTS DAPSAADIEN DLDEMEDFDE LSD(HHHHHH) (SEQ ID NO:115). The six "H" at the end is optional.

The Rb69 UvsX H64S 2xLDE sequence is as follows: MSDLKSRLIK ASTSKMTADL TKSKLFNNRD EVPTRIPMLN IALGGALNAG LQSGLTIFAA PSKSFKTLFG LTMVAAYMKK YKDAICLFYD SEFGASESYF RSMGVDLDRV VHTPIQSVEQ LKVDMTNQLD AIERGDKVII FIDSIGNTAS KKETEDALNE KVVGDMSRAK ALKSLFRIVT PYLTIKDIPC VAINHTAMEI GGLYPKEIMG GGTGILYSAN TVFFISKRQV KEGTELTGYD FTLKAEKSRT VKEKSTFPIT VNFDGGIDPF SGLLEMATEI GFVVKPKAGW YAREFLDEET GEMIREEKSW RAKATDCVEF WGPLFKHKPF RDAIETKYKL GAISSIKEVD DAVNDLINCK ATTKVPVKTS DAPSAADIEN DLDEMEDFDE LSD LDELDE (HHHHHH) (SEQ ID NO:116). The six "H" at the end is optional.

The Rb69 UvsX H64S T6/2xLDE sequence is as follows: MSDLKSRLIK ASTSKMTADL TKSKLFNNRD EVPTRIPMLN IALGGALNAG LQSGLTIFAA PSKSFKTLFG LTMVAAYMKK YKDAICLFYD SEFGASESYF RSMGVDLDRV VHTPIQSVEQ LKVDMTNQLD AIERGDKVII FIDSIGNTAS KKETEDALNE KVVGDMSRAK ALKSLFRIVT PYLTIKDIPC VAI NHTIETIEMFSKTVMTGGTGILYSAN TVFFISKRQV KEGTELTGYD FTLKAEKSRT VKEKSTFPIT VNFDGGIDPF SGLLEMATEI GFVVKPKAGW YAREFLDEET GEMIREEKSW RAKATDCVEF WGPLFKHKPF RDAIETKYKL GAISSIKEVD DAVNDLINCK ATTKVPVKTS DAPSAADIEN DLDEMEDFDE LSD LDELDE (HHHHHH) (SEQ ID NO:117). The six "H" at the end is optional.

The Rb69 UvsX H64S T4/2xLDE sequence is as follows: MSDLKSRLIK ASTSKMTADL TKSKLFNNRD EVPTRIPMLN IALGGALNAG LQSGLTIFAA PSKSFKTLFG LTMVAAYMKK YKDAICLFYD SEFGASESYF RSMGVDLDRV VHTPIQSVEQ LKVDMTNQLD AIERGDKVII FIDSIGNTAS KKETEDALNE KVVGDMSRAK ALKSLFRIVT PYLTIKDIPC VAI NHTYETQEMFSKTVMGGGTGILYSAN TVFFISKRQV KEGTELTGYD FTLKAEKSRT VKEKSTFPIT VNFDGGIDPF SGLLEMATEI GFVVKPKAGW YAREFLDEET GEMIREEKSW RAKATDCVEF WGPLFKHKPF RDAIETKYKL GAISSIKEVD DAVNDLINCK ATTKVPVKTS DAPSAADIEN DLDEMEDFDE LSD LDELDE (HHHHHH) (SEQ ID NO:118). The six "H" at the end is optional.

The Rb69 UvsX H64S T67S L68N T4/2xLDE sequence is as follows: MSDLKSRLIK ASTSKMTADL TKSKLFNNRD EVPTRIPMLN IALGGALNAG LQSGLTIFAA PSK SFKSNFG LTMVAAYMKK YKDAICLFYD SEFGASESYF RSMGVDLDRV VHTPIQSVEQ LKVDMTNQLD AIERGDKVII FIDSIGNTAS KKETEDALNE KVVGDMSRAK ALKSLFRIVT PYLTIKDIPC VAI NHTYETQEMFSKTVMGGGTGILYSAN TVFFISKRQV KEGTELTGYD FTLKAEKSRT VKEKSTFPIT VNFDGGIDPF SGLLEMATEI GFVVKPKAGW YAREFLDEET GEMIREEKSW RAKATDCVEF WGPLFKHKPF RDAIETKYKL GAISSIKEVD DAVNDLINCK ATTKVPVKTS DAPSAADIEN DLDEMEDFDE LSD LDELDE (HHHHHH) (SEQ ID NO:119). The six "H" at the end is optional.

Additional alterations to the parent clone of Rb69 UvsX in a modified pET21+ vector were generated. The overall layout of the coding/primary amino acid sequence of Rb69 drawing attention to additional regions of interest is shown at the top of the FIG. 21. Changes in the coding sequence were engineered, specifically in and around the DNA-binding loop 2. The entire DNA-binding loop2 sequence was replaced with the equivalent sequences from phage 133, phage Aeh1, phage KVP40, a representative (hybrid) cyanophage sequence, or the loop from *E. coli* RecA. A loop which was part Aeh1 and part Rb16 was also tested. The precise amino acid substitutions are indicated in FIG. 21. A summary remark regarding the behaviour/activity of the protein produced from these clones during expression/purification or testing in RPA is given on the left of FIGS. 20 and 21.

The Rb69 UvsX sequence is as follows: MSDLKSRLIK ASTSKMTADL TKSKLFNNRD EVPTRIPMLN IALGGALNAG LQSGLTIFAA PSKHFKTLFG LTMVAAYMKK YKDAICLFYD SEFGASESYF RSMGVDLDRV VHTPIQSVEQ LKVDMTNQLD AIERGDKVII FIDSIGNTAS KKETEDALNE KVVGDMSRAK ALKSLFRIVT PYLTIKDIPC VAINHTAMEIGGLYPKEIMGGGTGILYSAN TVFFISKRQV KEGTELTGYD FTLKAEKSRT VKEKSTFPIT VNFDGGIDPF SGLLEMATEI GFVVKPKAGW YAREFLDEET GEMIREEKSW RAKATDCVEF WGPLFKHKPF RDAIETKYKL GAISSIKEVD DAVNDLINCK ATTKVPVKTS DAPSAADIEN DLDEMEDFDE (SEQ ID NO:120)

The Rb69 Loop133 UvsX sequence is as follows: MSDLKSRLIK ASTSKMTADL TKSKLFNNRD EVPTRIPMLN IALGGALNAG LQSGLTIFAA PSKHFKTLFG LTMVAAYMKK YKDAICLFYD SEFGASESYF RSMGVDLDRV VHTPIQSVEQ LKVDMTNQLD AIERGDKVII FIDSIGNTAS KKETEDALNE KVVGDMSRAK ALKSLFRIVT PYLTIKDIPC VAI NHTLQTLEMFSKEVMTGGTGILYSAN TVFFISKRQV KEGTELTGYD FTLKAEKSRT VKEKSTFPIT VNFDGGIDPF SGLLEMATEI GFVVKPKAGW YAREFLDEET GEMIREEKSW RAKATDCVEF WGPLFKHKPF RDAIETKYKL GAISSIKEVD DAVNDLINCK ATTKVPVKTS DAPSAADIEN DLDEMEDFDE (SEQ ID NO:121)

The Rb69 LoopKVP40 UvsX sequence is as follows: MSDLKSRLIK ASTSKMTADL TKSKLFNNRD EVPTRIPMLN IALGGALNAG LQSGLTIFAA PSKHFKTLFG LTMVAAYMKK YKDAICLFYD SEFGASESYF RSMGVDLDRV VHTPIQSVEQ LKVDMTNQLD AIERGDKVII FIDSIGNTAS KKETEDALNE KVVGDMSRAK ALKSLFRIVT PYLTIKDIPC VAI NHTYQTQEWSKTVMSGGTGILYSAN TVFFISKRQV KEGTELTGYD FTLKAEKSRT VKEKSTFPIT VNFDGGIDPF SGLLEMATEI GFVVKPKAGW YAREFLDEET GEMIREEKSW RAKATDCVEF WGPLFKHKPF RDAIETKYKL GAISSIKEVD DAVNDLINCK ATTKVPVKTS DAPSAADIEN DLDEMEDFDE (SEQ ID NO:122)

Activity of Rb69 H64S

A kinetic study of the activity of mutant Rb69 H64S protein compared to wild type Rb69, or T4 UvsX, was made. A fluorescent probe based monitoring approach was taken. General conditions were as for the experiment shown in FIG. 13 with the exception of the type and concentrations of recombination components, and that PEG compound was employed at 7% w/v. Other changes are as follows: 120 ng/µl T4 UvsX, 900 ng/µl T4 gp32, 50 ng/µl T4 UvsY, OR 100 ng/µl Rb69 or Rb69 H64S UvsX, 400 ng/µl Rb69 gp32, 80 ng/µl Rb69 UvsY. Target DNA was present at 100 copies total. As shown in FIG. 22, the Rb69 H64S protein works according to this assay (although this experiment does not address the nature of the DNA generated during amplification) and seems to outperform the kinetics of the wild-type protein. In the next experiment performed the rate under apparently identical conditions (400 ng/µl Rb69 gp32) the outcome was slightly different. This is most likely due to slight pipetting errors in the latter experiment.

Rb69 H64S—Relative Resistance to gp32 Up-Titration

A kinetic study of the activity of mutant Rb69 H64S protein compared to wild type Rb69 was made in which the quantity of Rb69 gp32 was varied somewhat. A fluorescent probe based monitoring approach was taken. General conditions were as for the experiment shown in FIG. 22 with the exception of a variable concentration of gp32 protein, and that PEG compound was employed at 6% w/v. Conditions were: 100 ng/µl Rb69 or Rb69 H64S UvsX, Rb69 gp32 concentration as indicated, 80 ng/µl Rb69 UvsY. Target DNA was present at 100 copies total. As shown in FIG. 23, up-titration of gp32 had less impact on kinetics of Rb69 H64S compared to Rb69 protein. It was concluded that RbH64S is somewhat more resistant to competition by gp32.

Activity of Rb69 H64S Compared to Wild Type Rb69

A kinetic study of the activity of mutant Rb69 H64S protein compared to wild type Rb69 was made. A fluorescent probe based monitoring approach was taken. General conditions were as for the experiment shown in FIG. 22 with the exception of the type and concentrations of recombination components, and that PEG compound was used at 6% w/v. Other conditions are as follows: 100 ng/µl Rb69 or Rb69 H64S UvsX, 400 ng/µl Rb69 gp32, 80 ng/µl Rb69 UvsY. Target DNA was present at 0 copies, 100 copies, or 1000 copies total as indicated. As shown in FIG. 24, the Rb69 H64S protein works well according to this assay and outperforms the behaviour of the wild-type protein.

Activity of Rb69 UvsX H64S at 300-500 ng/µl gp32

Figure 25:
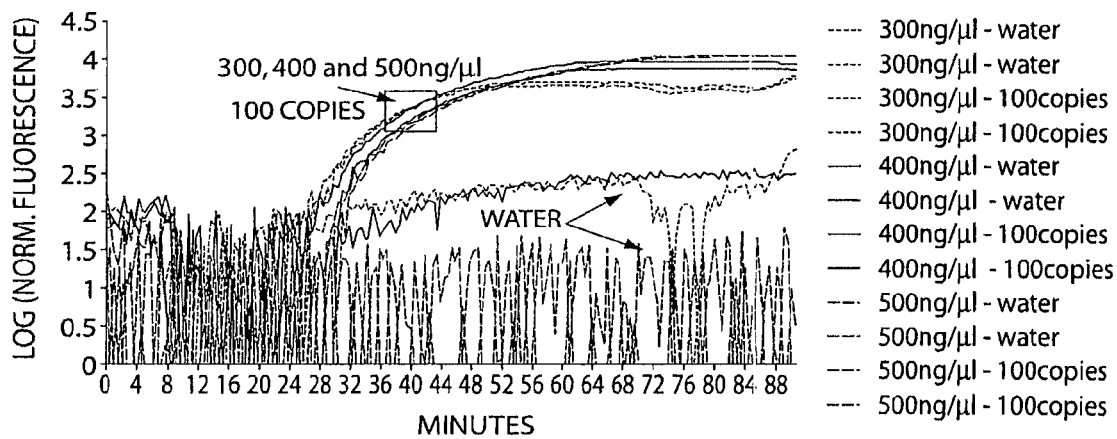
FIG. 25 is a graph showing mutant Rb69 H64S UvsX is functional in RPA over a range of Rb69 gp32 concentrations (300, 400, or 500 ng/µl of Rb69 gp32 protein). Samples were analyzed using a fluorescent probe.

A kinetic study of the activity of mutant Rb69 H64S protein was made under conditions of 300, 400, or 500 ng/µl of Rb69 gp32 protein. A fluorescent probe based monitoring approach was taken. General conditions were as for the experiment shown in FIG. 22 but gp32 concentrations were varied and PEG compound was used at 6% w/v. Protein concentrations were thus as follows: 100 ng/µl Rb69 H64S UvsX, 300-500 ng/µl Rb69 gp32, 80 ng/µl Rb69 UvsY. Target DNA was present at 0 (water control) or 100 copies total as indicated. As shown in FIG. 25, the Rb69 H64S protein works well according to this assay with little difference in kinetic behaviour over the tested range of Rb69 gp32 protein.

Titration of Rb69 UvsX H64S

Figure 26:
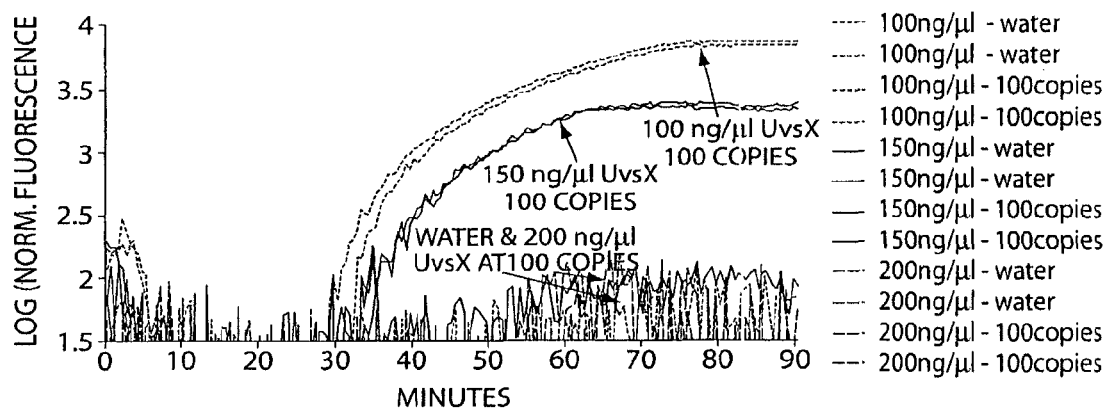
FIG. 26 is a graph showing a titration of mutant Rb69 H64S UvsX in RPA (00, 150 or 200 ng/µl Rb69 H64S UvsX). Samples were analyzed using a fluorescent probe.

A kinetic study of the activity of mutant Rb69 H64S UvsX protein was made under varying concentrations of UvsX protein. A fluorescent probe based monitoring approach was taken. General conditions were as for the experiment shown in FIG. 22 but the concentration of Rb69 H64S UvsX was varied and PEG compound was used at 6% w/v. Protein concentrations were thus as follows: 100, 150 or 200 ng/µl Rb69 H64S UvsX, 500 ng/µl Rb69 gp32, 80 ng/µl Rb69 UvsY. Target DNA was present at 0 (water control) or 100 copies total as indicated. As shown in FIG. 26, the Rb69 H64S protein works well according to this assay providing that the UvsX concentration does not significantly exceed 100 ng/µl.

Another kinetic study of the activity of mutant Rb69 H64S protein was performed under varying concentrations of UvsX protein using a fluorescent probe based monitoring approach. General conditions were as for the experiment shown in FIG. 22 but the concentration of Rb69 H64S UvsX was varied and PEG compound was employed at 6% w/v. Protein concentrations were thus as follows: 60, 80 or 100 ng/µl Rb69 H64S UvsX, 500 ng/µl Rb69 gp32, 80 ng/µl Rb69 UvsY. Target DNA was present at 0 (water control) or 100 copies total as indicated. As shown in FIG. 27, the Rb69 H64S protein works well according to this assay regardless of whether the protein was in the range 60-100 ng/µl.

Effectiveness of Rb69 gp32 in Reactions with T4 UvsX and UvsY

A kinetic study investigating the utility of Rb69 gp32 when combined with T4 UvsX and UvsY was performed. RPA reactions were established using primers J1 (120 ng/µl) and K2 (480 ng/µl) under the following conditions: 50 mM Tris. acetate pH 7.9, 100 mM Potassium acetate, 14 mM Magnesium acetate, 50 mM Creatine phosphate (Calbiochem), 3 mM ATP (Roche), 200 micromolar dNTPs, 50 ng/µl creatine kinase (Roche), 120 ng/µl T4 UvsX, 30 ng/µl T4 UvsY, 900 ng/µl T4 gp32 OR 500 ng/µl Rb69 gp32 OR 1000 ng/µl, 30 ng/µl Bsu polymerase, 6% PEG 35,000, 120 nM fluorescent probe BsFlc. Exonuclease III was included at 65 ng/µl. Reactions were established on ice in a 384-well plate, and then transferred to a BIOTEK Flx-800 fluorescence microplate reader with stage set to 38° C. at which time measurements were taken periodically from a bottom-reading probe. Samples contained either water or 100 copies of *B. subtilis* genomic DNA containing the target sequence as indicated in the legend. As shown in FIG. 28, all template positive samples worked effectively and there appeared to be little difference between using T4 and Rb69 gp32 protein.

T4 Outperforms Rb69 UvsX/UvsY System when Rb69 gp32 is Used in Both Cases

A kinetic study investigating the utility of Rb69 gp32 when combined with T4 UvsX and UvsY, or when combined with Rb69 UvsX and UvsY. RPA reactions were established using primers J1 (120 nM) and K2 (480 nM) under the following conditions: 50 mM Tris.acetate pH 7.9, 100 mM Potassium acetate, 14 mM Magnesium acetate, 50 mM Creatine phosphate (Calbiochem), 3 mM ATP (Roche), 200 micromolar dNTPs, 50 ng/µl creatine kinase (Roche), 120 ng/µl T4 UvsX, 30 ng/µl T4 UvsY, 1000 ng/µl Rb69 gp32, 30 ng/µl Bsu polymerase, 6% PEG 35,000, 300 nM amplification primers, 120 nM fluorescent probe BsFlc. Exonuclease III was included at 65 ng/µl. Alternatively similar conditions were employed but the recombinase was 100 ng/µl Rb69 UvsX and the loading protein was 80 ng/µl Rb69 UvsY protein. Reactions were established on ice in a 384-well plate, and then transferred to a BIOTEK Flx-800 fluorescence microplate reader with stage set to 38° C. at which time measurements were taken periodically from a bottom-reading probe. Samples contained either water or 100 copies of *B. subtilis* genomic DNA containing the target sequence as indicated in the legend. As shown in FIG. 29, all template positive samples developed positive signals, however the system established with T4 UvsX and UvsY develop much earlier and stronger signals. It was concluded that when the Rb69 gp32 concentration is raised to 1000 ng/µl Rb69 little inhibition of amplification occurs when the T4 components are used, but when Rb69 UvsX and UvsY are used there is significant inhibition (see effects of Rb69 gp32 overtitration with Rb69 UvsX and UvsY in FIG. 23).

Poor Activity of Rb69 UvsX H64T Protein

Figure 30:
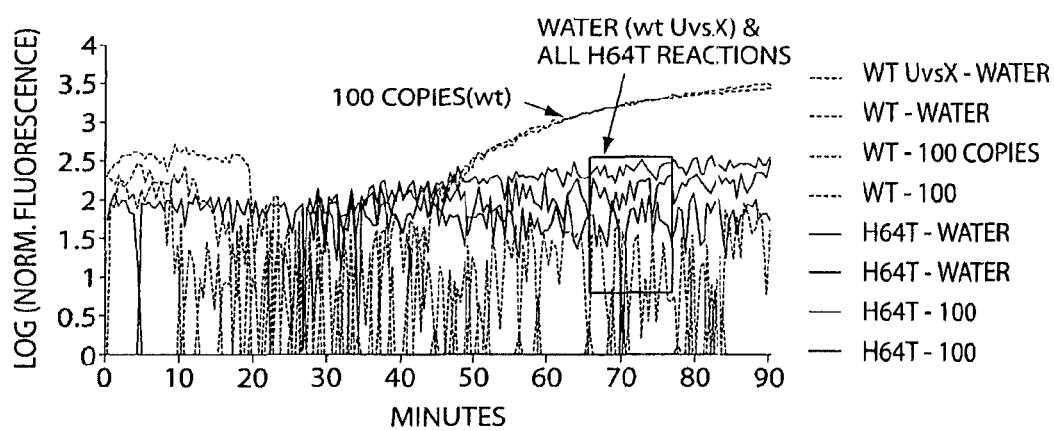
FIG. 30 is a graph showing the kinetic behaviour of mutant Rb69 UvsX H64T in RPA. Samples were analyzed using a fluorescent probe.

An RB69 UvsX-encoding clone was generated in which histidine 64 was altered to a threonine. This mutation was analogous to the Rb69 UvsX H64S protein assessed earlier, and was designed to test whether a threonine residue would be as effective as a serine residue at improving RPA behaviour. General reaction conditions were the same as described for the experiment in FIG. 29 with the following exceptions: UvsX was either Rb69 wild type UvsX at 100 ng/µl or Rb69 UvsX H64T at 100 ng/µl, Rb69 UvsY at 80 ng/µl, and 500 ng/µl Rb69 gp32. DNA target was present either at 0 or 100 copies. As shown in FIG. 30, reactions performed using Rb69 UvsX H64T barely developed signal and it was deduced that this amino acid substitution is not effective in contrast to when a serine is substituted at this position.

ATP Titration Using Rb69 UvsX

Figure 31:
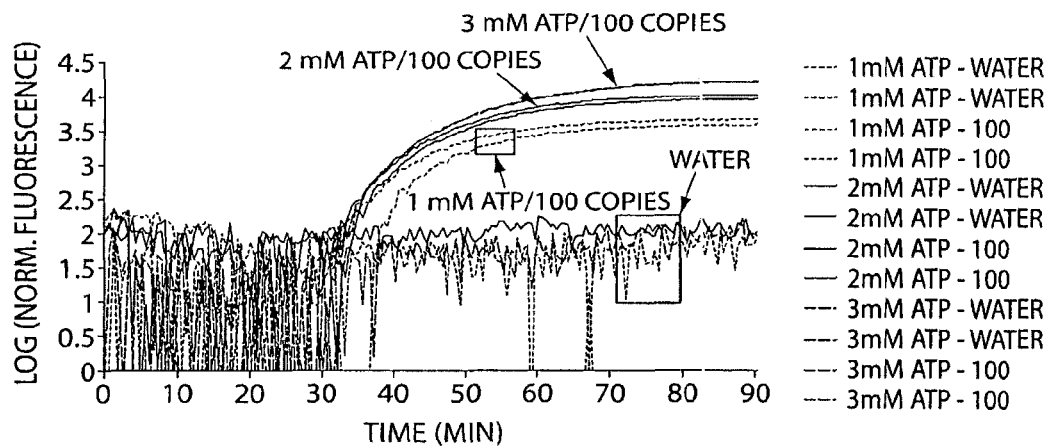
FIG. 31 is a graph showing ATP titration when using Rb69 UvsX in RPA. Samples were analyzed using a fluorescent probe.

The effects of different ATP concentrations on the amplification kinetics when using Rb69 UvsX protein were investigated. Reaction conditions were as in FIG. 30 but only wild-type Rb69 gp32, UvsX, and UvsY were used. The final concentration of ATP was adjusted to either 1 mM, 2 mM, or 3 mM. Target was present at either 0 or 100 copies as indicated. As shown in FIG. 31, amplification occurred in all cases that target DNA was present, but the strongest signals develop when 3 mM ATP is used.

Suppressing Effect of T4 gp32 on Rb69 UvsX and UvsY

The effects using T4 gp32 protein with Rb69 UvsX and UvsY proteins were investigated. Conditions were the same as those described in FIG. 29 with the following modifications. Rb69 UvsX was used at 100 ng/µl, Rb69 UvsY was used at 80 ng/µl, and gp32 was either Rb69 gp32 at 500 ng/µl OR T4 gp32 at 500 ng/µl OR T4 gp32 at 1000 ng/µl. As shown in FIG. 32, signals only develop when Rb69 gp32 is used, and not when T4 gp32 is employed contrasting with the full compatibility of Rb69 gp32 when used with T4 heterologous components.

Consequences of Modification to the C Terminus of Rb69 UvsX

A kinetic analysis of amplification reactions configured with Rb69 UvsX H64S, with Rb69 UvsX H64S LSD, and with Rb69 UvsX H64S 2xLDE was performed. General reaction conditions were as described in FIG. 29, except that different UvsX proteins were used in all cases at 100 ng/µl. Rb69 UvsY was used at 80 ng/µl. Rb69 gp32 was used at 500 ng/µl. DNA target was present at either 0 or 1000 copies. As shown in FIG. 33, strong signals develop in all target-containing samples and show similar kinetics. A very slight tendency for the proteins with more acidic C-termini (LSD and 2xLDE clones) to initiate signal very slightly later and to generate slightly stronger signals in total is seen.

A similar experiment to that described in FIG. 33 was performed. However in this case DNA target was present at either 0 or 100 copies. As shown in FIG. 34, strong signals develop in all target-containing samples and show, once again, fairly similar kinetics. In this case, a slightly stronger tendency for the proteins with more acidic C-termini (LSD and 2xLDE clones) to initiate signal slightly later and to generate stronger signals was observed.

Titration of PEG When Using Rb69 UvsX H64S/2xLDE

Figure 35:
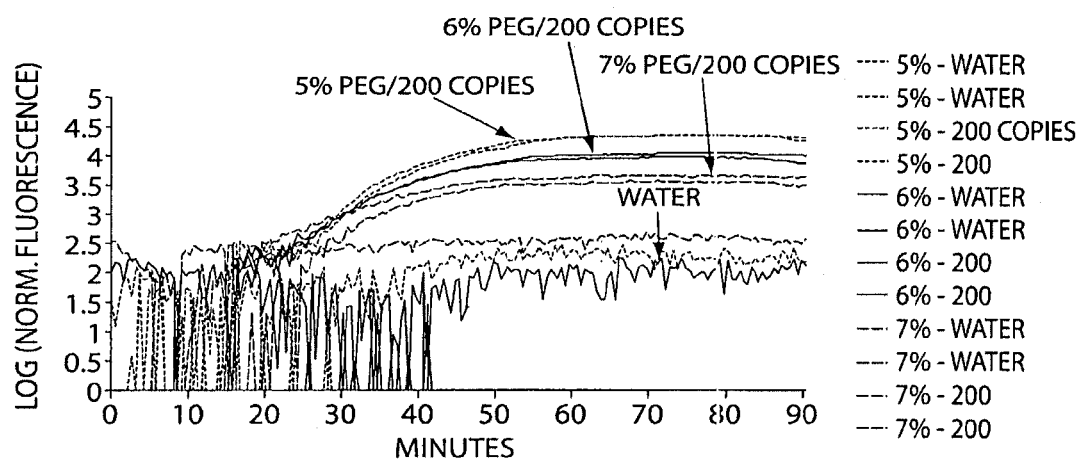
FIG. 35 is a graph showing the titration of PEG 35,000 when using mutant Rb69 UvsX H64S 2xLDE in an RPA reaction. Samples were analyzed using a fluorescent probe.

Similar conditions were employed as in the experiment described in FIG. 33. However in this case only Rb69 UvsX H64S 2xLDE was used and at a concentration of 100 ng/µl, Rb69 UvsY was used at 80 ng/µl, and Rb69 gp32 was used at 500 ng/µl. DNA target was present at either 0 or 200 copies per reaction as indicated. The concentration of polyethylene glycol (M.W. 35,000 Fluka) was tested at 5%, 6%, and 7%. As shown in FIG. 35, the best signals were obtained when polyethylene glycol M.W. 35,000 was used at 5% w/v.

Example 9

Engineered UvsY Constructs

Figure 36:
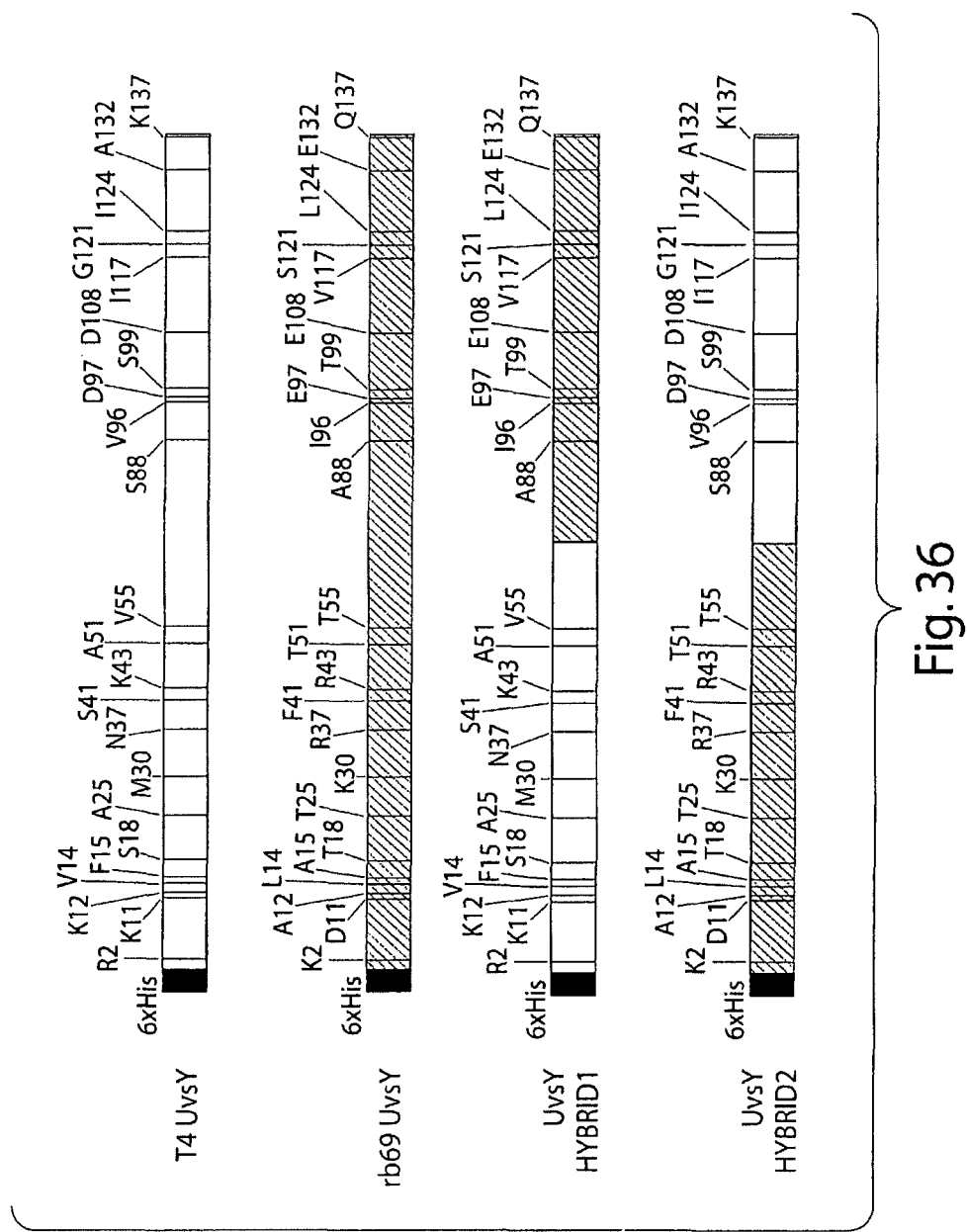
FIG. 36 is a schematic of novel, engineered, hybrid UvsY constructs.

A schematic representation is shown of the peptide sequence predicted to be encoded by the T4 UvsY and Rb69 UvsY genes is shown in FIG. 36. Residues that are substituted between these 2 proteins are indicated, all other residues are identical. Two chimeric clones which were used to express chimeric proteins were generated. Each chimera consisted of the N-terminal half of one UvsY molecule fused to the C-terminal half of the other. These are termed UvsY hybrid 1 and UvsY hybrid 2.

Activity of UvsY Hybrids with T4 UvsX and T4 gp32

An experiment was performed to address how well the T4, Rb69, and hybrid UvsY proteins described in FIG. 36 would function when combined with T4 UvsX and T4 gp32.

Standard conditions as described for the experiment in FIG. 29 were used but with the following modifications. T4 UvsX was employed at a concentration of 120 ng/µl, T4 gp32 was employed at 900 ng/µl, and the UvsY proteins tested were used at 80 ng/µl. DNA target was present at either 0 or 1000 copies in each reaction. PEG 35,000 (Fluka) was employed at 5% w/v. As shown in FIG. 37, all of the different forms of UvsY behaved excellently in this assay indicating that when T4 UvsX and T4 gp32 are employed there is little or no preference visible for T4 vs Rb69 UvsY, nor any significant distinction from the hybrid molecules.

Activity of UvsY Hybrids with Rb69 UvsX and Rb69 gp32

An experiment was performed to address how well the T4, Rb69, and hybrid UvsY proteins described in FIG. 36 would function when combined with Rb69 UvsX and Rb69 gp32. Standard conditions as described for the experiment in FIG. 37 were used but with the following modifications. Rb69 UvsX H64S 2xLDE was employed at a concentration of 100 ng/µl, Rb69 gp32 was employed at 500 ng/µl, and the UvsY proteins tested were used at 80 ng/µl. DNA target was present at either 0 or 1000 copies in each reaction. As shown in FIG. 38, all the forms of UvsY functioned in this assay, however there were strong differences in response time and signal strength. This indicates that when Rb69 UvsX and RB69 gp32 are employed there is a clear preference for Rb69 UvsY.

The sequence of UvsY hybrid 1 is as follows: HHHHHH-MRLEDLQEEL KKDVFIDSTK LQYEAANNVM LYSKWLNKHS SIKKEMLRIE AQKKVALKAR LDYYS-GRGDG DEFSMDRYEK SEMKTVLAAD KDVLKIETTL QYWGILLEFC SGALDAVKSR SFALKHIQDM REFEAGQ (SEQ ID NO:123). The N terminus six histidines are optional.

The sequence of UvsY hybrid 2 is as follows: HHHHHH-MKLEDLQEEL DADLAIDTTK LQYETANNVK LYSKWLRKHS FIRKEMLRIE TQKKT ALKAR LDYYS-GRGDG DEFSMDRYEK SEMKTVLSAD KDV-LKVDTSL QYWGILLDFC SGALDAIKSR GFAIKHIQDM RAFEAGK (SEQ ID NO:124). The N terminus six histidines are optional.

Example 10

Additional Analysis of Rb69 Engineered Constructs and Chimeras

No Activity for Rb69 UvsX H64S/T6-1/2xLDE

The activity of Rb69 UvsX H64S/T6-1 2xLDE in comparison to the robust activity of Rb69 UvsX H64S/2xLDE was investigated. Reactions were established according to standard conditions described in FIG. 29 with the following modifications. Rb69 UvsX H64S/2xLDE protein and Rb69 UvsX H64S/T6-1/2xLDE protein were used at 100 ng/µl, Rb69 gp32 was used at 600 ng/µl, and Rb69 UvsY was employed at 80 ng/µl. DNA target was present at either 0 or 1000 copies per reaction. As shown in FIG. 39, robust activity was exhibited by the Rb69 UvsX H64S/2xLDE protein, but no activity was detected with Rb69 UvsX H64S/T6-1/2xLDE protein. Apparently recoding the DNA-binding loop 2 sequence in this case resulted in a non-functional protein.

Titration of Rb69 gp32 in the Presence of Rb69 UvsX H64S/2xLDE

Figure 40:
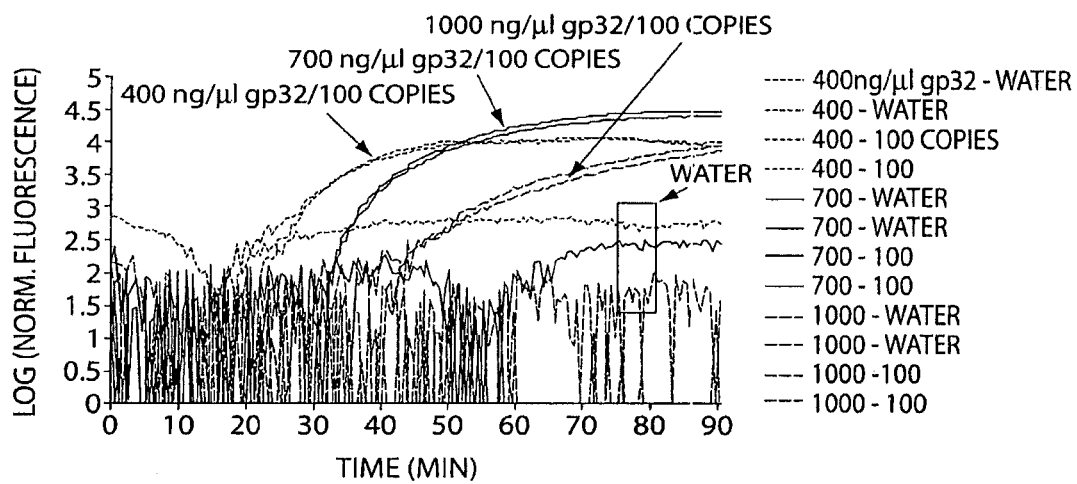
FIG. 40 is a graph showing the titration of Rb69 gp32 in the presence of mutant Rb69 UvsX H64S/2xLDE in RPA. Samples were analyzed using a fluorescent probe.

The effects of titrating Rb69 gp32 protein on amplification kinetics when employing the Rb69 UvsX/H64S 2xLDE protein were investigated. Reactions were established according to standard conditions described in FIG. 29 with the following modifications. PEG 35,000 (Fluka) was used at 5% w/v. Rb69 UvsX H64S/2xLDE protein was used at 100 ng/µl, Rb69 gp32 was used at 400, 700, or 1000 ng/µl, and Rb69 UvsY was employed at 80 ng/µl. DNA target was present at either 0 or 100 copies per reaction. As shown in FIG. 40, increasing quantities of Rb69 gp32 lead to a delay in onset of signal detection.

No activity for Rb69 UvsX H64S/F69M/G70S/T6-1/2xLDE

Figure 41:
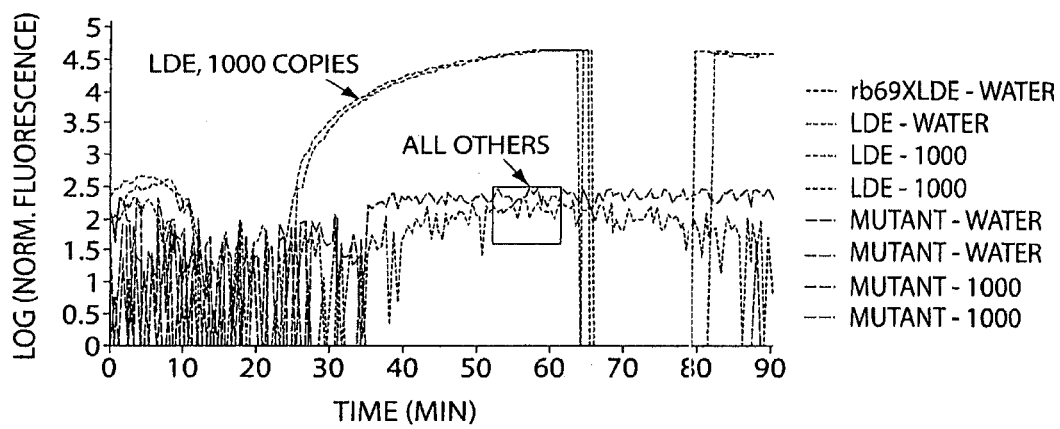
FIG. 41 is a graph showing the kinetic behaviour of mutant Rb69 UvsX H64S/2xLDE and Rb69 H64S/F69M/G70S/T6-1/2xLDE in RPA. Samples were analyzed using a fluorescent probe.

The effects of using Rb69 UvsX H64S/F69M/G70S/T6-1/2xLDE protein in amplification reactions were investigated. This clone was similar to that tested earlier containing most of the T6 UvsX DNA-binding loop 2, but also contained 2 additional T6-like residues near to the Walker A motif Reactions were established according to standard conditions described in FIG. 40 with the following modifications. Rb69 UvsX H64S/2xLDE protein or Rb69 UvsX H64S F69M/G70S/T6-1/2xLDE were used at 100 ng/µl, Rb69 gp32 was used at 500 ng/µl, and Rb69 UvsY was employed at 80 ng/µl. DNA target was present at either 0 or 1000 copies per reaction. As shown in FIG. 41, no activity is detected for the Rb69 UvsX H64S F69M/G70S/T6-1/2xLDE protein.

Strong Activity of Rb69 H64S T67S/L68N/T4/2xLDE and Rb69 H64S/T4/2xLDE

Figure 42:
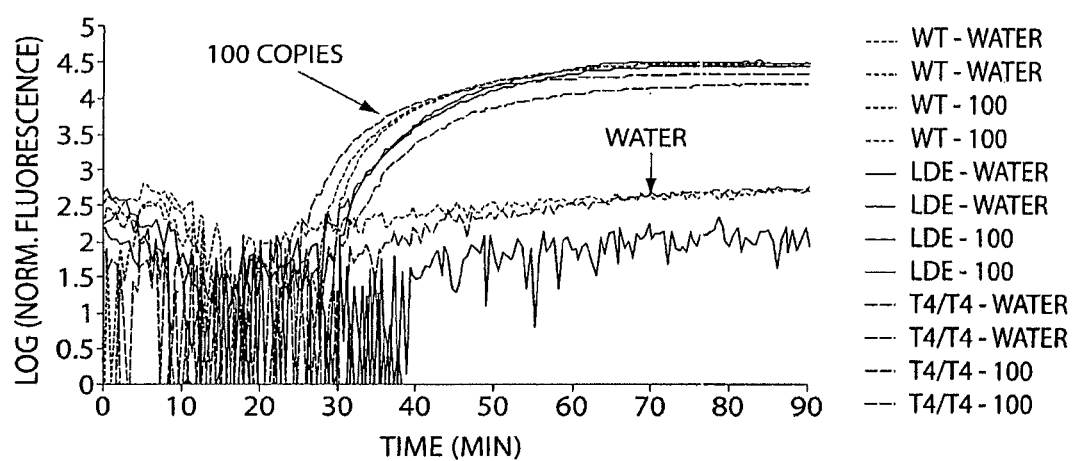
FIG. 42 is a graph showing the kinetic behaviour of mutant Rb69 H64S T68S/L68N/T4/2xLDE in RPA. Samples were analyzed using a fluorescent probe.

The effects of using Rb69 H64S T67S/L68N/T4/2xLDE and Rb69 H64S/T4/2xLDE protein in amplification reactions were investigated. These proteins were analogous to those tested earlier containing T6 UvsX DNA-binding loop 2 and/or additionally containing T6-like residues near to the Walker A motif, except that in this case the DNA-binding loop2 sequences and Walker A sequences were derived from T4 UvsX (see clone schematic chart). Reactions were established according to standard conditions described in FIG. 40 with the following modifications. Rb69 UvsX protein or Rb69 UvsX H64S/2xLDE or Rb69 UvsX H64S/T67S/L68N/T4/2xLDE were used at 100 ng/µl, Rb69 gp32 was used at 500 ng/µl, and Rb69 UvsY was employed at 80 ng/µl. DNA target was present at either 0 or 100 copies per reaction. As shown in FIG. 42, excellent activity was detected for all UvsX proteins tested indicating that the T4 DNA-binding loop and associated Walker A residues may be substituted successfully into the Rb69 UvsX protein.

Rb69 UvsX H64S/T67S/L68N/T4/2xLDE Protein is Relatively Resistant to Up-Titration of Rb69 gp32

The inhibitory effect of overtitration of Rb69 gp32 on reaction kinetics comparing wild-type Rb69 UvsX and Rb69 UvsX H64S/T67S/L68N/T4/2xLDE was investigated. Reactions were established according to standard conditions described in FIG. 40 with the following modifications. Rb69 UvsX protein or Rb69 UvsX H64S/T67S/L68/T4/2xLDE were used at 100 ng/µl, Rb69 gp32 was used at either 400 or 800 ng/µl, and Rb69 UvsY was employed at 80 ng/µl. DNA target was present at either 0 or 100 copies per reaction. As shown in FIG. 43, the slowing in time to detection experienced for Rb69 UvsX H64S/T67S/L68N/T4/2xLDE compared to wild-type Rb69 UvsX when increasing the gp32 concentration was only about half as much. It was concluded that the substituted protein is less sensitive to gp32 concentration.

Rb69 UvsX H64S/T67S/L68N/T4/2xLDE Protein can Function with T4 gp32

Figure 44:
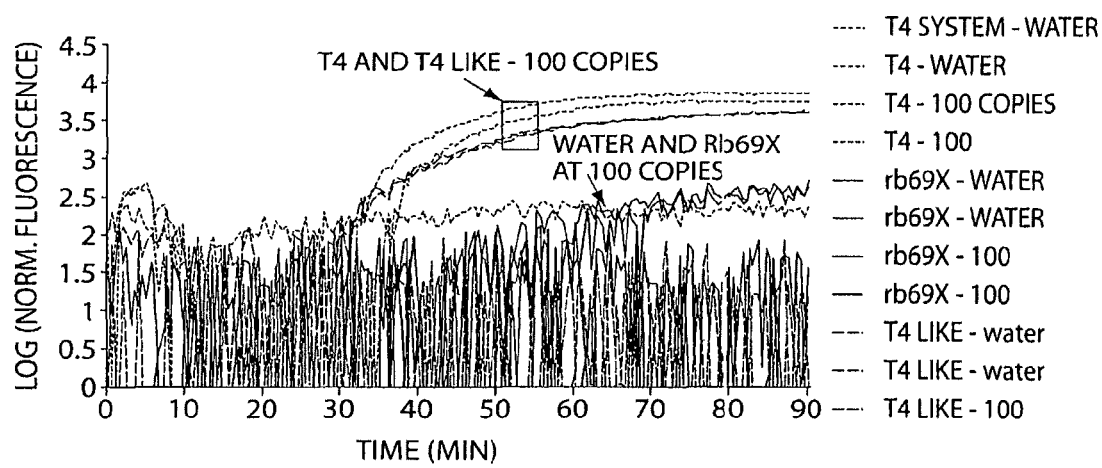
FIG. 44 is a graph showing the activity of mutant Rb69 UvsX H64S/T67S/L68N T4 2xLDE protein with T4 gp32 in RPA. Samples were analyzed using a fluorescent probe.

Whether or not the inhibitory effect of T4 gp32 on reactions configured with Rb69 UvsX and UvsY could be overcome by the use of Rb69 UvsX H64S/T67S/L68N/T4/2xLDE was investigated. Reactions were established according to standard conditions described in FIG. 40 with the following modifications. T4 UvsX protein or Rb69 UvsX or Rb69 UvsX H64S/T67S/L68N/T4/2xLDE were used at 120 ng/µl or 100 ng/µl or 100 ng/µl respectively, T4 gp32 was used at 700 ng/µl, and T4 or Rb69 UvsY was employed at 30 ng/µl or 80 ng/µl respectively. T4 UvsX was combined with T4 UvsY, and the Rb69 UvsX proteins were combined with Rb69 UvsY. DNA target was present at either 0 or 100 copies per reaction. As shown in FIG. 44, Rb69 UvsX H64S/T67S/L68N/T4/2xLDE functioned almost as well as the T4 components, while wild-type Rb69 UvsX was inactive when T4 gp32 was used. It was concluded that the substituted Rb69 protein has developed very good tolerance to T4 gp32.

Figure 45:
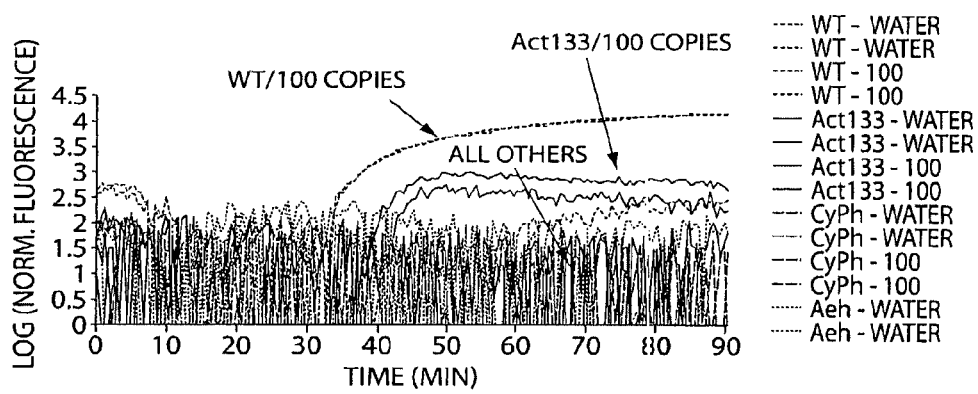
FIG. 45 is a graph showing the activity of Rb69 UvsX chimeras containing DNA-binding loops from phage 133, cyanophage, and Aeh1 in RPA. Samples were analyzed using a fluorescent probe.

Rb69 UvsX Chimeras Containing DNA-Binding Loops from Phage 133 Work Weakly, while Cyanophage and Aeh1 Loops are Non-Functional The activity of Rb69 UvsX proteins in which the DNA-binding loop2 had been replaced with sequences found in other diverse UvsX-like molecules was investigated. Reactions were established according to standard conditions described in FIG. 40 with the following modifications. Rb69 UvsX protein or Rb69 UvsX loop 133 or Rb69 loop Cyano or Rb69 loop Aeh1 were used at 100 ng/µl, Rb69 gp32 was used at either 500 ng/µl, and Rb69 UvsY was employed at 80 ng/µl. As shown in FIG. 45, no activity was detected for the proteins containing cyanophage or Aeh1 loops, while the protein containing the Phage 133 loop showed very weak activity.

Rb69 UvsX H64S/T6/2xLDE is Active Unlike the Equivalent Lacking the Final G to T Substitution of the DNA-Binding Loop2

The activity of Rb69 UvsX H64S/T6/2xLDE was tested, that is a protein in which the final residue that differs between T4 and T6 has been altered to the T6 equivalent unlike the case with Rb69 UvsX H64S T6-1 2xLDE. Also tested was a protein in which the DNA-binding loop2 had been replaced with a hybrid of the Aeh1 loop and the Rb16 loop (possessing the unusual alanine at the beginning of the Aeh1 loop instead of the cysteine found in Rb16) Reactions were established according to standard conditions described in FIG. 40 with the following modifications. Rb69 UvsX protein or Rb69 UvsX H64S/T6/2xLDE or Rb69 loop (hybrid Aeh1/Rb16) were used at 100 ng/µl, Rb69 gp32 was used at either 500 ng/µl, and Rb69 UvsY was employed at 80 ng/µl. As shown in FIG. 46, no activity was detected for the proteins containing the Aeh1/Rb16 hybrid loop, however the protein containing the repaired T6 loop showed excellent activity. It was concluded that a complete replacement of the T6-like DNA-binding loop 2 results in activity, but hybrids of the similar T4 and T6 loops are not active indicating that substitutions between T4 and T6 are not silent and must be exchanged in groups.

Example 11

Manganese Ions are Able to Support RPA Reactions

RPA reactions were established under the following conditions: 50 mM Tris. acetate pH8.3, 100 mM Potassium acetate, 200 µM dNTPs, 3 mM ATP, 50 mM phosphocreatine, 120 ng/µl T4 UvsX, 30 ng/µl T4 UvsY, 900 ng/µl T4 gp32, 5% PEG 35,000, 30 ng/µl Bsu polymerase, 1000 copies *B. sub-tilis* genomic DNA. Divalent manganese cations were supplied individually to each reaction to give final concentrations of 0.1 mM, 0.5 mM, 1 mM, 2 mM, 3 mM. Alternatively as a control 16 mM Magnesium was employed. Reactions were incubated at 37° C. for 90 minutes, purified on PCR clean-up columns (SIGMA) and then separated on a 2% agarose gel before visualization with ethidium bromide. As shown in FIG. 47, manganese ions efficiently supported RPA in the concentration range of 0.5 to 3 mM manganese. Significantly higher concentrations (from about 4-5 mM Manganese—not shown here) started to inhibit reactions behaviour which lead to progressively less product until at 10 mM manganese no product was detected with these primers after 90 minutes. Some carry-over of magnesium ions from buffers is anticipated, perhaps accounting for roughly 0.5 mM magnesium ions total per reaction.

Example 12: *Staphylococcus aureus* Polymerase I Large Fragment Functions Well in RPA Reactions RPA reactions were configured using alternative polymerases capable of strand displacement synthesis, including bacterial polymerase I repair enzymes which bear homology to the Pol I class of *E. coli, Bacillus subtilis*, and *Staphylococcus aureus*. In this experiment, either the *Bacillus subtilis* PolI large fragment described elsewhere and herein, or with the equivalent large fragment from *S. aureus*, generated in-house were used in RPA reactions. Reactions were configured under standard conditions, namely: 300 nM primer J1, 300 nM primer K2, 50 mM Tris.acetate pH 7.9, 100 mM Potassium acetate, 200 µM dNTPs, 3 mM ATP, 50 mM phosphocreatine, 120 ng/µl T4 UvsX, 30 ng/µl T4 UvsY, 900 ng/µl T4 gp32, 5% PEG compound (SIGMA), 70 ng/µl Bsu polymerase OR 70 ng/µl *S. aureus* (Sau) polymerase, and 0, 100, 1000 or 10,000 copies *B. subtilis* genomic DNA. Reactions were monitored by the inclusion of 1:50,000 dilution of SYBR green (Invitrogen). As shown in FIG. 48, iboth cases robust amplification occurred. If anything the temporal separation between water and target-containing samples was larger when *S. aureus* polymerase was employed. This could indicate that this polymerase displays slightly improved characteristics for sensitive RPA reactions.

Example 13

Use of Heparin in RPA Reactions

Heparin Slows the Development of Signals in Zero-Target Controls

RPA reactions were configured using the J1 and K2 primers used elsewhere in this disclosure but deliberately omitted target DNA. Reactions were configured under standard conditions, namely: 300 nM primer J1, 300 nM primer K2, 50 mM Tris.acetate pH 7.9, 100 mM Potassium acetate, 200 µM dNTPs, 3 mM ATP, 50 mM phosphocreatine, 120 ng/µl T4 UvsX, 30 ng/µl T4 UvsY, 900 ng/µl T4 gp32, 5% PEG compound (SIGMA), 30 ng/µl Bsu polymerase. Reactions were monitored by the inclusion of 1:50,000 dilution of SYBR green (Invitrogen). Heparin was either not included in the reaction, or present at 20 ng/µl. As shown in FIG. 49, after some time background signals develop in all reactions, however this occurs later for those samples containing heparin suggesting it slows noise development.

Heparin Improves Signal: Noise Ratios in RPA Reactions

A kinetic study was made to investigate the effects of heparin on the sensitivity and kinetics of amplification reactions monitored via a probe-based approach. RPA reactions were established using primers J1 (120 ng/μl) and K2 (480 ng/μl) under the following conditions: 50 mM Tris.acetate pH 7.9, 100 mM Potassium acetate, 14 mM Magnesium acetate, 50 mM Creatine phosphate (Calbiochem), 3 mM ATP (Roche), 200 micromolar dNTPs, 50 ng/μl creatine kinase (Roche), 120 ng/μl T4 UvsX, 30 ng/μl T4 UvsY, 1000 ng/μl Rb69 gp32, 30 ng/μl Bsu polymerase, 5% PEG compound, 120 nM fluorescent probe BsFlc. Exonuclease III was included at 65 ng/μl. Heparin was either absent or present at 20 ng/μl as indicated. Reactions were established on ice in a 384-well plate, and then transferred to a BIOTEK Flx-800 fluorescence microplate reader with stage set to 38° C. at which time measurements were taken periodically from a bottom-reading probe. Samples contained either water, 10, 100, 1000 or 10,000 copies of *B. subtilis* genomic DNA containing the target sequence as indicated in the legend. As shown in FIG. 50, all template positive samples developed positive signals, however the system established with heparin showed improvement in the consistency of signal development at 10 copies It was concluded that the heparin inclusion slowed noise development which lead to less of a breakdown of simultaneity of signal detection at low copy numbers.

Example 14

3'-Blocked Primers and *E. coli* Exonuclease III in RPA Reactions

Strong evidence was discovered which suggests that primers which were 3'-blocked with groups such as biotin, via a carbon-oxygen-carbon linkage at least, may be successfully employed as amplification primers if *E. coli* exonuclease III is included in the reaction. This experiment provides an example of this phenomenon. In this experiment RPA reactions were performed by amplifying a fragment from the *Bacillus subtilis* genome using the primers J1 and K2 used widely in this document. The use of a primer designated K2-epsilon which had been designed for other purposes. This primer has the same sequence as the K2 primer, but differs in its possession of a 3'-blocking biotin group which is attached via a linker and described as biotin-TEG (see suppliers website http://uk.eurogentec.com). This constitutes a biotin attached via a linker which is joined to the 3' sugar via an oxygen atom. The K2-epsilom primer also contains a deoxyuracil residue replacing a deoxythymidine residue within the body of the sequence, however this is considered of no relevance to this experiment. Reactions contained the J1 primer paired with the K2 primer OR the K2-epsilon 'blocked' primer, and either exonuclease III or *E. coli* Nfo protein. RPA reactions were established using primers J1 (120 ng/μl) and K2 or K2 epsilon (480 ng/μl) under the following conditions: 50 mM Tris.acetate pH 7.9, 100 mM Potassium acetate, 14 mM Magnesium acetate, 50 mM Creatine phosphate (Calbiochem), 3 mM ATP (Roche), 200 micromolar dNTPs, 50 ng/μl creatine kinase (Roche), 120 ng/μl T4 UvsX, 30 ng/μl T4 UvsY, 1000 ng/μl T4 gp32, 30 ng/μl Bsu polymerase, 5% PEG compound, 120 nM fluorescent probe BsFlc.

Figure 51:
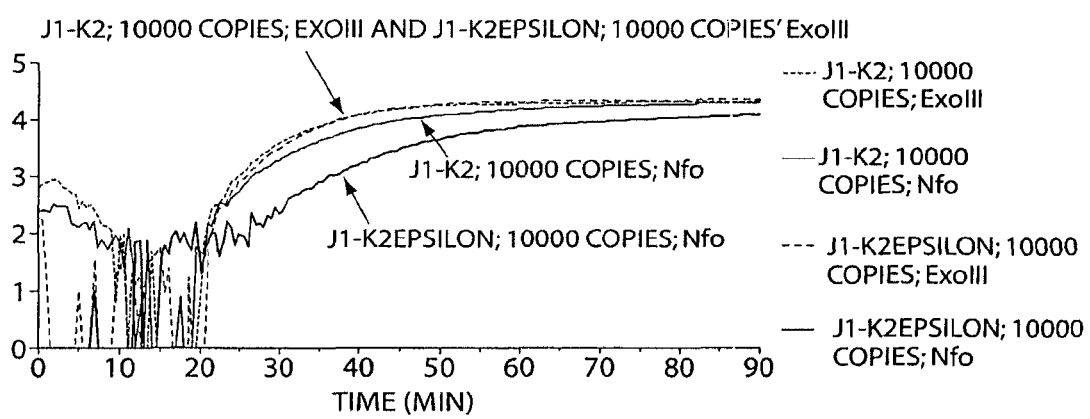
FIG. 51 is graph showing DNA amplification using blocked primers in RPA. Samples were analyzed using a fluorescent probe.

Exonuclease III was included at 65 ng/μl or endonuclease IV (Nfo) was included at 200 ng/μl. Despite the blocked nature of the K2 epsilon primer, when exonuclease III is used as the agent to process the probe to generate fluorescence, there is no difference in amplification kinetics between samples employing K2 and those employing K2-epsilon, as shown in FIG. 51. This suggests that exonuclease III rapidly processes non-extendable hybrids of template bound to K2-epsilon into extendable forms, presumably either by exo- nuclease activity or via the 3'-diesterase or phosphatase types of activity that have been attributed to this enzyme and Nfo (also known as endonuclease IV). In contrast, when Nfo was employed in place of Exo III, there was a general delay in amplification but this was much more marked for the J1 paired with K2-epsilon reaction. It was concluded that the 'activation' process works poorly when Nfo is employed, but very rapidly when exoIII is employed.

Example 15

UvsY-Free DNA Amplification

A series of experiments were performed to investigate the effects on DNA amplification by removing UvsY from the RPA reaction.

UvsY-Free DNA Amplication Using T6 H66S

In this experiment RPA was performed under the following conditions: 100 mM Potassium acetate, 50 mM Tris.acetate pH 8.3, 14 mM Magnesium acetate, 5 mM dTT, 200 mM dNTPs, 50 mM Creatine phosphate (Calbiochem), 2.5 mM ATP (Roche), 50 ng/μl Creatine Kinase (Roche), 300 nM amplification primers, 5% PEG 35,000, 43 ng/μl S.au Polymerase, 600 ng/μl Rb69 gp32, 120 ng/μl T6 H66S UvsX and 79 ng/μl Rb69 UvsY, where appropriate. Reactions were carried out using 1000 copies MS2 DNA template with primer MS2 downRT2 and primer MS2 up4, up5, up6 or up7, and in the presence or absence of Rb69 UvsY. Reactions were established on ice and then transferred to 37° C. for 1 hour. Following amplification, the products were purified using the GenElute PCR cleanup kit (Sigma) and visualised using gel electrophoresis. Discovered unexpectedly was that T6 H66S recombinase could effectively amplify DNA in RPA reactions in the absence of UvsY. As shown in FIG. 52, products of the correct size were amplified in the presence of UvsY. In the absence of UvsY, with the exception of the MS2 downRT2+MS2 up5 reaction products, the most abundant product appeared to be of the same size as that synthesised when UvsY is present. It was concluded that, with the template and primer pairs used, RPA DNA amplification is possible in the absence of UvsY and that such reactions often produce products of the correct size.

An additional experiment was carried out to explore whether the UvsY-independent amplification observed previously would occur using different primer pairs synthesising different sized products. The results for this additional experiment exquisitely show just how effective amplification can be using the T6 H66S recombinase in the absence of UvsY (although kinetics are not investigated). General reaction conditions were the same as described in for the experiment depicted in FIG. 52, with the following exceptions: reactions were carried out using primer MS2 down5 with primer MS2 up5, up6, up7 or up2. Reactions were also carried out using primers MS2 down2 and MS2 up4. Amplification products were made when using any of the primer combinations and in both presence and absence of UvsY. As shown in FIG. 53, all reactions worked well except with the MS2 down5/up5 primer pair, although this still produced a small amount of the correct product. The major product from each reaction was of the correct size regardless of whether UvsY was present in the reaction or not. In the absence of UvsY there appeared to be a greater abundance of incorrect products, however these were present in lower amounts than the correct product. It was concluded that different sized RPA products can be amplified using a variety of primer pairs and that the ability of the reaction to proceed in the absence of UvsY is unlikely to be dependent upon the primers used or the resultant product size.

UvsY-Free Amplification of Small Genomic DNA Targets

A study was performed to investigate whether, in the absence of UvsY, the size of the DNA target plays a role in the ability of RPA to amplify DNA. To this end, a small 305 bp RPA product, amplified from human genomic DNA, was used as the DNA target in an RPA reaction. Reaction conditions were the same as stated for the experiment depicted in FIG. 52, with the exception that the reactions were carried out using 1000 copies of DNA target with primer ApoB4 and either primer ApoB300, ApoB3, ApoB7 or ApoB10, which generate products of 305 bp, 210 bp, 143 bp and 141 bp, respectively. As shown in FIG. 54, in the absence of UvsY all of the reactions generated DNA amplicons, however despite an apparently robust capability to synthesise DNA products in the absence of UvsY, products generated using T6 H66S UvsX without UvsY were not always those of the expected size and the same size as those produced in the presence of UvsY. Presumably primer-related artefacts are sometimes dominant to bona fide product formation, although the reasons are unclear. It was concluded that in the absence of UvsY, DNA amplification occurs reasonably proficiently using a small DNA target but unlike when UvsY is present, the product is always of the correct size.

UvsY Free Amplification of Complex Genomic Targets

Figure 55:
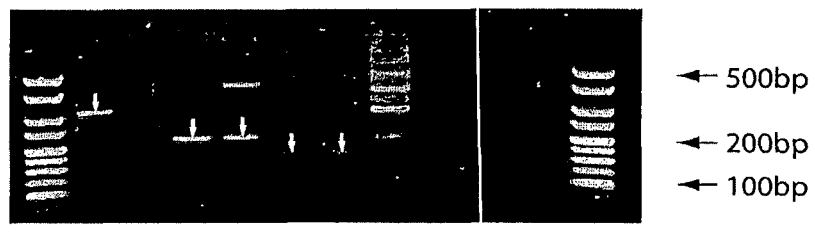
FIG. 55 is a picture of an ethidium bromide stained agarose gel showing DNA amplification of complex genomic DNA targets using T6 H66S UvsX and Rb69 gp32 in the presence or absence of UvsY loading agent.

This experiment addressed whether low copy numbers of complex genomic targets may be amplified in the absence of UvsY. Reaction conditions were the same as described for the experiment depicted in FIG. 52, with the exception that reactions were carried out using 1000 copies of human genomic DNA with primer ApoB4 and either primer ApoB300, ApoB3, ApoB7 or ApoB10, which generate products of 305 bp, 210 bp, 143 bp and 141 bp, respectively. As shown in FIG. 55, in the absence of UvsY, DNA amplification occurred for all reactions, however the products generated using T6 H66S UvsX without UvsY were not always those of the expected size and the same size as those produced in the presence of UvsY. It was concluded that in the absence of UvsY, DNA amplification occurs efficiently using a complex genomic DNA target but unlike reactions performed in the presence of UvsY, where the correct product is usually synthesised, the product is always of the correct size.

UvsY Free DNA Amplification Requires PEG

An experiment was performed to address whether the UvsY-independent behaviour exhibited by T6 H66S recombinase extended further to a lack of requirement for PEG. These reactions were conducted as described for the experiment depicted in FIG. 52, with the following exceptions: reactions were performed using 1000 copies of human genomic DNA and primer ApoB4 with either primer ApoB300 or ApoB3, both with and without the presence of PEG. As shown in FIG. 56, the results demonstrated a stark difference in reaction productivity between when PEG is present or absent. This experiment demonstrated the criticality of the use of polyethylene glycol inclusion in RPA reactions to permit effective amplification. In the absence of PEG, amplification of bona fide products generally does not occur, although a very faint artifact may be present in one lane, perhaps indicating a low level of loaded filaments when the T6 H66S recombinase is employed (although this does not occur in the presence of UvsY). It was concluded that for correct and effective amplification of target DNA, regardless of the presence or absence of UvsY, PEG is necessary in the reaction.

UvsY-Free DNA Amplification Using T4 gp32 with T6 H66S Recombinase

This experiment was performed to investigate whether the UvsY-independent amplification would occur when T4 gp32 was used together with T6 H66S UvsX. The general reaction conditions were as described for the experiment depicted in FIG. 52, except that here reactions were conducted using either Rb69 gp32 or 337.5 ng/µl T4 gp32. Where T4 gp32 was used in the presence of UvsY, 30 ng/µl T4 UvsY was used. 1000 copies of human genomic DNA were used per reaction in conjunction with primer ApoB4 and either primer ApoB300 or ApoB3. As shown in FIG. 57, this experiment shows that the UvsY-independent activity of T6 H66S recombinase is still found when T4 gp32, rather than Rb69 gp32, is utilized. The production of clean expected products is less efficient than when using Rb69 gp32, however there can be no doubt that large numbers of recombinationally active filaments are present. It was concluded that DNA amplification plainly occurs when using T4 gp32 in reaction, although, in the terms of correct products, this process is less efficient than if Rb69 gp32 is used.

UvsY-Free DNA Amplification Using T6 H66S and Aeh1 gp32

This experiment was performed to investigate whether the UvsY-independent amplification would occur when Aeh1 gp32 was used together with T6 H66S UvsX. Reaction conditions were the same as described for the experiment depicted in FIG. 52, with the exception that reactions were carried out using 400 ng/µl Rb69 gp32 or 360 ng/µl Aeh1 gp32, and 1000 copies human genomic DNA with primer ApoB4 and either primer ApoB300 or ApoB3. As shown in FIG. 58, the results demonstrate when UvsY was omitted and T6 H66S was used, Aeh1 gp32 was unable to support RPA in producing a correct product. However, some small amount of amplification did occur. It was concluded that, when combined with T6 H66S, Aeh1 promotes only limited DNA amplification. This data, when combined with the data previously described, suggests that the efficiency of UvsY-independent behaviour of T6 H66S RPA reactions is to some extent dependent on gp32 type.

UvsY-Free DNA Amplification Using T4 UvsX

An experiment was performed to investigate whether the presence of UvsY was needed for DNA amplification to occur when using T4 UvsX with Rb69 gp32. These reactions were conducted as described in the experiment depicted in FIG. 52, with the following exceptions: reactions were performed using either T6 H66S UvsX or 123.5 ng/µl T4 UvsX, and 1000 copies of human genomic DNA with primer ApoB4 and either primer ApoB300 or ApoB3. Where T4 UvsX was used with UvsY, 30 ng/µl T4 UvsY was utilized. As shown in FIG. 59, the results demonstrate that in the presence of UvsY, T4 UvsX reactions generate products of the expected size, as when T6 H66S UvsX is used. However, unlike T6 H66S reactions, when UvsY is omitted no amplification products whatsoever are generated. This experiment shows that under the standard conditions employed T4 UvsX, unlike T6 H66S UvsX, is totally dependent on the presence of UvsY protein. This data confirms a large body of earlier evidence, which showed that UvsY and PEG were both obligate components of RPA systems configured with T4 reagents.

An additional experiment was performed to investigate if by using T4 gp32 instead of Rb69 gp32, whether UvsY-deficient T4 UvsX reactions would continue to fail to produce amplification product. The general reaction conditions were as described for the experiment depicted in FIG. 52 with the exception that reactions were performed using either Rb69 gp32 with T6 H66S UvsX or 337 ng/µl T4 gp32 with 123 ng/µl T4 UvsX. 1000 copies of human genomic DNA were used per reaction in conjunction with primer ApoB4 and either primer ApoB300 or ApoB3. Where T4 gp32 and UvsX were used with UvsY, 30 ng/µl T4 UvsY was utilized. As shown in FIG. 60, the results demonstrate that, similar to that shown previously, in the presence of UvsY, reactions utilizing T4 components generate products of the correct size and the absence of UvsY negates this. This data confirms the conclusion that under the standard conditions, T4 UvsX, unlike T6 H66S UvsX, is totally dependent on the presence of UvsY protein. In this case T4 gp32 was employed as the single-stranded DNA binding protein.

Yet another experiment was performed to investigate the requirement for UvsY when using T4 UvsX in RPA amplification/detection reactions that utilize a fluorescent probe system to sense DNA accumulation. In this experiment RPA was performed under the following conditions: 100 mM Potassium acetate, 50 mM Tris.acetate pH 8.3, 14 mM Magnesium acetate, 5 mM dTT, 200 mM dNTPs, 50 mM Creatine phosphate (Calbiochem), 2.5 mM ATP (Roche), 50 ng/µl Creatine Kinase (Roche), amplification primers J1 (120 nM) and K2 (480 nM), 120 nM fluorescent probe BsFlc, 5% PEG 35,000, 43.33 ng/µl Sau Polymerase, 600 ng/µl Rb69 gp32, 120 ng/µl T6 H66S UvsX and 79 ng/µl Rb69 UvsY, where appropriate. Nfo was included at 100 ng/µl. Samples contained either water or 200 copies of *B. subtilis* genomic DNA, and were either in the presence or absence of Rb69 UvsY. Reactions were established on ice in a 384-well plate, and then transferred to a BIOTEK Flx-800 fluorescence microplate reader with stage set to 38'C at which time measurements were taken periodically from a bottom-reading probe.

As shown in FIG. 61, signal accumulated in a template-dependent manner in reactions configured with T6 H66S recombinase with or without UvsY, and also with reactions containing T4 UvsX in the presence of UvsY. However, in the absence of UvsY, T4 UvsX reactions displayed no DNA amplification capability. It was concluded that under these standard conditions, for DNA amplification to occur, unlike T6 H66S UvsX, T4 UvsX has a strict requirement for UvsY.

Figure 69:
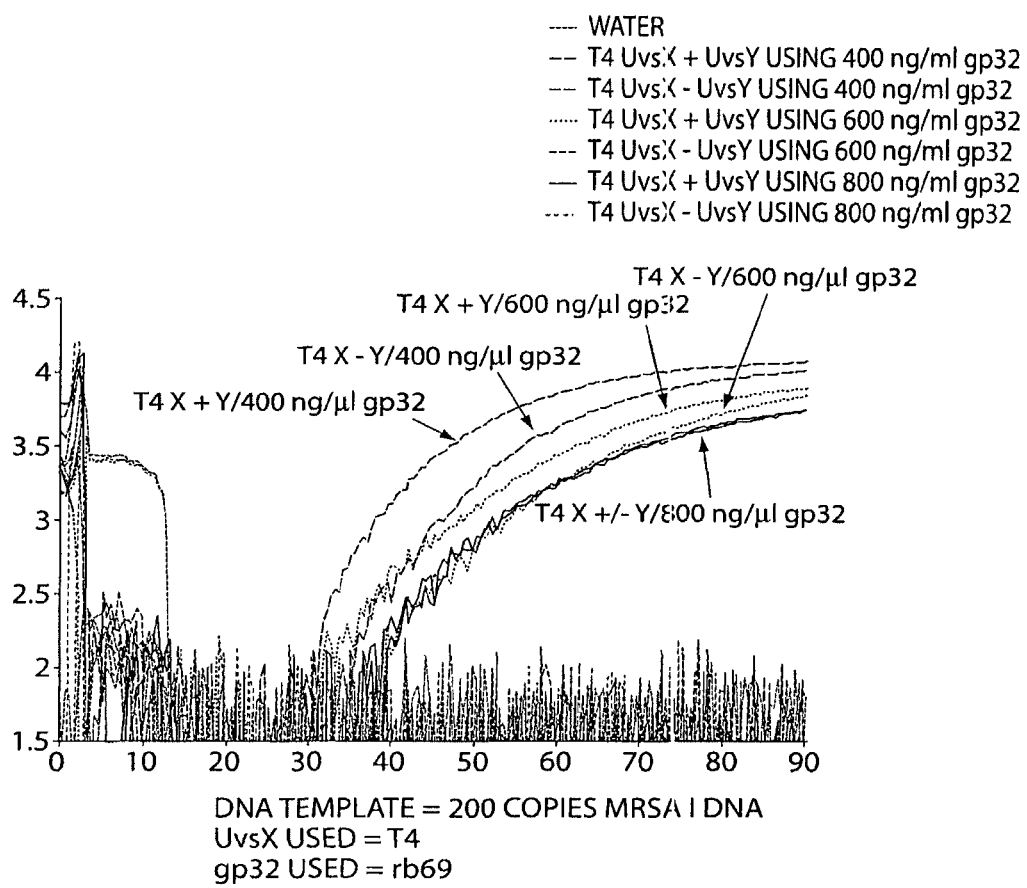
FIG. 69 is a graph showing the comparison of DNA amplification in RPA reactions using T4 UvsX with Rb69 gp32, in the presence and absence of UvsY loading agent. Samples were analyzed using a fluorescent probe.

An additional experiment was carried out in order to investigate the effects of titrating Rb69 gp32 concentrations on the requirement of T4 UvsX for UvsY. These reactions were conducted as described for the experiment depicted in FIG. 61, with the exception that reactions were performed using amplification primers Sccii35IV (480 nM) and OrfX45a (120 nM), 120 nM fluorescent probe SA Tamra2, 125 ng/µl T4 UvsX and 30 ng/µl T4 UvsY, where appropriate. Rb69 gp32 was used at 400 ng/µl, 600 ng/µl or 800 ng/µl. Samples contained either water or 200 copies of MRSA I genomic DNA, and were either in the presence or absence of Rb69 UvsY. As shown in FIG. 69, DNA amplification occurred in all template samples containing UvsY, regardless of the concentration of Rb69 used. No template sample demonstrated DNA amplification when UvsY was missing. It was concluded that under the standard conditions employed, for DNA amplification to occur, the T4 UvsX protein is dependent on UvsY and that this dependency is not altered by variation of gp32 concentration.

Figure 70:
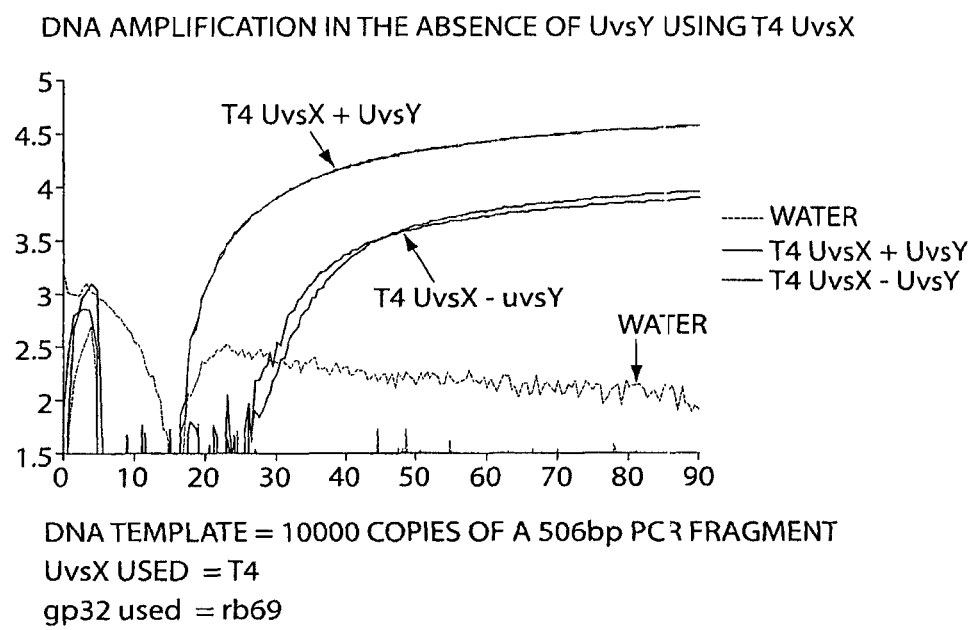
FIG. 70 is an additional graph showing the comparison of DNA amplification in RPA reactions using T4 UvsX with Rb69 gp32, in the presence and absence of UvsY loading agent. Samples were analyzed using a fluorescent probe.

Yet another experiment was carried out to further investigate the requirement of the T4 UvsX protein for UvsY. The reaction conditions used were the same as described for the experiment depicted in FIG. 61, with the following exceptions: reactions were performed using amplification primers Sciii (480 nM) and OrfX45a (120 nM), 120 nM fluorescent probe BsFlc beta, 123.5 ng/µl T4 UvsX, 500 ng/µl Rb69 gp32 and 18 ng/µl Sau Polymerase. Samples contained either water or 10000 copies of 506 bp PCR DNA fragment, and were either in the presence or absence of Rb69 UvsY. As shown in FIG. 70, under these conditions, T4 UvsX reactions efficiently amplify DNA, both in the presence and absence of UvsY. However, DNA amplification in samples that contained UvsY preceded those where UvsY was missing, and at experiment termination more DNA had been amplified in the presence of UvsY than the absence of UvsY. It was concluded that depending upon the conditions employed, T4 UvsX may or may not require the presence of UvsY for DNA amplification to occur. However, even where the conditions allow amplification to occur in the absence of UvsY, the addition of UvsY improves the reaction rate and increases the amplified DNA output.

Figure 71:
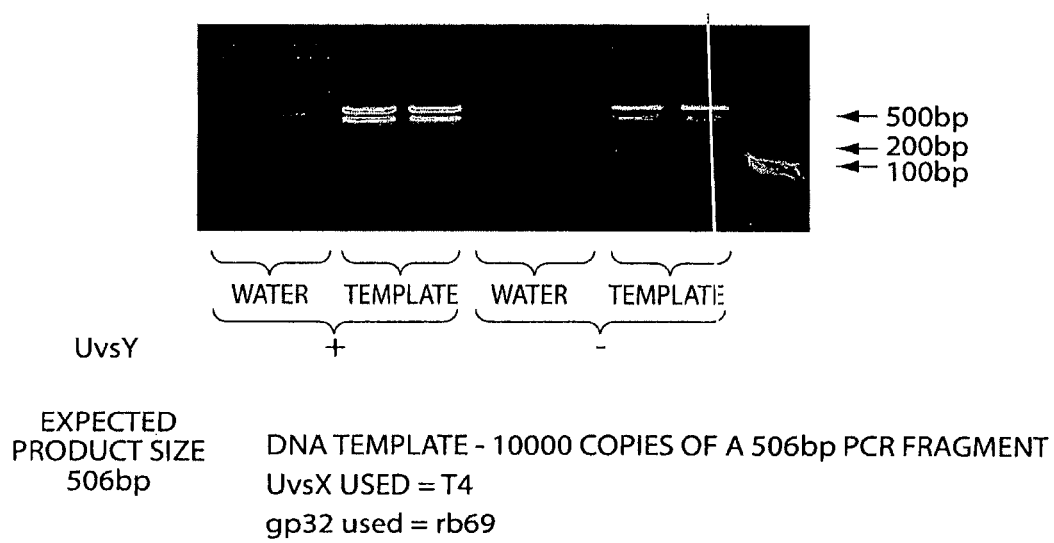
FIG. 71 is a picture of an ethidium bromide stained agarose gel showing RPA products using T4 UvsX and Rb69 gp32 in the presence or absence of UvsY loading agent.

To further elucidate the requirement of T4 UvsX protein for UvsY, a further experiment was performed. The reaction conditions and samples were those described in FIG. 70. Following reaction completion, each of the samples was purified using the GenElute PCR cleanup kit (Sigma) and visualized using gel electrophoresis. As shown in FIG. 71, gel electorphoresis can be used as an additional method (process) of visualizing the data collected for DNA amplification using RPA, such as the experiment described in FIG. 70. The results shown in FIG. 71 further demonstrate that under these conditions, T4 UvsX enables DNA amplification to occur both in the presence and absence of UvsY. However, as described for the experiment depicted in FIG. 70, more DNA was amplified in the presence of UvsY than in the absence of UvsY. These results confirm that under certain conditions, T4 UvsX can support DNA amplification in the absence of UvsY, however the amount of DNA amplification is improved in the presence of UvsY.

UvsY-Free DNA Amplification Using T6 UvsX

This experiment was performed to determine whether the unmodified T6 UvsX protein exhibits the capacity to amplify DNA in the absence of UvsY. The reaction conditions used were as described for the experiment depicted in FIG. 52, with the exception that the reactions were performed using T6 H66S UvsX or 120 ng/µl T6 UvsX, and 1000 copies of human genomic DNA with primer ApoB4 and either primer ApoB300 or ApoB3. As shown in FIG. 62, one of the two amplicons examined was efficiently amplified, while one was not, in the absence of UvsY. Furthermore, the relative efficiency of amplification of fragments between T6 and T6 H66S recombinase with or without UvsY were variant. While one cannot exclude preparation-dependent variations in between the recombinase proteins, this data is consistent with the suggestion that the unmodified and modified recombinase demonstrate variant activities as indicated earlier. It was concluded that in the absence of UvsY, DNA amplification can occur with T6 UvsX, although the efficiency to do this is different from T6 H66S UvsX.

UvsY-Free DNA Amplification Using Rb69 UvsX

This experiment investigated whether Rb69 UvsX requires UvsY for efficient amplification. The reactions were conducted as described for the experiment depicted in FIG. 52, with the exception that the reactions were performed using T6 H66S UvsX or 120 ng/µl Rb69 UvsX, 400 ng/µl Rb69 gp32, and 1000 copies of human genomic DNA with primer ApoB4 and either primer ApoB300 or ApoB3. As shown in FIG. 63, no amplification was seen in the absence of UvsY consistent with a strict dependence on the presence of UvsY under the conditions employed. Even with UvsY present, amplification was poor, so some caution should be placed on the interpretation. Without intending to be bound by any theory, the simplest explanation is that like with T4 UvsX, UvsY is required to achieve filament-loading levels required for effective and sensitive amplification. It was concluded that under the standard conditions employed, Rb69 UvsX is likely to require UvsY for efficient DNA amplification to be achieved.

UvsY-Free DNA Amplification Using Aeh1 UvsX

This experiment was performed to address whether Aeh1 UvsX requires UvsY for efficient amplification. Reaction conditions were as described for the experiment depicted in FIG. 52, with the exception that the reactions were carried out using 400 ng/μl Rb69 gp32 for reactions with T6 H66S UvsX, and for reactions with Aeh1: 500 ng/μl Rb69 gp32 UvsX, 200 ng/μl Aeh1 UvsX and 80 ng/μl Aeh1 UvsY, where UvsY was included. 1000 copies of human genomic DNA were used per reaction in conjunction with primer ApoB4 and either primer ApoB300 or ApoB3. As shown in FIG. 64, no amplification was seen in the absence of UvsY where Aeh1 proteins were used, while with the presence of UvsY, correct sized products were evident. It was concluded that Aeh1 proteins are unable to undergo DNA amplification in the absence of UvsY, consistent with a strict dependence on the presence of UvsY under the conditions employed.

UvsY-Free DNA Amplification Using Modified Rb69 UvsX (T6 DNA Binding Loop2, Modification of Histidine 64 to Serine, and Modified C Terminus (LDEx2))

Figure 65:
FIG. 65 is a picture of an ethidium bromide stained agarose gel showing RPA products using T6 H66S UvsX or Rb69T6loop2H64S UvsX with Rb69 gp32 in the presence or absence of UvsY loading agent.

This experiment was performed to investigate whether modified Rb69 UvsX containing the DNA binding loop2 of T6UvsX requires UvsY for efficient amplification, and to determine whether the variant DNA binding loop2 of T6 recombinase accounted for the UvsY-independent activity of T6 recombinases. Reaction conditions employed were as described for the experiment depicted in FIG. 52, with the following exceptions: reactions were performed using 400 ng/μl Rb69 gp32 and either T6 H66S UvsX or 120 ng/μl T6 H64S 2xLDE UvsX. 1000 copies of human genomic DNA were used per reaction in conjunction with primer ApoB4 and either primer ApoB300 or ApoB3. As shown in FIG. 65, no amplification was seen in the absence of UvsY consistent with dependence on the presence of UvsY under the conditions employed.

Without intending to be bound by any theory, one interpretation of this experiment is that the DNA binding loop 2, in isolation, may be insufficient to confer UvsY-independent activity on hybrid recombinases. However caution should be exercised as poor amplification was observed with this protein even in the presence of UvsY. It was concluded that, under the standard conditions employed, T6 H64S 2xLDE UvsX is likely to require UvsY for efficient DNA amplification to be achieved.

Example 16 gp32 Activity

The ability to measure the effectiveness of gp32 in regulating the cutting rate proves to be a very accurate approach to assess gp32 activity, something which has been historically difficult to assess. An experiment was performed to demonstrate a useful assay for the activity of gp32 preparations. Experimental conditions were as follows: reactions were performed in 50 μl volume; final concentration of probe (SA-Tamra2; 5'-tgttaattgagcaagtgtatagagcattraygabtatgcgtggag-3' (SEQ ID NO:125), here y=thf, b=BHQ2-dT, r=TAMRA-dT, 3'=Bio-TEG) was 100 nM; Rb69 pg32 was used at final concentration of 0, 40, 50, 63, 83, 100, 125, 167, or 250 ng/μl; Nfo was present at 33 ng/μl; buffer conditions were 20 mM Tris-acetate, 50 mM potassium acetate (pH 7.9), 10 mM Magnesium Acetate, 1 mM Dithiothreitol.

As depicted in FIG. 66, the results of this experiment show that a single-stranded probe which contains a fluorophore and quencher separated by a tetrahydrofuran residue (THF) can be rapidly cut by an excess of Nfo nuclease when present in an aqueous buffered solution, and in the absence of gp32 protein. This activity was robust under these conditions despite claims in the literature that Nfo targets only duplex DNA substrates. Without intending to be bound by any theory, the activity may arise by formation of transient duplex structures, hairpins and the like, under the conditions used here. This activity was entirely suppressed by an excess of gp32 protein when included in the reaction mixture. When the mass of gp32 was progressively decreased, cutting activity was once again detected (monitored by increasing fluorescence over time) and the rate of cutting was regulated by the mass of gp32 added at these limiting final concentrations. Furthermore, by setting the concentration of gp32 at limiting levels in experiments it was possible to assess consequences of a variety of manipulations such as the effects of competitor nucleic acids or temperature on gp32 behaviour and turnover.

Biochemical Distinction Among Different Species of gp32 Molecules

An experiment was performed to assess whether gp32 molecules from different species of origin were biochemically distinct from one another. Experimental conditions were as follows: reactions were performed in 50u1 volume; final concentration of probe (SA-Tamra2; 5'-tgttaattgagcaagtgtatagagcattraygabtatgcgtggag-3' (SEQ ID NO:126), here y=thf, b=BHQ2-dT, r=TAMRA-dT, 3'=Bio-TEG) was 100 nM; Rb69 pg32 was used at final concentration of 80 ng/μl, Nfo was present at 33 ng/μl; after 350 sec either water, dsDNA (550 ng human genomic DNA; i.e. approximately 10× mass of oligonucleotide probe) or ssDNA (28 pmol oligonucleotide of sequence 5' ctgtattagaagtacatgctgatcaagtgaca-3' (SEQ ID NO:127)) was added; buffer conditions were 20 mM Tris-acetate, 50 mM potassium acetate (pH 7.9), 10 mM Magnesium Acetate, 1 mM Dithiothreitol. Measurements were made in a fluorometer manufactured by Embedded System Engineering (ESE,GmbH) with LED excitation of 520 nM and emission at 585 nM.

Initially, a concentration of gp32 was established which permitted only a very low cutting activity by Nfo nuclease on the fluorophore/quencher probe. At this concentration the availability of gp32 was limited to a minimal quantity for substantial probe protection, and under these conditions it was possible to assess very sensitively whether gp32 was partitioned away from the probe in competition experiments. After monitoring the slow probe cutting for a while, excess double-stranded DNA or single-stranded oligonucleotides were added to assess whether this affected the distribution of gp32 on the probe. In all cases the addition of excess in single-stranded oligonucleotide lead to a sudden and pronounced increase in fluorescence and hence probe cutting. However, rather interestingly, it was discovered that T4 gp32 was strongly influenced by the addition of the duplex DNA as cutting became very pronounced indicating loss of gp32 from the probe DNA, while Rb69 and Aeh1 gp32 species showed only slight increases in cutting. Clearly Rb69 and Aeh1 gp32 molecules differentiated and partitioned much more effectively in favour of single-stranded DNA than T4 gp32. The results are depicted in FIG. 67, which shows that T4 and Rb69 gp32 molecules are biochemically distinct in regard to partitioning between single-stranded and duplex DNAs.

Temperature Limits for Different gp32 Species

An experiment was performed using the probe protection assay to assess at what upper temperature different species of gp32 failed to function correctly. Experimental conditions were as follows: reactions were performed in 50 μl volume; final concentration of probe (SA-Tamra2; 5'-tgttaattgagcaagtgtatagagcattraygabtatgcgtggag-3' (SEQ ID NO:128), where y=thf, b=BHQ2-dT, r=TAMRA-dT, 3'=Bio-TEG) was 100 nM; Rb69 pg32 was used at final concentration of 80 ng/µl, Nfo was present at 33 ng/µl; after 350 sec the temperature was gradually raised (see graph); buffer conditions were 20 mM Tris-acetate, 50 mM potassium acetate (pH 7.9), 10 mM Magnesium Acetate, 1 mM Dithiothreitol. Measurements were made in a fluorometer manufactured by Embedded System Engineering (ESE,GmbH) with LED excitation of 520 nM and emission at 585 nM.

Concentrations of gp32 were used that lead to a situation in which gp32 were just limiting with regard to probe protection. Reactions were then continuously monitored after a heat source was applied such that temperature gradually increased in the reaction environment. Indicated temperatures referred to those read from a thermocouple in the fluorescent probe device utilized which was close to the tube containing the reaction and thus a good indicator of the reaction temperature. As shown in FIG. 68, there were differences in upper temperature activity limits for different gp32 species. As the temperature rises the slope of the fluorescence curves initially remained constant, but at some point began to increase. Without intending to be bound by any theory, this evidence indicated that the gp32 was losing its effectiveness because the protein was becoming structurally unstable. Support for this interpretation rather than an interpretation in which Nfo activity progressively increases, is provided by the fact that T4 gp32 does not show any rate changes until relatively high temperatures, while when other gp32 molecules are used, changes begin much earlier. In particular it was noted that Aeh1 gp32 became highly ineffective at about 40° C., and displayed a pronounced loss of activity in the assay above this point. Rb69 gp32 also appeared to be less tolerant of higher temperatures than T4 gp32 and became partially affected by about 42° C. T4 gp32 is much more resistant and was still functioning at a temperature of at least 47° C.

The data describes herein supports the discovery of novel, diverse, hybrid and engineered recombinase enzymes and the utility of such enzymes for carrying out RPA reactions. The data further supports the identification of optimal conditions for carrying out RPA reactions using the novel, diverse, hybrid and engineered recombinase agents described herein and associated recombination factors. While specific embodiments of the subject invention have been discussed, the above specification is illustrative and not restrictive. Many variations of the invention will become apparent to those skilled in the art upon review of this specification. The appendant claims are not intended to claim all such embodiments and variations, and the full scope of the invention should be determined by reference to the claims, along with their full scope of equivalents, and the specification, along with such variations.

All publications, patent applications, and patents mentioned herein, including those items listed below, are hereby incorporated by reference in their entireties as if each individual publication or patent was specifically and individually indicated to be incorporated by reference. In case of conflict, the present application, including any definitions herein, will control.

References

Amasino R. M., Acceleration of nucleic acid hybridization rate by polyethylene glycol. Anal Biochem, Volume 152, Issue 2, 304-7, Feb. 1, 1986. Armes N. A. and Stemple D. L., Recombinase Polymerase Amplification, U.S. patent application Ser. No. 10/371,641. Benedict R. C. and Kowalczykowski S. C. Increase in the DNA strand assimilation activity of RecA protein by removal of the C terminus and structure-function studies of the resulting protein fragment. J. Biol. Chem. 1988 Oct. 25; 263(30):15513-20. Chan E. W., Dale P. J., Greco I. L., Rose J. G., O'Connor T. E., Biochim Biophys Acta, Volume 606, Issue 2, 353-61, Feb. 29, 1980. Eggler A. L., Lusetti S. L., Cox M. M. The C terminus of the *Escherichia coli* RecA protein modulates the DNA binding competition with single-stranded DNA-binding protein. J. Biol. Chem. 2003 May 2; 278(18): 16389-96. Ellouze C., Takahashi M., Wittung P., Mortensen K., Schnarr M., Norden B. Eur. J. Biochem. 1995 Oct. 15; 233(2):579-83. Formosa T. and Alberts B. M. Purification and characterization of the T4 bacteriophage UvsX protein. J. Biol. Chem. 1986 May 5; 261 (13):6107-18. Giedroc D. P., Gin H. W, Khan R., King G. C., Chen K. Zn(II) coordination domain mutants of T4 gp32 protein. Biochemistry. 1992 Jan. 28; 31 (3):765-74. Giedroc D. P., Keating K. M., Williams K. R., and Coleman J. E. The function of zinc in gene 32 protein from T4. Biochemistry 1987 Aug. 25; 26(17):5251-9. Layery P. E. and Kowalczykowski S. C., J. Biol. Chem., Vol. 267, Issue 13, 9307-14, May 5, 1992. Lerman L. S., A transition to a Compact Form of DNA in Polymer Solutions. Proc Natl Acad Sci USA. 1971 April; 68(8):1886-1890. Lusetti S. L., Shaw J. J., Cox M. M. Magnesium ion-dependent activation of the RecA protein involves the C terminus. J. Biol. Chem. 2003 May 2; 278(18):16389-96. Malkov V. A. and Camerini-Otero R. D. Photocross-links between single-stranded DNA and *Escherichia coli* RecA protein map to loops L1 (amino acid residues 157-164) and L2 (amino acid residues 195-209). J. Biol. Chem. 1995 Dec. 15, Volume 270, Issue 50, 30230-3. Minton A. P. The Influence of Macromolecular Crowding and Macromolecular Confinement on Biochemical Reactions in Physiological Media. J. Biol. Chem., Vol. 276, Issue 14, 10577-10580, Apr. 6, 2001. Naimushin A. N., Quach M., Fujimoto B. S., Schurr J. M. Effect of polyethylene glycol on the supercoiling free energy of DNA. Biopolymers. 2001, Volume 58, Issue 2, 204-17. Nadler S. G., Roberts W. J., Shamoo Y., Williams K. R. A novel function for Zinc(II) in a nucleic acid-binding protein. Contribution of Zinc(II) toward the cooperativity of bacteriophage T4 gp32 protein binding. J. Biol. Chem. 1990 Jun. 25; 265(18):10389-94. Qiu H. and Giedroc D. P. Effects of substitution of proposed Zn(II) ligand His81 or His64 in phage gp32 protein:spectroscopic evidence for a novel zinc coordination complex. Biochemistry 1994 Jul. 5; 33(26): 8139-48. Rivas G., Ferrone F., Herzfeld J. Life in a crowded world—Workshop on the Biological Implications of Macromolecular Crowding. EMBO reports 5, 1, 23-27 (2004) doi:10.1038/sj.embor.7400056 Published online: 19 Dec. 2003. Story R. M., Bishop D. K., Kleckner N., Steitz, T. A. Structural relationship of bacterial RecA proteins to recombination proteins from bacteriophage T4 and yeast. Science. 1993 Mar. 26, 259(5103):1892-6. Voloshin O. N., Wang L., Camerini-Otero R. D. Homologous DNA pairing Promoted by a 20-Amino Acid Peptide Derived from RecA. Science 10 May 1996. Vol 272 Number 5263, pages 868-872. Voloshin O. N., Wang L., Camerini-Otero R. D. The homologous pairing domain of RecA also mediates the allosteric regulation of DNA binding and ATP hydrolysis: a remarkable concentration of functional residues. J. Mol. Biol. 2000 Nov. 10; 303(5):709-20. Walker J. E., Saraste M., Runswick M., and Gay N. J. 1982 EMBO J. Volume 1. Pages 945-51. Zarling, D. A., Sena E. P., Green C. J., U.S. Pat. No. 5,223,414 filed May 7, 1990. Zimmerman SB and Harrison B. Macromolecular crowding increases binding of DNA polymerase to DNA: an adaptive effect. Proc Natl Acad Sci USA. 1987 April; 84(7):1871-5. Zinchenko A. A. and Yoshikawa, K. Biophysical Journal. June 2005.

We claim:

1. A method, comprising:
   (a) contacting UvsX, UvsY, and Rb69 gp32 proteins with first and second single stranded nucleic acid primers specific for a double stranded target nucleic acid molecule to provide first and second nucleoprotein primers, the UvsX and UvsY proteins each being derived from a myoviridae phage;
   (b) contacting the first nucleoprotein primer with the double stranded target nucleic acid molecule to create a first D loop structure at a first portion of the double stranded target nucleic acid molecule;
   (c) contacting the second nucleoprotein primer with the double stranded target nucleic acid molecule to create a second D loop structure at a second portion of the double stranded target nucleic acid molecule so that the 3' ends of the first and second nucleic acid primers are oriented toward each other on the same double stranded target nucleic acid molecule without completely denaturing the target nucleic acid molecule; and
   (d) extending the 3' end of the first and second nucleoprotein primers with one or more polymerases capable of strand displacement synthesis and dNTPs to provide first and second double stranded target nucleic acid molecules and first and second displaced strands of nucleic acid.

2. The method of claim 1, further comprising repeating (b) through (d).

3. The method of claim 1, wherein the first and second displaced strands of nucleic acid hybridize to each other after (d) to form a third double stranded target nucleic acid molecule.

4. The method of claim 1, wherein the myoviridae phage is selected from the group consisting of T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, phage 44RR2.8t, Rb49, phage Rb3 and phage LZ2.

5. The method of claim 1, wherein the UvsX and UvsY are selected from the group consisting of:
   (a) Rb69 UvsX and Rb69 UvsY;
   (b) Aeh1 UvsX and Aeh1 UvsY; and
   (c) T4 UvsX and T4 UvsY.

6. The method of claim 1, wherein the UvsX, UvsY, and Rb69 gp32 are native, hybrid, or mutant proteins from the same or different myoviridae phage sources.

7. The method of claim 6, wherein the hybrid protein comprises one or more amino acid residues from two different species of myoviridae phages to yield a protein with improved performance characteristics in the method.

8. The method of claim 6, wherein the UvsX is a mutant UvsX.

9. The method of claim 8, wherein the mutant UvsX is an Rb69 UvsX comprising at least one modification the Rb69 UvsX amino acid sequence, wherein the modification is selected from the group consisting of:
   an amino acid which is not histidine at position 64;
   a serine at position 64;
   the addition of one or more glutamic acid residues at the C-terminus;
   the addition of one or more aspartic acid residues at the C-terminus; and
   a combination thereof.

10. The method of claim 8, wherein the mutant UvsX is a T6 UvsX having at least one modification in the T6 UvsX amino acid sequence, wherein the modification is selected from the group consisting of:
    an amino acid which is not histidine at position 66;
    a serine at position 66;
    the addition of one or more glutamic acid residues at the C-terminus;
    the addition of one or more aspartic acid residues at the C-terminus; and
    a combination thereof 11. The method of claim 7, wherein the hybrid protein is a UvsX protein comprising at least one region which comprises an amino acid sequence from a different UvsX species.

12. The method of claim 11, wherein the at least one region is the DNA-binding loop-2 region of UvsX.

13. The method of claim 1, wherein the method is performed in the presence of a crowding agent selected from the group consisting of polyethylene glycol, polyethylene oxide, polystyrene, Ficoll, dextran, PVP, and albumin, such that the crowding agent stimulates amplification.

14. The method of claim 13, wherein the crowding agent has a molecular weight of less than 200,000.

15. The method of claim 13, wherein the crowding agent is present in an amount of about 0.5% to about 15% w/v.

16. The method of claim 1, wherein the polymerase is a large fragment polymerase selected from the group consisting of *E. coli* Pol I, *Bacillus subtilis* Pol I, *Staphylococcus aureus* Pol I, and homologues thereof.

17. The method of claim 1, wherein the method is performed in the presence of heparin.

18. The method of claim 1, wherein the first or second nucleic acid primer is a blocked primer, and the method is performed in the presence of *E. coli* exonuclease III or *E. coli* endonuclease IV.

19. The method of claim 1, wherein the method is performed in the presence of about 1 mM to about 8 mM divalent manganese ions.

20. The method of claim 1, wherein the UvsX protein comprises an amino acid sequence selected from the group consisting of SEQ ID NO: 105, SEQ ID NO: 106, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122; or the UvsY protein comprises an amino acid sequence of SEQ ID NO: 123 or SEQ ID NO: 124.

21. The method of claim 20, wherein the UvsX comprises the amino acid sequence SEQ ID NO: 105, the UvsY is a Rb69 UvsY, and the one or more polymerases capable of strand displacement synthesis is a DNA polymerase I.

22. The method of claim 1, wherein the myoviridae phage is Phage 31.

23. A method, comprising:
(a) contacting UvsX, UvsY, and Rb69 gp32 proteins with first and second single stranded nucleic acid primers specific for a double stranded target nucleic acid molecule to provide first and second nucleoprotein primers, the UvsX and UvsY each being derived from a myoviridae phage selected from the group consisting of T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2;
(b) contacting the first nucleoprotein primer with the double stranded target nucleic acid molecule to create a first D loop structure at a first portion of the double stranded target nucleic acid molecule;
(c) contacting the second nucleoprotein primer with the double stranded target nucleic acid molecule to create a second D loop structure at a second portion of the double stranded target nucleic acid molecule so that the 3' ends of the first and second nucleic acid primers are oriented toward each other on the same double stranded target nucleic acid molecule without completely denaturing the target nucleic acid molecule; and
(d) extending the 3' end of the first and second nucleoprotein primers with one or more polymerases capable of strand displacement synthesis and dNTPs to provide first and second double stranded target nucleic acid molecules and first and second displaced strands of nucleic acid.

24. The method of claim 23, further comprising repeating (b) through (d).

25. The method of claim 23, wherein the first and second displaced strands of nucleic acid hybridize to each other after (d) to form a third double stranded target nucleic acid molecule.

26. The method of claim 23, wherein the UvsX and UvsY are selected from the group consisting of:
(a) Rb69 UvsX and Rb69 UvsY;
(b) Aeh1 UvsX and Aeh1 UvsY; and
(c) T4 UvsX and T4 UvsY.

27. The method of claim 23, wherein the UvsX is T4 UvsX, and the UvsY is Rb69 UvsY.

28. The method of claim 23, wherein the UvsX, UvsY, and Rb69 gp32 are native, hybrid, or mutant proteins from the same or different myoviridae phage sources.

29. The method of claim 28, wherein the hybrid protein comprises one or more amino acid residues from two different species of myoviridae phages to yield a protein with improved performance characteristics in the method.

30. The method of claim 28, wherein the UvsX is a mutant UvsX.

31. The method of claim 30, wherein the mutant UvsX is an Rb69 UvsX comprising at least one modification in the Rb69 UvsX amino acid sequence, wherein the modification is selected from the group consisting of:
an amino acid which is not histidine at position 64;
a serine at position 64;
the addition of one or more glutamic acid residues at the C-terminus;
the addition of one or more aspartic acid residues at the C-terminus; and
a combination thereof.

32. The method of claim 30, wherein the mutant UvsX is a T6 UvsX having at least one modification in the T6 UvsX amino acid sequence, wherein the modification is selected from the group consisting of:
an amino acid which is not histidine at position 66;
a serine at position 66;
the addition of one or more glutamic acid residues at the C-terminus;
the addition of one or more aspartic acid residues at the C-terminus; and
a combination thereof.

33. The method of claim 29, wherein the hybrid protein is a UvsX protein comprising at least one region which comprises an amino acid sequence from a different UvsX species.

34. The method of claim 33, wherein the at least one region is the DNA-binding loop-2 region of UvsX.

35. The method of claim 23, wherein the method is performed in the presence of a crowding agent selected from the group consisting of polyethylene glycol, polyethylene oxide, polystyrene, Ficoll, dextran, PVP, and albumin, such that the crowding agent stimulates amplification.

36. The method of claim 35, wherein the crowding agent has a molecular weight of less than 200,000.

37. The method of claim 35, wherein the crowding agent is present in an amount of about 0.5% to about 15% w/v.

38. The method of claim 23, wherein the polymerase is a large fragment polymerase selected from the group consisting of *E. coli* Pol I, *Bacillus subtilis* Pol I, *Staphylococcus aureus* Pol I, and homologues thereof.

39. The method of claim 23, wherein the method is performed in the presence of heparin.

40. The method of claim 23, wherein the first or second nucleic acid primer is a blocked primer, and the method is performed in the presence of *E. coli* exonuclease III or *E. coli* endonuclease IV.

41. The method of claim 23, wherein the method is performed in the presence of about 1 mM to about 8 mM divalent manganese ions.

42. The method of claim 23, wherein the UvsX protein comprises an amino acid sequence selected from the group consisting of: SEQ ID NO: 105, SEQ ID NO: 106, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122; or the UvsY protein comprises an amino acid sequence of SEQ ID NO: 123 or SEQ ID NO: 124.

43. The method of claim 42, wherein the UvsX comprises the amino acid sequence SEQ ID NO: 105, the UvsY is a Rb69 UvsY, and the one or more polymerases capable of strand displacement synthesis is a DNA polymerase I.

44. A method, comprising:
(a) contacting UvsX and Rb69 gp32 proteins with first and second single stranded nucleic acid primers specific for a double stranded target nucleic acid molecule to provide first and second nucleoprotein primer, the UvsX being derived from a myoviridae phage;
(b) contacting the first nucleoprotein primer to the double stranded target nucleic acid molecule to create a first D loop structure at a first portion of the double stranded target nucleic acid molecule;
(c) contacting the second nucleoprotein primer to the double stranded target nucleic acid molecule to create a second D loop structure at a second portion of the double stranded target nucleic acid molecule so that the 3' ends of the first and second nucleic acid primers are oriented toward each other on the same double stranded target nucleic acid molecule without completely denaturing the target nucleic acid molecule; and (d) extending the 3' ends of the first and second nucleoprotein primers with one or more polymerases capable of strand displacement synthesis and dNTPs to generate first and second double stranded target nucleic acid molecules and first and second displaced strands of nucleic acid, wherein the method is performed in the absence of UvsY.

45. The method of claim 44, further comprising repeating (b) through (d).

46. A method, comprising:
(a) contacting UvsX, UvsY, and Rb69 gp32 proteins with a first single stranded nucleic acid primer specific for a double stranded target nucleic acid molecule to provide a population of first nucleoprotein primer, the UvsX and UvsY each being derived from a myoviridae phage;
(b) contacting the first nucleoprotein primer with the double stranded target nucleic acid molecule to provide a first D loop structure at a first portion of the double stranded target nucleic acid molecule without completely denaturing the target nucleic acid molecule;
(c) extending the 3' end of the first nucleoprotein primer with one or more polymerases capable of strand displacement synthesis and dNTPs to provide a double stranded target nucleic acid molecule and a displaced strand of nucleic acid molecule;
(d) hybridizing a second single stranded nucleic acid primer with the displaced strand of nucleic acid molecule to form a hybridized second single stranded nucleic acid primer; and
(e) elongating the hybridized second single stranded nucleic acid primer to provide a double stranded target nucleic acid molecule.

47. The method of claim 46, further comprising repeating (b) through (e).

* * * * *

UNITED STATES PATENT AND TRADEMARK OFFICE
CERTIFICATE OF CORRECTION

PATENT NO. : 8,637,253 B2
APPLICATION NO. : 13/307293
DATED : January 28, 2014
INVENTOR(S) : Olaf Piepenburg et al.

It is certified that error appears in the above-identified patent and that said Letters Patent is hereby corrected as shown below:

On the Title Page

Page 2, Col. 1, line 29, Item (56), delete "Assimiliation" and insert -- Assimilation --

Page 3, Col. 1, line 61, Item (56), delete "Characteirzation" and insert -- Characterization --

Page 3, Col. 2, line 8, Item (56), delete "Mixturre" and insert -- Mixture --

Page 3, Col. 2, line 65, Item (56), delete "bacteriophage ω0" and insert -- bacteriophage λ O --

Page 4, Col. 1, line 15, Item (56), delete "Hydridization." and insert -- Hybridization. --

Page 4, Col. 1, line 34, Item (56), delete "$^C$hannel" and insert -- Channel --

Page 4, Col. 1, line 66, Item (56), delete "Quantification f" and insert -- Quantification of --

Page 5, Col. 1, line 8, Item (56), delete "Bacteriphage" and insert -- Bacteriophage --

Page 5, Col. 2, line 55, Item (56), delete "Expressiono f" and insert -- Expression of --

Page 6, Col. 2, line 19, Item (56), delete "32350347?sat= I 38zsatkey = 7100722" and insert -- 32350347?sat=13&satkey=7100722 --

Page 6, Col. 2, line 22, Item (56), delete "38639939?&satkey=85157 9" and insert -- 3R639939?sat=12&satkey=851579 --

Signed and Sealed this
Sixth Day of May, 2014

Michelle K. Lee
*Deputy Director of the United States Patent and Trademark Office*

In the Claims

Col. 179, line 65, claim 9, delete "modification" and insert -- modification in --

Col. 180, line 29, claim 10, delete "thereof" and insert -- thereof. --

SEQUENCE LISTING

<160> NUMBER OF SEQ ID NOS: 132

<210> SEQ ID NO 1
<211> LENGTH: 391
<212> TYPE: PRT
<213> ORGANISM: Enterobacteria phage T4

<400> SEQUENCE: 1

```
Met Ser Asp Leu Lys Ser Arg Leu Ile Lys Ala Ser Thr Ser Lys Leu
 1               5                  10                  15

Thr Ala Glu Leu Thr Ala Ser Lys Phe Phe Asn Glu Lys Asp Val Val
             20                  25                  30

Arg Thr Lys Ile Pro Met Met Asn Ile Ala Leu Ser Gly Glu Ile Thr
         35                  40                  45

Gly Gly Met Gln Ser Gly Leu Leu Ile Leu Ala Gly Pro Ser Lys Ser
     50                  55                  60

Phe Lys Ser Asn Phe Gly Leu Thr Met Val Ser Ser Tyr Met Arg Gln
 65                  70                  75                  80

Tyr Pro Asp Ala Val Cys Leu Phe Tyr Asp Ser Glu Phe Gly Ile Thr
                 85                  90                  95

Pro Ala Tyr Leu Arg Ser Met Gly Val Asp Pro Glu Arg Val Ile His
            100                 105                 110

Thr Pro Val Gln Ser Leu Glu Gln Leu Arg Ile Asp Met Val Asn Gln
        115                 120                 125

Leu Asp Ala Ile Glu Arg Gly Glu Lys Val Val Phe Ile Asp Ser
    130                 135                 140

Leu Gly Asn Leu Ala Ser Lys Lys Glu Thr Glu Asp Ala Leu Asn Glu
145                 150                 155                 160

Lys Val Val Ser Asp Met Thr Arg Ala Lys Thr Met Lys Ser Leu Phe
                165                 170                 175

Arg Ile Val Thr Pro Tyr Phe Ser Thr Lys Asn Ile Pro Cys Ile Ala
            180                 185                 190

Ile Asn His Thr Tyr Glu Thr Gln Glu Met Phe Ser Lys Thr Val Met
        195                 200                 205

Gly Gly Gly Thr Gly Pro Met Tyr Ser Ala Asp Thr Val Phe Ile Ile
    210                 215                 220

Gly Lys Arg Gln Ile Lys Asp Gly Ser Asp Leu Gln Gly Tyr Gln Phe
225                 230                 235                 240

Val Leu Asn Val Glu Lys Ser Arg Thr Val Lys Glu Lys Ser Lys Phe
                245                 250                 255

Phe Ile Asp Val Lys Phe Asp Gly Gly Ile Asp Pro Tyr Ser Gly Leu
            260                 265                 270

Leu Asp Met Ala Leu Glu Leu Gly Phe Val Val Lys Pro Lys Asn Gly
        275                 280                 285

Trp Tyr Ala Arg Glu Phe Leu Asp Glu Glu Thr Gly Glu Met Ile Arg
    290                 295                 300

Glu Glu Lys Ser Trp Arg Ala Lys Asp Thr Asn Cys Thr Thr Phe Trp
305                 310                 315                 320

Gly Pro Leu Phe Lys His Gln Pro Phe Arg Asp Ala Ile Lys Arg Ala
                325                 330                 335

Tyr Gln Leu Gly Ala Ile Asp Ser Asn Glu Ile Val Glu Ala Glu Val
            340                 345                 350

Asp Glu Leu Ile Asn Ser Lys Val Glu Lys Phe Lys Ser Pro Glu Ser
        355                 360                 365
```

```
Lys Ser Lys Ser Ala Ala Asp Leu Glu Thr Asp Leu Glu Gln Leu Ser
    370                 375                 380

Asp Met Glu Glu Phe Asn Glu
385                 390

<210> SEQ ID NO 2
<211> LENGTH: 353
<212> TYPE: PRT
<213> ORGANISM: Escherichia coli

<400> SEQUENCE: 2

Met Ala Ile Asp Glu Asn Lys Gln Lys Ala Leu Ala Ala Ala Leu Gly
  1               5                  10                  15

Gln Ile Glu Lys Gln Phe Gly Lys Gly Ser Ile Met Arg Leu Gly Glu
                 20                  25                  30

Asp Arg Ser Met Asp Val Glu Thr Ile Ser Thr Gly Ser Leu Ser Leu
             35                  40                  45

Asp Ile Ala Leu Gly Ala Gly Gly Leu Pro Met Gly Arg Ile Val Glu
         50                  55                  60

Ile Tyr Gly Pro Glu Ser Ser Gly Lys Thr Thr Leu Thr Leu Gln Val
 65                  70                  75                  80

Ile Ala Ala Ala Gln Arg Glu Gly Lys Thr Cys Ala Phe Ile Asp Ala
                 85                  90                  95

Glu His Ala Leu Asp Pro Ile Tyr Ala Arg Lys Leu Gly Val Asp Ile
            100                 105                 110

Asp Asn Leu Leu Cys Ser Gln Pro Asp Thr Gly Glu Gln Ala Leu Glu
        115                 120                 125

Ile Cys Asp Ala Leu Ala Arg Ser Gly Ala Val Asp Val Ile Val Val
    130                 135                 140

Asp Ser Val Ala Ala Leu Thr Pro Lys Ala Glu Ile Glu Gly Glu Ile
145                 150                 155                 160

Gly Asp Ser His Met Gly Leu Ala Ala Arg Met Met Ser Gln Ala Met
                165                 170                 175

Arg Lys Leu Ala Gly Asn Leu Lys Gln Ser Asn Thr Leu Leu Ile Phe
            180                 185                 190

Ile Asn Gln Ile Arg Met Lys Ile Gly Val Met Phe Gly Asn Pro Glu
        195                 200                 205

Thr Thr Thr Gly Gly Asn Ala Leu Lys Phe Tyr Ala Ser Val Arg Leu
    210                 215                 220

Asp Ile Arg Arg Ile Gly Ala Val Lys Glu Gly Glu Asn Val Val Gly
225                 230                 235                 240

Ser Glu Thr Arg Val Lys Val Val Lys Asn Lys Ile Ala Ala Pro Phe
                245                 250                 255

Lys Gln Ala Glu Phe Gln Ile Leu Tyr Gly Glu Gly Ile Asn Phe Tyr
            260                 265                 270

Gly Glu Leu Val Asp Leu Gly Val Lys Glu Lys Leu Ile Glu Lys Ala
        275                 280                 285

Gly Ala Trp Tyr Ser Tyr Lys Gly Glu Lys Ile Gly Gln Gly Lys Ala
    290                 295                 300

Asn Ala Thr Ala Trp Leu Lys Asp Asn Pro Glu Thr Ala Lys Glu Ile
305                 310                 315                 320

Glu Lys Lys Val Arg Glu Leu Leu Leu Ser Asn Pro Asn Ser Thr Pro
                325                 330                 335

Asp Phe Ser Val Asp Asp Ser Glu Gly Val Ala Glu Thr Asn Glu Asp
            340                 345                 350
```

Phe

<210> SEQ ID NO 3
<211> LENGTH: 302
<212> TYPE: PRT
<213> ORGANISM: Artificial Sequence
<220> FEATURE:
<223> OTHER INFORMATION: Description of Artificial Sequence: Synthetic construct

<400> SEQUENCE: 3

```
Met Phe Lys Arg Lys Ser Thr Ala Glu Leu Ala Ala Gln Met Ala Lys
 1               5                  10                  15

Leu Ala Gly Asn Lys Gly Gly Phe Ser Ser Glu Asp Lys Gly Glu Trp
             20                  25                  30

Lys Leu Lys Leu Asp Asn Ala Gly Asn Gly Gln Ala Val Ile Arg Phe
         35                  40                  45

Leu Pro Ser Lys Asn Asp Glu Gln Ala Pro Phe Ala Ile Leu Val Asn
     50                  55                  60

His Gly Phe Lys Lys Asn Gly Lys Trp Tyr Ile Glu Thr Cys Ser Ser
 65                  70                  75                  80

Thr His Gly Asp Tyr Asp Ser Cys Pro Val Cys Gln Tyr Ile Ser Lys
                 85                  90                  95

Asn Asp Leu Tyr Asn Thr Asp Asn Lys Glu Tyr Ser Leu Val Lys Arg
            100                 105                 110

Lys Thr Ser Tyr Trp Ala Asn Ile Leu Val Val Lys Asp Pro Ala Ala
        115                 120                 125

Pro Glu Asn Glu Gly Lys Val Phe Lys Tyr Arg Phe Gly Lys Lys Ile
    130                 135                 140

Trp Asp Lys Ile Asn Ala Met Ile Ala Val Asp Val Glu Met Gly Glu
145                 150                 155                 160

Thr Pro Val Asp Val Thr Cys Pro Trp Glu Gly Ala Asn Phe Val Leu
                165                 170                 175

Lys Val Lys Gln Val Ser Gly Phe Ser Asn Tyr Asp Glu Ser Lys Phe
            180                 185                 190

Leu Asn Gln Ser Ala Ile Pro Asn Ile Asp Asp Glu Ser Phe Gln Lys
        195                 200                 205

Glu Leu Phe Glu Gln Met Val Asp Leu Ser Glu Met Thr Ser Lys Asp
    210                 215                 220

Lys Phe Lys Ser Phe Glu Glu Leu Ser Thr Lys Phe Ser Gln Val Met
225                 230                 235                 240

Gly Thr Ala Ala Met Gly Gly Ala Ala Thr Ala Ala Lys Lys Ala
                245                 250                 255

Asp Lys Val Ala Asp Asp Leu Asp Ala Phe Asn Val Asp Asp Phe Asn
            260                 265                 270

Thr Lys Thr Glu Asp Asp Phe Met Ser Ser Ser Gly Ser Ser Ser
        275                 280                 285

Ser Ala Asp Asp Thr Asp Leu Asp Asp Leu Asn Asp Leu
    290                 295                 300
```

<210> SEQ ID NO 4
<211> LENGTH: 301
<212> TYPE: PRT
<213> ORGANISM: Artificial Sequence
<220> FEATURE:
<223> OTHER INFORMATION: Description of Artificial Sequence: Synthetic construct

<400> SEQUENCE: 4

```
Met Phe Lys Arg Lys Ser Thr Ala Glu Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Asn Ala Gly Asn Gly Gln Ala Val Ile Arg Phe Leu
        35                  40                  45

Pro Ser Lys Asn Asp Glu Gln Ala Pro Phe Ala Ile Leu Val Asn His
50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asp Asn Lys Glu Tyr Ser Leu Val Lys Arg Lys
                100                 105                 110

Thr Ser Tyr Trp Ala Asn Ile Leu Val Val Lys Asp Pro Ala Ala Pro
            115                 120                 125

Glu Asn Glu Gly Lys Val Phe Lys Tyr Arg Phe Gly Lys Lys Ile Trp
130                 135                 140

Asp Lys Ile Asn Ala Met Ile Ala Val Asp Val Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
210                 215                 220

Phe Lys Ser Phe Glu Glu Leu Asn Thr Lys Phe Gly Gln Val Met Gly
225                 230                 235                 240

Thr Ala Val Met Gly Gly Ala Ala Ala Thr Ala Ala Lys Lys Ala Asp
                245                 250                 255

Lys Val Ala Asp Asp Leu Asp Ala Phe Asn Val Asp Asp Phe Asn Thr
            260                 265                 270

Lys Thr Glu Asp Asp Phe Met Ser Ser Ser Gly Ser Ser Ser Ser
        275                 280                 285

Ala Asp Asp Thr Asp Leu Asp Asp Leu Leu Asn Asp Leu
290                 295                 300
```

<210> SEQ ID NO 5
<211> LENGTH: 137
<212> TYPE: PRT
<213> ORGANISM: Artificial Sequence
<220> FEATURE:
<223> OTHER INFORMATION: Description of Artificial Sequence: Synthetic construct

<400> SEQUENCE: 5

```
Met Arg Leu Glu Asp Leu Gln Glu Glu Leu Lys Lys Asp Val Phe Ile
1               5                   10                  15

Asp Ser Thr Lys Leu Gln Tyr Glu Ala Ala Asn Asn Val Met Leu Tyr
            20                  25                  30

Ser Lys Trp Leu Asn Lys His Ser Ser Ile Lys Lys Glu Met Leu Arg
        35                  40                  45

Ile Glu Ala Gln Lys Lys Val Ala Leu Lys Ala Arg Leu Asp Tyr Tyr
```

```
                    50                  55                  60
Ser Gly Arg Gly Asp Gly Asp Glu Phe Ser Met Asp Arg Tyr Glu Lys
 65                  70                  75                  80

Ser Glu Met Lys Thr Val Leu Ser Ala Asp Lys Asp Val Leu Lys Val
                 85                  90                  95

Asp Thr Ser Leu Gln Tyr Trp Gly Ile Leu Leu Asp Phe Cys Ser Gly
            100                 105                 110

Ala Leu Asp Ala Ile Lys Ser Arg Gly Phe Ala Ile Lys His Ile Gln
        115                 120                 125

Asp Met Arg Ala Phe Glu Ala Gly Lys
    130                 135

<210> SEQ ID NO 6
<211> LENGTH: 137
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 6

Met Arg Leu Glu Asp Leu Gln Glu Glu Leu Lys Lys Asp Val Phe Ile
  1               5                  10                  15

Asp Ser Thr Lys Leu Gln Tyr Glu Ala Ala Asn Asn Val Met Leu Tyr
                 20                  25                  30

Ser Lys Trp Leu Asn Lys His Ser Ser Ile Leu Lys Glu Met Leu Arg
             35                  40                  45

Ile Asp Ala Gln Lys Lys Val Ala Leu Lys Ala Lys Leu Asp Tyr Tyr
         50                  55                  60

Ser Gly Arg Gly Asp Gly Asp Glu Phe Ser Met Asp Arg Tyr Glu Lys
 65                  70                  75                  80

Ser Glu Met Lys Thr Val Leu Ser Ala Asp Lys Asp Val Leu Lys Val
                 85                  90                  95

Asp Thr Ser Leu Gln Tyr Trp Gly Ile Leu Leu Asp Phe Cys Ser Gly
            100                 105                 110

Ala Leu Asp Ala Ile Lys Ser Arg Gly Phe Ala Ile Lys His Ile Gln
        115                 120                 125

Asp Met Arg Ala Phe Glu Ala Gly Lys
    130                 135

<210> SEQ ID NO 7
<211> LENGTH: 391
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7

Met Ser Asp Leu Lys Ser Arg Leu Ile Lys Ala Ser Thr Ser Lys Leu
  1               5                  10                  15

Thr Ala Glu Leu Thr Ala Ser Lys Phe Phe Asn Glu Lys Asp Val Val
                 20                  25                  30

Arg Thr Lys Ile Pro Met Met Asn Ile Ala Leu Ser Gly Glu Ile Thr
             35                  40                  45

Gly Gly Met Gln Ser Gly Leu Leu Ile Leu Ala Gly Pro Ser Lys Ser
         50                  55                  60

Phe Lys Ser Asn Phe Gly Leu Thr Met Val Ser Ser Tyr Met Arg Gln
 65                  70                  75                  80
```

```
Tyr Pro Asp Ala Val Cys Leu Phe Tyr Asp Ser Glu Phe Gly Ile Thr
                85                  90                  95

Pro Ala Tyr Leu Arg Ser Met Gly Val Asp Pro Glu Arg Val Ile His
            100                 105                 110

Thr Pro Val Gln Ser Leu Glu Gln Leu Arg Ile Asp Met Val Asn Gln
        115                 120                 125

Leu Asp Ala Ile Glu Arg Gly Glu Lys Val Val Phe Ile Asp Ser
130                 135                 140

Leu Gly Asn Leu Ala Ser Lys Lys Glu Thr Glu Asp Ala Leu Asn Glu
145                 150                 155                 160

Lys Val Val Ser Asp Met Thr Arg Ala Lys Thr Met Lys Ser Leu Phe
                165                 170                 175

Arg Ile Val Thr Pro Tyr Phe Ser Thr Lys Asn Ile Pro Cys Ile Ala
            180                 185                 190

Ile Asn His Thr Tyr Glu Thr Gln Glu Met Phe Ser Lys Thr Val Met
        195                 200                 205

Gly Gly Gly Thr Gly Pro Met Tyr Ser Ala Asp Thr Val Phe Ile Ile
210                 215                 220

Gly Lys Arg Gln Ile Lys Asp Gly Ser Asp Leu Gln Gly Tyr Gln Phe
225                 230                 235                 240

Val Leu Asn Val Glu Lys Ser Arg Thr Val Lys Glu Lys Ser Lys Phe
                245                 250                 255

Phe Ile Asp Val Lys Phe Asp Gly Gly Ile Asp Pro Tyr Ser Gly Leu
            260                 265                 270

Leu Asp Met Ala Leu Glu Leu Gly Phe Val Val Lys Pro Lys Asn Gly
        275                 280                 285

Trp Tyr Ala Arg Glu Phe Leu Asp Glu Glu Thr Gly Glu Met Ile Arg
290                 295                 300

Glu Glu Lys Ser Trp Arg Ala Lys Asp Thr Asn Cys Thr Thr Phe Trp
305                 310                 315                 320

Gly Pro Leu Phe Lys His Gln Pro Phe Arg Asp Ala Ile Lys Arg Ala
                325                 330                 335

Tyr Gln Leu Gly Ala Ile Asp Ser Asn Glu Ile Val Glu Ala Glu Val
            340                 345                 350

Asp Glu Leu Ile Asn Ser Lys Val Glu Lys Phe Lys Ser Pro Glu Ser
        355                 360                 365

Lys Ser Lys Ser Ala Ala Asp Leu Glu Thr Asp Leu Glu Gln Leu Ser
370                 375                 380

Asp Met Glu Glu Phe Asn Glu
385                 390

<210> SEQ ID NO 8
<211> LENGTH: 393
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45
```

Ile Asp Gly Gly Met Gln Ser Gly Leu Thr Ile Phe Ala Gly Pro Ser
        50                  55                  60

Lys His Phe Lys Ser Asn Met Ser Leu Thr Met Val Ala Ala Tyr Leu
 65                  70                  75                  80

Asn Lys Tyr Pro Asp Ala Val Cys Leu Phe Tyr Asp Ser Glu Phe Gly
                 85                  90                  95

Ile Thr Pro Ala Tyr Leu Arg Ser Met Gly Val Asp Pro Glu Arg Val
            100                 105                 110

Ile His Thr Pro Ile Gln Ser Val Glu Gln Leu Lys Ile Asp Met Val
            115                 120                 125

Asn Gln Leu Glu Ala Ile Glu Arg Gly Glu Lys Val Ile Val Phe Ile
130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
                180                 185                 190

Val Ala Val Asn His Thr Ile Glu Thr Ile Glu Met Phe Ser Lys Thr
                195                 200                 205

Val Met Thr Gly Gly Thr Gly Val Met Tyr Ser Ala Asp Thr Val Phe
210                 215                 220

Ile Ile Gly Lys Arg Gln Ile Lys Asp Gly Ser Asp Leu Gln Gly Tyr
225                 230                 235                 240

Gln Phe Val Leu Asn Val Lys Ser Arg Thr Val Lys Glu Lys Ser
                245                 250                 255

Lys Phe Phe Ile Asp Val Lys Phe Asp Gly Gly Ile Asp Pro Tyr Ser
                260                 265                 270

Gly Leu Leu Asp Met Ala Leu Glu Leu Gly Phe Val Val Lys Pro Lys
                275                 280                 285

Asn Gly Trp Tyr Ala Arg Glu Phe Leu Asp Glu Thr Gly Glu Met
290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
                340                 345                 350

Glu Val Asp Glu Leu Ile Asn Ser Lys Val Glu Lys Phe Lys Ser Pro
                355                 360                 365

Glu Ser Lys Ser Lys Ser Ala Ala Asp Leu Glu Thr Asp Leu Glu Gln
                370                 375                 380

Leu Ser Asp Met Glu Glu Phe Asn Glu
385                 390

<210> SEQ ID NO 9
<211> LENGTH: 387
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 9

Met Ser Ser Leu Lys Glu Arg Leu Ile Lys Ala Ser Thr Ser Lys Met
 1               5                   10                  15

```
Thr Ala Glu Leu Thr Lys Ser Lys Phe Phe Asn Asp Lys Thr Val Val
             20                  25                  30

Arg Thr Arg Ile Pro Met Leu Asn Ile Ala Ile Ser Gly Ala Leu Asn
         35                  40                  45

Gly Gly Met Gln Ser Gly Leu Thr Ile Phe Ala Gly Pro Ser Lys His
     50                  55                  60

Phe Lys Ser Asn Met Gly Leu Thr Met Val Ala Ala Tyr Met Lys Ala
 65                  70                  75                  80

Phe Pro Asp Ala Val Cys Met Phe Tyr Asp Ser Glu Phe Gly Ile Thr
                 85                  90                  95

Pro Ala Tyr Leu Lys Ala Met Gly Val Asp Pro Asp Arg Val Ile His
            100                 105                 110

Thr Pro Val Gln Ser Val Glu Gln Leu Lys Ile Asp Met Thr Asn Gln
        115                 120                 125

Leu Glu Glu Val Lys Arg Gly Glu Lys Val Ile Val Phe Ile Asp Ser
    130                 135                 140

Ile Gly Asn Leu Ala Ser Lys Lys Glu Thr Glu Asp Ala Leu Asn Glu
145                 150                 155                 160

Lys Thr Thr Ala Asp Met Thr Arg Ala Lys Ala Leu Lys Ser Leu Phe
                165                 170                 175

Arg Ile Val Thr Pro Tyr Phe Ser Ile Lys Asp Ile Pro Cys Val Ala
            180                 185                 190

Val Asn His Thr Leu Gln Thr Leu Glu Met Phe Ser Lys Glu Val Met
        195                 200                 205

Thr Gly Gly Thr Gly Val Met Tyr Ser Ala Asp Thr Val Phe Phe Ile
    210                 215                 220

Gly Lys Arg Gln Val Lys Asp Gly Thr Glu Leu Ala Gly Tyr Glu Phe
225                 230                 235                 240

Ile Leu Lys Ala Glu Lys Ser Arg Met Val Lys Glu Lys Ser Val Phe
                245                 250                 255

Pro Ile Thr Val Lys Phe Asp Gly Gly Ile Asp Pro Tyr Ser Gly Leu
            260                 265                 270

Leu Glu Met Ala Thr Asp Leu Gly Phe Val Val Lys Pro Lys Val Gly
        275                 280                 285

Trp Tyr Lys Arg Ala Met Met Val Asp Gly Val Met Gln His Glu Glu
    290                 295                 300

Lys Ser Trp Arg Ala Lys Asp Thr Asp Ser Ile Asp Phe Trp Gly Pro
305                 310                 315                 320

Leu Phe Lys His Asp Glu Phe Arg Lys Ala Ile Glu Thr Arg Tyr Gln
                325                 330                 335

Leu Gly Ser Ile Glu Ser Asp Ala Glu Val Ala Glu Val Asp Ala
            340                 345                 350

Leu Ile Gly Ser Lys Thr Thr Ala Lys Ile Ser Gly Val Asn Phe Gly
        355                 360                 365

Pro Ala Glu Ser Ala Ala Asp Lys Gly Gln Gln Leu Glu Asp Phe Val
    370                 375                 380

Asp Glu Asp
385

<210> SEQ ID NO 10
<211> LENGTH: 390
<212> TYPE: PRT
<213> ORGANISM: Artificial Sequence
<220> FEATURE:
<223> OTHER INFORMATION: Description of Artificial Sequence: Synthetic
``` construct

<400> SEQUENCE: 10

```
Met Ser Asp Leu Lys Ser Arg Leu Ile Lys Ala Ser Thr Ser Lys Met
 1               5                  10                  15

Thr Ala Asp Leu Thr Lys Ser Lys Leu Phe Asn Asn Arg Asp Glu Val
            20                  25                  30

Pro Thr Arg Ile Pro Met Leu Asn Ile Ala Leu Gly Gly Ala Leu Asn
        35                  40                  45

Ala Gly Leu Gln Ser Gly Leu Thr Ile Phe Ala Ala Pro Ser Lys His
    50                  55                  60

Phe Lys Thr Leu Phe Gly Leu Thr Met Val Ala Ala Tyr Met Lys Lys
65                  70                  75                  80

Tyr Lys Asp Ala Ile Cys Leu Phe Tyr Asp Ser Glu Phe Gly Ala Ser
                85                  90                  95

Glu Ser Tyr Phe Arg Ser Met Gly Val Asp Leu Asp Arg Val Val His
            100                 105                 110

Thr Pro Ile Gln Ser Val Glu Gln Leu Lys Val Asp Met Thr Asn Gln
        115                 120                 125

Leu Asp Ala Ile Glu Arg Gly Asp Lys Val Ile Phe Ile Asp Ser
    130                 135                 140

Ile Gly Asn Thr Ala Ser Lys Lys Glu Thr Glu Asp Ala Leu Asn Glu
145                 150                 155                 160

Lys Val Val Gly Asp Met Ser Arg Ala Lys Ala Leu Lys Ser Leu Phe
                165                 170                 175

Arg Ile Val Thr Pro Tyr Leu Thr Ile Lys Asp Ile Pro Cys Val Ala
            180                 185                 190

Ile Asn His Thr Ala Met Glu Ile Gly Gly Leu Tyr Pro Lys Glu Ile
        195                 200                 205

Met Gly Gly Gly Thr Gly Ile Leu Tyr Ser Ala Asn Thr Val Phe Phe
    210                 215                 220

Ile Ser Lys Arg Gln Val Lys Glu Gly Thr Glu Leu Thr Gly Tyr Asp
225                 230                 235                 240

Phe Thr Leu Lys Ala Glu Lys Ser Arg Thr Val Lys Glu Lys Ser Thr
                245                 250                 255

Phe Pro Ile Thr Val Asn Phe Asp Gly Gly Ile Asp Pro Phe Ser Gly
            260                 265                 270

Leu Leu Glu Met Ala Thr Glu Ile Gly Phe Val Val Lys Pro Lys Ala
        275                 280                 285

Gly Trp Tyr Ala Arg Glu Phe Leu Asp Glu Glu Thr Gly Glu Met Ile
    290                 295                 300

Arg Glu Glu Lys Ser Trp Arg Ala Lys Ala Thr Asp Cys Val Glu Phe
305                 310                 315                 320

Trp Gly Pro Leu Phe Lys His Lys Pro Phe Arg Asp Ala Ile Glu Thr
                325                 330                 335

Lys Tyr Lys Leu Gly Ala Ile Ser Ser Ile Lys Glu Val Asp Asp Ala
            340                 345                 350

Val Asn Asp Leu Ile Asn Cys Lys Ala Thr Thr Lys Val Pro Val Lys
        355                 360                 365

Thr Ser Asp Ala Pro Ser Ala Ala Asp Ile Glu Asn Asp Leu Asp Glu
    370                 375                 380

Met Glu Asp Phe Asp Glu
385                 390
```

```
<210> SEQ ID NO 11
<211> LENGTH: 411
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 11

Met Ala Lys Gly Ile Lys Thr Ala Lys Thr Gly Asn Leu Gly Ser Leu
 1               5                  10                  15

Met Ser Lys Leu Ala Gly Thr Ser Ser Asn Lys Met Ser Ser Val Leu
                20                  25                  30

Ala Asp Ser Lys Phe Phe Asn Asp Lys Asp Cys Val Arg Thr Arg Val
            35                  40                  45

Pro Leu Leu Asn Leu Ala Met Ser Gly Glu Leu Asp Gly Gly Leu Thr
        50                  55                  60

Pro Gly Leu Thr Val Leu Ala Gly Pro Ser Lys His Phe Lys Ser Asn
65                  70                  75                  80

Leu Ser Leu Val Phe Ala Ala Tyr Leu Arg Lys Tyr Pro Asp Ala
                85                  90                  95

Val Cys Ile Phe Phe Asp Asn Glu Phe Gly Ser Thr Pro Gly Tyr Phe
                100                 105                 110

Glu Ser Gln Gly Val Asp Ile Ser Arg Val Ile His Cys Pro Phe Lys
                115                 120                 125

Asn Ile Glu Glu Leu Lys Phe Asp Ile Val Lys Lys Leu Glu Ala Ile
                130                 135                 140

Glu Arg Gly Asp Arg Val Ile Val Phe Val Asp Ser Ile Gly Asn Ala
145                 150                 155                 160

Ala Ser Lys Lys Glu Ile Asp Asp Ala Ile Asp Glu Lys Ser Val Ser
                165                 170                 175

Asp Met Thr Arg Ala Lys Gln Ile Lys Ser Leu Thr Arg Met Met Thr
                180                 185                 190

Pro Tyr Leu Thr Val Asn Asp Ile Pro Ala Ile Met Val Ala His Thr
                195                 200                 205

Tyr Asp Thr Gln Glu Met Tyr Ser Lys Lys Val Val Ser Gly Gly Thr
            210                 215                 220

Gly Ile Thr Tyr Ser Ser Asp Thr Val Ile Ile Gly Arg Gln Gln
225                 230                 235                 240

Glu Lys Asp Gly Lys Glu Leu Leu Gly Tyr Asn Phe Val Leu Asn Met
                245                 250                 255

Glu Lys Ser Arg Phe Val Lys Glu Gln Ser Lys Leu Pro Leu Glu Val
                260                 265                 270

Thr Phe Gln Gly Gly Ile Asn Thr Tyr Ser Gly Met Leu Asp Ile Ala
                275                 280                 285

Leu Glu Val Gly Phe Val Val Lys Pro Ser Asn Gly Trp Phe Ser Arg
            290                 295                 300

Ala Phe Leu Asp Glu Glu Thr Gly Glu Leu Val Glu Glu Asp Arg Lys
305                 310                 315                 320

Trp Arg Arg Ala Asp Thr Asn Cys Leu Glu Phe Trp Lys Pro Met Phe
                325                 330                 335

Ala His Gln Pro Phe Lys Thr Ala Cys Ser Asp Met Phe Lys Leu Lys
                340                 345                 350

Ser Val Ala Val Lys Asp Glu Val Phe Asp Glu Val Asp Glu Leu Phe
                355                 360                 365

Ser Gly Glu Ala Glu Met Pro Val Asn Met Gly Arg Lys Leu Asp Thr
```

```
                    370                 375                 380
Ala Asp Gln Glu Glu Ile Asp Gln Leu Glu Glu Val Asp Val Glu Gly
385                 390                 395                 400

Ser Asp Ser Asp Glu Leu Phe Ala Asn Leu Asp
                405                 410

<210> SEQ ID NO 12
<211> LENGTH: 368
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

Met Ala Lys Lys Ala Lys Val Val Asn Ser Gly Asp Leu Leu Glu Arg
  1               5                  10                  15

Leu Asn Gly Thr Ser Ser Asn Lys Met Ser Ala Met Leu Ala Glu Ser
                 20                  25                  30

Ile Phe Phe Asn Glu Lys Asp Thr Ile Arg Thr Arg Val Pro Ile Ile
             35                  40                  45

Asn Leu Met Met Ser Gly Arg Leu Asp Gly Gly Ile Thr Pro Gly Leu
 50                  55                  60

Thr Cys Ile Ala Gly Pro Ser Lys His Phe Lys Ser Asn Leu Ser Leu
 65                  70                  75                  80

Val Met Val Ser Ala Tyr Leu Arg Lys Tyr Pro Lys Ala Val Cys Leu
                 85                  90                  95

Phe Phe Asp Asn Glu Phe Gly Ser Thr Pro Asp Tyr Phe Thr Ser Gln
            100                 105                 110

Gly Val Asp Ile Ser Arg Val Val His Cys Pro Phe Ile Asp Val Glu
        115                 120                 125

Glu Leu Lys Phe Asp Ile Val Lys Lys Leu Glu Ser Ile Thr Arg Gly
130                 135                 140

Asp Lys Val Ile Ile Tyr Ile Asp Ser Ile Gly Asn Val Ala Ser Lys
145                 150                 155                 160

Lys Glu Leu Gln Asp Ala Lys Asp Glu Lys Ser Ala Gln Asp Met Thr
                165                 170                 175

Arg Ala Lys Gln Ile Lys Ser Leu Phe Arg Met Val Thr Pro Tyr Leu
            180                 185                 190

Thr Val Leu Asp Ile Pro Cys Ile Ala Val Asn His Thr Tyr Glu Thr
        195                 200                 205

Gln Glu Met Phe Ser Lys Thr Val Met Ser Gly Gly Thr Gly Pro Met
210                 215                 220

Tyr Ser Ala Asp Thr Val Ile Ile Leu Gly Lys Gln Gln Asp Lys Asp
225                 230                 235                 240

Gly Lys Glu Leu Leu Gly Tyr Asn Phe Val Met Asn Ala Glu Lys Ser
                245                 250                 255

Arg Ala Ile Lys Glu Lys Ser Lys Leu Asp Leu Met Val Ser Phe Glu
            260                 265                 270

Gly Gly Ile Asn Thr Tyr Ser Gly Leu Leu Lys Ile Ala Gln Glu Leu
        275                 280                 285

Gly Phe Val Thr Lys Pro Gln Asn Ala Arg Tyr Gln Arg Asn Phe Leu
290                 295                 300

Asp Leu Glu Pro Gly Glu Met Val Ile Pro Glu Asp Glu Lys Lys Trp
305                 310                 315                 320

Thr Glu Glu Glu Ser Asp Ser Leu Glu Phe Trp Lys Pro Met Phe Ser
```

-continued

```
                325                 330                 335
His Lys Pro Phe Met Asp Ala Val Ser Asn Ala Tyr Lys Leu Lys Ala
                    340                 345                 350

Val Glu Val Ser Gln Glu Val Phe Asp Glu Val Asp Gln Leu Phe Gly
            355                 360                 365

<210> SEQ ID NO 13
<211> LENGTH: 366
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 13

Met Ser Asp Leu Met Lys Ser Leu Lys Lys Ser Ser Thr Ser Gly Tyr
  1               5                  10                  15

Ala Gln Val Leu Ser Glu Ser Gln Phe Met Phe Asp Lys Asp His Thr
             20                  25                  30

Arg Thr Tyr Val Pro Ala Ile Asn Ile Ala Phe Ser Gly Glu Val Asp
         35                  40                  45

Gly Gly Leu Thr Ser Gly Leu Thr Val Leu Ala Gly Pro Ser Lys His
     50                  55                  60

Phe Lys Ser Asn Leu Gly Leu Val Gly Val Ala Ala Tyr Leu Lys Lys
 65                  70                  75                  80

Tyr Pro Asp Ala Val Cys Val Phe Ile Asp Thr Glu Phe Gly Ile Thr
                 85                  90                  95

Pro Ser Tyr Leu Arg Ser Gln Gly Val Asp Pro Asp Arg Val Leu His
            100                 105                 110

Ile Gln Cys Glu Ser Val Glu Arg Met Lys Phe Glu Met Ala Asn Gln
        115                 120                 125

Leu Lys Asp Leu Ala Glu Arg Lys Arg Ala Lys Lys Ala Gly Glu Glu
    130                 135                 140

Pro Asp Arg Val Ile Phe Phe Ile Asp Ser Val Gly Asn Val Ala Ser
145                 150                 155                 160

Ala Lys Glu Ile Asp Asp Ala Gln Asn Glu Lys Ser Val Ala Asp Met
                165                 170                 175

Ser Arg Ala Lys Gln Leu Lys Ser Leu Phe Arg Ile Ile Thr Pro Tyr
            180                 185                 190

Phe Thr Met Leu Asp Ile Pro Cys Ile Ala Ile Asn His Thr Tyr Gln
        195                 200                 205

Thr Gln Glu Ile Tyr Ser Lys Thr Val Met Ser Gly Thr Gly Ile
    210                 215                 220

Met Tyr Ser Ala Asp Thr Val Ile Ile Leu Gly Lys Gln Gln Glu Lys
225                 230                 235                 240

Asp Gly Lys Asp Ile Ile Gly Tyr His Phe Ile Met Asn Ile Glu Lys
                245                 250                 255

Ser Arg Phe Val Lys Glu Lys Met Lys Val Pro Leu Thr Val Thr Tyr
            260                 265                 270

Glu Asn Gly Ile Asp Pro Phe Ser Gly Leu Leu Asp Ile Ala Leu Gln
        275                 280                 285

Thr Gly His Val Val Lys Pro Ser Asn Gly Trp Tyr Gln Arg Ala Thr
    290                 295                 300

Val Asp Glu Glu Thr Gly Glu Met Ile Val Glu Glu Lys Lys Tyr Arg
305                 310                 315                 320

Ala Lys Glu Thr Gln Thr Ile Ser Phe Trp Lys Asp Ile Ile Asn Ser
```

325                 330                 335
Pro Thr Phe Lys Glu Gly Val Lys Arg Ile Tyr Cys Leu Gly Gln Leu
            340                 345                 350

Asp Glu Ser Glu Leu Phe Gly Glu Val Asp Ser Leu Phe Asp
            355                 360                 365

<210> SEQ ID NO 14
<211> LENGTH: 386
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 14

Met Ser Asn Lys Ala Leu Leu Lys Lys Leu Ile Lys Asn Ser Asn Ser
 1               5                  10                  15

Gln Ser Ala Ala Ile Leu Ser Glu Ser Asp Val Phe Asn Asn Ile Thr
            20                  25                  30

Lys Thr Arg Thr Arg Val Pro Ile Leu Asn Leu Ala Leu Ser Gly Ala
        35                  40                  45

Phe Asp Gly Gly Leu Thr Ser Gly Leu Thr Leu Phe Ala Gly Pro Ser
    50                  55                  60

Lys His Phe Lys Ser Asn Leu Gly Leu Val Thr Val Ser Ala Tyr Leu
65                  70                  75                  80

Lys Ala Asn Glu Asp Ala Val Cys Leu Phe Tyr Asp Ser Glu Lys Gly
                85                  90                  95

Val Thr Lys Ser Tyr Leu Lys Ser Met Gly Val Asp Pro Asp Arg Val
            100                 105                 110

Val Tyr Thr Arg Ile Thr Thr Val Glu Gln Leu Arg Asn Asp Val Val
        115                 120                 125

Ser Gln Leu Asp Ala Leu Glu Arg Gly Asp Lys Val Ile Ile Phe Val
    130                 135                 140

Asp Ser Val Gly Asn Thr Ala Ser Lys Lys Glu Leu Ala Asp Ala Leu
145                 150                 155                 160

Ser Asp Asn Asp Lys Gln Asp Met Thr Arg Ala Lys Ala Leu Lys Gly
                165                 170                 175

Met Phe Arg Met Val Thr Pro Tyr Leu Ala Asp Leu Asp Ile Pro Met
            180                 185                 190

Val Cys Ile Cys His Thr Tyr Asp Thr Gln Glu Met Tyr Ser Lys Lys
        195                 200                 205

Val Ile Ser Gly Gly Thr Gly Leu Met Tyr Ser Ala Asp Thr Ala Ile
    210                 215                 220

Ile Leu Gly Lys Gln Val Lys Glu Gly Thr Glu Val Val Gly Tyr
225                 230                 235                 240

Asp Phe Ile Met Asn Ile Glu Lys Ser Arg Phe Val Lys Glu Lys Ser
                245                 250                 255

Lys Phe Pro Leu His Val Thr Tyr Glu Gly Gly Ile Ser Met Tyr Ser
            260                 265                 270

Gly Leu Leu Asp Leu Ala Met Glu Met Asn Phe Val Gln Thr Pro Thr
        275                 280                 285

Lys Gly Trp Arg Gly Arg Ala Phe Leu Asn Thr Glu Thr Gly Glu Leu
    290                 295                 300

Glu Leu Glu Glu Lys Lys Trp Arg Glu Ser Thr Asn Ser Ile Glu
305                 310                 315                 320

Phe Trp Arg Pro Leu Phe Thr His Gln Pro Phe Leu Asp Ala Ile Gln

```
                    325                 330                 335
Asp Lys Tyr Arg Ile Pro Asp Lys Glu Ile Thr Asp Gly Ala Ala Leu
                340                 345                 350

Glu Asp Leu Tyr Ser Thr Asp Glu Pro Glu Ser Asn Lys Ile Asp Leu
            355                 360                 365

Asp Asp Asp Ile Pro Asp Asp Ile Gly Ile Asp Gln Asp Glu Glu Pro
        370                 375                 380

Ile Met
385

<210> SEQ ID NO 15
<211> LENGTH: 335
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 15

Met Asp Phe Leu Lys Glu Ile Val Lys Glu Ile Gly Asp Glu Tyr Thr
 1               5                  10                  15

Gln Val Ala Ala Asp Ile Gln Glu Asn Glu Arg Phe Ile Asp Thr Gly
            20                  25                  30

Ser Tyr Ile Phe Asn Gly Leu Val Ser Gly Ser Ile Phe Gly Gly Val
        35                  40                  45

Ser Ser Ser Arg Ile Thr Ala Ile Ala Gly Glu Ser Ser Thr Gly Lys
    50                  55                  60

Thr Tyr Phe Ser Leu Ala Val Val Lys Asn Phe Leu Asp Asn Asn Pro
65                  70                  75                  80

Asp Gly Tyr Cys Leu Tyr Phe Asp Thr Glu Ala Ala Val Asn Lys Gly
                85                  90                  95

Leu Leu Glu Ser Arg Gly Ile Asp Met Asn Arg Leu Val Val Val Asn
            100                 105                 110

Val Val Thr Ile Glu Glu Phe Arg Ser Lys Ala Leu Arg Ala Val Asp
        115                 120                 125

Ile Tyr Leu Lys Thr Ser Glu Glu Arg Lys Pro Cys Met Phe Val
    130                 135                 140

Leu Asp Ser Leu Gly Met Leu Ser Thr Glu Lys Glu Ile Arg Asp Ala
145                 150                 155                 160

Leu Asp Asp Lys Gln Val Arg Asp Met Thr Lys Ser Gln Leu Val Lys
                165                 170                 175

Gly Ala Phe Arg Met Leu Thr Leu Lys Leu Gly Gln Ala Asn Ile Pro
            180                 185                 190

Leu Ile Val Thr Asn His Thr Tyr Asp Val Ile Gly Ser Tyr Val Pro
        195                 200                 205

Thr Lys Glu Met Gly Gly Gly Ser Gly Leu Lys Tyr Ala Ala Ser Thr
    210                 215                 220

Ile Ile Tyr Leu Ser Lys Lys Lys Glu Lys Asp Gln Lys Glu Val Ile
225                 230                 235                 240

Gly Asn Leu Ile Lys Ala Lys Thr His Lys Ser Arg Leu Ser Lys Glu
                245                 250                 255

Asn Lys Glu Val Gln Ile Arg Leu Tyr Tyr Asp Glu Arg Gly Leu Asp
            260                 265                 270

Arg Tyr Tyr Gly Leu Leu Glu Leu Gly Glu Ile Gly Gly Met Trp Lys
        275                 280                 285

Asn Val Ala Gly Arg Tyr Glu Met Asn Gly Lys Lys Ile Tyr Ala Lys
```

```
            290                 295                 300
Glu Ile Leu Lys Asn Pro Thr Glu Tyr Phe Thr Asp Asp Ile Met Glu
305                 310                 315                 320

Gln Leu Asp Asn Ile Ala Lys Glu His Phe Ser Tyr Gly Thr Asn
                325                 330                 335

<210> SEQ ID NO 16
<211> LENGTH: 336
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 16

Met Asn Phe Leu Lys Asp Ile Ala Lys Glu Ile Gly Asn Asp Tyr Ala
1               5                   10                  15

Ser Leu Val Ser Glu Gly Val Ser Ala Gly Asp Thr Ala Gly Phe Ile
            20                  25                  30

Asp Thr Gly Ser Tyr Ile Phe Asn Ala Leu Leu Ser Gly Ser Ile Tyr
        35                  40                  45

Gly Gly Ile Pro Asn Asn Lys Ile Thr Ala Ile Ala Gly Glu Thr Ser
    50                  55                  60

Thr Gly Lys Thr Phe Phe Cys Leu Gly Met Val Gln His Phe Leu Glu
65                  70                  75                  80

Ser Asn Pro Asp Ala Gly Val Ile Tyr Phe Glu Ser Glu Ser Ala Ile
                85                  90                  95

Ser Lys Gln Met Ile Glu Asp Arg Gly Ile Asp Ser Asn Arg Met Leu
            100                 105                 110

Leu Val Pro Val Thr Thr Val Gln Glu Phe Arg Leu Gln Ala Ile Lys
        115                 120                 125

Ile Leu Asp Lys Tyr Asn Glu Gln Thr Ala Glu Glu Arg Lys Pro Leu
    130                 135                 140

Met Phe Val Leu Asp Ser Leu Gly Met Leu Ser Thr Ser Lys Glu Val
145                 150                 155                 160

Glu Asp Ser Glu Ala Gly Lys Glu Thr Arg Asp Met Thr Arg Ala Gln
                165                 170                 175

Val Val Lys Ser Ile Phe Arg Val Leu Thr Leu Lys Leu Gly Lys Ala
            180                 185                 190

Asn Val Pro Leu Ile Val Thr Asn His Thr Tyr Asp Val Val Gly Ala
        195                 200                 205

Tyr Ile Pro Thr Lys Glu Met Gly Gly Gly Ser Gly Leu Lys Tyr Ala
    210                 215                 220

Ala Ser Thr Ile Val Tyr Leu Ser Lys Lys Glu Lys Asn Gly Lys
225                 230                 235                 240

Glu Val Val Gly Asn Ile Ile Lys Cys Lys Thr Ala Lys Ser Arg Leu
                245                 250                 255

Thr Lys Glu Asn Ser Asp Val Glu Thr Arg Leu Tyr Tyr Asp Arg Gly
            260                 265                 270

Leu Asp Arg Tyr Tyr Gly Leu Leu Glu Leu Gly Glu Lys His Gly Val
        275                 280                 285

Phe Ser Arg Lys Gly Asn Arg Val Val Gly Asp Ser Ser Val Tyr
    290                 295                 300

Pro Ser Ala Ile Leu Ala Asp Pro Asp Lys Tyr Phe Thr Glu Glu Leu
305                 310                 315                 320

Met Glu Lys Leu Asp Glu Ala Ala Ala Lys Glu Phe Arg Tyr Gly Asn
```

325                 330                 335

<210> SEQ ID NO 17
<211> LENGTH: 137
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 17

Met Arg Leu Glu Asp Leu Gln Glu Glu Leu Lys Lys Asp Val Phe Ile
1               5                   10                  15

Asp Ser Thr Lys Leu Gln Tyr Glu Ala Ala Asn Asn Val Met Leu Tyr
            20                  25                  30

Ser Lys Trp Leu Asn Lys His Ser Ser Ile Lys Lys Glu Met Leu Arg
        35                  40                  45

Ile Glu Ala Gln Lys Lys Val Ala Leu Lys Ala Arg Leu Asp Tyr Tyr
    50                  55                  60

Ser Gly Arg Gly Asp Gly Asp Glu Phe Ser Met Asp Arg Tyr Glu Lys
65                  70                  75                  80

Ser Glu Met Lys Thr Val Leu Ser Ala Asp Lys Asp Val Leu Lys Val
                85                  90                  95

Asp Thr Ser Leu Gln Tyr Trp Gly Ile Leu Leu Asp Phe Cys Ser Gly
            100                 105                 110

Ala Leu Asp Ala Ile Lys Ser Arg Gly Phe Ala Ile Lys His Ile Gln
        115                 120                 125

Asp Met Arg Ala Phe Glu Ala Gly Lys
    130                 135

<210> SEQ ID NO 18
<211> LENGTH: 137
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 18

Met Arg Leu Glu Asp Leu Gln Glu Glu Leu Lys Lys Asp Val Phe Ile
1               5                   10                  15

Asp Ser Thr Lys Leu Gln Tyr Glu Ala Ala Asn Asn Val Met Leu Tyr
            20                  25                  30

Ser Lys Trp Leu Asn Lys His Ser Ser Ile Lys Lys Glu Met Leu Arg
        35                  40                  45

Ile Asp Ala Gln Lys Lys Val Ala Leu Lys Ala Lys Leu Asp Tyr Tyr
    50                  55                  60

Ser Gly Arg Gly Asp Gly Asp Glu Phe Ser Met Asp Arg Tyr Glu Lys
65                  70                  75                  80

Ser Glu Met Lys Thr Val Leu Ser Ala Asp Lys Asp Val Leu Lys Val
                85                  90                  95

Asp Thr Ser Leu Gln Tyr Trp Gly Ile Leu Leu Asp Phe Cys Ser Gly
            100                 105                 110

Ala Leu Asp Ala Ile Lys Ser Arg Gly Phe Ala Ile Lys His Ile Gln
        115                 120                 125

Asp Met Arg Ala Phe Glu Ala Gly Lys
    130                 135

<210> SEQ ID NO 19

<211> LENGTH: 137
<212> TYPE: PRT
<213> ORGANISM: Artificial Sequence
<220> FEATURE:
<223> OTHER INFORMATION: Description of Artificial Sequence: Synthetic construct

<400> SEQUENCE: 19

```
Met Lys Leu Glu Asp Leu Gln Glu Glu Leu Asp Ala Asp Leu Ala Ile
  1               5                  10                  15
Asp Thr Thr Lys Leu Gln Tyr Glu Thr Ala Asn Asn Val Lys Leu Tyr
                 20                  25                  30
Ser Lys Trp Leu Arg Lys His Ser Phe Ile Arg Lys Glu Met Leu Arg
             35                  40                  45
Ile Glu Thr Gln Lys Lys Thr Ala Leu Lys Ala Arg Leu Asp Tyr Tyr
         50                  55                  60
Ser Gly Arg Gly Asp Gly Asp Glu Phe Ser Met Asp Arg Tyr Glu Lys
 65                  70                  75                  80
Ser Glu Met Lys Thr Val Leu Ala Ala Asp Lys Asp Val Leu Lys Ile
                 85                  90                  95
Glu Thr Leu Gln Tyr Trp Gly Ile Leu Leu Glu Phe Cys Ser Gly
             100                 105                 110
Ala Leu Asp Ala Val Lys Ser Arg Ser Phe Ala Leu Lys His Ile Gln
         115                 120                 125
Asp Met Arg Glu Phe Glu Ala Gly Gln
         130                 135
```

<210> SEQ ID NO 20
<211> LENGTH: 135
<212> TYPE: PRT
<213> ORGANISM: Artificial Sequence
<220> FEATURE:
<223> OTHER INFORMATION: Description of Artificial Sequence: Synthetic construct

<400> SEQUENCE: 20

```
Met Thr Leu Glu Asp Leu Gln Ala Glu Leu Lys Lys Asp Leu Val Leu
  1               5                  10                  15
Asp Met Thr Gln Leu Gln Thr Glu Ala Ala Glu Asn Ile Asn Leu Tyr
                 20                  25                  30
Cys Lys Trp Ser Thr Lys Tyr Ser Asn Ile Arg Lys Ser Ile Leu Ser
             35                  40                  45
Leu Asp Ala Gln Arg Lys Lys His Thr Lys Thr Lys Leu Asp Tyr Tyr
         50                  55                  60
Ser Gly Arg Gly Asp Glu Val Ser Met Asp Arg Tyr Glu Arg Ser Glu
 65                  70                  75                  80
Met Lys Thr Val Leu Ser Gly Asp Ala Asp Ile Leu Thr Val Glu Thr
                 85                  90                  95
Lys Ile Gln Tyr Phe Thr Ile Met Leu Glu Phe Cys Gly Asn Ala Met
             100                 105                 110
Asp Ala Ile Lys Ser Arg Gly Phe Ala Ile Lys Asn Ile Ile Asp Leu
         115                 120                 125
Arg Gln Phe Glu Ala Gly Lys
         130                 135
```

<210> SEQ ID NO 21
<211> LENGTH: 136
<212> TYPE: PRT
<213> ORGANISM: Artificial Sequence
<220> FEATURE:

<223> OTHER INFORMATION: Description of Artificial Sequence: Synthetic
      construct

<400> SEQUENCE: 21

Met Thr Leu Asp Glu Leu Lys Glu Leu Lys Ala Asp Leu Pro Ile
1               5                   10                  15

Lys Leu Thr Ala Val Gln Thr Glu Val Ala Glu Asn Pro Val Leu Tyr
            20                  25                  30

Gly Lys Trp Asn Arg Tyr Leu Ala Asp Ile Asn Arg Glu Ile Thr Arg
        35                  40                  45

Leu Asp Ala Glu Arg Lys Lys Met Leu Arg Asp Arg Phe Met Phe Tyr
    50                  55                  60

Thr Gly Arg Ser Glu Asp Glu Val Cys Met Asp Val Tyr Ser Pro Thr
65                  70                  75                  80

Glu Leu Lys Thr Val Ile Ala Gly Asp Glu Val Ile Lys Lys Asn
                85                  90                  95

Ala Ala Val Glu Leu Ser Gln Ala Lys Ala Asp Phe Cys Arg Gln Ser
            100                 105                 110

Met Glu Ala Val Arg Gln Arg Gly Phe Ser Leu Arg Ala Ile Ile Asp
        115                 120                 125

Cys Arg Lys Leu Glu Ala Gly Glu
    130                 135

<210> SEQ ID NO 22
<211> LENGTH: 140
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 22

Met Thr Glu Leu Lys Leu Glu Asp Leu Gln Ala Glu Leu Gly Gln Asp
1               5                   10                  15

Met Leu Ile Asp Pro Leu Lys Leu Gln Ser Glu Ser Ala Asp Ile Pro
            20                  25                  30

Lys Ile Trp Ser Lys Trp Leu Arg Tyr His Ser Asn Ala Lys Lys Lys
        35                  40                  45

Leu Ile Gln Leu Gln Ala Arg Lys Glu Ala Asp Val Lys Glu Arg Leu
    50                  55                  60

Leu Tyr Tyr Thr Gly Arg His Glu Thr Glu Met Thr Asp Val Ile Tyr
65                  70                  75                  80

Thr Gly Ser Gly Glu Ile Lys Ile Ala Ile Asn Gly Asp Pro Lys Ile
                85                  90                  95

Val Glu Val Asn Lys Leu Ile Gln Tyr Phe Glu Leu Ile Ala Glu Phe
            100                 105                 110

Thr Ser Lys Ala Leu Asp Ile Val Lys Asn Lys Gly Tyr Ser Ile Lys
        115                 120                 125

Asn Met Leu Glu Ile Arg Lys Leu Glu Ser Gly Ala
    130                 135                 140

<210> SEQ ID NO 23
<211> LENGTH: 137
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 23

```
Met Lys Leu Gln Asp Leu Lys Ala Glu Tyr His Glu Asp Val Lys Ile
1               5                   10                  15

Asp Thr Thr Ala Leu Glu Thr Ala Ala Ile Arg Ile Pro Val Leu His
                20                  25                  30

Ala Lys Trp Leu Ala Tyr Arg Ala Asp Ala Arg Gln Leu Leu Ile Lys
            35                  40                  45

Ala Glu Met Lys Met Glu Ala Val Arg Lys Asp Arg Trp Leu Phe Tyr
        50                  55                  60

Ser Gly Lys His Asp Asp Glu Val Cys Asp Phe Ile Val Glu Lys Ser
65                  70                  75                  80

Glu Met Lys Tyr Ala Leu Ala Gly Asp Glu Ala Leu Gln Leu Ala Ile
                85                  90                  95

Ala Arg Phe Gln His Met Lys Asp Val Leu Ser Phe Ile Glu Glu Ala
            100                 105                 110

Leu Lys Gly Ile Ser Gln Met Gly Phe Thr Ile Lys His Ile Ile Asp
        115                 120                 125

Asn Arg Lys Ile Glu Ser Gly Ile Val
    130                 135
```

<210> SEQ ID NO 24
<211> LENGTH: 142
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 24

```
Met Asn Leu Asp Lys Ile Gln Glu Met Trp Glu Arg Asp Ala Val Ile
1               5                   10                  15

Asp Pro Asp Asn Leu His Asp Glu Ser Leu Lys Ile Pro Gln Leu His
                20                  25                  30

Ser Lys Tyr Tyr Thr Val Tyr Asn Thr Val Thr Leu Met Arg Glu Lys
            35                  40                  45

Ala Arg Glu Gln Tyr Asn Lys Thr Arg Leu Glu Arg His Asn Tyr Tyr
        50                  55                  60

Thr Gly Lys Ala Pro Ala Glu Val Tyr Ile Glu Glu Pro Phe Gly Tyr
65                  70                  75                  80

Lys Val Arg Glu Lys Asp Ala Ile Gln Arg Tyr Met Glu Ala Asp Glu
                85                  90                  95

Lys Met Ser Lys Ile Asp Leu Lys Ile Arg Tyr Tyr Asp Thr Thr Leu
            100                 105                 110

Lys Phe Leu Glu Glu Ile Ile Lys Asn Ile Ser Asn Arg Thr Phe Gln
        115                 120                 125

Ile Lys Asn Ala Ile Glu Trp Asn Lys Phe Gln Ala Gly Met
130                 135                 140
```

<210> SEQ ID NO 25
<211> LENGTH: 142
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 25

```
Met Asn Leu Glu Gln Ile Gln Glu Met Trp Lys Lys Asp Ser Val Ile
1               5                   10                  15
```

```
Asp Asn Asp Leu Tyr Cys Glu Glu Ser Thr Lys Ile Pro Gln Leu His
             20                  25                  30

Met Arg Tyr Met Glu Leu Tyr Thr Thr Phe Gly Leu Met Lys Lys Glu
         35                  40                  45

Arg Glu Ile Glu Met Lys Arg Leu Ile Arg Glu Lys Trp Leu Tyr Tyr
     50                  55                  60

Lys Gly Lys Ala Pro Ser Ser Val Tyr Lys Glu Leu Pro Phe Asp Leu
 65                  70                  75                  80

Lys Leu Thr Thr Lys Glu Val Asn Met Phe Ile Glu Gly Asp Asp
             85                  90                  95

Asp Val Arg Lys Leu Gln Tyr Lys Ile Glu Tyr Val Glu Gln Cys Leu
             100                 105                 110

Asn Tyr Leu Asp Gly Val Leu Arg Gln Ile Asn Asn Arg Asn Phe Gln
             115                 120                 125

Ile Lys Asn Ala Ile Asp Trp Thr Lys Phe Gln Asn Gly Leu
             130                 135                 140
```

<210> SEQ ID NO 26
<211> LENGTH: 301
<212> TYPE: PRT
<213> ORGANISM: Artificial Sequence
<220> FEATURE:
<223> OTHER INFORMATION: Description of Artificial Sequence: Synthetic
      construct <400> SEQUENCE: 26

```
Met Phe Lys Arg Lys Ser Thr Ala Glu Leu Ala Ala Gln Met Ala Lys
  1               5                  10                  15

Leu Asn Gly Asn Lys Gly Phe Ser Ser Glu Asp Lys Gly Glu Trp Lys
             20                  25                  30

Leu Lys Leu Asp Asn Ala Gly Asn Gly Gln Ala Val Ile Arg Phe Leu
         35                  40                  45

Pro Ser Lys Asn Asp Glu Gln Ala Pro Phe Ala Ile Leu Val Asn His
     50                  55                  60

Gly Phe Lys Lys Asn Gly Lys Trp Tyr Ile Glu Thr Cys Ser Ser Thr
 65                  70                  75                  80

His Gly Asp Tyr Asp Ser Cys Pro Val Cys Gln Tyr Ile Ser Lys Asn
             85                  90                  95

Asp Leu Tyr Asn Thr Asp Asn Lys Glu Tyr Ser Leu Val Lys Arg Lys
             100                 105                 110

Thr Ser Tyr Trp Ala Asn Ile Leu Val Val Lys Asp Pro Ala Ala Pro
         115                 120                 125

Glu Asn Glu Gly Lys Val Phe Lys Tyr Arg Phe Gly Lys Lys Ile Trp
     130                 135                 140

Asp Lys Ile Asn Ala Met Ile Ala Val Asp Val Glu Met Gly Glu Thr
145                 150                 155                 160

Pro Val Asp Val Thr Cys Pro Trp Glu Gly Ala Asn Phe Val Leu Lys
                 165                 170                 175

Val Lys Gln Val Ser Gly Phe Ser Asn Tyr Asp Glu Ser Lys Phe Leu
             180                 185                 190

Asn Gln Ser Ala Ile Pro Asn Ile Asp Asp Glu Ser Phe Gln Lys Glu
         195                 200                 205

Leu Phe Glu Gln Met Val Asp Leu Ser Glu Met Thr Ser Lys Asp Lys
     210                 215                 220

Phe Lys Ser Phe Glu Glu Leu Asn Thr Lys Phe Gly Gln Val Met Gly
225                 230                 235                 240
```

```
Thr Ala Val Met Gly Gly Ala Ala Thr Ala Ala Lys Lys Ala Asp
            245                 250                 255

Lys Val Ala Asp Asp Leu Asp Ala Phe Asn Val Asp Asp Phe Asn Thr
            260                 265                 270

Lys Thr Glu Asp Asp Phe Met Ser Ser Ser Gly Ser Ser Ser Ser
        275                 280                 285

Ala Asp Asp Thr Asp Leu Asp Asp Leu Leu Asn Asp Leu
    290                 295                 300

<210> SEQ ID NO 27
<211> LENGTH: 293
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 27

Met Phe Lys Arg Lys Ser Thr Ala Glu Leu Ala Ala Gln Met Ala Lys
  1               5                  10                  15

Leu Ala Gly Asn Lys Gly Gly Phe Ser Ser Glu Asp Lys Gly Glu Trp
            20                  25                  30

Lys Leu Lys Leu Asp Asn Ala Gly Asn Gly Gln Ala Val Ile Arg Phe
        35                  40                  45

Leu Pro Ser Lys Asn Asp Glu Gln Ala Pro Phe Ala Ile Leu Val Asn
    50                  55                  60

His Gly Phe Lys Lys Asn Gly Lys Trp Tyr Ile Glu Thr Cys Ser Ser
 65                 70                  75                  80

Thr His Gly Asp Tyr Asp Ser Cys Pro Val Cys Gln Tyr Ile Ser Lys
                85                  90                  95

Asn Asp Leu Tyr Asn Thr Asp Asn Lys Glu Tyr Ser Leu Val Lys Arg
            100                 105                 110

Lys Thr Ser Tyr Trp Ala Asn Ile Leu Val Val Lys Asp Pro Ala Ala
        115                 120                 125

Pro Glu Asn Glu Gly Lys Val Phe Lys Tyr Arg Phe Gly Lys Lys Ile
    130                 135                 140

Trp Asp Lys Ile Asn Ala Met Ile Ala Val Asp Val Glu Met Gly Glu
145                 150                 155                 160

Thr Pro Val Asp Val Thr Cys Pro Trp Glu Gly Ala Asn Phe Val Leu
                165                 170                 175

Lys Val Lys Gln Val Ser Gly Pro Ser Asn Tyr Asp Gly Ser Lys Phe
            180                 185                 190

Leu Asn Gln Ser Ala Ile Pro Asn Ile Asp Asp Glu Ser Phe Gln Lys
        195                 200                 205

Glu Leu Phe Glu Gln Met Val Asp Leu Ser Glu Met Thr Ser Lys Asp
    210                 215                 220

Lys Phe Lys Ser Phe Glu Glu Leu Ser Thr Lys Phe Ser Gln Val Met
225                 230                 235                 240

Gly Thr Ala Ala Met Gly Gly Ala Ala Thr Ala Ala Lys Lys Ala
                245                 250                 255

Asp Lys Val Ala Asp Asp Leu Asp Ala Phe Asn Val Asp Asp Phe Asn
            260                 265                 270

Thr Lys Thr Glu Asp Asp Phe Met Ser Ser Ser Ser Gly Ser Ser Ser
        275                 280                 285

Ser Ala Asp Asp Thr
    290
```

<210> SEQ ID NO 28
<211> LENGTH: 299
<212> TYPE: PRT
<213> ORGANISM: Artificial Sequence
<220> FEATURE:
<223> OTHER INFORMATION: Description of Artificial Sequence: Synthetic construct

<400> SEQUENCE: 28

```
Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Ala Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Ser Asp
        275                 280                 285

Asp Gly Asp Leu Asp Asp Leu Leu Ala Gly Leu
    290                 295
```

<210> SEQ ID NO 29
<211> LENGTH: 302
<212> TYPE: PRT
<213> ORGANISM: Artificial Sequence
<220> FEATURE:
<223> OTHER INFORMATION: Description of Artificial Sequence: Synthetic construct

<400> SEQUENCE: 29

Met Ser Ile Phe Lys Arg Lys Asp Pro Ser Gln Leu Gln Gln Gln Leu

```
                1               5              10              15
        Ala Ala Phe Ser Ala Lys Lys Gly Phe Glu Ser Asp Ala Thr Glu Trp
                           20                  25                  30
        Lys Leu Thr Gln Gly Lys Asp Gly Asn Gly Ala Ala Val Ile Arg Phe
                   35                  40                  45
        Leu Pro Ala Lys Gly Asp Asn Ala Thr Thr Phe Val Lys Leu Val Asn
               50                  55                  60
        His Gly Phe Gln Arg Asn Gly Lys Trp Tyr Ile Glu Asn Cys Ser Ser
           65                  70                  75                  80
        Thr His Gly Asp Tyr Asp Asn Cys Pro Ala Cys Gln Trp Ile Lys Glu
                           85                  90                  95
        Gln Asn Trp Asp Tyr Asn Val Glu Ala Asp Lys Lys Ala Met Tyr Ala
                       100                 105                 110
        Ser Gly Val Thr Arg Lys Thr Ala Phe Trp Ala Asn Ile Leu Val Ile
                   115                 120                 125
        Lys Asp Pro Ala Asn Pro Asp Asn Glu Gly Lys Val Phe Lys Phe Arg
               130                 135                 140
        Phe Gly Lys Lys Ile Met Asp Lys Ile Gln Ala Glu Val Asp Val Asn
        145                 150                 155                 160
        Thr Asp Leu Gly Glu Glu Pro Cys Asp Val Thr Cys Pro Phe Glu Gly
                           165                 170                 175
        Lys Asn Phe Thr Ile Lys Ile Lys Val Gly Gly Asn Asn Asn Tyr
                       180                 185                 190
        Asp Asp Ser Val Phe Gly Lys Gln Ser Gln Ile Ala Asn Ile Glu Asp
                   195                 200                 205
        Glu Ala Tyr Gln Ala Gln Leu Phe Glu Gln Met His Asp Ile Met Asp
               210                 215                 220
        Leu Ile Ala Lys Asp Lys Phe Lys Ser Met Glu Asp Leu Thr Thr Val
        225                 230                 235                 240
        Phe Asn Arg Val Met Gly Ala Glu Lys Arg Ser Asn Ala Arg Ala Ala
                           245                 250                 255
        Asp Asp Phe Glu Lys Gln Met Glu Gln Phe Glu Asn Thr Pro Ala Ser
                       260                 265                 270
        Lys Pro Glu Lys Glu Asp Asp Val Pro Phe Asn Thr Gly Ser Ala
                   275                 280                 285
        Gly Thr Val Asp Thr Asp Leu Asp Leu Leu Asn Glu Ile
               290                 295                 300

<210> SEQ ID NO 30
<211> LENGTH: 326
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 30

Met Ser Phe Phe Lys Arg Gln Asp Pro Thr Lys Leu Gln Glu Gln Val
        1               5                  10                  15

Ala Ala Leu Lys Gly Ser Ser Gly Phe Gln Lys Asp Glu Lys Glu Trp
                           20                  25                  30

Lys Leu Thr Leu Asp Ala Gln Lys Asn Gly Ser Ala Val Ile Arg Phe
                       35                  40                  45

Leu Pro Asn Arg Ser Asp Asp Glu Leu Ala Phe Val Arg Ile Val Asn
                   50                  55                  60

His Ser Phe Lys Lys Gln Asn Gln Trp Tyr Ile Glu Asn Cys Pro Ser
```

```
                 65                  70                  75                  80
Thr His Gly Asp Tyr Asp Gly Cys Pro Val Cys Gln Tyr Ile Thr Asp
                     85                  90                  95

Asn Asp Leu Phe Glu Lys Ala Lys Asn Lys Gly Gly Glu Ala Asp
                100                 105                 110

Lys Leu Leu Gly Gln Ile Gly Arg Lys Gln Ser Phe Trp Ala Asn Ile
            115                 120                 125

Leu Val Ile Lys Asp Pro Gly Asn Pro Glu Asn Glu Gly Lys Val Phe
        130                 135                 140

Lys Phe Arg Phe Gly Lys Lys Ile Met Asp Lys Ile Thr Ala Thr Ile
145                 150                 155                 160

Ala Gly Asn Pro Asp Leu Asp Glu Pro Gly Ile Ala Val Thr Cys Pro
                165                 170                 175

Phe Ala Gly Ala Asn Phe Thr Leu Lys Ala Lys Val Gly Asp Trp
                180                 185                 190

Pro Asn Tyr Asp Asp Ser Thr Phe Gly Val Pro Gly Pro Ile Lys Gly
                195                 200                 205

Ile Asp Asp Glu Ala Val Gln Lys Ala Ile Phe Glu Gly Met Ser Asp
        210                 215                 220

Leu Arg Pro Ile Thr Ala Pro Asp Gln Phe Lys Pro Thr Ala Glu Leu
225                 230                 235                 240

Thr Ala Lys Phe Thr Lys Val Phe Gly Gly Ala Ala Met Gly Ala
                245                 250                 255

Gly Ser Ser Ala Gly Ala Asp Leu Asp Ser Glu Leu Asn Ser Phe Asp
                260                 265                 270

Ala Asp Leu Lys Asn Phe Asp Asn Gly Asn Gln Ser Gly Ser Val Lys
            275                 280                 285

Glu Ser Gly Gly Val Asn Gln Leu Asn Val Gly Gly Ser Val Pro Glu
        290                 295                 300

Asp Asp Thr Pro Phe Asp Leu Asp Asn Thr Ser Gly Asp Asp Leu
305                 310                 315                 320

Asp Lys Leu Leu Asp Leu
                325

<210> SEQ ID NO 31
<211> LENGTH: 302
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 31

Met Phe Lys Arg Lys Ser Pro Ala Gln Leu Gln Glu Lys Leu Glu Lys
  1               5                  10                  15

Met Ser Ser Lys Lys Ser Phe Asp Asn Ala Asp Glu Trp Lys Leu Thr
             20                  25                  30

Thr Asp Lys Leu Gly Asn Gly Ser Ala Val Ile Arg Phe Leu Pro Ala
         35                  40                  45

Lys Gly Glu Asp Asp Leu Pro Phe Val Lys Ile Phe Thr His Gly Phe
     50                  55                  60

Lys Glu Asn Gly Asn Trp Phe Ile Glu Asn Cys Pro Ser Thr Ile Asp
 65                  70                  75                  80

Leu Pro Cys Pro Cys Cys Ala Ala Asn Gly Glu Leu Trp Lys Thr Glu
                 85                  90                  95

Ile Glu Asp Asn Gln Asn Ile Ala Arg Lys Arg Lys Arg Thr Leu Ser
```

```
                100                 105                 110
Tyr Trp Ala Asn Ile Val Val Ile Lys Asp Asp Ala Pro Glu Asn
            115                 120                 125

Glu Gly Lys Val Phe Lys Tyr Arg Phe Gly Lys Lys Ile Leu Asp Lys
        130                 135                 140

Ile Thr Gln Ala Ala Gln Ala Asp Glu Asp Leu Gly Val Pro Gly Met
145                 150                 155                 160

Asp Val Thr Cys Val Phe Asp Gly Ala Asn Phe Ser Leu Lys Ala Lys
                165                 170                 175

Lys Val Ser Gly Phe Pro Asn Tyr Asp Asp Ser Lys Phe Gly Pro Ser
            180                 185                 190

Thr Glu Leu Tyr Gly Gly Asp Glu Ala Lys Leu Lys Glu Val Trp Asp
        195                 200                 205

Ala Met His Asp Leu Asn Ala Ile Ile Ala Pro Ser Ala Phe Lys Ser
    210                 215                 220

Glu Ala Glu Leu Gln Lys Arg Phe Leu Gln Val Thr Gly Ala Ala Gln
225                 230                 235                 240

Pro Lys Ala Ser Ala Ala Gln Asn Leu Glu Ala Gln Leu Asn Thr Ser
                245                 250                 255

Ala Pro Ala Gln Ala Asn Ala Pro Lys Ala Ala Lys Pro Ala Ala
            260                 265                 270

Ala Ser Val Asp Val Asp Ser Glu Pro Val Thr Asp Ser Val Asp Asp
        275                 280                 285

Glu Leu Asp Ala Leu Leu Ala Asp Leu Glu Leu Gly Asp Asp
    290                 295                 300

<210> SEQ ID NO 32
<211> LENGTH: 297
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 32

Met Ser Phe Ala Lys Leu Lys Lys Gln Ser Lys Leu Gly Ser Leu Thr
 1               5                  10                  15

Gln Lys Leu Val Lys Glu Val Gly Lys Met Asn Asn Thr Gly Gly Gln
            20                  25                  30

Gly Asp Asp Arg Leu Trp Lys Leu Glu Val Asp Lys Gly Gly Asn Gly
        35                  40                  45

Tyr Asp Val Ile Arg Phe Leu Pro Ala Pro Asp Gly Glu Asp Leu Pro
    50                  55                  60

Phe Val Lys Leu Tyr Ser His Ala Phe Gln Gly Pro Gly Gly Trp Tyr
65                  70                  75                  80

Ile Glu Asn Ser Leu Thr Thr Leu Gly Gln Lys Asp Pro Val Ser Glu
                85                  90                  95

Phe Asn Ser Gln Leu Trp Asn Asn Gly Thr Asp Ala Gly Lys Asp Thr
            100                 105                 110

Ala Arg Lys Gln Lys Arg Lys Leu Thr Tyr Ile Ser Asn Ile Tyr Val
        115                 120                 125

Val Lys Asp Pro Ala Asn Pro Glu Asn Glu Gly Lys Thr Phe Leu Tyr
    130                 135                 140

Lys Tyr Gly Lys Lys Ile Phe Asp Lys Leu Thr Ala Ala Met Gln Pro
145                 150                 155                 160

Glu Phe Glu Asp Glu Glu Ala Ile Asp Pro Phe Asp Phe Trp Gln Gly
```

165                 170                 175
Ala Asn Phe Lys Leu Lys Ala Lys Asn Val Ala Gly Tyr Arg Asn Tyr
                180                 185                 190

Asp Ser Ser Glu Phe Ala Ala Thr Ser Ala Leu Leu Asp Asp Asp
            195                 200                 205

Ala Met Glu Ala Ile Trp Lys Lys Glu Tyr Ser Leu Ala Glu Leu Val
210                 215                 220

Ala Thr Asp Gln Phe Lys Ser Tyr Asp Glu Leu Lys Thr Arg Leu Gly
225                 230                 235                 240

Tyr Val Leu Gly Asn Lys Pro Val Arg Asn Asp Ala Glu Thr Val Glu
                245                 250                 255

Gln Glu Val Glu Asp Val Arg Ala Ser Ala Pro Val Val Glu Thr Val
            260                 265                 270

Glu Ser Val Ser Arg Ser Ser Ala Thr Glu Asp Glu Asp Thr Leu
        275                 280                 285

Ser Tyr Phe Ala Lys Leu Ala Glu Ser
    290                 295

<210> SEQ ID NO 33
<211> LENGTH: 307
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 33

Met Ser Phe Ala Ser Leu Lys Lys Ala Ala Ser Ala Gly Ser Thr Leu
1               5                   10                  15

Ser Lys Leu Thr Gln Glu Ile Glu Lys Ile Asn Gln Pro Gln Gln Asn
            20                  25                  30

Asn Ser Ala Asp Glu Arg Phe Trp Lys Pro Glu Leu Asp Lys Ser Gly
        35                  40                  45

Asn Gly Phe Ala Val Ile Arg Phe Leu Pro Ala Pro Glu Gly Glu Glu
    50                  55                  60

Met Pro Trp Ala Lys Val Trp Ser His Ala Phe Lys Gly Pro Gly Gly
65                  70                  75                  80

Gln Trp Tyr Ile Glu Asn Ser Leu Thr Thr Ile Gly Lys Asp Asp Pro
                85                  90                  95

Val Gly Glu Tyr Asn Arg Glu Leu Trp Asn Ser Gly Lys Glu Ser Asp
            100                 105                 110

Lys Asn Ile Ala Arg Ala Gln Lys Arg Lys Leu Ser Tyr Tyr Ser Asn
        115                 120                 125

Ile Tyr Val Val Ser Asp Pro Ala His Pro Glu Asn Glu Gly Lys Val
    130                 135                 140

Phe Leu Tyr Lys Tyr Gly Lys Lys Ile Phe Asp Lys Leu Val Glu Ala
145                 150                 155                 160

Met Gln Pro Ala Phe Ala Asp Glu Thr Pro Leu Asp Pro Phe Asn Phe
                165                 170                 175

Trp Lys Gly Ala Asp Phe Lys Leu Lys Ile Arg Lys Leu Asp Gly Tyr
            180                 185                 190

Trp Asn Tyr Asp Lys Ser Glu Phe Ala Ala Thr Ser Thr Leu Gly Gly
        195                 200                 205

Phe Asp Asp Ser Lys Leu Glu Ser Ile Trp Lys Glu Gly Tyr Ser Leu
    210                 215                 220

Thr Glu Phe Glu Ser Ala Lys Asn Phe Lys Asp Tyr Asp Ala Leu Lys

```
                    225                 230                 235                 240
Lys Arg Leu Asp Leu Val Leu Gly Leu Thr Ile Pro His Pro Thr Thr
                245                 250                 255

Glu Asp Glu Ser Leu Glu Asp Leu Ser Glu Gly Lys Thr Pro Ser Ser
            260                 265                 270

Trp Gly Gln Glu Val Ser Asp Phe Arg Glu Lys Ala Val Ala Ser Ser
        275                 280                 285

Pro Val Gln Asp Glu Asp Thr Leu Ser Tyr Phe Ser Arg Leu Ala
    290                 295                 300

Glu Glu Asp
305

<210> SEQ ID NO 34
<211> LENGTH: 38
<212> TYPE: DNA
<213> ORGANISM: Homo sapiens

<400> SEQUENCE: 34
cctttctttg ggactgtgtg gaccaaggag cttccatc                          38

<210> SEQ ID NO 35
<211> LENGTH: 36
<212> TYPE: DNA
<213> ORGANISM: Homo sapiens

<400> SEQUENCE: 35
cctgaaggag acagccttga aaccttgaag gattcc                            36

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asn His Thr Ala Met Glu Ile Gly Gly Leu Tyr Pro Lys Glu Ile Met
  1               5                  10                  15

Gly Gly Gly

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asn His Thr Leu Gln Thr Leu Glu Met Phe Ser Lys Glu Val Met Thr
  1               5                  10                  15

Gly Gly

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38
```

Ala His Thr Tyr Asp Thr Gln Glu Met Tyr Ser Lys Lys Val Ile Ser
1               5                   10                  15

Gly Gly

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala His Thr Tyr Asp Thr Gln Glu Met Tyr Ser Lys Lys Val Val Ser
1               5                   10                  15

Gly Gly

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asn His Thr Tyr Gln Thr Gln Glu Ile Tyr Ser Lys Thr Val Met Ser
1               5                   10                  15

Gly Gly

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asn His Thr Tyr Asp Val Val Gly Ser Tyr Val Pro Thr Lys Glu Met
1               5                   10                  15

Gly Gly Gly

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Gln Ile Arg Met Lys Ile Gly Val Met Phe Gly Asn Pro Glu Thr
1               5                   10                  15

Thr Thr Gly Gly
            20

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)
<223> OTHER INFORMATION: A or G
<220> FEATURE:
<221> NAME/KEY: MOD_RES
<222> LOCATION: (2)...(5)
<223> OTHER INFORMATION: Variable amino acid
<220> FEATURE:
<221> NAME/KEY: MOD_RES
<222> LOCATION: (8)
<223> OTHER INFORMATION: S or T

<400> SEQUENCE: 43

Xaa Xaa Xaa Xaa Xaa Gly Lys Xaa
 1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Pro Ser Lys His Phe Lys Ser
 1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Pro Ser Lys His Phe Lys Thr
 1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Pro Ser Lys Ser His Phe Lys Ser
1               5

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asn His Thr Ile Glu Thr Ile Glu Met Phe Ser Lys Thr Val Met Thr
 1               5                  10                  15

Gly Gly

<210> SEQ ID NO 48
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 48

Asn His Thr Ile Glu Thr Ile Glu Met Phe Ser Lys Thr Val Met Thr
 1               5                  10                  15

Gly Gly

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asn His Thr Ile Glu Thr Ile Glu Met Phe Ser Lys Thr Val Met Thr
 1               5                  10                  15

Gly Gly

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asn His Thr Ile Glu Thr Ile Glu Met Phe Ser Lys Thr Val Met Thr
 1               5                  10                  15

Gly Gly

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn His Thr Ile Glu Thr Ile Glu Met Phe Ser Lys Thr Val Met Thr
 1               5                  10                  15

Gly Gly

<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asn His Thr Leu Gln Thr Leu Glu Met Phe Ser Lys Glu Val Met Thr
 1               5                  10                  15

Gly Gly

<210> SEQ ID NO 53
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 53

Asn His Thr Tyr Glu Thr Gln Glu Met Phe Ser Lys Thr Val Met Gly
 1               5                  10                  15

Gly Gly

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asn His Thr Tyr Glu Thr Gln Glu Met Phe Ser Lys Thr Val Met Ser
 1               5                  10                  15

Gly Gly

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn His Thr Tyr Glu Thr Gln Glu Met Phe Ser Lys Thr Val Met Ser
 1               5                  10                  15

Gly Gly

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn His Thr Tyr Glu Thr Gln Glu Met Phe Ser Lys Thr Val Met Ser
 1               5                  10                  15

Gly Gly

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Cys His Thr Tyr Asp Thr Gln Glu Met Tyr Ser Lys Lys Val Ile Ser
 1               5                  10                  15

Gly Gly

<210> SEQ ID NO 58
<211> LENGTH: 18
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 58

Cys His Thr Tyr Asp Thr Gln Glu Met Tyr Ser Lys Lys Val Ile Ser
 1               5                  10                  15

Gly Gly

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala His Thr Tyr Asp Thr Gln Glu Met Tyr Ser Lys Lys Val Val Ser
 1               5                  10                  15

Gly Gly

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asn His Thr Tyr Gln Thr Gln Glu Ile Tyr Ser Lys Thr Val Met Ser
 1               5                  10                  15

Gly Gly

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn His Thr Tyr Gln Thr Gln Glu Met Tyr Ser Lys Thr Val Met Ser
 1               5                  10                  15

Gly Gly

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn His Thr Tyr Asp Val Ile Gly Ser Tyr Val Pro Thr Lys Glu Met
 1               5                  10                  15

Gly Gly Gly

<210> SEQ ID NO 63
<211> LENGTH: 19
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 63

Asn His Thr Tyr Asp Val Val Gly Ala Tyr Ile Pro Thr Lys Glu Met
  1               5                  10                  15

Gly Gly Gly

<210> SEQ ID NO 64
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asn His Thr Tyr Asp Val Val Gly Ser Tyr Val Pro Thr Lys Glu Met
  1               5                  10                  15

Gly Gly Gly

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asn His Thr Ala Met Glu Ile Gly Gly Leu Tyr Pro Lys Glu Ile Met
  1               5                  10                  15

Gly Gly Gly

<210> SEQ ID NO 66
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asn His Thr Ala Met Glu Ile Gly Gly Met Tyr Pro Lys Glu Ile Met
  1               5                  10                  15

Gly Gly Gly

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ile Arg Met Lys Ile Gly Val Met Phe Gly Asn Pro Glu Thr Thr
  1               5                  10                  15

Thr Gly Gly

<210> SEQ ID NO 68
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 68

Asn His Thr Ala Met Glu Ile Gly Gly Leu Tyr Pro Lys Glu Ile Met
  1               5                  10                  15

Gly Gly Gly

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asn His Thr Ile Glu Thr Ile Glu Met Phe Ser Lys Thr Val Met Thr
  1               5                  10                  15

Gly Gly

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Thr Leu Phe Gly Leu
  1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Ser Asn Phe Gly Leu
  1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Thr Leu Phe Gly Leu
  1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Ser Asn Met Ser Leu
```

-continued

```
<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Lys Ser Asn Phe Gly Leu
 1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys Ser Asn Met Ser Leu
 1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Thr Leu Met Ser Leu
 1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Ser Asn Phe Gly Leu
 1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Ser Asn Met Ser Leu
 1               5

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 79

Asn His Thr Ile Glu Thr Ile Glu Met Phe Ser Lys Thr Val Met Thr
 1               5                  10                  15

Gly Gly

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Lys Ser Asn Met Ser Leu
 1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys Ser Asn Met Ser Leu
 1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Lys Ser Asn Phe Gly Leu
 1               5

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

His Gln His Gln His Gln His Gln His Gln
 1               5                  10

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

His Gln His Gln His Gln
 1               5

<210> SEQ ID NO 85
```

```
<211> LENGTH: 45
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (29)
<223> OTHER INFORMATION: TAMRA-dT
<220> FEATURE:
<221> NAME/KEY: modified_base
<222> LOCATION: (31)
<223> OTHER INFORMATION: THF
<220> FEATURE:
<221> NAME/KEY: modified_base
<222> LOCATION: (34)
<223> OTHER INFORMATION: BHQ1-dT

<400> SEQUENCE: 85
tgttaattga acaagtgtac agagcattna ngantatgcg tggag            45

<210> SEQ ID NO 86
<211> LENGTH: 45
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (29)
<223> OTHER INFORMATION: TAMRA-dT
<220> FEATURE:
<221> NAME/KEY: modified_base
<222> LOCATION: (31)
<223> OTHER INFORMATION: THF
<220> FEATURE:
<221> NAME/KEY: modified_base
<222> LOCATION: (34)
<223> OTHER INFORMATION: BHQ2-dT

<400> SEQUENCE: 86
tgttaattga gcaagtgtat agagcattna ngantatgcg tggag            45

<210> SEQ ID NO 87
<211> LENGTH: 42
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (26)
<223> OTHER INFORMATION: dT-Fluorescein
<220> FEATURE:
<221> NAME/KEY: modified_base
<222> LOCATION: (28)
<223> OTHER INFORMATION: THF
<220> FEATURE:
<221> NAME/KEY: modified_base
<222> LOCATION: (30)
<223> OTHER INFORMATION: dT-DDQ1

<400> SEQUENCE: 87
catgattgga tgaataagct gcagcngntn aaaggaaact ta              42

<210> SEQ ID NO 88
<211> LENGTH: 35
<212> TYPE: DNA
<213> ORGANISM: Artificial Sequence
<220> FEATURE:
<223> OTHER INFORMATION: Description of Artificial Sequence: Synthetic
```

```
                    primer

<400> SEQUENCE: 88
acggcattaa caaacgaact gattcatctg cttgg                              35

<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ccttaatttc tccgagaact tcatattcaa gcgtc                              35

<210> SEQ ID NO 90
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ccaatatttc atatatgtaa ttcctccaca tctca                              35

<210> SEQ ID NO 91
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
cccaagggca aagcgacttt gtattcgtca ttggcggatc aaacg                   45

<210> SEQ ID NO 92
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ctcaaagcta gaactttgct tcactataag tattc                              35

<210> SEQ ID NO 93
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cttaagtaag caattgctgt aaagtcgtca c                                  31

<210> SEQ ID NO 94
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 94
ccagtagcga cagaagcaat tgattggtaa att        33

<210> SEQ ID NO 95
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ttccgactgc gagcttattg ttaaggcaat g        31

<210> SEQ ID NO 96
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
cctcgcgatc tttctctcga aatttaccaa tca        33

<210> SEQ ID NO 97
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ccatgtcgaa gacaacaaag aagttcaact ctt        33

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
catctactaa tagacgccgg ccattcaaac atg        33

<210> SEQ ID NO 99
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cccgattccc tcagcaatcg cagcaaactc cgg        33

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cagtgtatct ggaaagccta caggacacca aaa 33

<210> SEQ ID NO 101
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tgctttcata cgtttagccc aatcttggat ag 32

<210> SEQ ID NO 102
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tgacaagtgt gctataaacc tggcctacca gag 33

<210> SEQ ID NO 103
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ttgatacatt cggtctcgtg tatcttctat a 31

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gatacattcg gtctcgtgta tcttctagg 29

<210> SEQ ID NO 105
<211> LENGTH: 393
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 105

Met Ser Ile Ala Asp Leu Lys Ser Arg Leu Ile Lys Ala Ser Thr Ser
 1               5                  10                  15

Lys Met Thr Ala Glu Leu Thr Thr Ser Lys Phe Phe Asn Glu Lys Asp
                20                  25                  30

Val Ile Arg Thr Lys Ile Pro Met Leu Asn Ile Ala Ile Ser Gly Ala
            35                  40                  45

Ile Asp Gly Gly Met Gln Ser Gly Leu Thr Ile Phe Ala Gly Pro Ser
        50                  55                  60

Lys Ser Phe Lys Ser Asn Met Ser Leu Thr Met Val Ala Ala Tyr Leu
65                  70                  75                  80

```
Asn Lys Tyr Pro Asp Ala Val Cys Leu Phe Tyr Asp Ser Glu Phe Gly
                85                  90                  95
Ile Thr Pro Ala Tyr Leu Arg Ser Met Gly Val Asp Pro Glu Arg Val
            100                 105                 110
Ile His Thr Pro Ile Gln Ser Val Glu Gln Leu Lys Ile Asp Met Val
        115                 120                 125
Asn Gln Leu Glu Ala Ile Glu Arg Gly Glu Lys Val Ile Val Phe Ile
    130                 135                 140
Asp Ser Ile Gly Asn Met Ala Ser Lys Lys Glu Thr Glu Asp Ala Leu
145                 150                 155                 160
Asn Glu Lys Ser Val Ala Asp Met Thr Arg Ala Lys Ser Leu Lys Ser
                165                 170                 175
Leu Phe Arg Ile Val Thr Pro Tyr Phe Ser Ile Lys Asn Ile Pro Cys
            180                 185                 190
Val Ala Val Asn His Thr Ile Glu Thr Ile Glu Met Phe Ser Lys Thr
        195                 200                 205
Val Met Thr Gly Gly Thr Gly Val Met Tyr Ser Ala Asp Thr Val Phe
    210                 215                 220
Ile Ile Gly Lys Arg Gln Ile Lys Asp Gly Ser Asp Leu Gln Gly Tyr
225                 230                 235                 240
Gln Phe Val Leu Asn Val Glu Lys Ser Arg Thr Val Lys Glu Lys Ser
                245                 250                 255
Lys Phe Phe Ile Asp Val Lys Phe Asp Gly Ile Asp Pro Tyr Ser
            260                 265                 270
Gly Leu Leu Asp Met Ala Leu Glu Leu Gly Phe Val Val Lys Pro Lys
        275                 280                 285
Asn Gly Trp Tyr Ala Arg Glu Phe Leu Asp Glu Glu Thr Gly Glu Met
    290                 295                 300
Ile Arg Glu Glu Lys Ser Trp Arg Ala Lys Asp Thr Asn Cys Thr Thr
305                 310                 315                 320
Phe Trp Gly Pro Leu Phe Lys His Gln Pro Phe Arg Asp Ala Ile Lys
                325                 330                 335
Arg Ala Tyr Gln Leu Gly Ala Ile Asp Ser Asn Glu Ile Val Glu Ala
            340                 345                 350
Glu Val Asp Glu Leu Ile Asn Ser Lys Val Glu Lys Phe Lys Ser Pro
        355                 360                 365
Glu Ser Lys Ser Lys Ser Ala Ala Asp Leu Gly Thr Asp Leu Glu Gln
    370                 375                 380
Leu Ser Asp Met Glu Glu Phe Asn Glu
385                 390

<210> SEQ ID NO 106
<211> LENGTH: 393
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 106

Met Ser Ile Ala Asp Leu Lys Ser Arg Leu Ile Lys Ala Ser Thr Ser
1               5                   10                  15
Lys Met Thr Ala Glu Leu Thr Thr Ser Lys Phe Phe Asn Glu Lys Asp
            20                  25                  30
Val Ile Arg Thr Lys Ile Pro Met Leu Asn Ile Ala Ile Ser Gly Ala
        35                  40                  45
```

Ile Asp Gly Gly Met Gln Ser Gly Leu Thr Ile Phe Ala Gly Pro Ser
            50                  55                  60

Lys His Phe Lys Ser Asn Met Ser Leu Thr Met Val Ala Ala Tyr Leu
 65                  70                  75                  80

Asn Lys Tyr Pro Asp Ala Val Cys Leu Phe Tyr Asp Ser Glu Phe Gly
                 85                  90                  95

Ile Thr Pro Ala Tyr Leu Arg Ser Met Gly Val Asp Pro Glu Arg Val
            100                 105                 110

Ile His Thr Pro Ile Gln Ser Val Glu Gln Leu Lys Ile Asp Met Val
            115                 120                 125

Asn Gln Leu Glu Ala Ile Glu Arg Gly Glu Lys Val Ile Val Phe Ile
        130                 135                 140

Asp Ser Ile Gly Asn Met Ala Ser Lys Lys Glu Thr Glu Asp Ala Leu
145                 150                 155                 160

Asn Glu Lys Val Val Ser Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
            195                 200                 205

Val Met Thr Gly Gly Thr Gly Val Met Tyr Ser Ala Asp Thr Val Phe
        210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Phe Ile Asp Val Lys Phe Asp Gly Ile Asp Pro Tyr Ser
            260                 265                 270

Gly Leu Leu Asp Met Ala Leu Glu Leu Gly Phe Val Val Lys Pro Lys
            275                 280                 285

Asn Gly Trp Tyr Ala Arg Glu Phe Leu Asp Glu Glu Thr Gly Glu Met
        290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
            325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
        355                 360                 365

Glu Ser Lys Ser Lys Ser Ala Ala Asp Leu Thr Asp Leu Glu Gln
        370                 375                 380

Leu Ser Asp Met Glu Glu Phe Asn Glu
385                 390

<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asn His Thr Ala Met Glu Ile Gly Gly Leu Tyr Pro Lys Glu Ile Met
 1               5                  10                  15

Gly Gly Gly

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asn His Thr Ile Glu Thr Ile Glu Met Phe Ser Lys Thr Val Met Gly
 1               5                  10                  15

Gly Gly

<210> SEQ ID NO 109
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asn His Thr Ile Glu Thr Ile Glu Met Phe Ser Lys Thr Val Met Thr
 1               5                  10                  15

Gly Gly

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asn His Thr Tyr Glu Thr Gln Glu Met Phe Ser Lys Thr Val Met Gly
 1               5                  10                  15

Gly Gly

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Glu Asn Asp Leu Asp Glu Met Glu Asp Phe Asp Glu
 1               5                  10

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Glu Asn Asp Leu Asp Glu Leu Ser Asp Met Glu Asp Phe Asp Glu
 1               5                  10                  15

<210> SEQ ID NO 113

```
-continued

<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Glu Asn Asp Leu Asp Glu Met Glu Asp Phe Asp Glu Leu Asp Glu Leu
 1               5                  10                  15

Asp Glu

<210> SEQ ID NO 114
<211> LENGTH: 396
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (391)..(396)
<223> OTHER INFORMATION: Region may or may not be present

<400> SEQUENCE: 114

Met Ser Asp Leu Lys Ser Arg Leu Ile Lys Ala Ser Thr Ser Lys Met
 1               5                  10                  15

Thr Ala Asp Leu Thr Lys Ser Lys Leu Phe Asn Asn Arg Asp Glu Val
                20                  25                  30

Pro Thr Arg Ile Pro Met Leu Asn Ile Ala Leu Gly Gly Ala Leu Asn
            35                  40                  45

Ala Gly Leu Gln Ser Gly Leu Thr Ile Phe Ala Ala Pro Ser Lys Ser
        50                  55                  60

Phe Lys Thr Leu Phe Gly Leu Thr Met Val Ala Ala Tyr Met Lys Lys
65                  70                  75                  80

Tyr Lys Asp Ala Ile Cys Leu Phe Tyr Asp Ser Glu Phe Gly Ala Ser
                85                  90                  95

Glu Ser Tyr Phe Arg Ser Met Gly Val Asp Leu Asp Arg Val Val His
            100                 105                 110

Thr Pro Ile Gln Ser Val Glu Gln Leu Lys Val Asp Met Thr Asn Gln
        115                 120                 125

Leu Asp Ala Ile Glu Arg Gly Asp Lys Val Ile Ile Phe Ile Asp Ser
    130                 135                 140

Ile Gly Asn Thr Ala Ser Lys Lys Glu Thr Glu Asp Ala Leu Asn Glu
145                 150                 155                 160

Lys Val Val Gly Asp Met Ser Arg Ala Lys Ala Leu Lys Ser Leu Phe
                165                 170                 175

Arg Ile Val Thr Pro Tyr Leu Thr Ile Lys Asp Ile Pro Cys Val Ala
            180                 185                 190

Ile Asn His Thr Ala Met Glu Ile Gly Gly Leu Tyr Pro Lys Glu Ile
        195                 200                 205

Met Gly Gly Gly Thr Gly Ile Leu Tyr Ser Ala Asn Thr Val Phe Phe
    210                 215                 220

Ile Ser Lys Arg Gln Val Lys Glu Gly Thr Glu Leu Thr Gly Tyr Asp
225                 230                 235                 240

Phe Thr Leu Lys Ala Glu Lys Ser Arg Thr Val Lys Glu Lys Ser Thr
                245                 250                 255

Phe Pro Ile Thr Val Asn Phe Asp Gly Gly Ile Asp Pro Phe Ser Gly
            260                 265                 270
```

```
Leu Leu Glu Met Ala Thr Glu Ile Gly Phe Val Val Lys Pro Lys Ala
            275                 280                 285

Gly Trp Tyr Ala Arg Glu Phe Leu Asp Glu Glu Thr Gly Glu Met Ile
        290                 295                 300

Arg Glu Glu Lys Ser Trp Arg Ala Lys Ala Thr Asp Cys Val Glu Phe
305                 310                 315                 320

Trp Gly Pro Leu Phe Lys His Lys Pro Phe Arg Asp Ala Ile Glu Thr
                325                 330                 335

Lys Tyr Lys Leu Gly Ala Ile Ser Ser Ile Lys Glu Val Asp Asp Ala
            340                 345                 350

Val Asn Asp Leu Ile Asn Cys Lys Ala Thr Thr Lys Val Pro Val Lys
        355                 360                 365

Thr Ser Asp Ala Pro Ser Ala Ala Asp Ile Glu Asn Asp Leu Asp Glu
    370                 375                 380

Met Glu Asp Phe Asp Glu His His His His His
385                 390                 395

<210> SEQ ID NO 115
<211> LENGTH: 399
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (393)..(399)
<223> OTHER INFORMATION: Region may or may not be present

<400> SEQUENCE: 115

Met Ser Asp Leu Lys Ser Arg Leu Ile Lys Ala Ser Thr Ser Lys Met
1               5                   10                  15

Thr Ala Asp Leu Thr Lys Ser Lys Leu Phe Asn Asn Arg Asp Glu Val
            20                  25                  30

Pro Thr Arg Ile Pro Met Leu Asn Ile Ala Leu Gly Gly Ala Leu Asn
        35                  40                  45

Ala Gly Leu Gln Ser Gly Leu Thr Ile Phe Ala Ala Pro Ser Lys Ser
    50                  55                  60

Phe Lys Thr Leu Phe Gly Leu Thr Met Val Ala Ala Tyr Met Lys Lys
65                  70                  75                  80

Tyr Lys Asp Ala Ile Cys Leu Phe Tyr Asp Ser Glu Phe Gly Ala Ser
                85                  90                  95

Glu Ser Tyr Phe Arg Ser Met Gly Val Asp Leu Asp Arg Val Val His
            100                 105                 110

Thr Pro Ile Gln Ser Val Glu Gln Leu Lys Val Asp Met Thr Asn Gln
        115                 120                 125

Leu Asp Ala Ile Glu Arg Gly Asp Lys Val Ile Ile Phe Ile Asp Ser
130                 135                 140

Ile Gly Asn Thr Ala Ser Lys Lys Glu Thr Glu Asp Ala Leu Asn Glu
145                 150                 155                 160

Lys Val Val Gly Asp Met Ser Arg Ala Lys Ala Leu Lys Ser Leu Phe
                165                 170                 175

Arg Ile Val Thr Pro Tyr Leu Thr Ile Lys Asp Ile Pro Cys Val Ala
            180                 185                 190

Ile Asn His Thr Ala Met Glu Ile Gly Gly Leu Tyr Pro Lys Glu Ile
        195                 200                 205

Met Gly Gly Gly Thr Gly Ile Leu Tyr Ser Ala Asn Thr Val Phe Phe
210                 215                 220
```

```
Ile Ser Lys Arg Gln Val Lys Glu Gly Thr Glu Leu Thr Gly Tyr Asp
225                 230                 235                 240

Phe Thr Leu Lys Ala Glu Lys Ser Arg Thr Val Lys Glu Lys Ser Thr
            245                 250                 255

Phe Pro Ile Thr Val Asn Phe Asp Gly Gly Ile Asp Pro Phe Ser Gly
            260                 265                 270

Leu Leu Glu Met Ala Thr Glu Ile Gly Phe Val Val Lys Pro Lys Ala
            275                 280                 285

Gly Trp Tyr Ala Arg Glu Phe Leu Asp Glu Thr Gly Glu Met Ile
            290                 295                 300

Arg Glu Glu Lys Ser Trp Arg Ala Lys Ala Thr Asp Cys Val Glu Phe
305                 310                 315                 320

Trp Gly Pro Leu Phe Lys His Lys Pro Phe Arg Asp Ala Ile Glu Thr
                325                 330                 335

Lys Tyr Lys Leu Gly Ala Ile Ser Ser Ile Lys Glu Val Asp Asp Ala
                340                 345                 350

Val Asn Asp Leu Ile Asn Cys Lys Ala Thr Thr Lys Val Pro Val Lys
                355                 360                 365

Thr Ser Asp Ala Pro Ser Ala Asp Ile Glu Asn Asp Leu Asp Glu
370                 375                 380

Met Glu Asp Phe Asp Glu Leu Ser Asp His His His His His
385                 390                 395
```

<210> SEQ ID NO 116
<211> LENGTH: 405
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (400)..(405)
<223> OTHER INFORMATION: Region may or may not be present

<400> SEQUENCE: 116

```
Met Ser Asp Leu Lys Ser Arg Leu Ile Lys Ala Ser Thr Ser Lys Met
1               5                   10                  15

Thr Ala Asp Leu Thr Lys Ser Lys Leu Phe Asn Asn Arg Asp Glu Val
            20                  25                  30

Pro Thr Arg Ile Pro Met Leu Asn Ile Ala Leu Gly Gly Ala Leu Asn
        35                  40                  45

Ala Gly Leu Gln Ser Gly Leu Thr Ile Phe Ala Ala Pro Ser Lys Ser
    50                  55                  60

Phe Lys Thr Leu Phe Gly Leu Thr Met Val Ala Ala Tyr Met Lys Lys
65                  70                  75                  80

Tyr Lys Asp Ala Ile Cys Leu Phe Tyr Asp Ser Glu Phe Gly Ala Ser
                85                  90                  95

Glu Ser Tyr Phe Arg Ser Met Gly Val Asp Leu Asp Arg Val Val His
                100                 105                 110

Thr Pro Ile Gln Ser Val Glu Gln Leu Lys Val Asp Met Thr Asn Gln
            115                 120                 125

Leu Asp Ala Ile Glu Arg Gly Asp Lys Val Ile Phe Ile Asp Ser
        130                 135                 140

Ile Gly Asn Thr Ala Ser Lys Lys Glu Thr Glu Asp Ala Leu Asn Glu
145                 150                 155                 160

Lys Val Val Gly Asp Met Ser Arg Ala Lys Ala Leu Lys Ser Leu Phe
```

```
                    165                 170                 175

Arg Ile Val Thr Pro Tyr Leu Thr Ile Lys Asp Ile Pro Cys Val Ala
            180                 185                 190

Ile Asn His Thr Ala Met Glu Ile Gly Gly Leu Tyr Pro Lys Glu Ile
        195                 200                 205

Met Gly Gly Gly Thr Gly Ile Leu Tyr Ser Ala Asn Thr Val Phe Phe
    210                 215                 220

Ile Ser Lys Arg Gln Val Lys Glu Gly Thr Leu Thr Gly Tyr Asp
225                 230                 235                 240

Phe Thr Leu Lys Ala Glu Lys Ser Arg Thr Val Lys Glu Lys Ser Thr
                245                 250                 255

Phe Pro Ile Thr Val Asn Phe Asp Gly Gly Ile Asp Pro Phe Ser Gly
            260                 265                 270

Leu Leu Glu Met Ala Thr Glu Ile Gly Phe Val Val Lys Pro Lys Ala
        275                 280                 285

Gly Trp Tyr Ala Arg Glu Phe Leu Asp Glu Thr Gly Glu Met Ile
    290                 295                 300

Arg Glu Glu Lys Ser Trp Arg Ala Lys Ala Thr Asp Cys Val Glu Phe
305                 310                 315                 320

Trp Gly Pro Leu Phe Lys His Lys Pro Phe Arg Asp Ala Ile Glu Thr
                325                 330                 335

Lys Tyr Lys Leu Gly Ala Ile Ser Ser Ile Lys Glu Val Asp Asp Ala
            340                 345                 350

Val Asn Asp Leu Ile Asn Cys Lys Ala Thr Thr Lys Val Pro Val Lys
        355                 360                 365

Thr Ser Asp Ala Pro Ser Ala Ala Asp Ile Glu Asn Asp Leu Asp Glu
    370                 375                 380

Met Glu Asp Phe Asp Glu Leu Ser Asp Leu Asp Glu Leu Asp Glu His
385                 390                 395                 400

His His His His
            405

<210> SEQ ID NO 117
<211> LENGTH: 404
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (399)..(404)

<400> SEQUENCE: 117

Met Ser Asp Leu Lys Ser Arg Leu Ile Lys Ala Ser Thr Ser Lys Met
  1               5                  10                  15

Thr Ala Asp Leu Thr Lys Ser Lys Leu Phe Asn Asn Arg Asp Glu Val
             20                  25                  30

Pro Thr Arg Ile Pro Met Leu Asn Ile Ala Leu Gly Gly Ala Leu Asn
         35                  40                  45

Ala Gly Leu Gln Ser Gly Leu Thr Ile Phe Ala Ala Pro Ser Lys Ser
     50                  55                  60

Phe Lys Thr Leu Phe Gly Leu Thr Met Val Ala Ala Tyr Met Lys Lys
 65                  70                  75                  80

Tyr Lys Asp Ala Ile Cys Leu Phe Tyr Asp Ser Glu Phe Gly Ala Ser
                 85                  90                  95

Glu Ser Tyr Phe Arg Ser Met Gly Val Asp Leu Asp Arg Val Val His
```

```
                100             105             110
Thr Pro Ile Gln Ser Val Glu Gln Leu Lys Val Asp Met Thr Asn Gln
            115                 120                 125

Leu Asp Ala Ile Glu Arg Gly Asp Lys Val Ile Ile Phe Ile Asp Ser
    130                 135                 140

Ile Gly Asn Thr Ala Ser Lys Lys Glu Thr Glu Asp Ala Leu Asn Glu
145                 150                 155                 160

Lys Val Val Gly Asp Met Ser Arg Ala Lys Ala Leu Lys Ser Leu Phe
                165                 170                 175

Arg Ile Val Thr Pro Tyr Leu Thr Ile Lys Asp Ile Pro Cys Val Ala
            180                 185                 190

Ile Asn His Thr Ile Glu Thr Ile Glu Met Phe Ser Lys Thr Val Met
            195                 200                 205

Thr Gly Gly Thr Gly Ile Leu Tyr Ser Ala Asn Thr Val Phe Phe Ile
210                 215                 220

Ser Lys Arg Gln Val Lys Glu Gly Thr Glu Leu Thr Gly Tyr Asp Phe
225                 230                 235                 240

Thr Leu Lys Ala Glu Lys Ser Arg Thr Val Lys Glu Lys Ser Thr Phe
                245                 250                 255

Pro Ile Thr Val Asn Phe Asp Gly Gly Ile Asp Pro Phe Ser Gly Leu
            260                 265                 270

Leu Glu Met Ala Thr Glu Ile Gly Phe Val Val Lys Pro Lys Ala Gly
            275                 280                 285

Trp Tyr Ala Arg Glu Phe Leu Asp Glu Glu Thr Gly Glu Met Ile Arg
            290                 295                 300

Glu Glu Lys Ser Trp Arg Ala Lys Ala Thr Asp Cys Val Glu Phe Trp
305                 310                 315                 320

Gly Pro Leu Phe Lys His Lys Pro Phe Arg Asp Ala Ile Glu Thr Lys
                325                 330                 335

Tyr Lys Leu Gly Ala Ile Ser Ser Ile Lys Glu Val Asp Asp Ala Val
            340                 345                 350

Asn Asp Leu Ile Asn Cys Lys Ala Thr Thr Lys Val Pro Val Lys Thr
            355                 360                 365

Ser Asp Ala Pro Ser Ala Ala Asp Ile Glu Asn Asp Leu Asp Glu Met
370                 375                 380

Glu Asp Phe Asp Glu Leu Ser Asp Leu Asp Glu Leu Asp Glu His His
385                 390                 395                 400

His His His His

<210> SEQ ID NO 118
<211> LENGTH: 404
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (399)..(404)
<223> OTHER INFORMATION: Region may or may not be present

<400> SEQUENCE: 118

Met Ser Asp Leu Lys Ser Arg Leu Ile Lys Ala Ser Thr Ser Lys Met
1               5                   10                  15

Thr Ala Asp Leu Thr Lys Ser Lys Leu Phe Asn Asn Arg Asp Glu Val
            20                  25                  30

Pro Thr Arg Ile Pro Met Leu Asn Ile Ala Leu Gly Gly Ala Leu Asn
```

```
                35                  40                  45
Ala Gly Leu Gln Ser Gly Leu Thr Ile Phe Ala Ala Pro Ser Lys Ser
 50                  55                  60

Phe Lys Thr Leu Phe Gly Leu Thr Met Val Ala Ala Tyr Met Lys Lys
 65                  70                  75                  80

Tyr Lys Asp Ala Ile Cys Leu Phe Tyr Asp Ser Glu Phe Gly Ala Ser
                 85                  90                  95

Glu Ser Tyr Phe Arg Ser Met Gly Val Asp Leu Asp Val Val His
            100                 105                 110

Thr Pro Ile Gln Ser Val Glu Gln Leu Lys Val Asp Met Thr Asn Gln
        115                 120                 125

Leu Asp Ala Ile Glu Arg Gly Asp Lys Val Ile Ile Phe Ile Asp Ser
130                 135                 140

Ile Gly Asn Thr Ala Ser Lys Lys Glu Thr Glu Asp Ala Leu Asn Glu
145                 150                 155                 160

Lys Val Val Gly Asp Met Ser Arg Ala Lys Ala Leu Lys Ser Leu Phe
                165                 170                 175

Arg Ile Val Thr Pro Tyr Leu Thr Ile Lys Asp Ile Pro Cys Val Ala
            180                 185                 190

Ile Asn His Thr Tyr Glu Thr Gln Glu Met Phe Ser Lys Thr Val Met
        195                 200                 205

Gly Gly Gly Thr Gly Ile Leu Tyr Ser Ala Asn Thr Val Phe Phe Ile
210                 215                 220

Ser Lys Arg Gln Val Lys Glu Gly Thr Glu Leu Thr Gly Tyr Asp Phe
225                 230                 235                 240

Thr Leu Lys Ala Glu Lys Ser Arg Thr Val Lys Glu Lys Ser Thr Phe
                245                 250                 255

Pro Ile Thr Val Asn Phe Asp Gly Gly Ile Asp Pro Phe Ser Gly Leu
            260                 265                 270

Leu Glu Met Ala Thr Glu Ile Gly Phe Val Val Lys Pro Lys Ala Gly
        275                 280                 285

Trp Tyr Ala Arg Glu Phe Leu Asp Glu Glu Thr Gly Glu Met Ile Arg
290                 295                 300

Glu Glu Lys Ser Trp Arg Ala Lys Ala Thr Asp Cys Val Glu Phe Trp
305                 310                 315                 320

Gly Pro Leu Phe Lys His Lys Pro Phe Arg Asp Ala Ile Glu Thr Lys
                325                 330                 335

Tyr Lys Leu Gly Ala Ile Ser Ser Ile Lys Glu Val Asp Asp Ala Val
            340                 345                 350

Asn Asp Leu Ile Asn Cys Lys Ala Thr Thr Lys Val Pro Val Lys Thr
        355                 360                 365

Ser Asp Ala Pro Ser Ala Ala Asp Ile Glu Asn Asp Leu Asp Glu Met
370                 375                 380

Glu Asp Phe Asp Glu Leu Ser Asp Leu Asp Glu Leu Asp Glu His His
385                 390                 395                 400

His His His His

<210> SEQ ID NO 119
<211> LENGTH: 404
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
```

```
<222> LOCATION: (399)..(404)
<223> OTHER INFORMATION: Region may or may not be present

<400> SEQUENCE: 119
```

| | | | | | | | | | | | | | | | |
|---|---|---|---|---|---|---|---|---|---|---|---|---|---|---|---|
| Met | Ser | Asp | Leu | Lys | Ser | Arg | Leu | Ile | Lys | Ala | Ser | Thr | Ser | Lys | Met |
| 1 | | | | 5 | | | | | 10 | | | | | 15 | |
| Thr | Ala | Asp | Leu | Thr | Lys | Ser | Lys | Leu | Phe | Asn | Asn | Arg | Asp | Glu | Val |
| | | | | 20 | | | | | 25 | | | | | 30 | |
| Pro | Thr | Arg | Ile | Pro | Met | Leu | Asn | Ile | Ala | Leu | Gly | Gly | Ala | Leu | Asn |
| | | | | 35 | | | | | 40 | | | | | 45 | |
| Ala | Gly | Leu | Gln | Ser | Gly | Leu | Thr | Ile | Phe | Ala | Ala | Pro | Ser | Lys | Ser |
| | 50 | | | | | 55 | | | | | 60 | | | | |
| Phe | Lys | Ser | Asn | Phe | Gly | Leu | Thr | Met | Val | Ala | Ala | Tyr | Met | Lys | Lys |
| 65 | | | | | 70 | | | | | 75 | | | | | 80 |
| Tyr | Lys | Asp | Ala | Ile | Cys | Leu | Phe | Tyr | Asp | Ser | Glu | Phe | Gly | Ala | Ser |
| | | | | 85 | | | | | 90 | | | | | 95 | |
| Glu | Ser | Tyr | Phe | Arg | Ser | Met | Gly | Val | Asp | Leu | Asp | Arg | Val | Val | His |
| | | | | 100 | | | | | 105 | | | | | 110 | |
| Thr | Pro | Ile | Gln | Ser | Val | Glu | Gln | Leu | Lys | Val | Asp | Met | Thr | Asn | Gln |
| | | | | 115 | | | | | 120 | | | | | 125 | |
| Leu | Asp | Ala | Ile | Glu | Arg | Gly | Asp | Lys | Val | Ile | Ile | Phe | Ile | Asp | Ser |
| | 130 | | | | | 135 | | | | | 140 | | | | |
| Ile | Gly | Asn | Thr | Ala | Ser | Lys | Lys | Glu | Thr | Glu | Asp | Ala | Leu | Asn | Glu |
| 145 | | | | | 150 | | | | | 155 | | | | | 160 |
| Lys | Val | Val | Gly | Asp | Met | Ser | Arg | Ala | Lys | Ala | Leu | Lys | Ser | Leu | Phe |
| | | | | 165 | | | | | 170 | | | | | 175 | |
| Arg | Ile | Val | Thr | Pro | Tyr | Leu | Thr | Ile | Lys | Asp | Ile | Pro | Cys | Val | Ala |
| | | | | 180 | | | | | 185 | | | | | 190 | |
| Ile | Asn | His | Thr | Tyr | Glu | Thr | Gln | Glu | Met | Phe | Ser | Lys | Thr | Val | Met |
| | | | | 195 | | | | | 200 | | | | | 205 | |
| Gly | Gly | Gly | Thr | Gly | Ile | Leu | Tyr | Ser | Ala | Asn | Thr | Val | Phe | Phe | Ile |
| | 210 | | | | | 215 | | | | | 220 | | | | |
| Ser | Lys | Arg | Gln | Val | Lys | Glu | Gly | Thr | Glu | Leu | Thr | Gly | Tyr | Asp | Phe |
| 225 | | | | | 230 | | | | | 235 | | | | | 240 |
| Thr | Leu | Lys | Ala | Glu | Lys | Ser | Arg | Thr | Val | Lys | Glu | Lys | Ser | Thr | Phe |
| | | | | 245 | | | | | 250 | | | | | 255 | |
| Pro | Ile | Thr | Val | Asn | Phe | Asp | Gly | Gly | Ile | Asp | Pro | Phe | Ser | Gly | Leu |
| | | | | 260 | | | | | 265 | | | | | 270 | |
| Leu | Glu | Met | Ala | Thr | Glu | Ile | Gly | Phe | Val | Val | Lys | Pro | Lys | Ala | Gly |
| | | | | 275 | | | | | 280 | | | | | 285 | |
| Trp | Tyr | Ala | Arg | Glu | Phe | Leu | Asp | Glu | Glu | Thr | Gly | Glu | Met | Ile | Arg |
| | 290 | | | | | 295 | | | | | 300 | | | | |
| Glu | Glu | Lys | Ser | Trp | Arg | Ala | Lys | Ala | Thr | Asp | Cys | Val | Glu | Phe | Trp |
| 305 | | | | | 310 | | | | | 315 | | | | | 320 |
| Gly | Pro | Leu | Phe | Lys | His | Lys | Pro | Phe | Arg | Ala | Ile | Glu | Thr | Lys | |
| | | | | 325 | | | | | 330 | | | | | 335 | |
| Tyr | Lys | Leu | Gly | Ala | Ile | Ser | Ser | Ile | Lys | Glu | Val | Asp | Asp | Ala | Val |
| | | | | 340 | | | | | 345 | | | | | 350 | |
| Asn | Asp | Leu | Ile | Asn | Cys | Lys | Ala | Thr | Thr | Lys | Val | Pro | Val | Lys | Thr |
| | | | | 355 | | | | | 360 | | | | | 365 | |
| Ser | Asp | Ala | Pro | Ser | Ala | Ala | Asp | Ile | Glu | Asn | Asp | Leu | Asp | Glu | Met |
| | 370 | | | | | 375 | | | | | 380 | | | | |
| Glu | Asp | Phe | Asp | Glu | Leu | Ser | Asp | Leu | Asp | Glu | Leu | Asp | Glu | His | His |
| 385 | | | | | 390 | | | | | 395 | | | | | 400 |

His His His His

<210> SEQ ID NO 120
<211> LENGTH: 390
<212> TYPE: PRT
<213> ORGANISM: Artificial Sequence
<220> FEATURE:
<223> OTHER INFORMATION: Description of Artificial Sequence: Synthetic construct

<400> SEQUENCE: 120

```
Met Ser Asp Leu Lys Ser Arg Leu Ile Lys Ala Ser Thr Ser Lys Met
 1               5                  10                  15

Thr Ala Asp Leu Thr Lys Ser Lys Leu Phe Asn Asn Arg Asp Glu Val
             20                  25                  30

Pro Thr Arg Ile Pro Met Leu Asn Ile Ala Leu Gly Gly Ala Leu Asn
         35                  40                  45

Ala Gly Leu Gln Ser Gly Leu Thr Ile Phe Ala Ala Pro Ser Lys His
     50                  55                  60

Phe Lys Thr Leu Phe Gly Leu Thr Met Val Ala Ala Tyr Met Lys Lys
 65                  70                  75                  80

Tyr Lys Asp Ala Ile Cys Leu Phe Tyr Asp Ser Glu Phe Gly Ala Ser
                 85                  90                  95

Glu Ser Tyr Phe Arg Ser Met Gly Val Asp Leu Asp Arg Val Val His
            100                 105                 110

Thr Pro Ile Gln Ser Val Glu Gln Leu Lys Val Asp Met Thr Asn Gln
        115                 120                 125

Leu Asp Ala Ile Glu Arg Gly Asp Lys Val Ile Ile Phe Ile Asp Ser
    130                 135                 140

Ile Gly Asn Thr Ala Ser Lys Lys Glu Thr Glu Asp Ala Leu Asn Glu
145                 150                 155                 160

Lys Val Val Gly Asp Met Ser Arg Ala Lys Ala Leu Lys Ser Leu Phe
                165                 170                 175

Arg Ile Val Thr Pro Tyr Leu Thr Ile Lys Asp Ile Pro Cys Val Ala
            180                 185                 190

Ile Asn His Thr Ala Met Glu Ile Gly Gly Leu Tyr Pro Lys Glu Ile
        195                 200                 205

Met Gly Gly Gly Thr Gly Ile Leu Tyr Ser Ala Asn Thr Val Phe Phe
    210                 215                 220

Ile Ser Lys Arg Gln Val Lys Glu Gly Thr Glu Leu Thr Gly Tyr Asp
225                 230                 235                 240

Phe Thr Leu Lys Ala Glu Lys Ser Arg Thr Val Lys Glu Lys Ser Thr
                245                 250                 255

Phe Pro Ile Thr Val Asn Phe Asp Gly Gly Ile Asp Pro Phe Ser Gly
            260                 265                 270

Leu Leu Glu Met Ala Thr Glu Ile Gly Phe Val Val Lys Pro Lys Ala
        275                 280                 285

Gly Trp Tyr Ala Arg Glu Phe Leu Asp Glu Gly Thr Gly Glu Met Ile
    290                 295                 300

Arg Glu Glu Lys Ser Trp Arg Ala Lys Ala Thr Asp Cys Val Glu Phe
305                 310                 315                 320

Trp Gly Pro Leu Phe Lys His Lys Pro Phe Arg Asp Ala Ile Glu Thr
                325                 330                 335

Lys Tyr Lys Leu Gly Ala Ile Ser Ser Ile Lys Glu Val Asp Asp Ala
            340                 345                 350

Val Asn Asp Leu Ile Asn Cys Lys Ala Thr Thr Lys Val Pro Val Lys
```

-continued

```
                    355                 360                 365
Thr Ser Asp Ala Pro Ser Ala Ala Asp Ile Glu Asn Asp Leu Asp Glu
        370                 375                 380

Met Glu Asp Phe Asp Glu
385                 390

<210> SEQ ID NO 121
<211> LENGTH: 389
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 121

Met Ser Asp Leu Lys Ser Arg Leu Ile Lys Ala Ser Thr Ser Lys Met
1               5                   10                  15

Thr Ala Asp Leu Thr Lys Ser Lys Leu Phe Asn Asn Arg Asp Glu Val
            20                  25                  30

Pro Thr Arg Ile Pro Met Leu Asn Ile Ala Leu Gly Gly Ala Leu Asn
        35                  40                  45

Ala Gly Leu Gln Ser Gly Leu Thr Ile Phe Ala Ala Pro Ser Lys His
    50                  55                  60

Phe Lys Thr Leu Phe Gly Leu Thr Met Val Ala Ala Tyr Met Lys Lys
65                  70                  75                  80

Tyr Lys Asp Ala Ile Cys Leu Phe Tyr Asp Ser Glu Phe Gly Ala Ser
                85                  90                  95

Glu Ser Tyr Phe Arg Ser Met Gly Val Asp Leu Asp Arg Val Val His
            100                 105                 110

Thr Pro Ile Gln Ser Val Glu Gln Leu Lys Val Asp Met Thr Asn Gln
        115                 120                 125

Leu Asp Ala Ile Glu Arg Gly Asp Lys Val Ile Ile Phe Ile Asp Ser
    130                 135                 140

Ile Gly Asn Thr Ala Ser Lys Lys Glu Thr Glu Asp Ala Leu Asn Glu
145                 150                 155                 160

Lys Val Val Gly Asp Met Ser Arg Ala Lys Ala Leu Lys Ser Leu Phe
                165                 170                 175

Arg Ile Val Thr Pro Tyr Leu Thr Ile Lys Asp Ile Pro Cys Val Ala
            180                 185                 190

Ile Asn His Thr Leu Gln Thr Leu Glu Met Phe Ser Lys Glu Val Met
        195                 200                 205

Thr Gly Gly Thr Gly Ile Leu Tyr Ser Ala Asn Thr Val Phe Phe Ile
    210                 215                 220

Ser Lys Arg Gln Val Lys Glu Gly Thr Glu Leu Thr Gly Tyr Asp Phe
225                 230                 235                 240

Thr Leu Lys Ala Glu Lys Ser Arg Thr Val Lys Glu Lys Ser Thr Phe
                245                 250                 255

Pro Ile Thr Val Asn Phe Asp Gly Gly Ile Asp Pro Phe Ser Gly Leu
            260                 265                 270

Leu Glu Met Ala Thr Glu Ile Gly Phe Val Val Lys Pro Lys Ala Gly
        275                 280                 285

Trp Tyr Ala Arg Glu Phe Leu Asp Glu Thr Gly Glu Met Ile Arg
    290                 295                 300

Glu Glu Lys Ser Trp Arg Ala Lys Ala Thr Asp Cys Val Glu Phe Trp
305                 310                 315                 320

Gly Pro Leu Phe Lys His Lys Pro Phe Arg Asp Ala Ile Glu Thr Lys
```

```
                    325                 330                 335
Tyr Lys Leu Gly Ala Ile Ser Ser Ile Lys Glu Val Asp Asp Ala Val
            340                 345                 350

Asn Asp Leu Ile Asn Cys Lys Ala Thr Thr Lys Val Pro Val Lys Thr
            355                 360                 365

Ser Asp Ala Pro Ser Ala Ala Asp Ile Glu Asn Asp Leu Asp Glu Met
        370                 375                 380

Glu Asp Phe Asp Glu
385

<210> SEQ ID NO 122
<211> LENGTH: 389
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 122

Met Ser Asp Leu Lys Ser Arg Leu Ile Lys Ala Ser Thr Ser Lys Met
  1               5                  10                  15

Thr Ala Asp Leu Thr Lys Ser Lys Leu Phe Asn Asn Arg Asp Glu Val
             20                  25                  30

Pro Thr Arg Ile Pro Met Leu Asn Ile Ala Leu Gly Gly Ala Leu Asn
         35                  40                  45

Ala Gly Leu Gln Ser Gly Leu Thr Ile Phe Ala Ala Pro Ser Lys His
     50                  55                  60

Phe Lys Thr Leu Phe Gly Leu Thr Met Val Ala Ala Tyr Met Lys Lys
 65                  70                  75                  80

Tyr Lys Asp Ala Ile Cys Leu Phe Tyr Asp Ser Glu Phe Gly Ala Ser
                 85                  90                  95

Glu Ser Tyr Phe Arg Ser Met Gly Val Asp Leu Asp Arg Val Val His
            100                 105                 110

Thr Pro Ile Gln Ser Val Glu Gln Leu Lys Val Asp Met Thr Asn Gln
        115                 120                 125

Leu Asp Ala Ile Glu Arg Gly Asp Lys Val Ile Ile Phe Ile Asp Ser
    130                 135                 140

Ile Gly Asn Thr Ala Ser Lys Lys Glu Thr Glu Asp Ala Leu Asn Glu
145                 150                 155                 160

Lys Val Val Gly Asp Met Ser Arg Ala Lys Ala Leu Lys Ser Leu Phe
                165                 170                 175

Arg Ile Val Thr Pro Tyr Leu Thr Ile Lys Asp Ile Pro Cys Val Ala
            180                 185                 190

Ile Asn His Thr Tyr Gln Thr Gln Glu Ile Tyr Ser Lys Thr Val Met
        195                 200                 205

Ser Gly Gly Thr Gly Ile Leu Tyr Ser Ala Asn Thr Val Phe Phe Ile
    210                 215                 220

Ser Lys Arg Gln Val Lys Glu Gly Thr Glu Leu Thr Gly Tyr Asp Phe
225                 230                 235                 240

Thr Leu Lys Ala Glu Lys Ser Arg Thr Val Lys Glu Lys Ser Thr Phe
                245                 250                 255

Pro Ile Thr Val Asn Phe Asp Gly Gly Ile Asp Pro Phe Ser Gly Leu
            260                 265                 270

Leu Glu Met Ala Thr Glu Ile Gly Phe Val Val Lys Pro Lys Ala Gly
        275                 280                 285

Trp Tyr Ala Arg Glu Phe Leu Asp Glu Glu Thr Gly Glu Met Ile Arg
```

```
                290                 295                 300
Glu Glu Lys Ser Trp Arg Ala Lys Ala Thr Asp Cys Val Glu Phe Trp
305                 310                 315                 320

Gly Pro Leu Phe Lys His Lys Pro Phe Arg Asp Ala Ile Glu Thr Lys
                325                 330                 335

Tyr Lys Leu Gly Ala Ile Ser Ser Ile Lys Glu Val Asp Asp Ala Val
                340                 345                 350

Asn Asp Leu Ile Asn Cys Lys Ala Thr Thr Lys Val Pro Val Lys Thr
                355                 360                 365

Ser Asp Ala Pro Ser Ala Ala Asp Ile Glu Asn Asp Leu Asp Glu Met
                370                 375                 380

Glu Asp Phe Asp Glu
385

<210> SEQ ID NO 123
<211> LENGTH: 143
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(6)
<223> OTHER INFORMATION: Region may or may not be present

<400> SEQUENCE: 123

His His His His His His Met Arg Leu Glu Asp Leu Gln Glu Glu Leu
  1               5                  10                  15

Lys Lys Asp Val Phe Ile Asp Ser Thr Lys Leu Gln Tyr Glu Ala Ala
                 20                  25                  30

Asn Asn Val Met Leu Tyr Ser Lys Trp Leu Asn Lys His Ser Ser Ile
             35                  40                  45

Lys Lys Glu Met Leu Arg Ile Glu Ala Gln Lys Lys Val Ala Leu Lys
         50                  55                  60

Ala Arg Leu Asp Tyr Tyr Ser Gly Arg Gly Asp Gly Asp Glu Phe Ser
 65                  70                  75                  80

Met Asp Arg Tyr Glu Lys Ser Glu Met Lys Thr Val Leu Ala Ala Asp
                 85                  90                  95

Lys Asp Val Leu Lys Ile Glu Thr Thr Leu Gln Tyr Trp Gly Ile Leu
                100                 105                 110

Leu Glu Phe Cys Ser Gly Ala Leu Asp Ala Val Lys Ser Arg Ser Phe
            115                 120                 125

Ala Leu Lys His Ile Gln Asp Met Arg Glu Phe Glu Ala Gly Gln
        130                 135                 140

<210> SEQ ID NO 124
<211> LENGTH: 143
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(6)
<223> OTHER INFORMATION: Region may or may not be present

<400> SEQUENCE: 124

His His His His His His Met Lys Leu Glu Asp Leu Gln Glu Glu Leu
  1               5                  10                  15
```

Asp Ala Asp Leu Ala Ile Asp Thr Thr Lys Leu Gln Tyr Glu Thr Ala
            20                  25                  30

Asn Asn Val Lys Leu Tyr Ser Lys Trp Leu Arg Lys His Ser Phe Ile
        35                  40                  45

Arg Lys Glu Met Leu Arg Ile Glu Thr Gln Lys Lys Thr Ala Leu Lys
    50                  55                  60

Ala Arg Leu Asp Tyr Tyr Ser Gly Arg Gly Asp Gly Asp Glu Phe Ser
65                  70                  75                  80

Met Asp Arg Tyr Glu Lys Ser Glu Met Lys Thr Val Leu Ser Ala Asp
                85                  90                  95

Lys Asp Val Leu Lys Val Asp Thr Ser Leu Gln Tyr Trp Gly Ile Leu
            100                 105                 110

Leu Asp Phe Cys Ser Gly Ala Leu Asp Ala Ile Lys Ser Arg Gly Phe
        115                 120                 125

Ala Ile Lys His Ile Gln Asp Met Arg Ala Phe Glu Ala Gly Lys
    130                 135                 140

<210> SEQ ID NO 125
<211> LENGTH: 45
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (29)
<223> OTHER INFORMATION: TAMRA-dT
<220> FEATURE:
<221> NAME/KEY: modified_base
<222> LOCATION: (31)
<223> OTHER INFORMATION: THF
<220> FEATURE:
<221> NAME/KEY: modified_base
<222> LOCATION: (34)
<223> OTHER INFORMATION: BHQ2-dT

<400> SEQUENCE: 125
tgttaattga gcaagtgtat agagcattna ngantatgcg tggag            45

<210> SEQ ID NO 126
<211> LENGTH: 45
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (29)
<223> OTHER INFORMATION: TAMRA-dT
<220> FEATURE:
<221> NAME/KEY: modified_base
<222> LOCATION: (31)
<223> OTHER INFORMATION: THF
<220> FEATURE:
<221> NAME/KEY: modified_base
<222> LOCATION: (34)
<223> OTHER INFORMATION: BHQ2-dT

<400> SEQUENCE: 126
tgttaattga gcaagtgtat agagcattna ngantatgcg tggag            45

<210> SEQ ID NO 127
<211> LENGTH: 32
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 127
ctgtattaga agtacatgct gatcaagtga ca                                    32

<210> SEQ ID NO 128
<211> LENGTH: 45
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (29)
<223> OTHER INFORMATION: TAMRA-dT
<220> FEATURE:
<221> NAME/KEY: modified_base
<222> LOCATION: (31)
<223> OTHER INFORMATION: THF
<220> FEATURE:
<221> NAME/KEY: modified_base
<222> LOCATION: (34)
<223> OTHER INFORMATION: BHQ2-dT

<400> SEQUENCE: 128
tgttaattga gcaagtgtat agagcattna ngantatgcg tggag                      45

<210> SEQ ID NO 129
<211> LENGTH: 4
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 129

Phe Lys Arg Lys
  1

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 130

Phe Lys Arg Gln
  1

<210> SEQ ID NO 131
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

His His His His His His
  1               5

<210> SEQ ID NO 132
<211> LENGTH: 6
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 132

Leu Asp Glu Leu Asp Glu
 1               5
```